United States Patent
Kadoma et al.

(10) Patent No.: US 11,937,498 B2
(45) Date of Patent: Mar. 19, 2024

(54) ORGANIC COMPOUND, LIGHT-EMITTING DEVICE, LIGHT-EMITTING APPARATUS, ELECTRONIC APPARATUS, AND LIGHTING APPARATUS

(71) Applicant: Semiconductor Energy Laboratory Co., Ltd., Kanagawa-ken (JP)

(72) Inventors: Hiroshi Kadoma, Kanagawa (JP); Satoshi Seo, Kanagawa (JP); Hiroki Suzuki, Aichi (JP); Naoaki Hashimoto, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 543 days.

(21) Appl. No.: 17/057,830

(22) PCT Filed: May 22, 2019

(86) PCT No.: PCT/IB2019/054218
§ 371 (c)(1),
(2) Date: Nov. 23, 2020

(87) PCT Pub. No.: WO2019/229591
PCT Pub. Date: Dec. 5, 2019

(65) Prior Publication Data
US 2021/0119133 A1    Apr. 22, 2021

(30) Foreign Application Priority Data

May 31, 2018  (JP) .................................. 2018-104950
Aug. 21, 2018  (JP) .................................. 2018-154845

(51) Int. Cl.
*H01L 51/50*    (2006.01)
*C07C 15/38*    (2006.01)
(Continued)

(52) U.S. Cl.
CPC .......... *H10K 85/626* (2023.02); *C07C 15/38* (2013.01); *H10K 50/11* (2023.02); *H10K 59/12* (2023.02);
(Continued)

(58) Field of Classification Search
None
See application file for complete search history.

(56) References Cited

U.S. PATENT DOCUMENTS 7,829,206 B2    11/2010    Kubota
8,030,646 B2    10/2011    Suzuki et al.
(Continued)

FOREIGN PATENT DOCUMENTS

CN    101445422 A    6/2009
CN    101679855 A    3/2010
(Continued)

OTHER PUBLICATIONS

International Search Report (Application No. PCT/IB2019/054218) dated Aug. 27, 2019.
(Continued)

*Primary Examiner* — Gregory D Clark
(74) *Attorney, Agent, or Firm* — Husch Blackwell LLP

(57) ABSTRACT

A novel compound is provided. A light-emitting device having high emission efficiency and a long lifetime is also provided. An organic compound is represented by General Formula (G2), in which a benzo[a]anthracene skeleton is bonded to the 2-position of an anthracene skeleton. In General Formula (G2), R1 to R3, R5 to R12, and R21 to R29 each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring. Another
(Continued)

embodiment of the present invention is a light-emitting device including the compound.

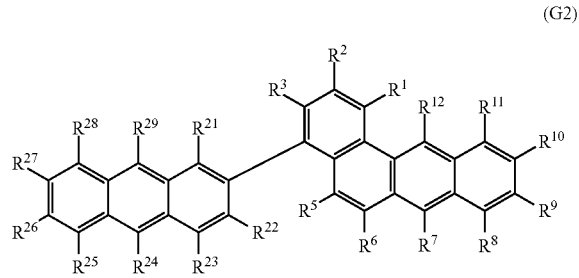

(G2)

13 Claims, 66 Drawing Sheets

(51) Int. Cl.
*H10K 85/60* (2023.01)
*H10K 50/11* (2023.01)
*H10K 59/12* (2023.01)
*H10K 59/38* (2023.01)
*H10K 59/40* (2023.01)
*H10K 101/10* (2023.01)

(52) U.S. Cl.
CPC ............ *H10K 59/38* (2023.02); *H10K 59/40* (2023.02); *H10K 2101/10* (2023.02)

(56) References Cited

U.S. PATENT DOCUMENTS

| | | | |
|---|---|---|---|
| 8,771,840 B2 | 7/2014 | Suzuki et al. | |
| 8,822,434 B2 | 9/2014 | Liang et al. | |
| 8,906,893 B2 | 12/2014 | Anemian et al. | |
| 8,986,852 B2 | 3/2015 | Stoessel et al. | |
| 9,093,649 B2 | 7/2015 | Kawakami et al. | |
| 9,142,782 B2 | 9/2015 | Pillow et al. | |
| 9,219,242 B2 | 12/2015 | Ogiwara et al. | |
| 9,303,053 B2 | 4/2016 | Liang et al. | |
| 9,499,459 B2 | 11/2016 | Parham et al. | |
| 9,526,739 B2 | 12/2016 | Liang et al. | |
| 9,586,924 B2 | 3/2017 | Kawakami et al. | |
| 9,614,170 B2 | 4/2017 | Ogiwara et al. | |
| 9,899,603 B2 | 2/2018 | Kawakami et al. | |
| 10,273,404 B2 | 4/2019 | Buesing et al. | |
| 2006/0046097 A1 | 3/2006 | Kim et al. | |
| 2007/0075312 A1* | 4/2007 | Chin ...................... H10K 59/32 257/40 |
| 2007/0224447 A1 | 9/2007 | Sotoyama et al. | |
| 2007/0247063 A1 | 10/2007 | Murase et al. | |
| 2008/0103279 A1 | 5/2008 | Heun et al. | |
| 2010/0069647 A1 | 3/2010 | Suzuki et al. | |
| 2010/0187505 A1 | 7/2010 | Stoessel et al. | |
| 2010/0295444 A1 | 11/2010 | Kuma et al. | |
| 2010/0301318 A1 | 12/2010 | Kuma et al. | |
| 2011/0137088 A1 | 6/2011 | Borden | |
| 2011/0233604 A1 | 9/2011 | Ikeda | |
| 2012/0126208 A1 | 5/2012 | Kawamura et al. | |
| 2012/0153268 A1 | 6/2012 | Kawamura et al. | |
| 2012/0217449 A1 | 8/2012 | Spreitzer et al. | |
| 2012/0326602 A1 | 12/2012 | Buesing et al. | |
| 2014/0319510 A1* | 10/2014 | Kageyama ........... H10K 85/633 564/429 |
| 2014/0339522 A1 | 11/2014 | Nonaka. et al. | |
| 2015/0031900 A1 | 1/2015 | Kawakami et al. | |
| 2015/0329514 A1 | 11/2015 | Kawakami et al. | |
| 2016/0104847 A1 | 4/2016 | Xia et al. | |
| 2016/0126463 A1 | 5/2016 | Kadoma et al. | |
| 2016/0166591 A1 | 6/2016 | Liang et al. | |
| 2017/0077418 A1 | 3/2017 | Stoessel et al. | |
| 2017/0125686 A1 | 5/2017 | Heil et al. | |
| 2017/0229648 A1 | 8/2017 | Kawakami et al. | |
| 2017/0244059 A1* | 8/2017 | Sasaki ................... H10K 50/82 |

FOREIGN PATENT DOCUMENTS

| | | |
|---|---|---|
| CN | 105683173 A | 6/2016 |
| CN | 106170476 A | 11/2016 |
| CN | 108101875 A | 6/2018 |
| DE | 10 2007 024 850 A1 | 12/2008 |
| DE | 10 2010 010 631 A1 | 9/2011 |
| DE | 11 2011 100 832 A5 | 1/2013 |
| EP | 2 148 909 | 2/2010 |
| EP | 3 132 476 | 2/2017 |
| JP | 2000-178548 A | 6/2000 |
| JP | 2002-193952 A | 7/2002 |
| JP | 2010-528070 | 8/2010 |
| JP | 2012-077069 A | 4/2012 |
| JP | 2013-512670 | 4/2013 |
| JP | 2013-521670 | 6/2013 |
| JP | 2013-232521 A | 11/2013 |
| JP | 5384482 B2 | 1/2014 |
| JP | 2015-042636 A | 3/2015 |
| JP | 2015-109407 A | 6/2015 |
| JP | 2015-181169 A | 10/2015 |
| JP | 2017-514807 | 6/2017 |
| JP | 2018-065791 A | 4/2018 |
| KR | 2009-0020542 A | 2/2009 |
| KR | 2012-0038422 A | 4/2012 |
| KR | 2016-0034937 A | 3/2016 |
| KR | 2016-0146826 A | 12/2016 |
| KR | 2017-0134793 A | 12/2017 |
| KR | 2019-0040106 A | 4/2019 |
| TW | 200914576 | 4/2009 |
| TW | 201604170 | 2/2016 |
| WO | WO 2008/145239 A2 | 12/2008 |
| WO | WO 2011/068708 A2 | 6/2011 |
| WO | WO 2011/103552 A2 | 8/2011 |
| WO | WO 2011/110276 A1 | 9/2011 |
| WO | WO 2015/011614 A1 | 1/2015 |
| WO | WO 2015/158409 A1 | 10/2015 |

OTHER PUBLICATIONS

Written Opinion (Application No. PCT/IB2019/054218) dated Aug. 27, 2019.

* cited by examiner

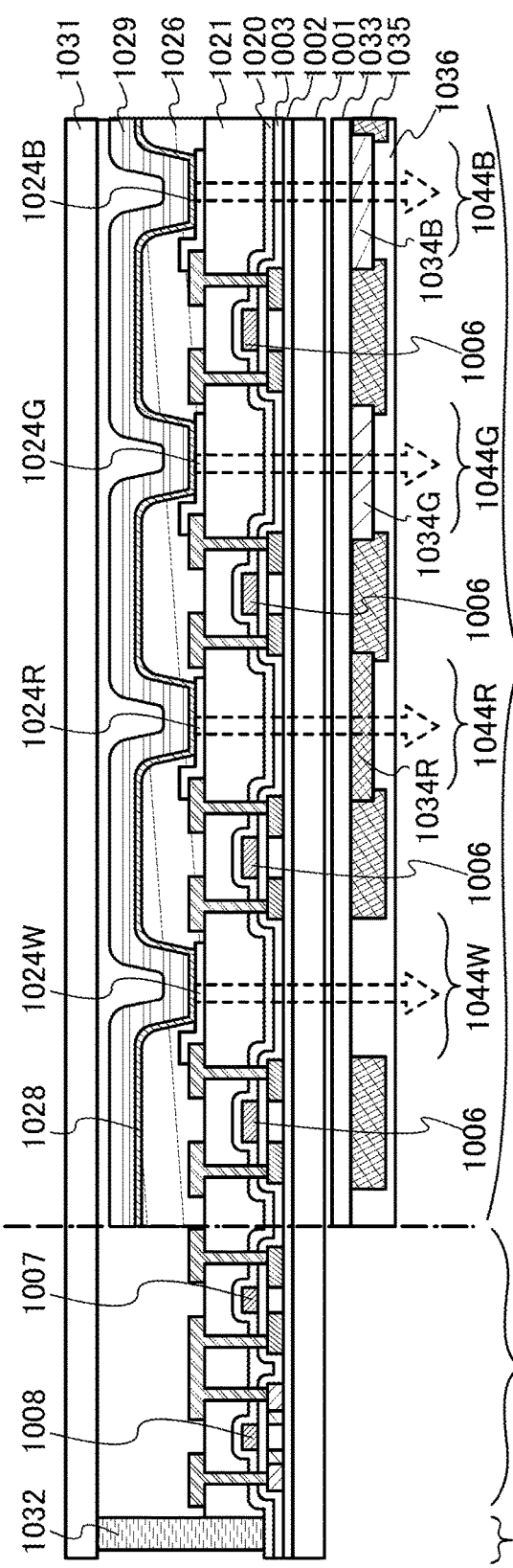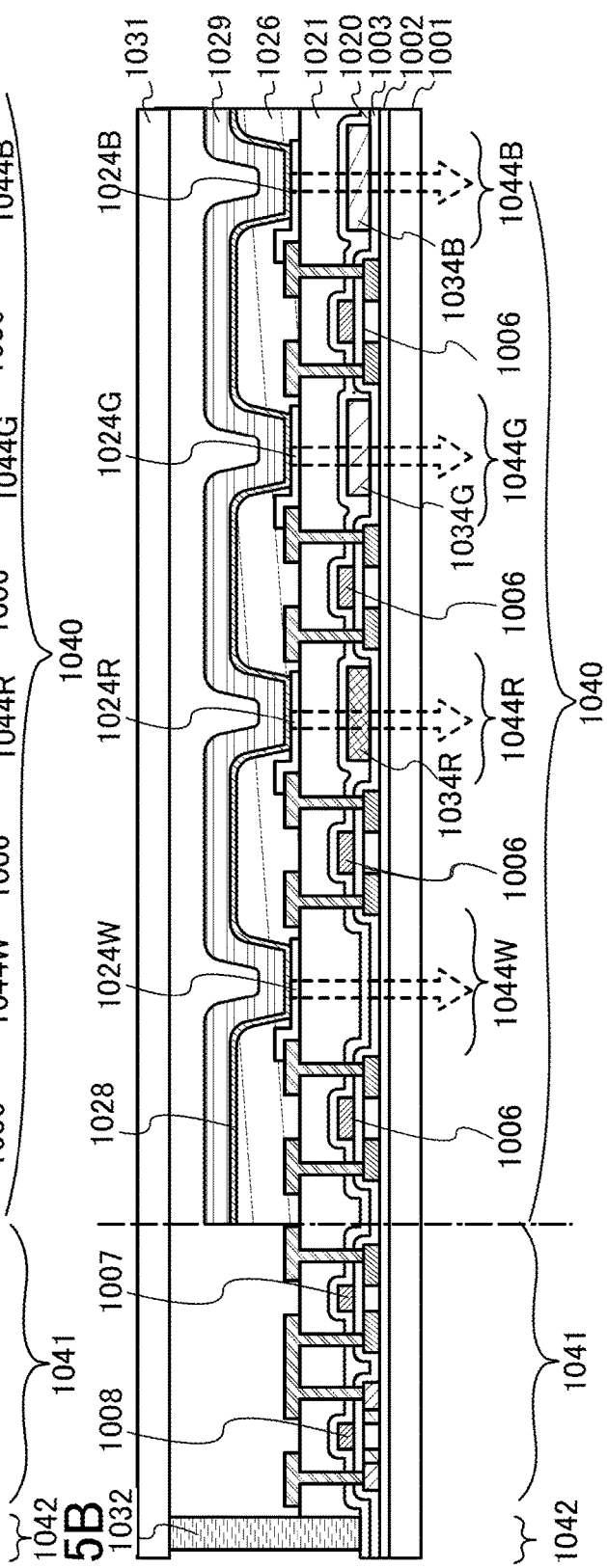

FIG. 9A
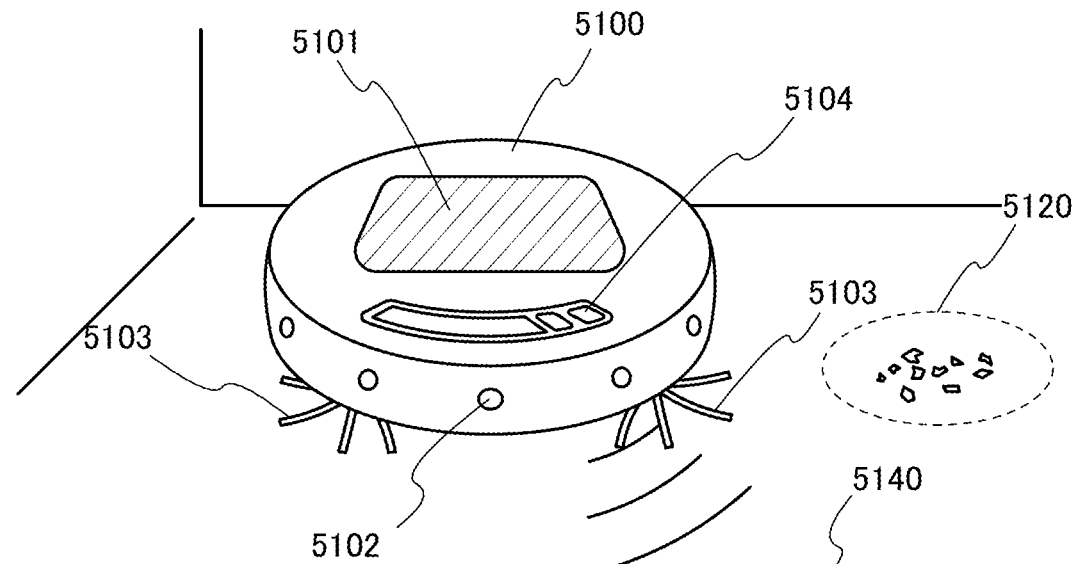
FIG. 9B
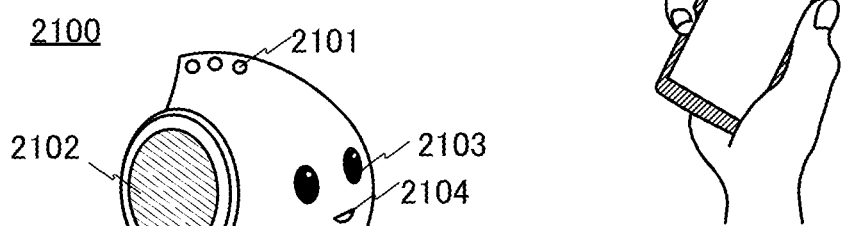
FIG. 9C
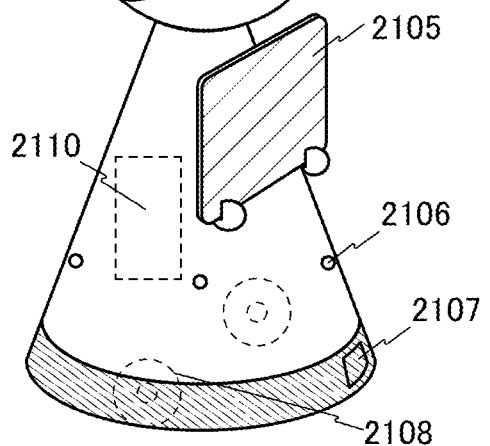
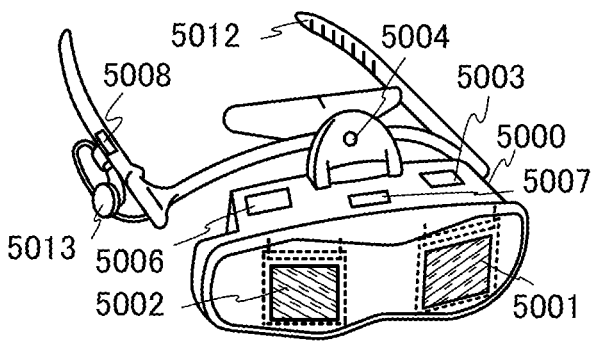

ORGANIC COMPOUND, LIGHT-EMITTING DEVICE, LIGHT-EMITTING APPARATUS, ELECTRONIC APPARATUS, AND LIGHTING APPARATUS

This application is a 371 of international application PCT/IB2019/054218 filed on May 22, 2019 which is incorporated herein by reference.

TECHNICAL FIELD

One embodiment of the present invention relates to a novel organic compound. One embodiment of the present invention relates particularly to an organic compound having a benzo[a]anthracene skeleton and an anthracene skeleton. In addition, one embodiment of the present invention relates to a light-emitting device, a light-emitting apparatus, an electronic apparatus, and a lighting apparatus each of which includes the organic compound.

Note that one embodiment of the present invention is not limited to the above technical field. One embodiment of the present invention relates to an object, a method, or a manufacturing method. In particular, one embodiment of the present invention relates to an organic compound, a light-emitting device, a light-emitting apparatus, and a lighting apparatus, and manufacturing methods therefor. One embodiment of the present invention relates to a novel method for synthesizing an organic compound having a benzo[a]anthracene skeleton and an anthracene skeleton. Thus, specific examples of one embodiment of the present invention disclosed in this specification include methods for manufacturing a light-emitting device, a light-emitting apparatus, a display apparatus, an electronic apparatus, and a lighting apparatus each of which includes the organic compound.

BACKGROUND ART

Light-emitting devices (organic EL devices) that use organic compounds and utilize electroluminescence (EL) have been put into practical use. In the basic structure of such light-emitting devices, an organic compound layer (EL layer) containing a light-emitting material is interposed between a pair of electrodes. Carriers are injected by application of voltage to this device, and recombination energy of the carriers is used, whereby light emission can be obtained from the light-emitting material.

Such light-emitting devices are of self-light-emitting type, and have advantages such as high visibility and no need for backlight when used in pixels of a display; accordingly, the light-emitting devices are suitable as flat panel display devices. Displays using such light-emitting devices are also highly advantageous in that they can be fabricated thin and lightweight. Moreover, an extremely fast response speed is also a feature.

Since light-emitting layers of such light-emitting devices can be successively formed two-dimensionally, planar light emission can be obtained. This is a feature difficult to obtain with point light sources typified by incandescent lamps and LEDs or linear light sources typified by fluorescent lamps. Furthermore, light emission from an organic compound can be light emission that does not include UV light by selecting a material; thus, the light-emitting devices also have great potential as planar light sources usable in lighting apparatuses and the like.

Displays and lighting apparatuses using organic EL devices are suitable for a variety of electronic apparatuses as described above; thus, research and development of light-emitting devices have progressed in seeking for higher efficiency or longer device lifetimes. White light is required for the above displays and lighting apparatuses; therefore, three colors of red (R), green (G), and blue (B) are mixed. Here, a fluorescent material is used for blue light because a blue phosphorescent material at present is insufficient in color purity and reliability. Thus, blue fluorescent materials with high color purity, reliability, and emission efficiency have been actively developed (e.g., Patent Document 1 and Patent Document 2).

For higher efficiency of a fluorescent device, a method using a triplet exciton is given. For example, a highly efficient fluorescent device using triplet-triplet annihilation (TTA) has been reported.

REFERENCE

Patent Document

[Patent Document 1] Japanese Published Patent Application No. 2012-77069
[Patent Document 2] Japanese Published Patent Application No. 2002-193952

SUMMARY OF THE INVENTION

Problems to be Solved by the Invention

Along with the demand for higher performance of electronic apparatuses and lighting apparatuses, a variety of properties are required for light-emitting devices, and in particular, a blue fluorescent material with high color purity is desired. In addition, higher emission efficiency and higher reliability are required for a material used for a light-emitting device.

As described above, an example of a way of increasing the efficiency of a fluorescent device is a method using TTA. In the case of using TTA, triplet excitons generated in a light-emitting layer need to be converted into singlet excitons. For this reason, a material that can efficiently convert triplet excitons into singlet excitons is required.

In view of the above, an object of one embodiment of the present invention is to provide a novel organic compound. Another object of one embodiment of the present invention is to provide a novel organic compound having a benzo[a]anthracene skeleton. Another object of one embodiment of the present invention is to provide a light-emitting device having high emission efficiency. Another object of one embodiment of the present invention is to provide a light-emitting device having a long lifetime. Another object of one embodiment of the present invention is to provide a light-emitting device having high color purity. Another object of one embodiment of the present invention is to provide a light-emitting device having low driving voltage. Another object of one embodiment of the present invention is to provide a light-emitting device having a large proportion of delayed fluorescence.

Another object of one embodiment of the present invention is to provide a light-emitting device, a light-emitting apparatus, and an electronic apparatus each having high reliability. Another object of one embodiment of the present invention is to provide a light-emitting device, a light-emitting apparatus, and an electronic apparatus each having low power consumption.

Note that the description of these objects does not preclude the existence of other objects. In one embodiment of the present invention, there is no need to achieve all of these objects. Other objects will be apparent from and can be derived from the description of the specification, the drawings, the claims, and the like.

Means for Solving the Problems

One embodiment of the present invention is an organic compound having a substituted or unsubstituted benzo[a]

anthracene skeleton and a substituted or unsubstituted anthracene skeleton, and the benzo[a]anthracene skeleton is bonded to the 2-position of the anthracene skeleton.

Another embodiment of the present invention is an organic compound represented by General Formula (G1) below.

[Chemical Formula 1]

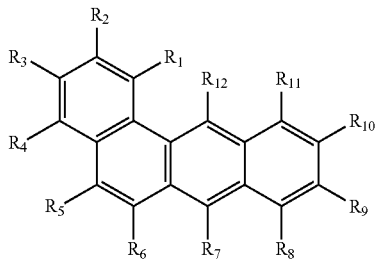
(G1)

In General Formula (G1), any one of $R^1$ to $R^{12}$ is a substituent represented by General Formula (g1), and the other $R^1$ to $R^{12}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring

[Chemical Formula 2]

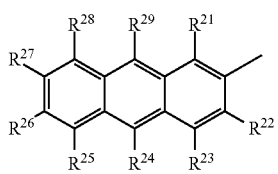
(g1)

In General Formula (g1), $R^{21}$ to $R^{29}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

Another embodiment of the present invention is an organic compound represented by General Formula (G2).

[Chemical Formula 3]

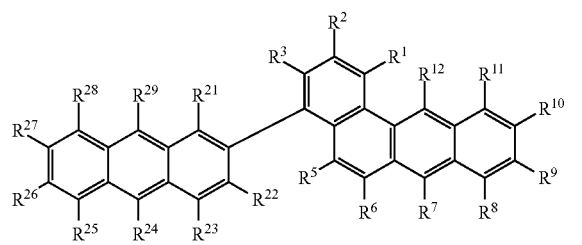
(G2)

In General Formula (G2), $R^1$ to $R^3$, $R^5$ to $R^{12}$, and $R^{21}$ to $R^{29}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

The skeletons are preferably bonded to each other at the 2-position of the anthracene skeleton and the 4-position of the benzo[a]anthracene skeleton. With this structure, an organic compound having high reliability can be obtained.

Another embodiment of the present invention is an organic compound represented by General Formula (G3).

[Chemical Formula 4]

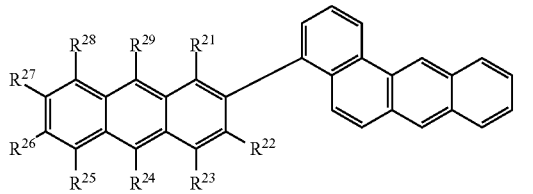
(G3)

In the above structures, in General Formula (G1) to General Formula (G3), $R^{24}$ and $R^{29}$ each independently represent preferably a substituted or unsubstituted aryl group having 6 to 13 carbon atoms, further preferably a substituted or unsubstituted phenyl group or a substituted or unsubstituted naphthyl group.

In the above structures, in General Formula (G1) to General Formula (G3), it is preferred that $R^{24}$ be a substituted or unsubstituted phenyl group and $R^{29}$ be a substituted or unsubstituted naphthyl group.

Another embodiment of the present invention is an organic compound represented by any one of Structural Formulae (100) to (104), (115), (120), (167), and (117) below.

[Chemical Formula 5]

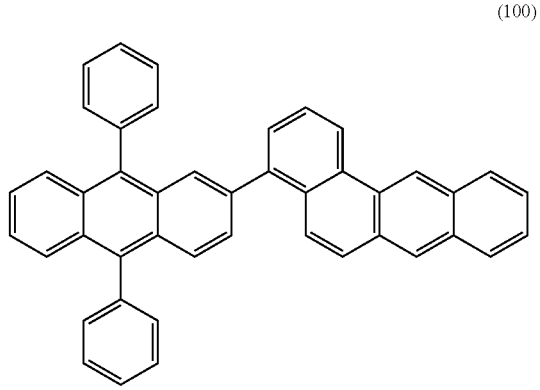
(100)

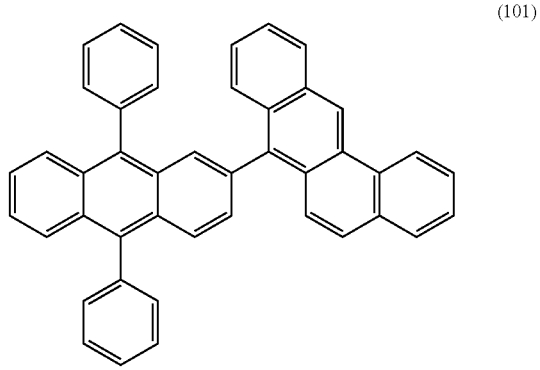
(101)

(102)
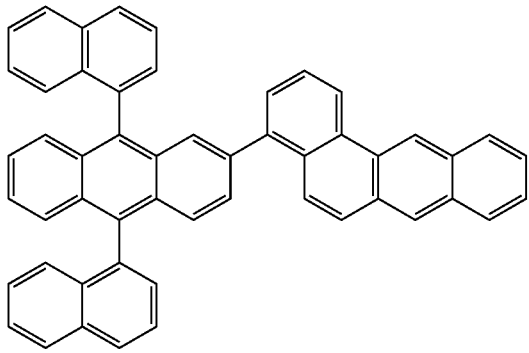

(103)
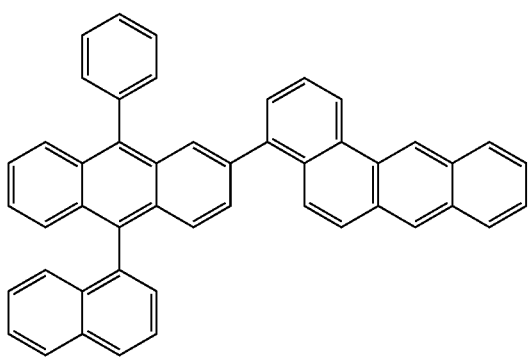

(104)
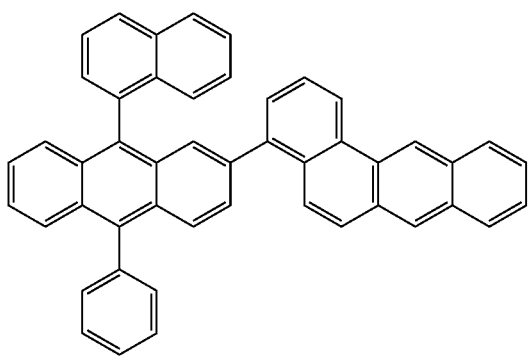

(120)
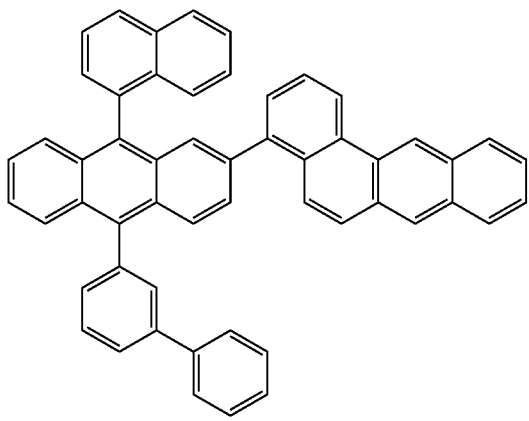

(115)
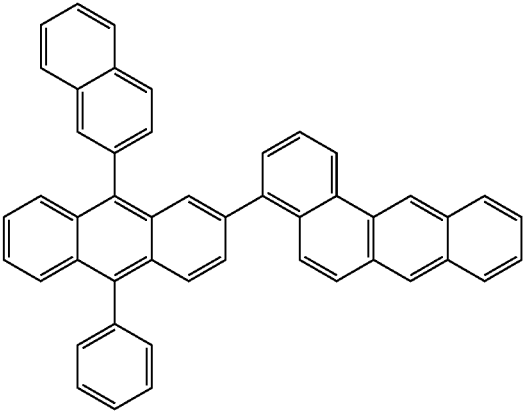

(167)
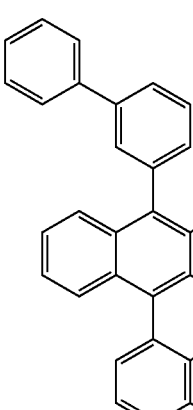

(117)
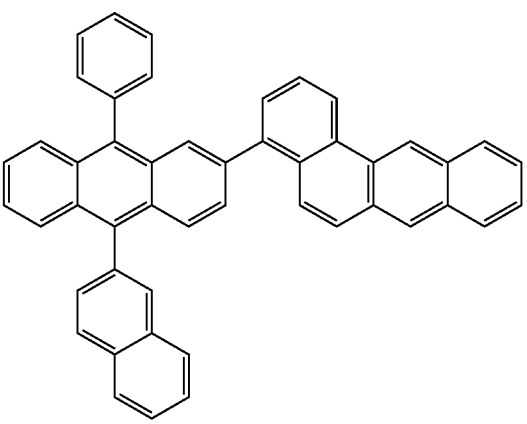

Another embodiment of the present invention is a light-emitting device that includes an EL layer between a pair of electrodes, and includes the organic compound described in any of the above structures in the EL layer. The organic compound is preferably included in a light-emitting layer in the EL layer.

Note that the light-emitting device having any of the above structures includes an EL layer between an anode and a cathode. The EL layer preferably includes at least a light-emitting layer. In addition, the EL layer may include a hole-injection layer, a hole-transport layer, an electron-transport layer, an electron-injection layer, and other functional layers.

Another embodiment of the present invention is a display apparatus including the light-emitting device having any of the above structures, and at least one of a color filter and a transistor. Another embodiment of the present invention is an electronic apparatus including the display apparatus, and at least one of a housing and a touch sensor. Another embodiment of the present invention is a lighting apparatus including the light-emitting device having any of the above structures, and at least one of a housing and a touch sensor. The category of one embodiment of the present invention includes not only a light-emitting apparatus including a light-emitting device but also an electronic apparatus including a light-emitting apparatus. Accordingly, a light-emitting apparatus in this specification refers to an image display device or a light source (including alighting apparatus). A display module in which a connector such as an FPC (Flexible Printed Circuit) or a TCP (Tape Carrier Package) is connected to a light-emitting device, a display module in which a printed wiring board is provided on the tip of a TCP, and a display module in which an IC (integrated circuit) is directly mounted on a light-emitting device by a COG (Chip On Glass) method are also embodiments of the present invention.

Effect of the Invention

According to one embodiment of the present invention, a novel organic compound can be provided. Alternatively, according to one embodiment of the present invention, a novel organic compound having a benzo[a]anthracene skeleton can be provided. Alternatively, according to one embodiment of the present invention, a light-emitting device having high emission efficiency can be provided. Alternatively, according to one embodiment of the present invention, a light-emitting device having a long lifetime can be provided. Alternatively, according to one embodiment of the present invention, a light-emitting device having high color purity can be provided. Alternatively, according to one embodiment of the present invention, a light-emitting device having low driving voltage can be provided. Alternatively, according to one embodiment of the present invention, a light-emitting device having a large proportion of delayed fluorescence can be provided.

According to another embodiment of the present invention, a light-emitting device, a light-emitting apparatus, and an electronic apparatus each having high reliability can be provided. According to another embodiment of the present invention, a light-emitting device, a light-emitting apparatus, and an electronic apparatus each having low power consumption can be provided.

Note that the description of these effects does not preclude the existence of other effects. Note that one embodiment of the present invention does not need to have all these effects. Other effects will be apparent from and can be derived from the description of the specification, the drawings, the claims, and the like.

BRIEF DESCRIPTION OF THE DRAWINGS

FIG. 5(A), (B) Conceptual views of active matrix light-emitting apparatuses of one embodiment of the present invention.

FIG. 9(A) to (C) Views illustrating electronic apparatuses of one embodiment of the present invention.

MODE FOR CARRYING OUT THE INVENTION

Figure 1A:
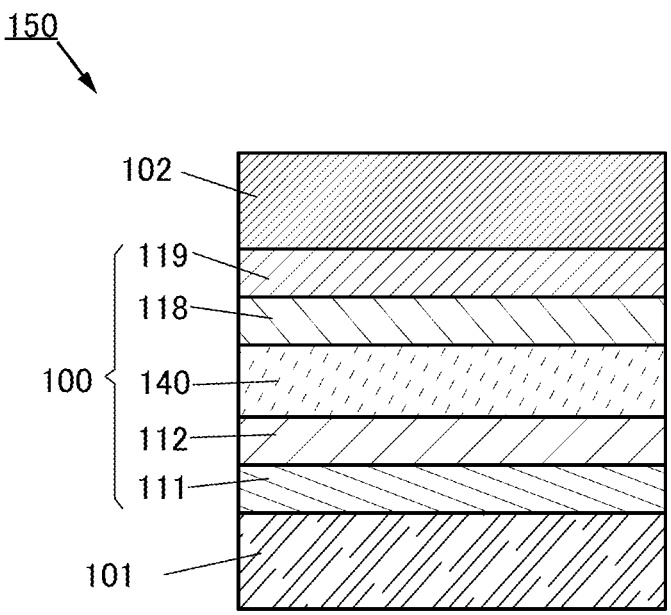
FIG. 1(A), (B) Schematic views of a light-emitting device of one embodiment of the present invention. (C) A diagram illustrating the correlation of energy levels in a light-emitting device of one embodiment of the present invention.

Hereinafter, embodiments of the present invention will be described. Note that the present invention can be implemented in many different modes, and it is easily understood by those skilled in the art that modes and details of the present invention can be changed in various ways without departing from the spirit and scope thereof. Thus, the present invention should not be interpreted as being limited to description of the embodiments.

Note that in each drawing described in this specification, the size and the thickness of an anode, an EL layer, an intermediate layer, a cathode, and the like are exaggerated for clarity in some cases. Therefore, the sizes of the components are not limited to the sizes in the drawings and relative sizes between the components.

Note that the ordinal numbers such as first, second, and third in this specification and the like are used for convenience and do not denote the order of steps, the positional relation, or the like. Therefore, for example, description can be made even when "first" is replaced with "second", "third", or the like as appropriate. In addition, the ordinal numbers in this specification and the like do not sometimes correspond to the ordinal numbers that are used to specify one embodiment of the present invention.

Note that in structures of the present invention described in this specification and the like, the same portions or portions having similar functions are denoted by common reference numerals in different drawings, and the description thereof is not repeated. Furthermore, the same hatch pattern is used for the portions having similar functions, and the portions are not especially denoted by reference numerals in some cases.

Note that the term "film" and the term "layer" can be interchanged with each other depending on the case or circumstances. For example, the term "conductive layer" can be changed into the term "conductive film" in some cases. As another example, the term "insulating film" can be changed into the term "insulating layer" in some cases.

Embodiment 1

In this embodiment, an organic compound of one embodiment of the present invention will be described below.

An organic compound of one embodiment of the present invention is an organic compound represented by General Formula (G1) below.

[Chemical Formula 6]

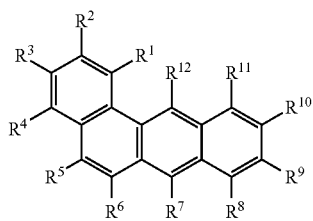

(G1)

In General Formula (G1), any one of $R^1$ to $R^{12}$ is a substituent represented by General Formula (g1) below, and the other $R^1$ to $R^{12}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

[Chemical Formula 7]

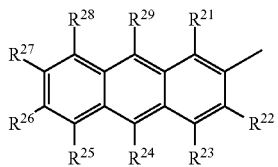

(g1)

In General Formula (g1), $R^{21}$ to $R^{29}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

The organic compound of one embodiment of the present invention includes a substituted or unsubstituted benzo[a]anthracene skeleton and a substituted or unsubstituted anthracene skeleton, and the benzo[a]anthracene skeleton is bonded to the 2-position of the anthracene skeleton. When the organic compound with this structure is used in a light-emitting device, the light-emitting device can have high emission efficiency and/or high reliability.

When the organic compound having the benzo[a]anthracene skeleton at the 2-position of the anthracene skeleton is used as a host material of a light-emitting layer in a light-emitting device, it is possible to obtain a light-emitting device in which delayed fluorescence components account for a large proportion of the total emission components (initial emission components+delayed fluorescence components). That is, TTA described later can be efficiently utilized, whereby a light-emitting device having high emission efficiency can be obtained.

The organic compound having the benzo[a]anthracene skeleton at the 2-position of the anthracene skeleton has a favorable electron-transport property because of having a large π-conjugated system. Thus, by using the organic compound of one embodiment of the present invention for a light-emitting layer and/or an electron-transport layer in an EL layer, a light-emitting device with low driving voltage can be fabricated.

In addition, an organic compound of one embodiment of the present invention is an organic compound represented by General Formula (G2) below.

[Chemical Formula 8]

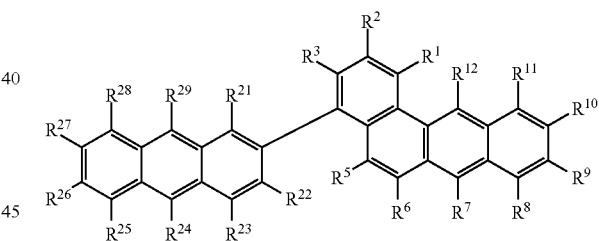

(G2)

In General Formula (G2), $R^1$ to $R^3$, $R^5$ to $R^{12}$, and $R^2$ to $R^{29}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

When the skeletons are bonded to each other at the 2-position of the anthracene skeleton and the 4-position of the benzo[a]anthracene skeleton, the conjugated system is not easily extended between the anthracene skeleton and the benzo[a]anthracene skeleton; thus, the organic compound can have a wide band gap. Accordingly, the organic compound can be favorably used in a blue fluorescent device. In addition, with the above structure, a highly reliable organic compound can be obtained. Moreover, TTA can be efficiently utilized.

By directly bonding an anthracene skeleton and a benzo[a]anthracene skeleton, which are electrochemically stable, a highly reliable organic compound can be obtained.

In addition, an organic compound of one embodiment of the present invention is an organic compound represented by General Formula (G3) below.

[Chemical Formula 9]

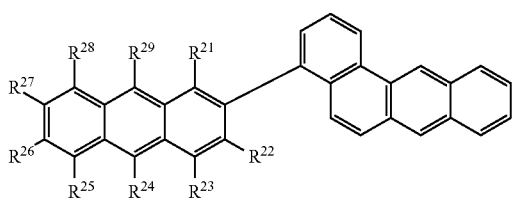

(G3)

In General Formula (G3), $R^{21}$ to $R^{29}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

Since a benzo[a]anthracene skeleton without a substituent is more electrochemically stable, the organic compound is preferable because of high reliability. It is also preferable because of easy synthesis.

In General Formulae (G1) to (G3), it is preferable that $R^{24}$ and $R^{29}$ each independently represent a substituted or unsubstituted aryl group having 6 to 13 carbon atoms. When an aryl group, which is electrochemically stable, is bonded at the substitution sites, the organic compound can have high reliability. Moreover, the organic compound can have a high molecular weight and thus can have excellent heat resistance.

In General Formulae (G1) to (G3), it is preferable that $R^{24}$ and $R^{29}$ each independently represent a substituted or unsubstituted phenyl group or a substituted or unsubstituted naphthyl group. The use of a bulky aryl group, such as a naphthyl group, is preferable, in which case heat resistance is increased. It is further preferable that $R^{24}$ represent a substituted or unsubstituted phenyl group and $R^{29}$ represent a substituted or unsubstituted naphthyl group. When different aryl groups are introduced into $R^{24}$ and $R^{29}$, a light-emitting device having high heat resistance and high reliability can be obtained.

Examples of Substituents

In General Formulae (G1) to (G3) and (g1), $R^1$ to $R^{12}$ and $R^{21}$ to $R^{29}$ each represent, for example, hydrogen, an alkyl group having 1 to 6 carbon atoms, a substituted or unsubstituted cycloalkyl group having 3 to 6 carbon atoms, or a substituted or unsubstituted aryl group having 6 to 13 carbon atoms in a ring. Specific examples of the alkyl group include a methyl group, an ethyl group, a propyl group, an isopropyl group, a butyl group, an isobutyl group, a tert-butyl group, and an n-hexyl group; specific examples of the cycloalkyl group include a cyclopropyl group, a cyclobutyl group, a cyclopentyl group, and a cyclohexyl group; and specific examples of the aryl group include a phenyl group, a naphthyl group, and a fluorenyl group. More specific examples include groups represented by Structural Formulae (R-1) to (R-22) below. Note that the groups represented by $R^1$ to $R^{29}$ are not limited thereto.

[Chemical Formula 10]

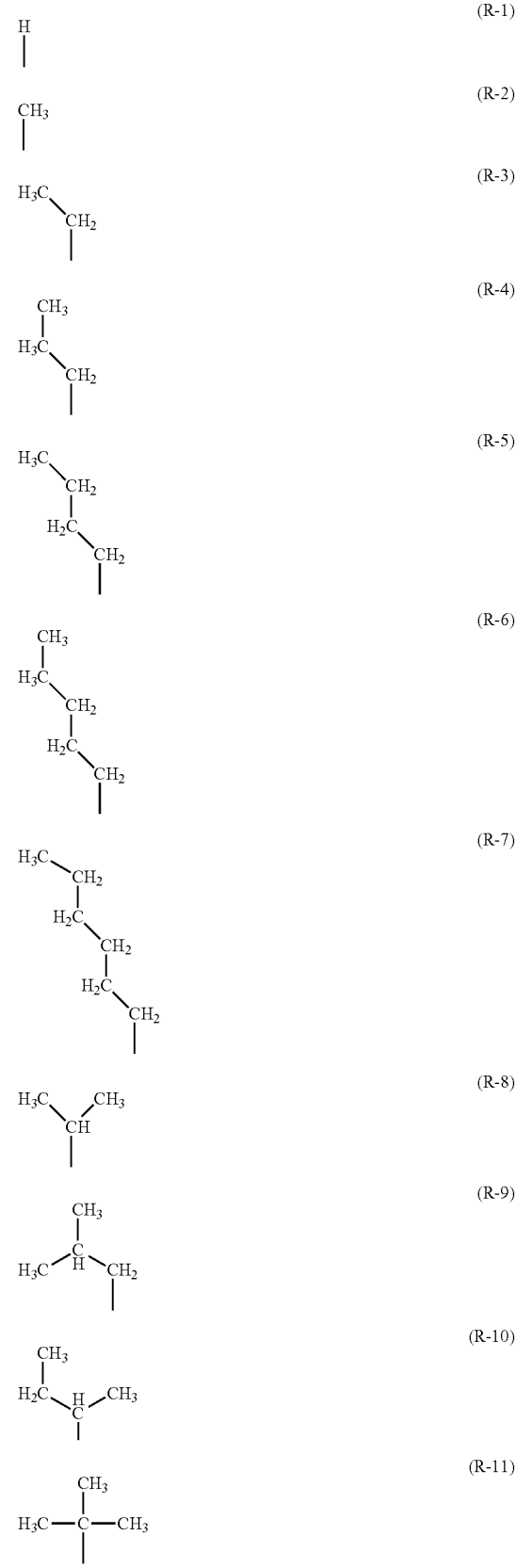

(R-12)

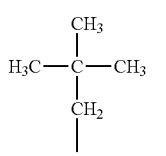

(R-13)

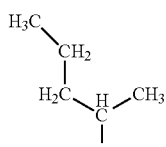

(R-14)

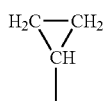

(R-15)

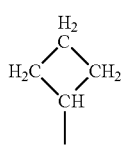

(R-16)

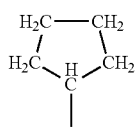

(R-17)

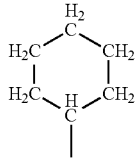

(R-18)

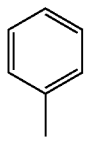

(R-19)

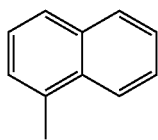

(R-20)

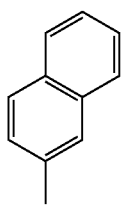

(R-21)

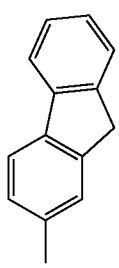

(R-22)

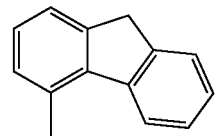

In the case where $R^1$ to $R^{12}$ and $R^{21}$ to $R^{29}$ are hydrogen, the organic compound of one embodiment of the present invention can be synthesized easily and at low cost, which is preferable because the organic compound achieves electrochemical stability and high reliability. In the case of using a substituent other than hydrogen, the heat resistance of the organic compound of one embodiment of the present invention can be increased. In the case of using an alkyl group or a cycloalkyl group as in (R-2) to (R-17), the organic compound of one embodiment of the present invention can have high solubility in an organic solvent and thus can be easily purified. Using an aryl group that does not include an alkyl group or a cycloalkyl group as in (R-18) to (R-22) achieves electrochemical stability and high reliability.

In the case where $R^1$ to $R^{29}$ in General Formulae (G1) to (G3) and (g1) above further include a substituent, examples of the substituent include an alkyl group having 1 to 6 carbon atoms, a substituted or unsubstituted cycloalkyl group having 3 to 7 carbon atoms, and a substituted or unsubstituted aryl group having 6 to 25 carbon atoms. Specific examples of the alkyl group include a methyl group, an ethyl group, a propyl group, an isopropyl group, a butyl group, an isobutyl group, a tert-butyl group, and an n-hexyl group; specific examples of the cycloalkyl group include a cyclopropyl group, a cyclobutyl group, a cyclopentyl group, and a cyclohexyl group; and specific examples of the aryl group include a phenyl group, a naphthyl group, and a fluorenyl group.

Specific Examples of Compounds

Specific structure examples of the compounds represented by General Formulae (G1) to (G3) include organic compounds represented by Structural Formulae (100) to (170) below. Note that the organic compounds represented by General Formulae (G1) to (G3) are not limited to the following examples.

[Chemical Formula 11]

(100)

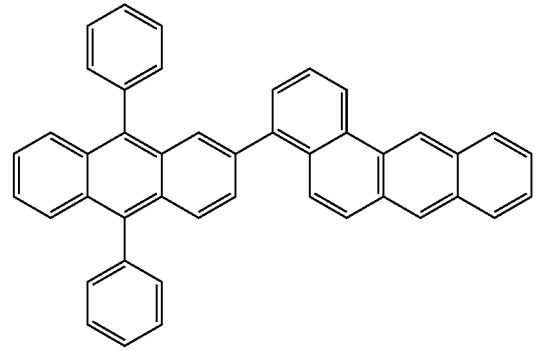

(101)
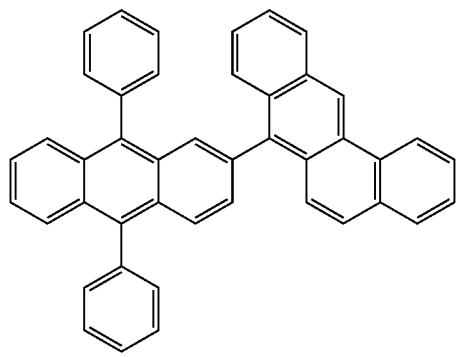
(102)
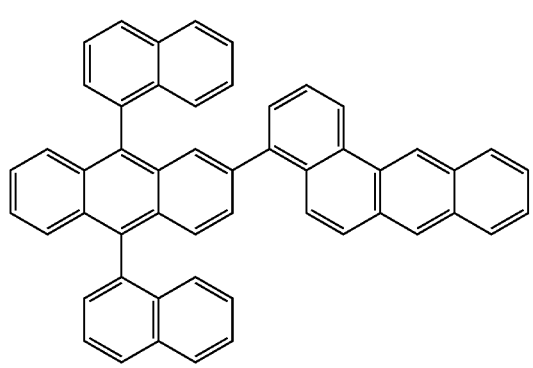
(103)
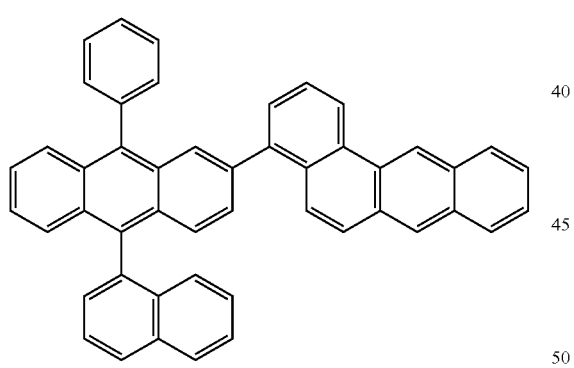
(104)
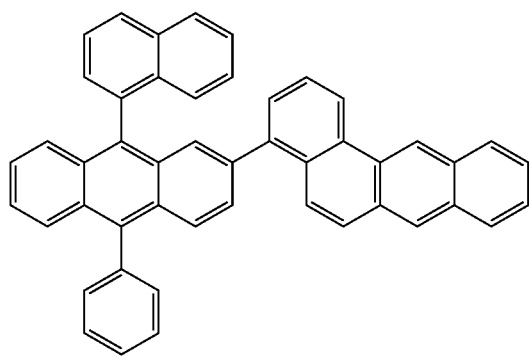
(105)
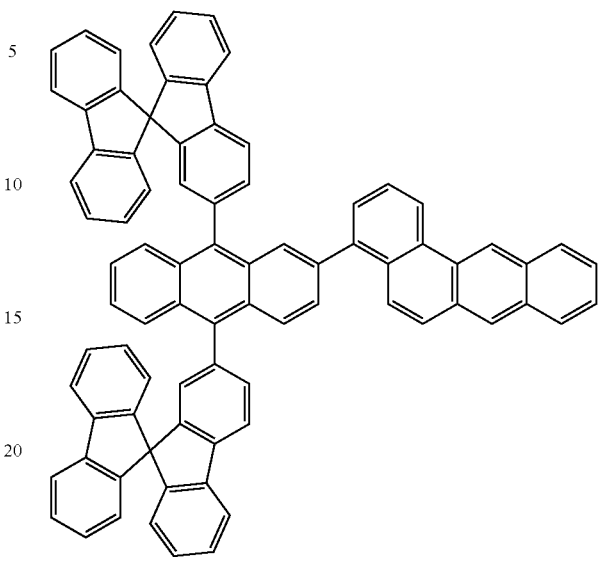
[Chemical Formula 12]
(106)
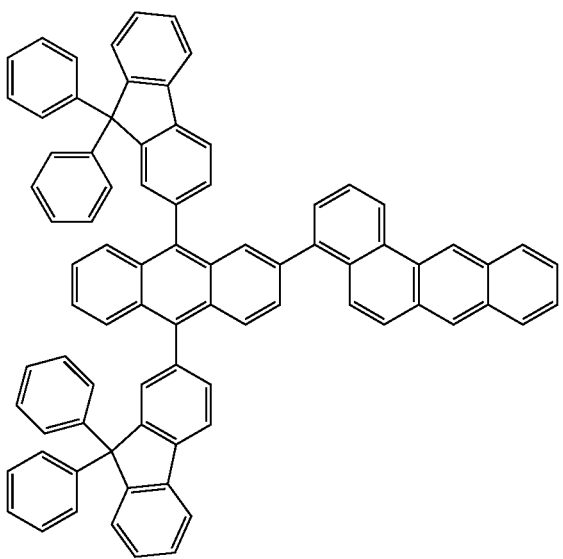

(107)
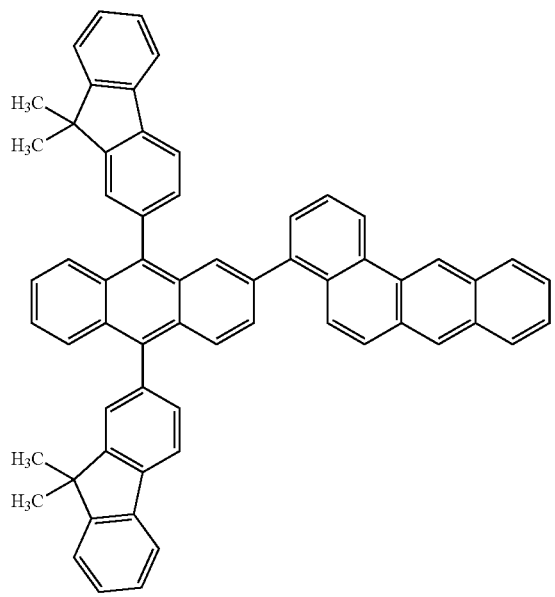
(110)
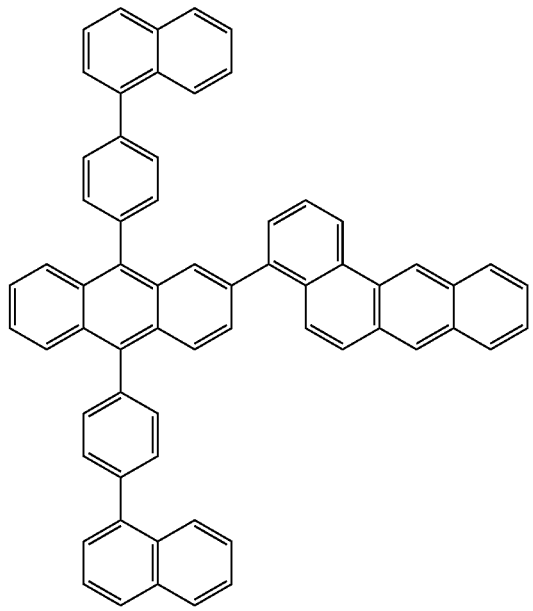
(108)
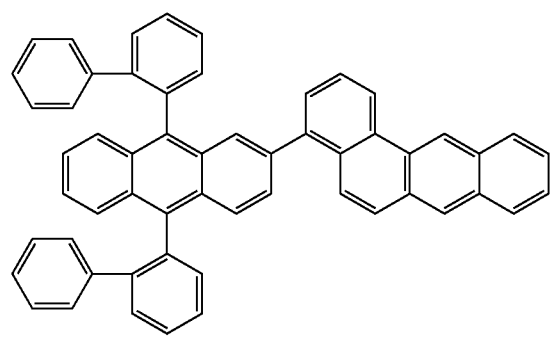
(111)
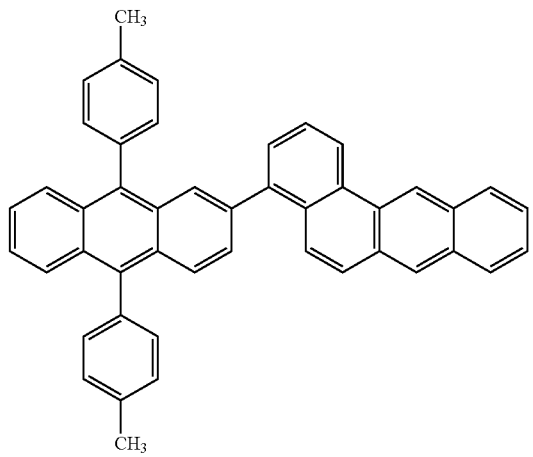
[Chemical Formula 13]
(109)
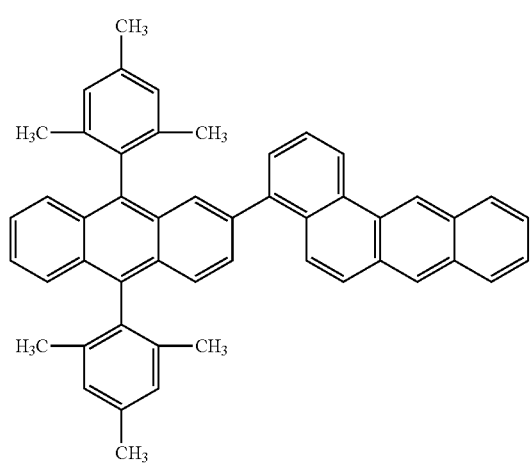
(112)
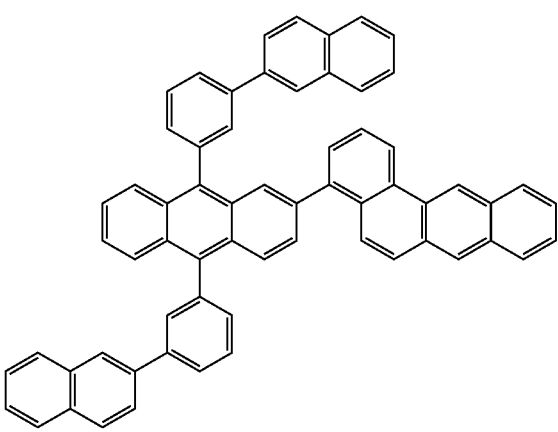

(113)
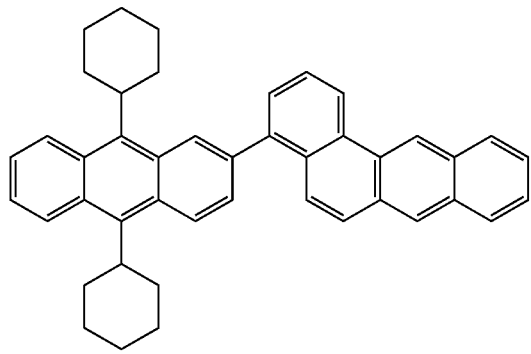
(114)
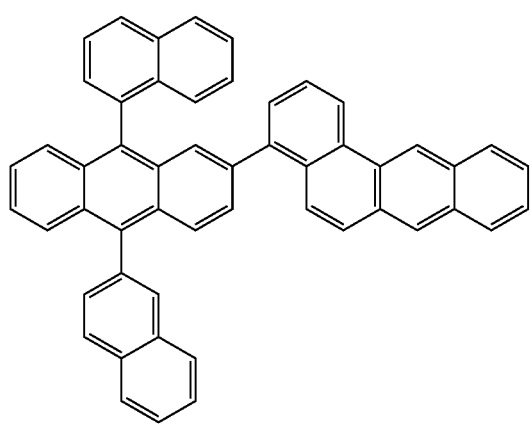
(115)
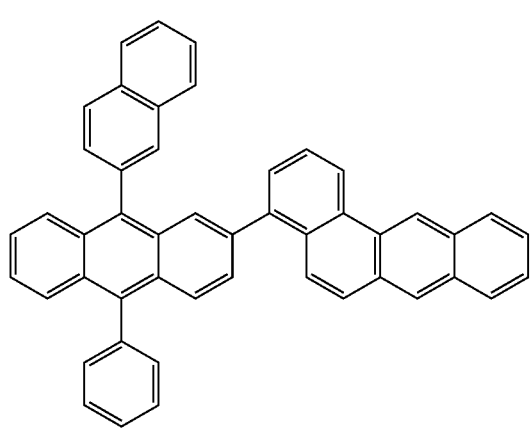
(116)
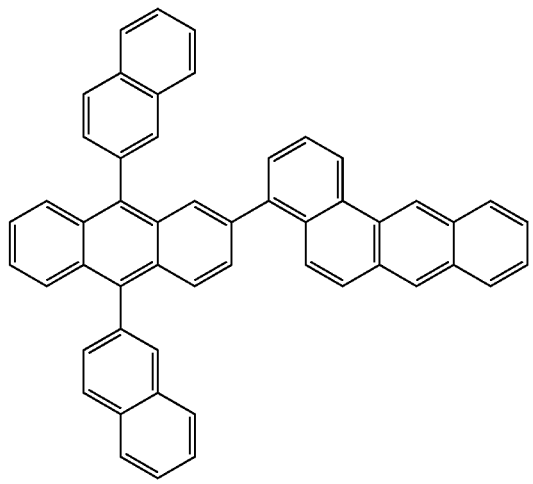
(117)
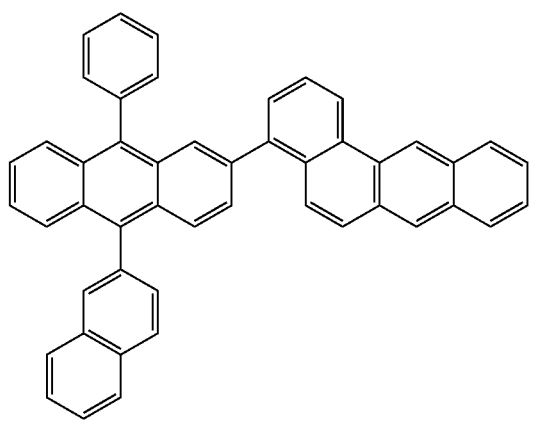
(118)
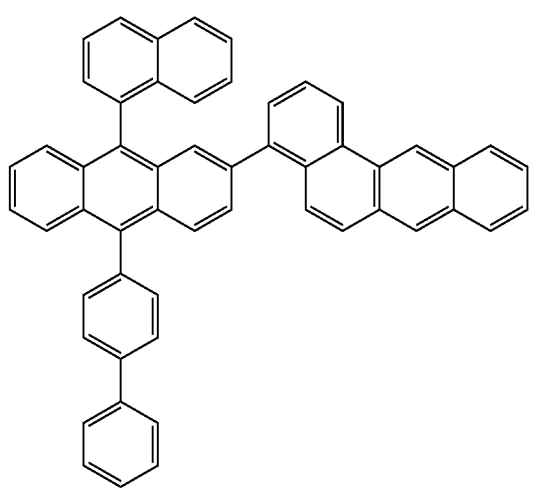

(119)
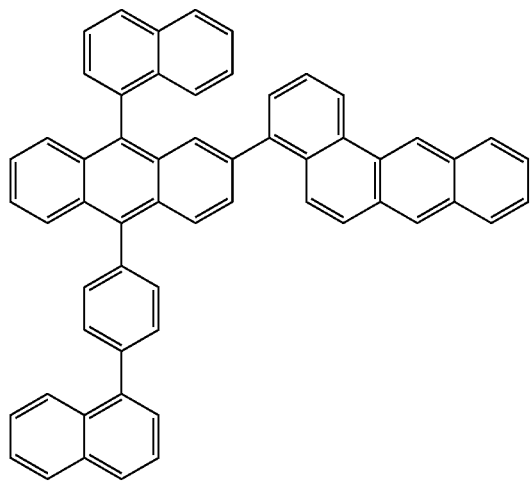
[Chemical Formula 14]
(120)
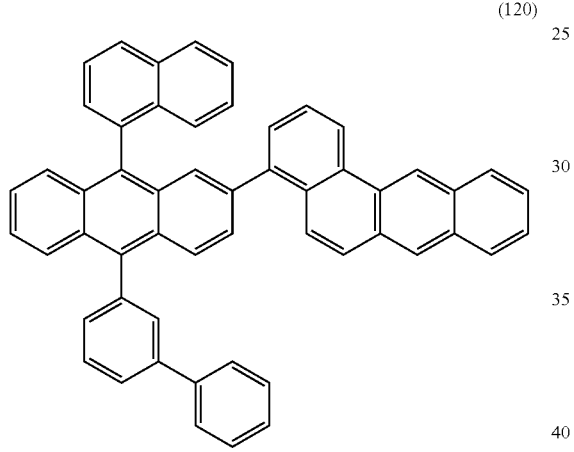
(121)
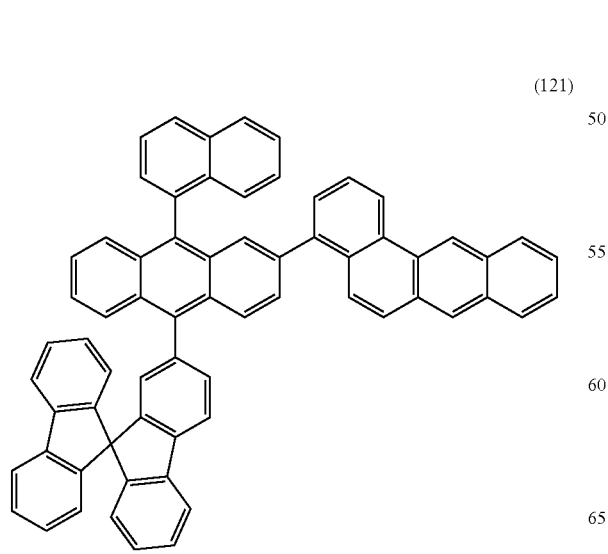
(122)
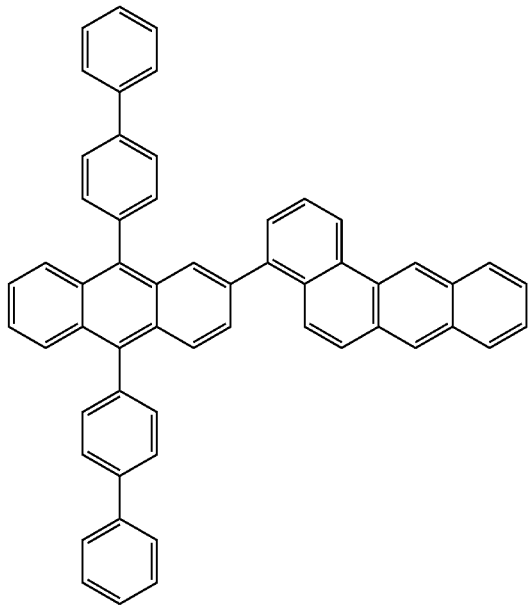
(123)
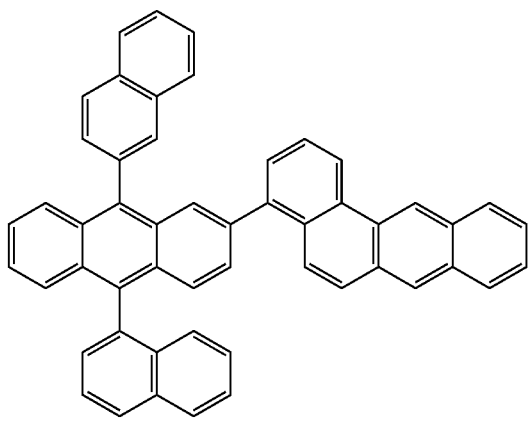
(124)
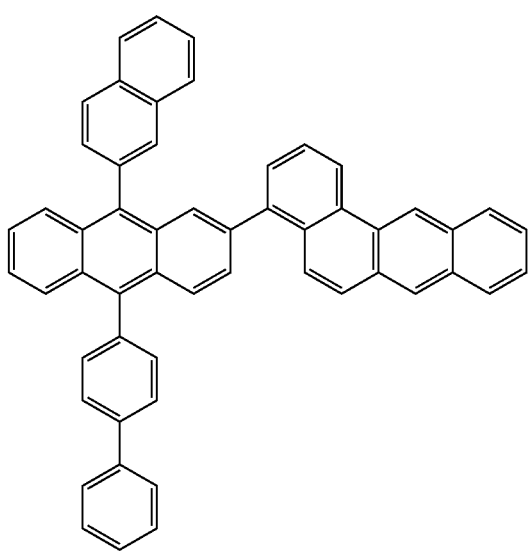

(125)
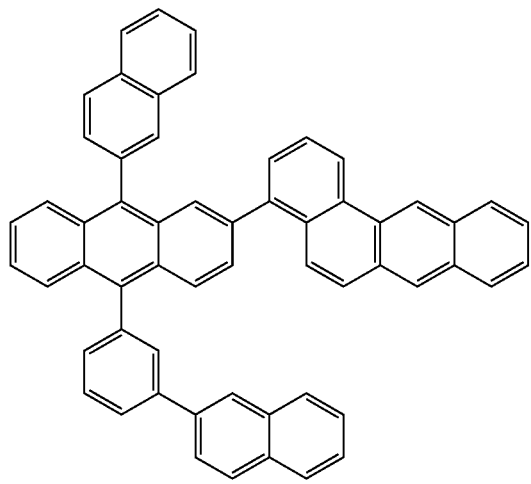
[Chemical Formula 15]
(126)
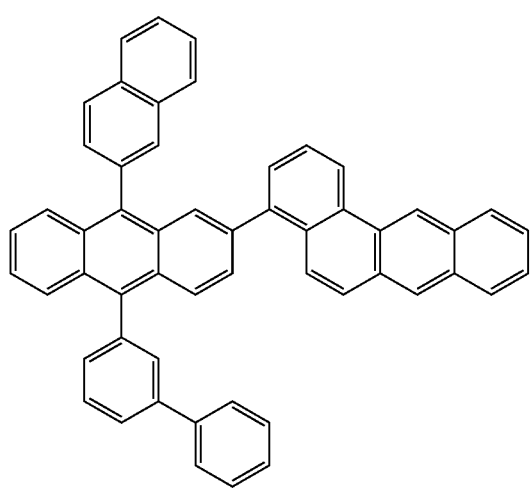
(127)
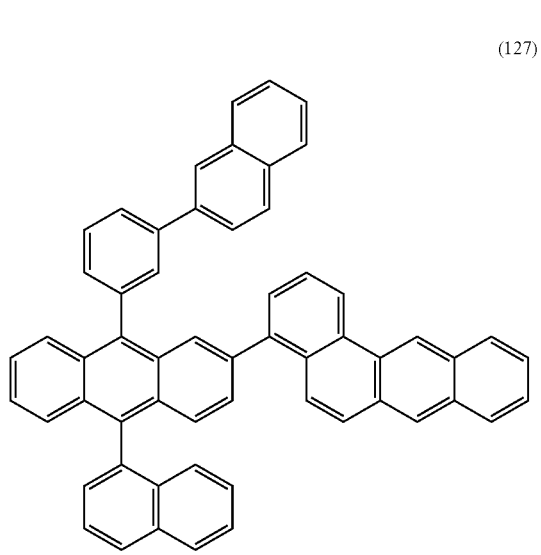
(128)
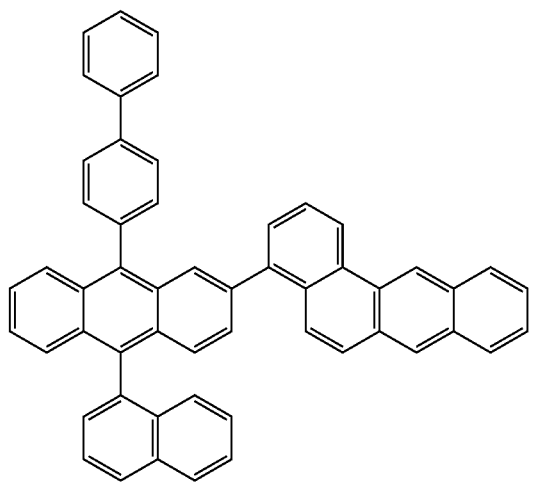
(129)
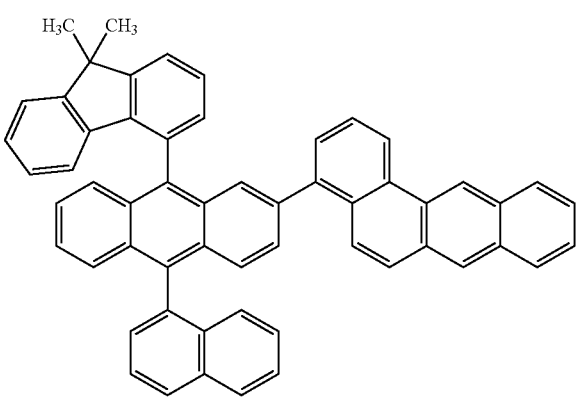
(130)
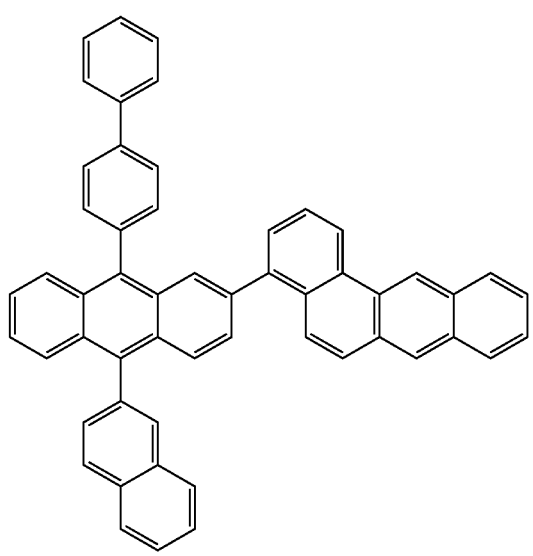

(131)
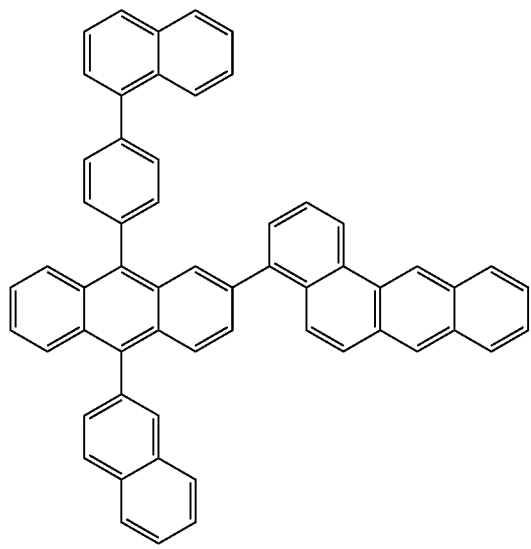
[Chemical Formula 16]
(132)
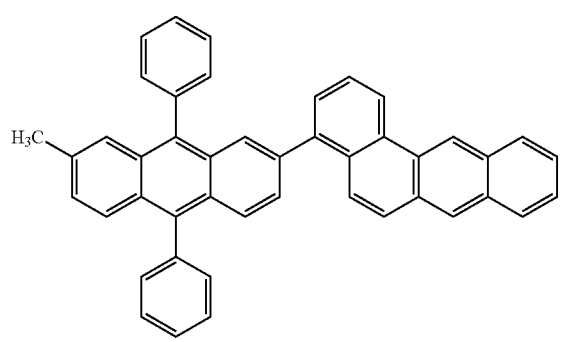
(133)
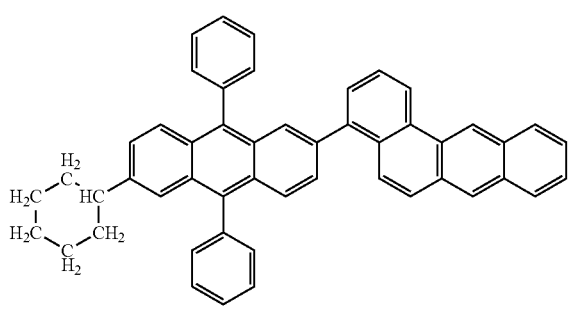
(134)
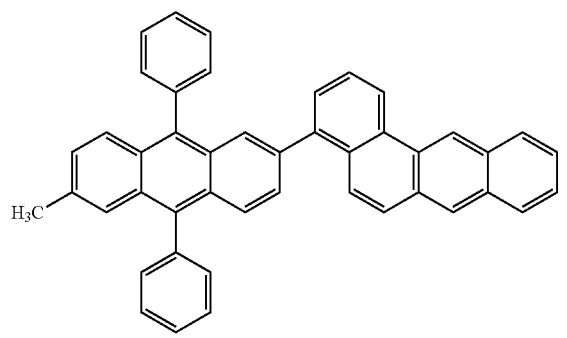
(135)
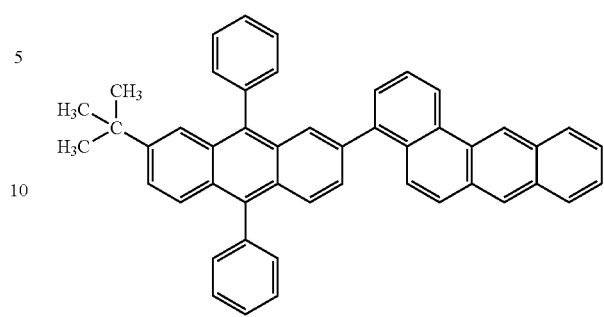
(136)
(137)
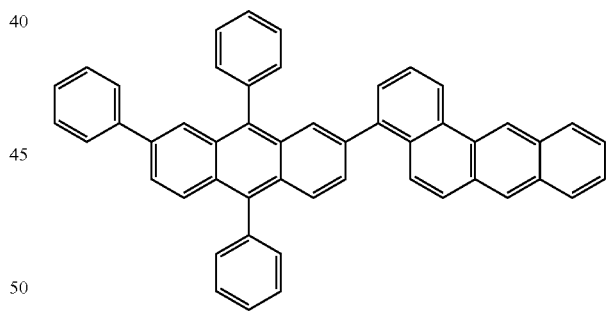
(138)

[Chemical Formula 17]
(139)
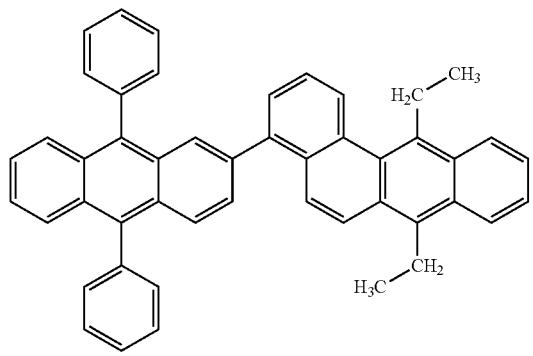
(140)
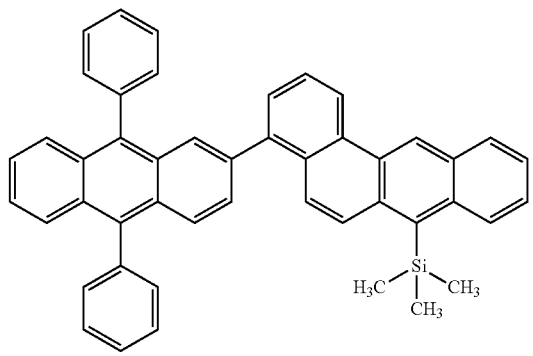
(141)
(142)
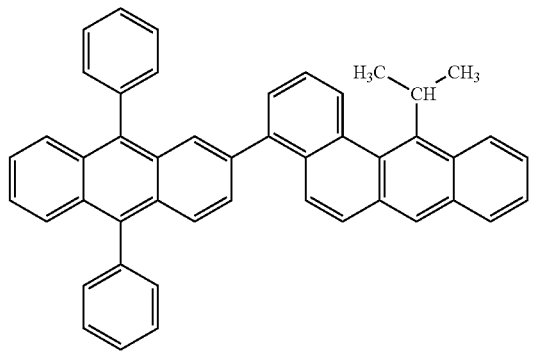
(143)
(144)
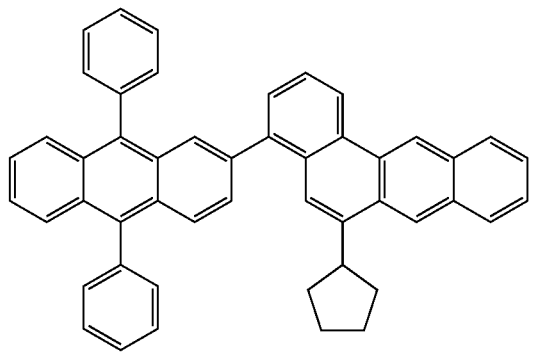
(145)
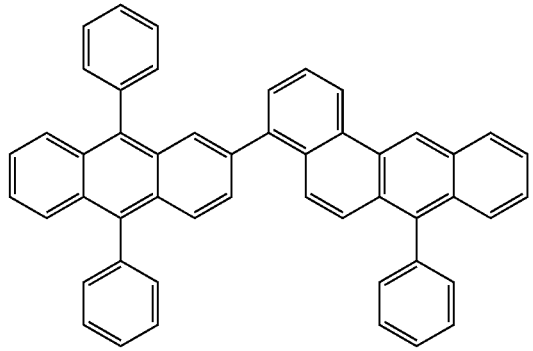

(146)
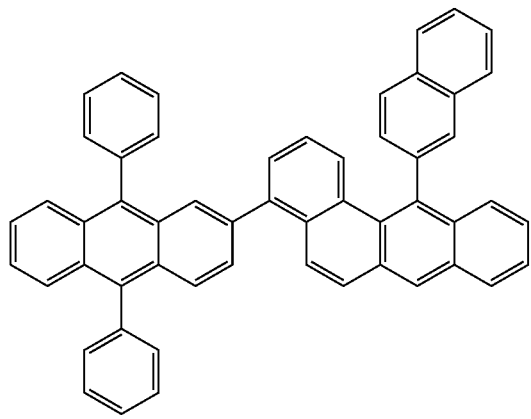
[Chemical Formula 18]
(147)
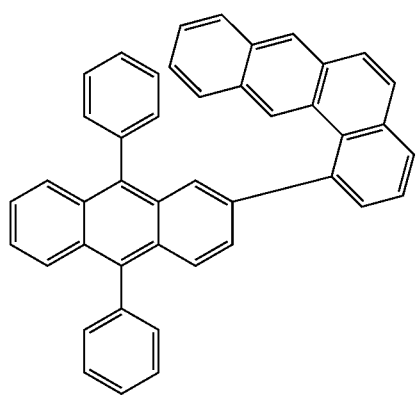
(148)
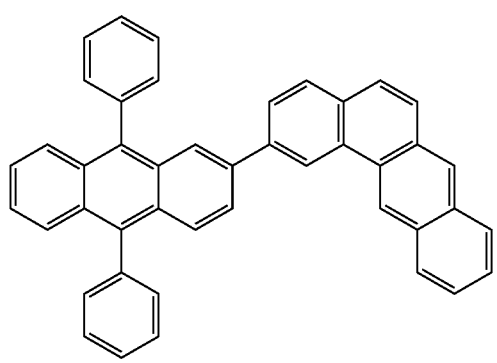
(149)
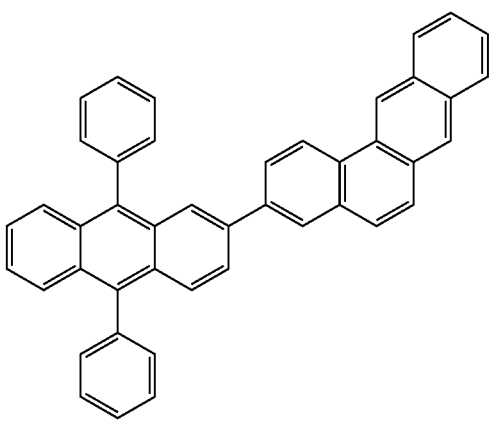
(150)
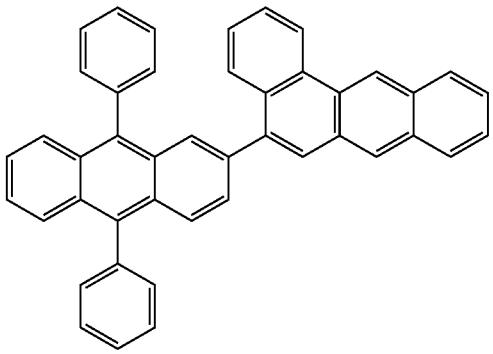
(151)
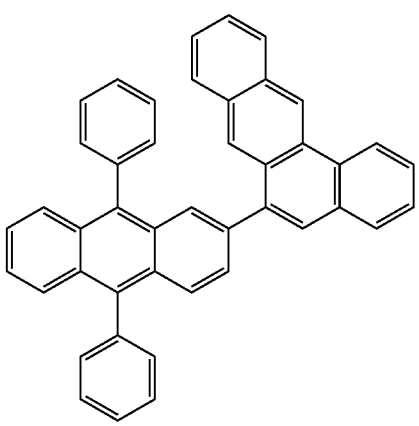

(152)
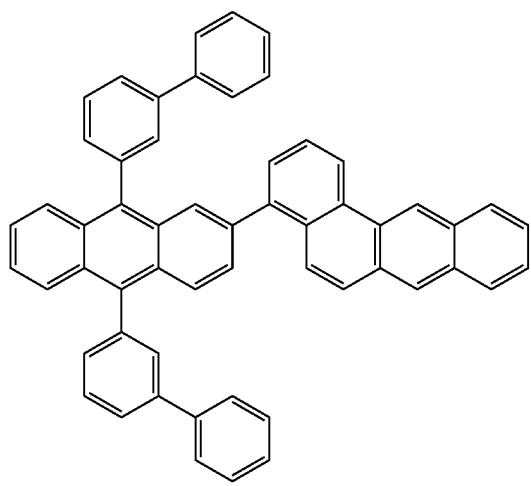
(153)
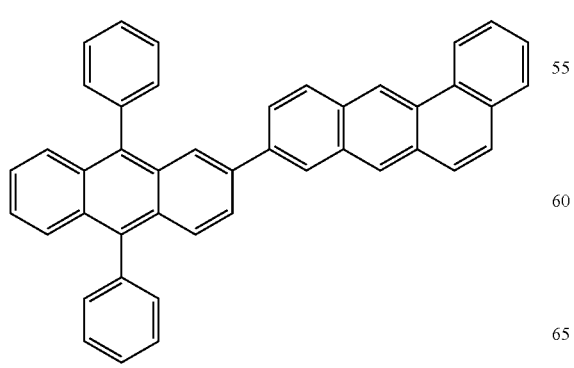
(154)
[Chemical Formula 19]
(155)
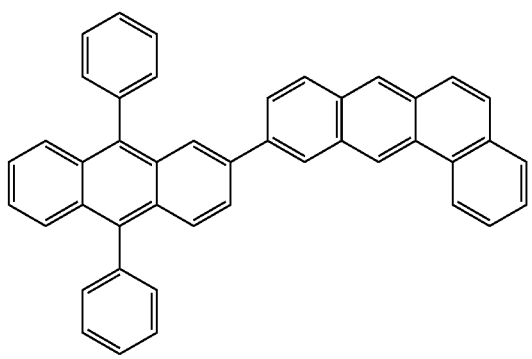
(156)
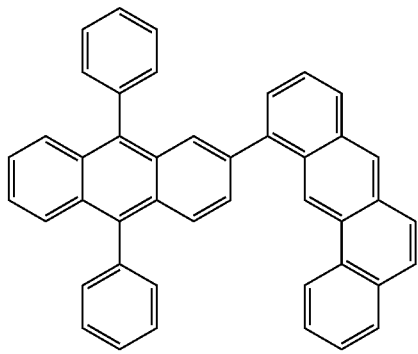
(157)
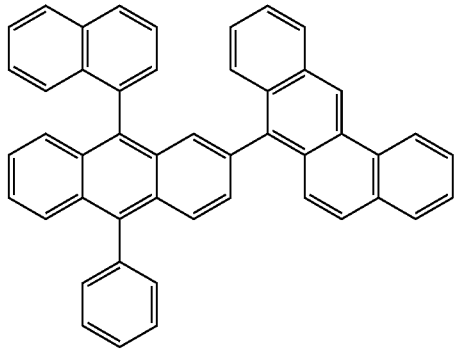
(158)
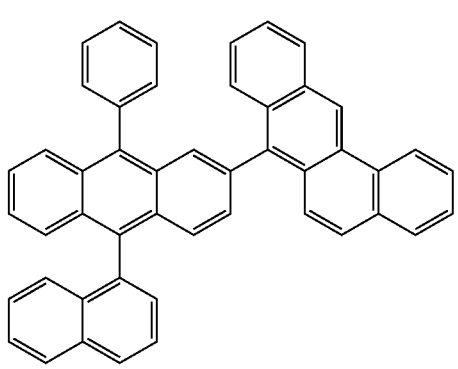

(159)
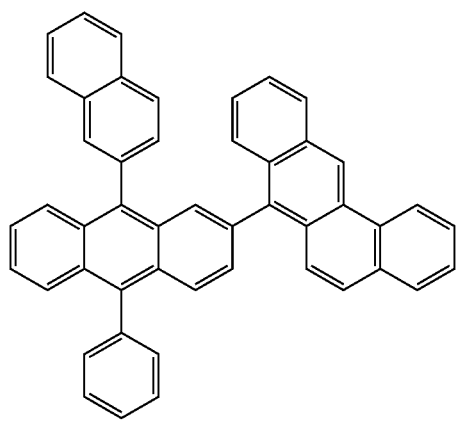
(160)
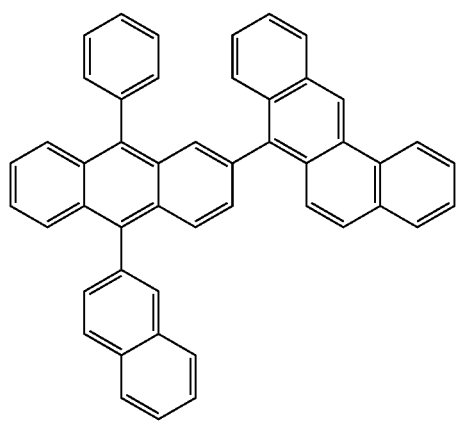
(161)
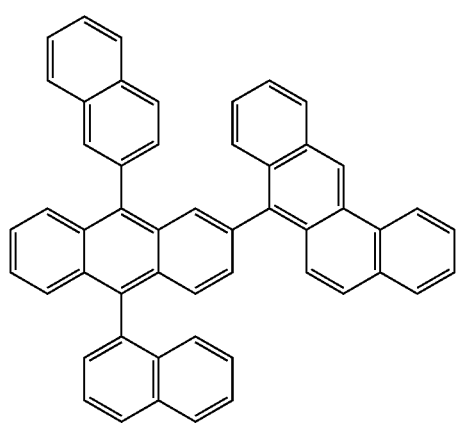
(162)
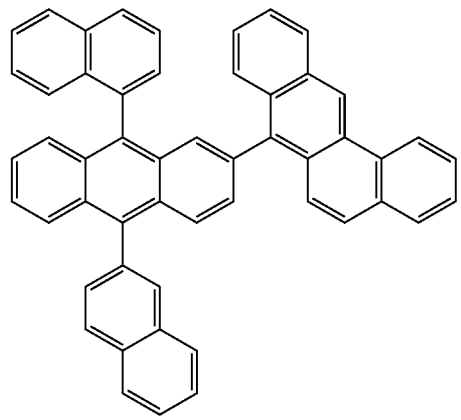
[Chemical Formula 20]
(163)
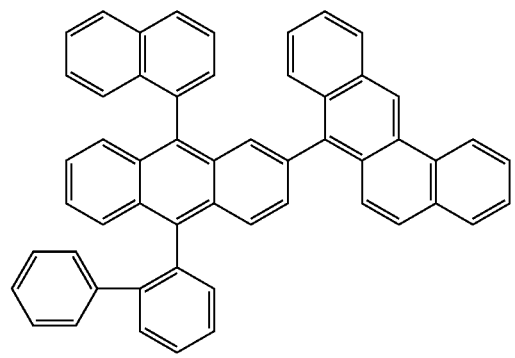
(164)
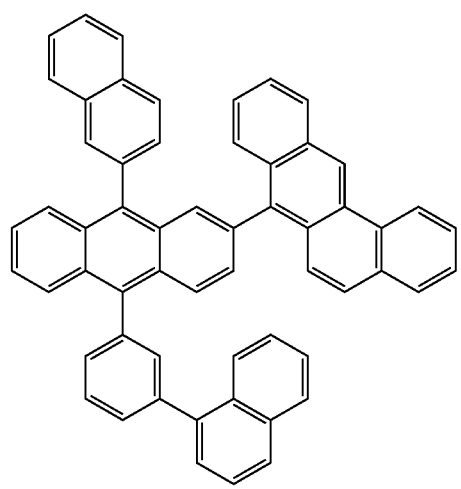

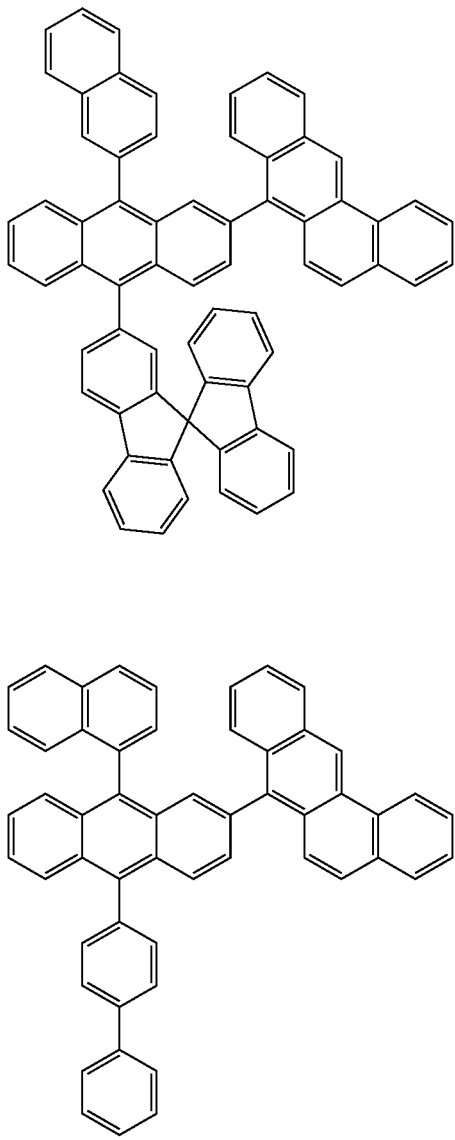

(165)

(166)

(167)

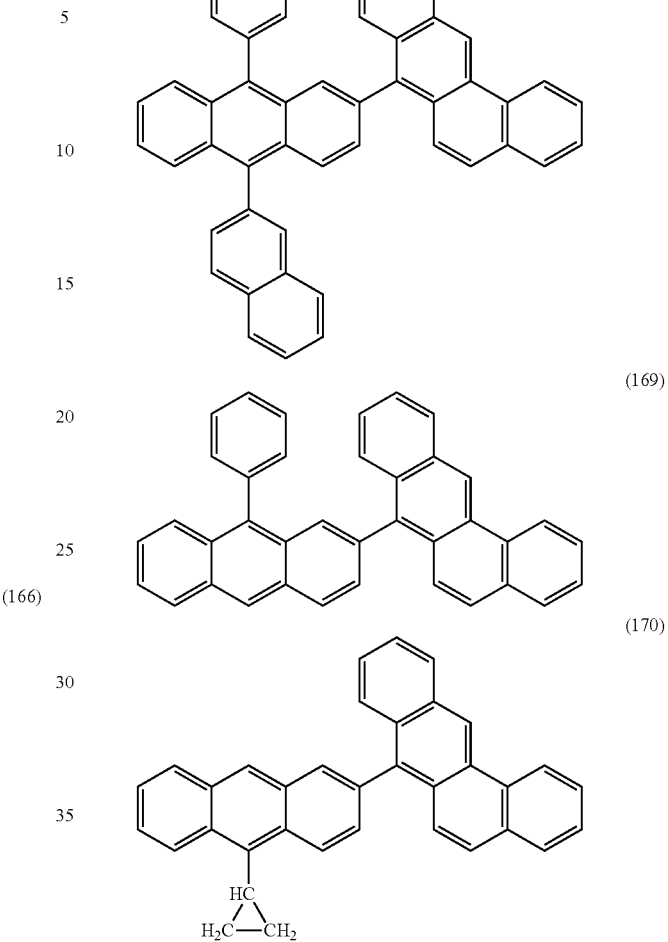

(168)

(169)

(170)

Note that the organic compound in this embodiment can be deposited by an evaporation method (including a vacuum evaporation method), an inkjet method, a coating method, a gravure printing method, or the like.

Note that this embodiment can be combined as appropriate with any of the other embodiments.

Embodiment 2

In this embodiment, an example of a method for synthesizing an organic compound of one embodiment of the present invention will be described using the organic compound represented by General Formula (G1) as an example.

[Chemical Formula 21]

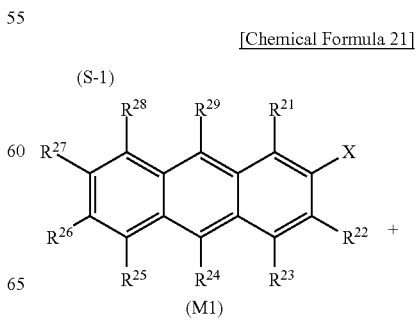

(S-1)

(M1)

-continued

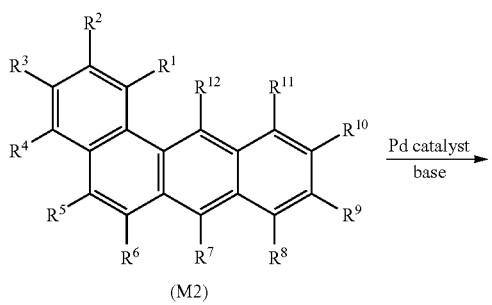

(M2)

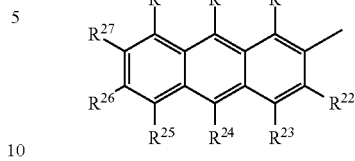

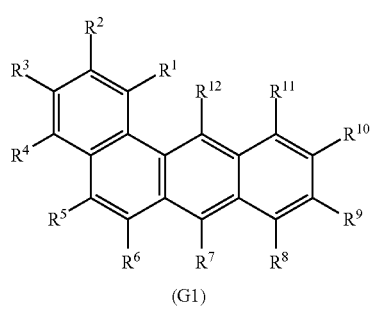

(G1)

In General Formula (M1), $R^{21}$ to $R^{29}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring. Furthermore, X represents a halogen or triflate.

In General Formula (M2), any one of $R^1$ to $R^{12}$ is a substituent represented by General Formula (m1) below, and the other $R^1$ to $R^{12}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

[Chemical Formula 22]

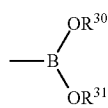

(m1)

In General Formula (m1), $R^{30}$ and $R^{31}$ each independently represent any one of hydrogen and an alkyl group having 1 to 6 carbon atoms. Moreover, $R^{30}$ and $R^{31}$ may be bonded to each other to form a ring.

In General Formula (G1), any one of $R^1$ to $R^{12}$ is a substituent represented by General Formula (g1) below, and the other $R^1$ to $R^{12}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

[Chemical Formula 23]

(g1)

In General Formula (g1), $R^{21}$ to $R^{29}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring.

As shown in Synthesis Scheme (S-1), an anthracene halide (Compound M1) and an organoboron compound or a boronic acid of benzo[a]anthracene (Compound M2) are coupled by the Suzuki-Miyaura reaction, thereby obtaining the objective compound.

Examples of a palladium (Pd) catalyst that can be used in Synthesis Scheme (S-1) include palladium(II) acetate, tetrakis(triphenylphosphine)palladium(0), and bis(triphenylphosphine)palladium(II) dichloride. The palladium catalyst is not limited thereto. Examples of a ligand of the palladium catalyst that can be used in Synthesis Scheme (S-1) include tri(ortho-tolyl)phosphine, triphenylphosphine, and tricyclohexylphosphine. The ligand is not limited thereto. Examples of a base that can be used in Synthesis Scheme (S-1) include an organic base such as sodium tert-butoxide and an inorganic base such as potassium carbonate and sodium carbonate. The base is not limited thereto. Examples of a solvent that can be used in Synthesis Scheme (S-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as ethylene glycol dimethyl ether. The solvent is not limited thereto. In addition, a mixed solvent of toluene and water, a mixed solvent of toluene, ethanol, and water, or a mixed solvent of water and an ether such as ethylene glycol dimethyl ether is more preferred.

In the Suzuki-Miyaura coupling reaction shown in Synthesis Scheme (S-1), a cross-coupling reaction using an organoaluminum, organozirconium, organozinc, or organotin compound or the like as well as the organoboron compound or boronic acid represented by Compound M2 may be used.

In the Suzuki-Miyaura coupling reaction shown in Synthesis Scheme (S-1), an organoboron compound or a boronic acid of anthracene may be coupled with a halide of benzo[a]anthracene or benzo[a]anthracene having triflate as a substituent by the Suzuki-Miyaura reaction.

Although the example of a method for synthesizing the organic compound of one embodiment of the present invention is described above, the present invention is not limited thereto and synthesis may be performed by any other synthesis method.

Embodiment 3

In this embodiment, a structure example of a light-emitting device including an organic compound of one embodiment of the present invention will be described below with reference to FIG. 1.

FIG. 1(A) is a schematic cross-sectional view of a light-emitting device 150 of one embodiment of the present invention. The light-emitting device 150 includes at least a pair of electrodes (an electrode 101 and an electrode 102) and an EL layer 100 between the electrodes.

The EL layer 100 includes at least a light-emitting layer 140 and a hole-transport layer 112. In addition, functional layers such as a hole-injection layer 111, an electron-transport layer 118, and an electron-injection layer 119 are included.

Although the description is given assuming that the electrode 101 serves as an anode and the electrode 102 serves as a cathode in this embodiment, the structure of the light-emitting device is not limited thereto. That is, a structure in which the electrode 101 serves as a cathode and the electrode 102 serves as an anode may be employed. In that case, the stacking order of the layers is reversed. In other words, the hole-injection layer, the hole-transport layer, the light-emitting layer, the electron-transport layer, and the electron-injection layer are stacked in this order from the anode side.

The structure of the EL layer 100 is not limited thereto, and for example, a functional layer that is capable of improving or inhibiting an electron- or hole-transport property or inhibiting diffusion of excitons may be included. The functional layers may be each a single layer or have a stacked-layer structure of a plurality of layers.

In the light-emitting device 150, any of the layers in the EL layer 100 contains the organic compound of one embodiment of the present invention. Note that the organic compound has a favorable quantum yield. Therefore, a light-emitting device with high emission efficiency can be obtained by using the organic compound as a guest material of the light-emitting layer 140. Furthermore, blue light emission with high color purity can be obtained.

Structure Example 1 of Light-Emitting Device

Figure 1B:
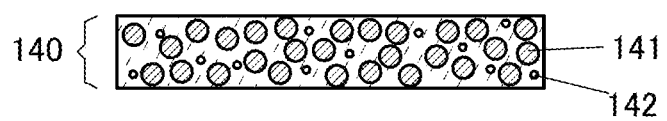

Next, a structure example of the blue fluorescent device will be described with reference to FIG. 1(A), FIG. 1(B), and FIG. 1(C).

The light-emitting device 150 illustrated in FIG. 1(A) is a device in which the organic compound of one embodiment of the present invention is used at least for the light-emitting layer 140. FIG. 1(B) illustrates a structure example of materials in the light-emitting layer 140, and FIG. 1(C) is a schematic diagram showing the correlation of energy levels of the materials in the light-emitting layer 140.

Here, the case where the T1 level of a host material 141 is lower than the T1 level of a guest material 142 is described. The following explains what terms and numerals in FIG. 1(C) represent. Note that the T1 level of the host material 121 may be higher than the T1 level of the guest material 122.

Host (141): the host material 141
Guest (142): the guest material 142 (fluorescent material)
$S_{FH}$: the S1 level of the host material 141
$T_{FH}$: the T1 level of the host material 141
$S_{FG}$: the S1 level of the guest material 142 (fluorescent material)
$T_{FG}$: the T1 level of the guest material 142 (fluorescent material)
Energy: energy
Emission: light emission
quench: quench The host material 141 preferably has a function of converting triplet excitation energy into singlet excitation energy by TTA. With this structure, triplet excitation energy that is generated in the light-emitting layer 140 and normally does not contribute to fluorescence can be partly converted into singlet excitation energy in the host material 141, and the singlet excitation energy is transferred to the guest material 142 (see Route $E_1$ in FIG. 1(C)) and thus extracted as fluorescence. Accordingly, the emission efficiency of the fluorescent device can be improved. Note that the fluorescence caused by TTA is obtained through a triplet excited state having a long lifetime; thus, delayed fluorescence is observed.

Figure 1C:
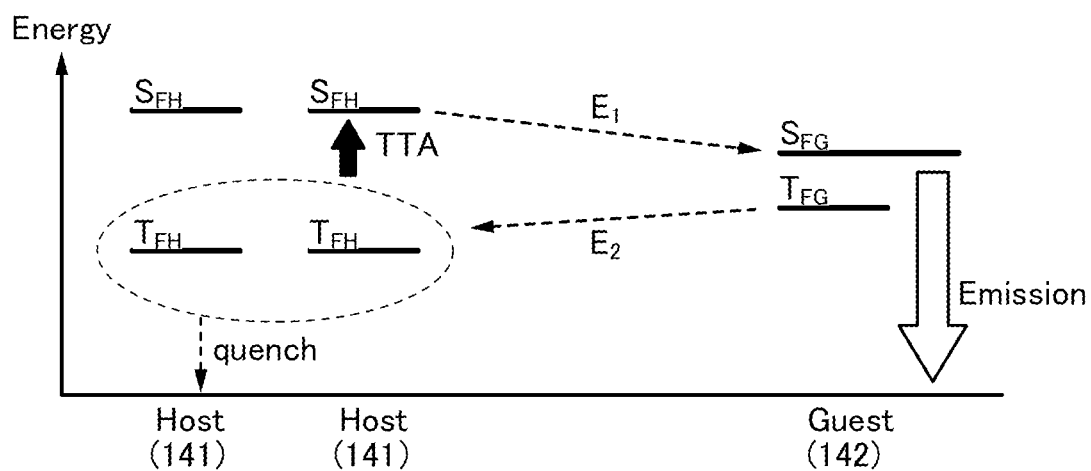

In order to transfer the singlet excitation energy to the guest material 142 efficiently in the light-emitting layer 140, the lowest level of the singlet excitation energy (S1 level) of the host material 141 is preferably higher than the S1 level of the guest material 142 as shown in FIG. 1(C). In addition, the lowest level of the triplet excitation energy (T1 level) of the host material 141 is preferably lower than the T1 level of the guest material 142 (see Route $E_2$ in FIG. 1(C)). With such a structure, TTA can be efficiently caused in the light-emitting layer 140.

Furthermore, the T1 level of the host material 141 is preferably lower than the T1 level of a material used for the hole-transport layer 112 that is in contact with the light-emitting layer 140. That is, the hole-transport layer 112 preferably has a function of inhibiting diffusion of excitons. Such a structure can inhibit diffusion of triplet excitons generated in the light-emitting layer 140 into the hole-transport layer 112, so that a device with high emission efficiency can be provided.

The organic compound of one embodiment of the present invention enables fabrication of a light-emitting device with a large proportion of delayed fluorescence components. Thus, it is suitably used as the host material in the light-emitting device utilizing TTA.

Structure Example 2 of Light-Emitting Device

It is preferred that a material having a benzo[a]anthracene skeleton be used as the host material 141 and a material having a benzofuran skeleton be used as a luminophore included in the guest material 142. The light-emitting device having this structure can have high emission efficiency and high reliability. As the material having a benzo[a]anthracene skeleton, the organic compound represented by any of General Formulae (G1) to (G3) can be suitably used.

Here, the luminophore refers to an atomic group (skeleton) that causes light emission in a fluorescent material. The luminophore generally has a π bond and preferably contains an aromatic ring, further preferably contains a condensed aromatic ring or a condensed heteroaromatic ring. As another embodiment, the luminophore can be regarded as an atomic group (skeleton) having an aromatic ring having a transition dipole vector on a ring plane.

The material having a benzo[a]anthracene skeleton has a large proportion of delayed fluorescence. Therefore, it is suitably used as the host material in the light-emitting device utilizing TTA. Accordingly, with the use of the host material having a benzo[a]anthracene skeleton, a light-emitting device having high emission efficiency can be obtained. Moreover, a light-emitting device having high reliability can be obtained because the benzo[a]anthracene skeleton is electrochemically stable.

A fluorescent material having a benzofuran skeleton in the luminophore has a high LUMO (Lowest Unoccupied Molecular Orbital) level and has a high S1 level. Therefore, the fluorescent material having a benzofuran skeleton in the luminophore can be suitably used in a blue light-emitting device.

Thus, by using the material having a benzo[a]anthracene skeleton as the host material 141 and the material having a benzofuran skeleton as the luminophore of the guest material 142, a blue fluorescent device with high emission efficiency and high reliability can be obtained.

A specific example of the material having a benzo[a]anthracene skeleton is the organic compound of one embodiment of the present invention. However, the material having a benzo[a]anthracene skeleton is not limited to the organic compound of one embodiment of the present invention.

Examples of the luminophore having a benzofuran skeleton include naphthobisbenzofuran, a dibenzo[b,b']furo[2,3-g:5,4-g']bisbenzofuran skeleton, a dibenzo[b,b']thieno[2,3-g:5,4-g]bisbenzofuranskeleton, aspiro[7H-zibenzo[b,b']cyclopenta[1,2-g:4,3-g']bisbenzofuran-7,9'-[9H]fluorene] skeleton, and a 7,7-diphenyl-7H-dibenzo[b,b']cyclopenta[1,2-g:4,3-g']bisbenzofuran skeleton. Specific examples of the fluorescent material having a benzofuran skeleton in the luminophore include organic compounds shown as Structural Formulae (300) to (310) below. Note that the fluorescent material having a benzofuran skeleton in the luminophore is not limited to the following examples.

[Chemical Formula 24]

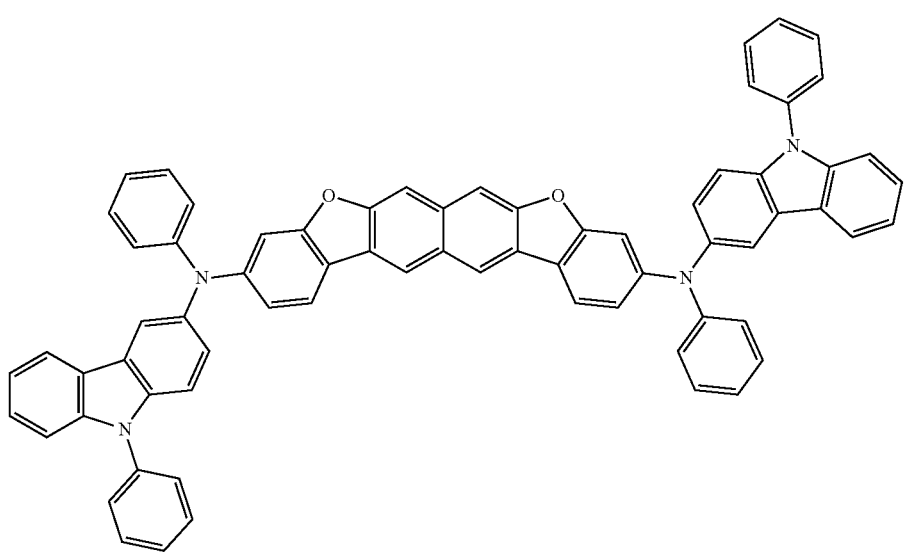

(300)

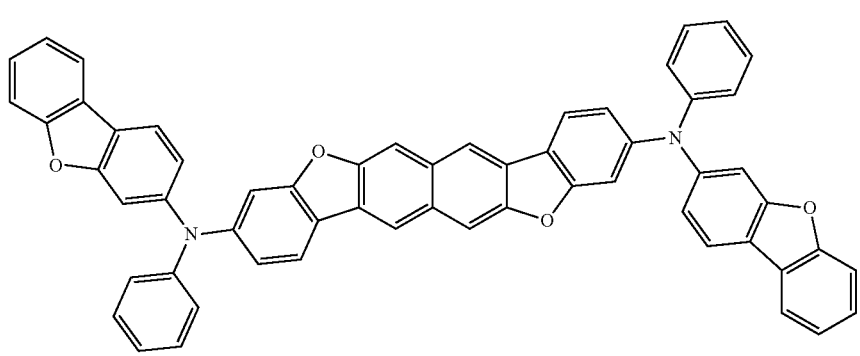

(301)

[Chemical Formula 25]

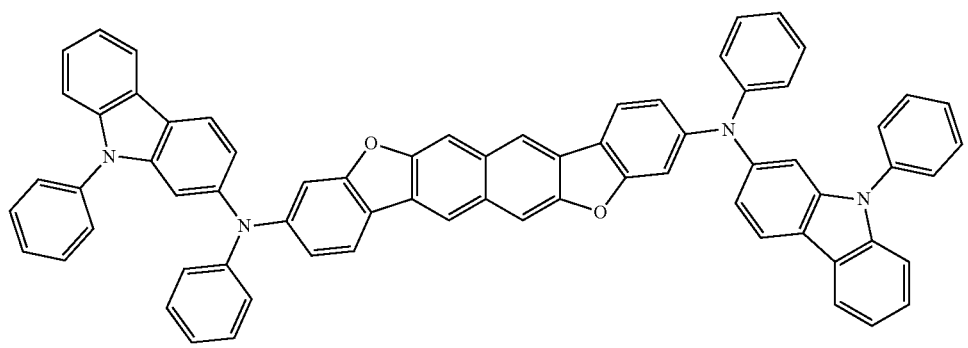

(302)

(303)
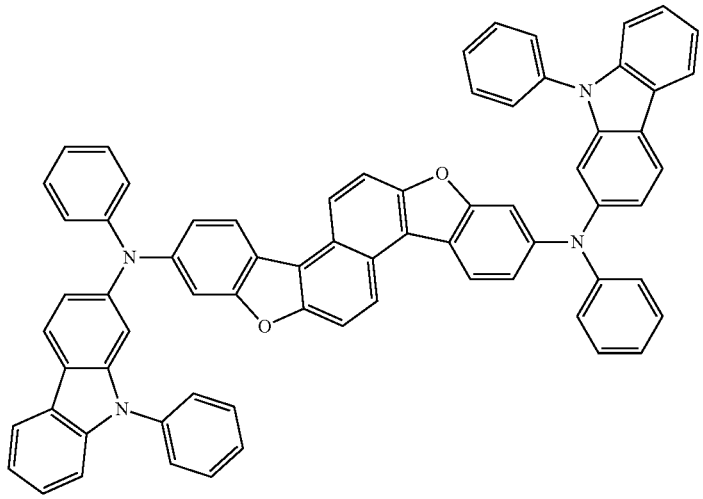
[Chemical Formula 26]
(304)
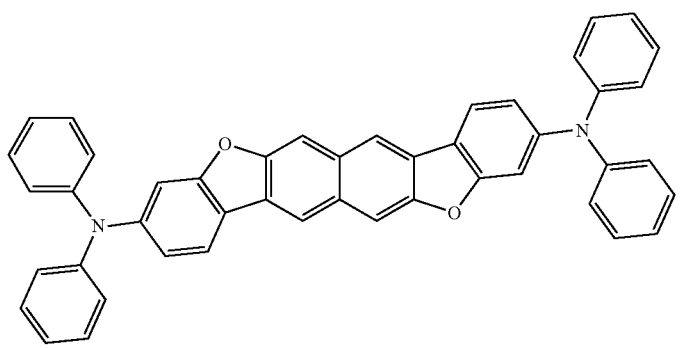
(305)
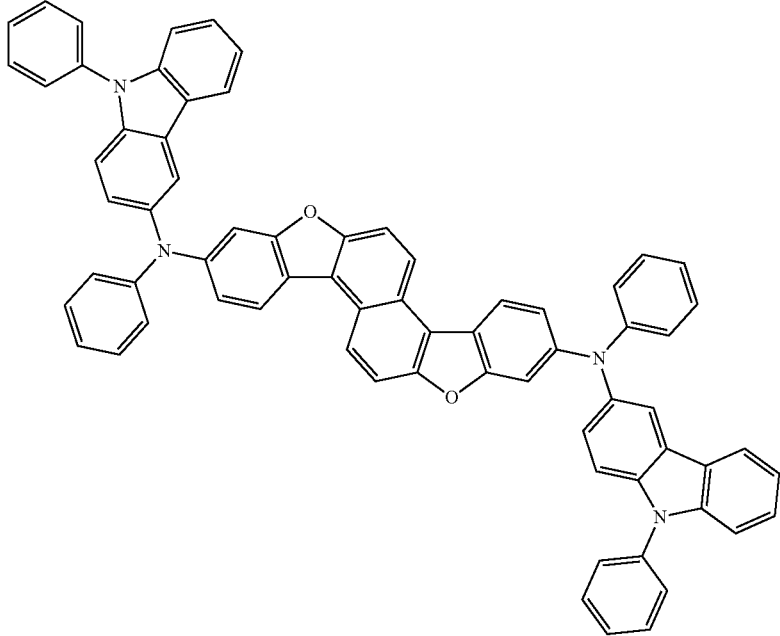

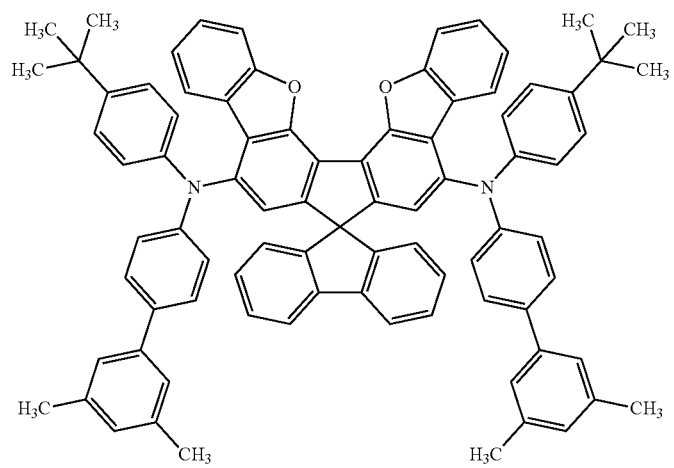
(306)
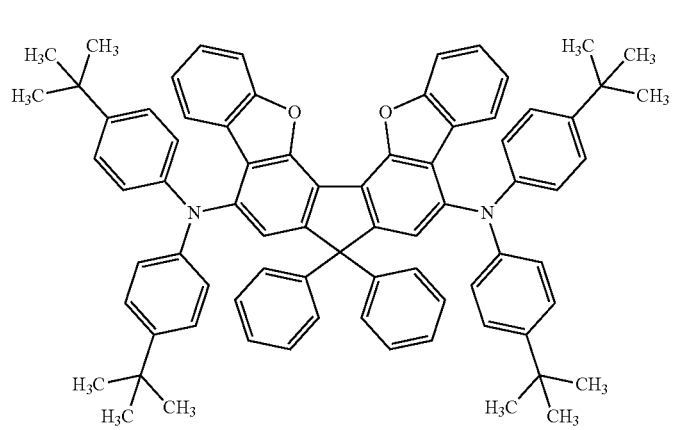
(307)
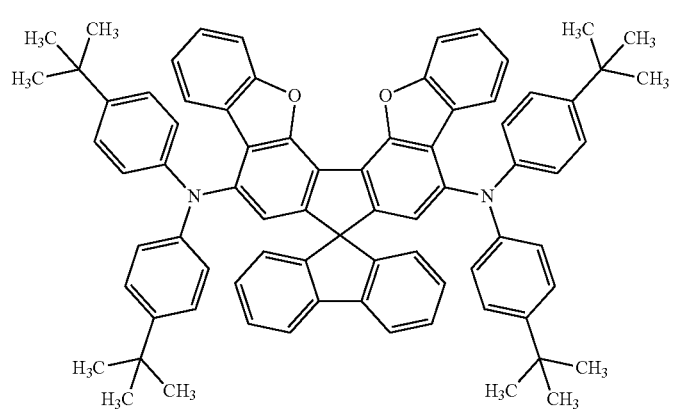
(308)
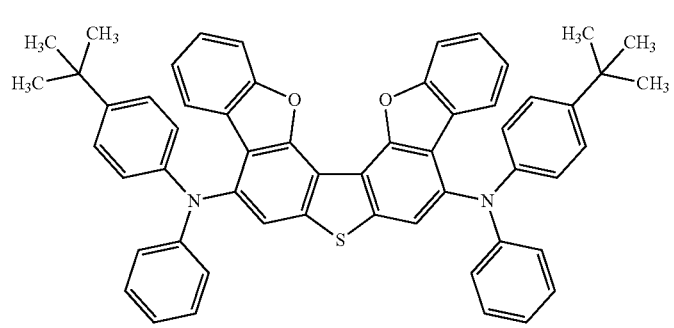
(309)

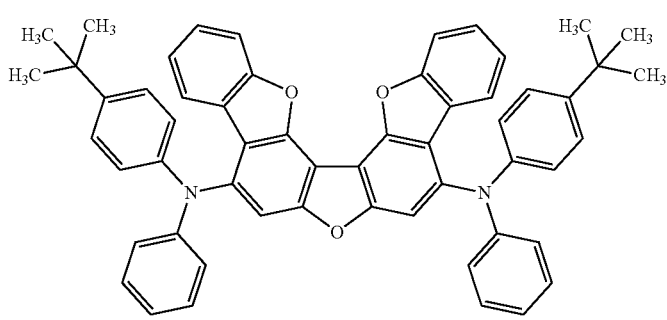

(310)

Note that the lowest singlet excitation energy level of an organic compound can be observed from an absorption spectrum at a transition from the singlet ground state to the lowest singlet excited state in the organic compound. Alternatively, the lowest singlet excitation energy level may be estimated from a peak wavelength of a fluorescence spectrum of the organic compound. Furthermore, the lowest triplet excitation energy level can be observed from an absorption spectrum at a transition from the singlet ground state to the lowest triplet excited state in the organic compound, but is difficult to observe in some cases because this transition is a forbidden transition. In such cases, the lowest triplet excitation energy level may be estimated from a peak wavelength of a phosphorescence spectrum of the organic compound.

Having a high T1 level and a favorable hole-transport property, the organic compound of one embodiment of the present invention can be suitably used as the hole-transport material in the light-emitting device utilizing TTA. Note that the organic compound of one embodiment of the present invention can also be used as the host material 121.

Note that the organic compound of one embodiment of the present invention can be used for an electronic device such as an organic thin film solar cell. Specifically, the organic compound can be used in a carrier-transport layer or a carrier-injection layer because it has a carrier-transport property. In addition, a mixed film of the organic compound and an acceptor substance can be used as a charge generation layer. The organic compound is photoexcited and thus can be used as a power generation layer.

Structure Example 3 of Light-Emitting Device

Figure 2A:
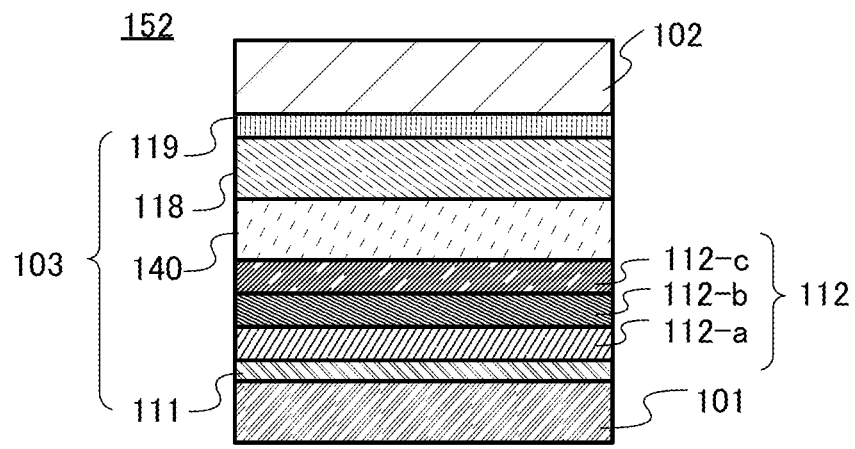
FIG. 2(A), (B) Schematic views of a light-emitting device of one embodiment of the present invention. (C) A diagram illustrating the correlation of energy levels in a light-emitting device of one embodiment of the present invention.
Figure 2B:
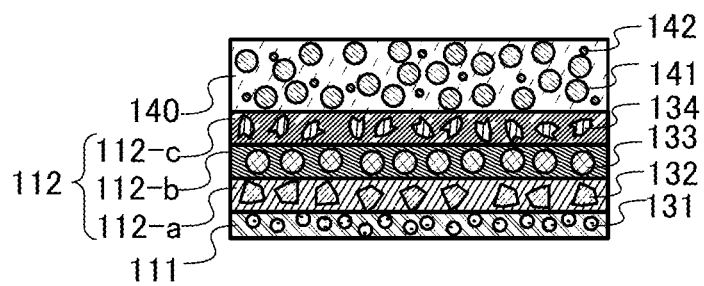
Figure 2C:
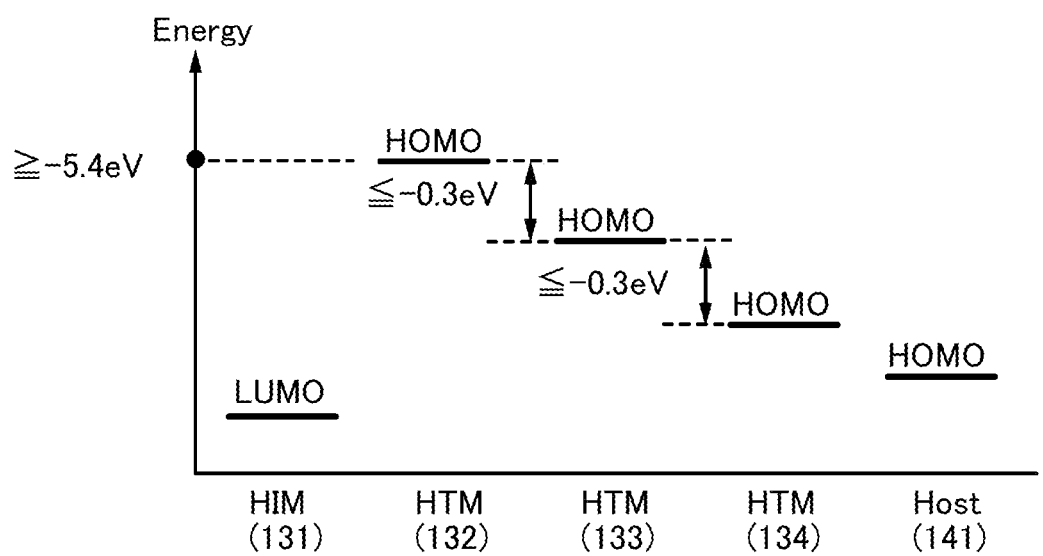

Next, an example of a light-emitting device different from the light-emitting device illustrated in FIG. 1 will be described with reference to FIG. 2. A light-emitting device 152 illustrated in FIG. 2(A) is a device in which the organic compound of one embodiment of the present invention is used at least for the light-emitting layer 140. FIG. 2(B) illustrates a structure example of materials in the hole-injection layer 111, the hole-transport layer, 112 and the light-emitting layer 140. FIG. 2(C) is a schematic diagram showing the correlation of energy levels of the materials in the hole-injection layer 111, the hole-transport layer 112, and the light-emitting layer 140.

FIG. 2(A) is a schematic cross-sectional view of the light-emitting device 152 of one embodiment of the present invention. The light-emitting device 152 includes at least a pair of electrodes (the electrode 101 and the electrode 102) and an EL layer 103 between the electrodes.

The EL layer 103 includes at least the light-emitting layer 140 and the hole-transport layer 112. In addition, functional layers such as the hole-injection layer 111, the electron-transport layer 118, and the electron-injection layer 119 are included.

When hole injection is performed using an organic compound having an electron-acceptor property, that is, when the hole-injection layer 111 is formed using an organic compound having an electron-acceptor property, the compound contained in the hole-transport layer 112, which is in contact with the hole-injection layer 111, is preferably a hole-transport material having a relatively high highest occupied molecular orbital (HOMO) level to facilitate electron extraction or hole injection by the organic compound having an electron-acceptor property. Meanwhile, the organic compound of one embodiment of the present invention does not include a hetero atom and thus has a low HOMO level. Therefore, when the organic compound of one embodiment of the present invention is used as the host material of the light-emitting layer 140, the use of the organic compound having an electron-acceptor property for the hole-injection layer 111 might form a hole injection barrier at the interface between the light-emitting layer 140 and the hole-transport layer 112.

For that reason, when the light-emitting layer 140 is formed in contact with the hole-transport layer 112 made of the above-described hole-transport material with a high HOMO level, carriers are accumulated at their interface, which might cause a decrease in lifetime and efficiency of the light-emitting device. Accordingly, when the hole-injection layer has a multilayer structure as illustrated in FIG. 2(A), holes can be injected smoothly into the light-emitting layer, which results in improved lifetime and efficiency of the light-emitting device.

The structure of the light-emitting device 152 in this case is described with reference to FIG. 2(B) and FIG. 2(C). Here, the description is made on the case where an organic compound having an acceptor property is used as a hole-injection layer material 131 and the LUMO level of the hole-injection layer material 131 is lower than the HOMO level of a first hole-transport material 132. FIG. 2(C) is a schematic diagram showing the correlation of the HOMO levels and the LUMO level of the materials in this case. The following explains what terms and numerals in FIG. 2(B) and FIG. 2(C) represent.

HIM (131): the hole-injection layer material 131
HTM (132): the first hole-transport material 132
HTM (133): a second hole-transport material 133
HTM (134): a third hole-transport material 134
Host (141): the host material 141
The guest material 142

The hole-transport layer 112 preferably has a stacked-layer structure of a plurality of layers, as illustrated in FIGS. 2(A) and 2(B). Specifically, it is preferred that the hole-transport layer 112 include a first hole-transport layer 112-a and a second hole-transport layer 112-b from the hole-injection layer 111 side, the first hole-transport layer 112-a contain the first hole-transport material 132, and the second hole-transport layer 112-b contain the second hole-transport material 133. With this structure, when the HOMO level of the second hole-transport material 133 is made lower than the HOMO level of the first hole-transport material 132 as shown in FIG. 2(C), the above-described hole injection barrier can be reduced and the light-emitting device can have a long lifetime and high efficiency. Note that the HOMO level of the first hole-transport material 132 is preferably greater than or equal to −5.4 eV, in which case electrons can be easily extracted from the hole-injection layer material 131 (see FIG. 1(C)).

As shown in FIG. 2(C), the difference between the HOMO level of the first hole-transport material 132 and the HOMO level of the second hole-transport material 133 is preferably less than or equal to 0.3 eV, further preferably less than or equal to 0.2 eV. Such a structure facilitates hole injection from the first hole-transport layer into the second hole-transport layer.

The hole-transport layer 112 may further include a third hole-transport layer 112-c between the second hole-transport layer 112-b and the light-emitting layer 140, and the third hole-transport layer 112-c may contain a third hole-transport material 134 (see FIG. 2(A) and FIG. 2(B)). In this case, it is preferred that the HOMO level of the third hole-transport material 134 be lower than that of the second hole-transport material 133, and that the difference be less than or equal to 0.3 eV, further preferably less than or equal to 0.2 eV, as shown in FIG. 2(C).

It can be said that a structure where the HOMO level of the third hole-transport material 134 is equal to or lower than the HOMO level of the host material 141 is more preferable, in which case holes are adequately transported into the light-emitting layer, leading to a favorable lifetime and efficiency.

Note that in FIG. 1(C), the LUMO level of the hole-injection layer material 131 is lower than the HOMO level of the host material 141; however, there is no limitation on the relation between these levels. That is, the LUMO level of the hole-injection layer material 131 may be higher than or equal to the HOMO level of the host material 141.

Note that in the case where the HOMO level of the guest material 142 is higher than the HOMO level of the host material 141, the proportion of holes injected into the guest material 142 may increase depending on the position of the HOMO level of the hole-transport layer, and furthermore, holes trapped in the guest material 141 might cause a decreased lifetime due to localization of a light-emitting region. An example of a light-emitting device that is likely to have such a structure is a light-emitting device using an aromatic diamine compound as the guest material. In the case of using the diamine compound as the guest material, the light-emitting device described in this structure example can have high efficiency and high reliability.

Although shown as a single layer in FIG. 2(A), the electron-transport layer 118 is not limited thereto and may have a stacked-layer structure of a plurality of layers. Alternatively, the electron-transport layer 118 may be a mixed film formed of a plurality of materials.

<Materials>

Next, the components of the light-emitting device of one embodiment of the present invention will be described in detail below.

<<Light-Emitting Layer>>

In the light-emitting layer 140, the host material 141 is present in a higher proportion by weight than at least the guest material 142, and the guest material 142 (fluorescent material) is dispersed in the host material 141. Note that in the light-emitting layer 140, the host material 141 may be composed of one kind of compound or a plurality of compounds.

In the light-emitting layer 140, as the guest material 142, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like can be used, and for example, the following materials can be used.

Specific examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N-bis[4-(9-phenyl-9H-fluoren-9-yl)phenyl]pyrene-1,6-diamine (abbreviation: 1,6FLPAPrn), N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-bis[4-(9-phenyl-9H-fluoren-9-yl)phenyl]-N,N'-bis(4-tert-butylphenyl)pyrene-1,6-diamine (abbreviation: 1,6tBu-FLPAPrn), N,N-bis[4-(9-phenyl-9H-fluoren-9-yl)phenyl]-N,N'-diphenyl-3,8-dicyclohexylpyrene-1,6-diamine (abbreviation: ch-1,6FLPAPrn), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyl-di-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2-YGABPhA), N,N,9-triphenylanthracen-9-amine (abbreviation: DPhAPhA), coumarin 6, coumarin 545 T, N,N-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and 5,10,15,20-tetraphenylbisbenzo[5,6]indeno[1,2,3-cd:1',2',3'-lm]perylene.

As described above, a fluorescent material having a benzofuran skeleton can also be used suitably as the guest material 142.

Note that the light-emitting layer 140 may contain a material other than the host material 141 and the guest material 142.

In the light-emitting layer 140, the organic compound of one embodiment of the present invention is preferably used as the host material 141.

Examples of the material that can be used for the light-emitting layer 140 are, but not limited to, condensed polycyclic aromatic compounds such as anthracene derivatives, phenanthrene derivatives, pyrene derivatives, chrysene derivatives, and dibenzo[g,p]chrysene derivatives. Specific examples include metal complexes such as tris(8-quinolinolato)aluminum(III) (abbreviation: Alq), tris(4-methyl-8-quinolinolato)aluminum(III) (abbreviation: Almq$_3$), bis(10-hydro- xybenzo[h]quinolinato)beryllium(II) (abbreviation: BeBq$_2$), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO-11); and aromatic amine compounds such as 4,4'-bis[N-(1-naphthyl)-N-phenylamino]biphenyl (abbreviation: NPB or α-NPD), N,N-bis(3-methylphenyl)-N,N-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). Other examples include condensed polycyclic aromatic compounds such as anthracene derivatives, phenanthrene derivatives, pyrene derivatives, chrysene derivatives, and dibenzo[g,p]chrysene derivatives, and specific examples include 9,10-diphenylanthracene (abbreviation: DPAnth), N,N-diphenyl-9-[4-(10-phenyl-9-anthryl)phenyl]-9H-carbazol-3-amine (abbreviation: CzA-1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: P-CAPBA), N,9-diphenyl-N-(9,10-diphenyl-2-anthryl)-9H-carbazol-3-amine (abbreviation: 2PCAPA), 7-[4-(10-phenyl-9-anthryl)phenyl]-7H-dibenzo[c,g]carbazole (abbreviation: cgDBCzPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl) diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). Alternatively, one or more substances having a wider energy gap than the guest material 142 are selected from these substances and known substances.

The light-emitting layer 140 can be formed of two or more layers. For example, in the case where the light-emitting layer 140 is formed by stacking a first light-emitting layer and a second light-emitting layer in this order from the hole-transport layer side, a substance having a hole-transport property is used as the host material of the first light-emitting layer and a substance having an electron-transport property is used as the host material of the second light-emitting layer.

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, an aromatic amine, or the like, for example. Examples of the transition metal oxide include molybdenum oxide, vanadium oxide, ruthenium oxide, tungsten oxide, and manganese oxide. Examples of the phthalocyanine derivative include phthalocyanine and metal phthalocyanine. Examples of the aromatic amine include a benzidine derivative and a phenylenediamine derivative. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron-accepting property and a layer containing a hole-transport material may be used. In a steady state or in the presence of an electric field, electric charge can be transferred between these materials. Examples of the material having an electron-accepting property include organic acceptors such as a quinodimethane derivative, a chloranil derivative, and a hexaazatriphenylene derivative. A specific example is a compound having an electron-withdrawing group (in particular, a cyano group or a halogen group such as a fluoro group), such as 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and 1,3,4,5,7,8-hexafluorotetracyanonaphthoquinodimethane (abbreviation: F6-TCNNQ). A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferable; specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile]. Alternatively, a transition metal oxide such as an oxide of metal from Group 4 to Group 8 can be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because of stability in the air, a low hygroscopic property, and easiness of handling.

A material having a property of transporting more holes than electrons can be used as the hole-transport material, and a material having a hole mobility of $1\times10^{-6}$ cm$^2$/Vs or higher is preferable. Specifically, an aromatic amine compound, a carbazole derivative, an aromatic hydrocarbon, a stilbene derivative, or the like can be used. Furthermore, the hole-transport material may be a high molecular compound.

Examples of the aromatic amine compound, which is a material having a high hole-transport property, include N,N-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Specific examples of the carbazole derivative include 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples of the carbazole derivative include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, and the like can be used. The aromatic hydrocarbon having a hole mobility of $1\times10^{-6}$ cm$^2$/Vs or higher and having 14 to 42 carbon atoms is particularly preferably used.

The aromatic hydrocarbon may include a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

It is also possible to use high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N-bis(4-butylphenyl)-N,N-bis(phenyl)benzidine] (abbreviation: poly-TPD).

As the material having a high hole-transport property, the following aromatic amine compounds can be used, for example: 4,4'-bis[N-(1-naphthyl)-N-phenylamino]biphenyl (abbreviation: NPB or α-NPD), N,N-bis(3-methylphenyl)-N,N-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N-bis(9-phenylcarbazol-3-yl)-N,N-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyl)phenylaniline (abbreviation: YGA1BP), and N,N-bis[4-(carbazol-9-yl)phenyl]-N,N-diphenyl-9,9-dimethylfluorene-2,7-diamine (abbreviation: YGA2F). Moreover, it is possible to use amine compounds, carbazole compounds, thiophene compounds, furan compounds, fluorene compounds, triphenylene compounds, and phenanthrene compounds, such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di (9H-carbazol-9-yl)-dibenzothiophene (abbreviation: Cz2DBT), 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl) phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), 4-[3-(triphenylen-2-yl)phenyl]dibenzothiophene (abbreviation: mDBTPTp-II), 3,6-bis[4-(2-naphthyl)phenyl]-9-phenyl-9H-carbazole (abbreviation: βNP2PC), and N,N-bis[4-(dibenzofuran-4-yl) phenyl]-4-amino-p-terphenyl (abbreviation: DBfBB1TP), for example. Among the above compounds, compounds including at least one of a pyrrole skeleton, a furan skeleton, a thiophene skeleton, and an aromatic amine skeleton are preferred because of their high stability and reliability. In addition, the compounds having such skeletons have a high hole-transport property to contribute to a reduction in driving voltage.

<<Hole-Transport Layer>>

The hole-transport layer 112 is a layer containing a hole-transport material and can be formed using any of the hole-transport materials described as examples of the material of the hole-injection layer 111. In order that the hole-transport layer 112 has a function of transporting holes injected into the hole-injection layer 111 to the light-emitting layer 140, the hole-transport layer 112 preferably has a HOMO level equal or close to the HOMO level of the hole-injection layer 111. Note that in the case where the hole-transport layer 112 is formed of a plurality of layers, the materials used for the hole-transport layer 112 are preferably selected so that their HOMO levels have a step-like shape as shown in FIG. 2(C).

A substance having a hole mobility of $1 \times 10^{-6}$ cm²/Vs or higher is preferred. However, other substances may also be used as long as they have a property of transporting more holes than electrons. Note that the layer containing a substance having a high hole-transport property is not limited to a single layer, and two or more layers containing the aforementioned substances may be stacked.

<<Electron-Transport Layer>>

The electron-transport layer 118 has a function of transporting, to the light-emitting layer 140, electrons injected from the other of the pair of electrodes (the electrode 101 or the electrode 102) through the electron-injection layer 119. A material having a property of transporting more electrons than holes can be used as the electron-transport material, and a material having an electron mobility of $1 \times 10^{-6}$ cm²/Vs or higher is preferable. The organic compound of one embodiment of the present invention is preferably used. As a compound that easily accepts electrons (a material having an electron-transport property), a π-electron deficient heteroaromatic compound such as a nitrogen-containing heteroaromatic compound or a metal complex can be used, for example. Specific examples include a metal complex having a quinoline ligand, a benzoquinoline ligand, an oxazole ligand, or a thiazole ligand; an oxadiazole derivative; a triazole derivative, a benzimidazole derivative; a quinoxaline derivative; a dibenzoquinoxaline derivative; a phenanthroline derivative; a pyridine derivative; a bipyridine derivative; a pyrimidine derivative; and a triazine derivative. Note that other substances may also be used for the electron-transport layer as long as they have a property of transporting more electrons than holes. The electron-transport layer 118 is not limited to a single layer, and two or more layers containing the aforementioned substances may be stacked.

Specific examples include metal complexes including a quinoline skeleton or a benzoquinoline skeleton, such as tris(8-quinolinolato)aluminum(III) (abbreviation: Alq), tris (4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq). Furthermore, metal complexes having an oxazole-based or thiazole-based ligand, such as bis[2-(2-benzoxazolyl)phenolato]zinc (II) (abbreviation: ZnPBO) and bis[2-(2-benzothiazolyl) phenolato]zinc(II) (abbreviation: ZnBTZ) can be used. Furthermore, other than metal complexes, the following can be used: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl] benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: Bphen), 2,9-bis (naphthalen-2-yl)-4,7-diphenyl-1,10-phenanthroline (abbreviation: NBPhen), and bathocuproine (abbreviation: BCP); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl] dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f, h]quinoxaline (abbreviation: 6mDBTPDBq-II), 2-[3-(3,9'-bi-9H-carbazol-9-yl)phenyl]dibenzo[f,h]quinoxaline (abbreviation: 2mCzCzPDBq), 4,6-bis[3-(phenanthren-9-yl) phenyl]pyrimidine (abbreviation: 4,6mPnP2Pm), 4,6-bis[3-(4-dibenzothienyl)phenyl]pyrimidine (abbreviation: 4,6-mDBTP2Pm-II), and 4,6-bis[3-(9H-carbazol-9-yl)phenyl] pyrimidine (abbreviation: 4,6mCzP2Pm); heterocyclic compounds having a triazine skeleton, such as 2-{4-[3-(N-phenyl-9H-carbazol-3-yl)-9H-carbazol-9-yl]phenyl}-4,6-diphenyl-1,3,5-triazine (abbreviation: PCCzPTzn); heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB); and heteroaromatic compounds such as 4,4'-bis(5-methylbenzoxazol-2-yl)stilbene (abbreviation: BzOs). Among the above-described heterocyclic compounds, the heterocyclic compounds having at least one of a triazine skeleton, a diazine (pyrimidine, pyrazine, pyridazine) skeleton, and a pyridine skeleton are preferred because of their high stability and reliability. In addition, the heterocyclic compounds having such skeletons have a high electron-transport property to contribute to a reduction in driving voltage. Furthermore, a high molecular compound such as poly(2,5-pyridinediyl) (abbreviation: PPy), poly[(9, 9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances listed here are mainly substances having an electron mobility of $1 \times 10^{-6}$ cm$^2$/Vs or higher.

Note that other substances may also be used for the electron-transport layer as long as they have a property of transporting more electrons than holes. The electron-transport layer 118 is not limited to a single layer, and two or more layers containing the aforementioned substances may be stacked.

A layer that controls transfer of carriers may be provided between the electron-transport layer 118 and the light-emitting layer 140. This layer is formed by addition of a small amount of a substance having a high electron-trapping property to the material having a high electron-transport property described above, and the layer is capable of adjusting carrier balance by suppressing transport of carriers. Such a structure is very effective in preventing a problem (such as a reduction in device lifetime) caused when electrons pass through the light-emitting layer.

An n-type compound semiconductor may also be used, and an oxide such as titanium oxide, zinc oxide, silicon oxide, tin oxide, tungsten oxide, tantalum oxide, barium titanate, barium zirconate, zirconium oxide, hafnium oxide, aluminum oxide, yttrium oxide, or zirconium silicate; a nitride such as silicon nitride; cadmium sulfide; zinc selenide; or zinc sulfide can be used, for example.

<<Electron-Injection Layer>>

The electron-injection layer 119 has a function of reducing a barrier for electron injection from the electrode 102 to promote electron injection, and a Group 1 metal, a Group 2 metal, or an oxide, a halide, a carbonate, or the like of them can be used, for example. Alternatively, a composite material of the electron-transport material described above and a material having a property of donating electrons thereto can be used. Examples of the material having an electron-donating property include a Group 1 metal, a Group 2 metal, and an oxide of them. Specifically, an alkali metal, an alkaline earth metal, or a compound thereof, such as lithium fluoride, sodium fluoride, cesium fluoride, calcium fluoride, or lithium oxide, can be used. A rare earth metal compound like erbium fluoride can also be used. Electride may also be used for the electron-injection layer 119. Examples of the electride include a substance in which electrons are added at high concentration to a mixed oxide of calcium and aluminum. The substance that can be used for the electron-transport layer 118 can be used for the electron-injection layer 119.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons; specifically, the above-listed substances contained in the electron-transport layer 118 (the metal complexes, heteroaromatic compounds, and the like) can be used, for example. As the electron donor, a substance showing an electron-donating property with respect to the organic compound is used. Specifically, an alkali metal, an alkaline earth metal, and a rare earth metal are preferable, and examples include lithium, sodium, cesium, magnesium, calcium, erbium, and ytterbium. In addition, an alkali metal oxide and an alkaline earth metal oxide are preferable, and examples include lithium oxide, calcium oxide, and barium oxide. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, gravure printing, or the like. Besides the above-mentioned materials, an inorganic compound such as a quantum dot or a high molecular compound (an oligomer, a dendrimer, a polymer, or the like) may be used for the light-emitting layer, the hole-injection layer, the hole-transport layer, the electron-transport layer, and the electron-injection layer described above.

<<Quantum Dot>>

A quantum dot is a semiconductor nanocrystal with a size of several nanometers to several tens of nanometers and contains approximately $1 \times 10^3$ to $1 \times 10^6$ atoms. Since energy shift of quantum dots depends on their size, quantum dots made of the same substance emit light with different emission wavelengths depending on their size. Thus, emission wavelengths can be easily changed by varying the size of quantum dots to be used.

Since a quantum dot has an emission spectrum with a narrow peak width, light emission with high color purity can be obtained. In addition, a quantum dot is said to have a theoretical internal quantum efficiency of approximately 100%, which far exceeds that of a fluorescent organic compound, i.e., 25%, and is comparable to that of a phosphorescent organic compound. Therefore, the use of a quantum dot as a light-emitting material enables a light-emitting device having high emission efficiency to be obtained. Furthermore, since a quantum dot, which is an inorganic material, has high inherent stability, a light-emitting device that is favorable also in terms of lifetime can be obtained.

Examples of a material of a quantum dot include a Group 14 element, a Group 15 element, a Group 16 element, a compound of a plurality of Group 14 elements, a compound of an element belonging to any of a Group 4 to a Group 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride; calcium sulfide; calcium selenide; calcium telluride; beryllium sulfide; beryllium selenide; beryllium telluride; magnesium sulfide; magnesium selenide; germanium sulfide;

germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; iron oxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur; a compound of cadmium, selenium, and tellurium; a compound of indium, gallium, and arsenic; a compound of indium, gallium, and selenium; a compound of indium, selenium, and sulfur; a compound of copper, indium, and sulfur; and combinations thereof. What is called an alloyed quantum dot, whose composition is represented by a given ratio, may be used. For example, an alloyed quantum dot of cadmium, selenium, and sulfur is a means effective in obtaining blue light emission because the emission wavelength can be changed by varying the content ratio of the elements.

As the structure of the quantum dot, any of a core type, a core-shell type, a core-multishell type, and the like may be used. When a core is covered with a shell formed of another inorganic material having a wider band gap, the influence of defects and dangling bonds existing at the surface of a nanocrystal can be reduced. Since this can significantly improve the quantum efficiency of light emission, it is preferable to use a core-shell or core-multishell quantum dot. Examples of the material of a shell include zinc sulfide and zinc oxide.

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It is also possible to reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

Since band gaps of quantum dots are increased as their size is decreased, the size is adjusted as appropriate so that light with a desired wavelength can be obtained. Light emission from the quantum dots is shifted to a blue color side, i.e., a high energy side, as the crystal size is decreased; thus, the emission wavelengths of the quantum dots can be adjusted over a wavelength range of a spectrum of an ultraviolet region, a visible light region, and an infrared region by changing the size of quantum dots. The range of size (diameter) of quantum dots which is usually used is greater than or equal to 0.5 nm and less than or equal to 20 nm, preferably greater than or equal to 1 nm and less than or equal to 10 nm. The emission spectra are narrowed as the size distribution of the quantum dots gets smaller, and thus light can be obtained with high color purity. The shape of the quantum dots is not particularly limited and may be a spherical shape, a rod shape, a circular shape, or the like. Quantum rods which are rod-like shape quantum dots have a function of emitting directional light; thus, quantum rods can be used as a light-emitting material to obtain a light-emitting device with higher external quantum efficiency.

In most organic EL devices, to improve emission efficiency, concentration quenching of the light-emitting materials is suppressed by dispersing light-emitting materials in host materials. The host materials need to be materials having singlet excitation energy levels or triplet excitation energy levels higher than or equal to those of the light-emitting materials. In the case of using blue phosphorescent materials as light-emitting materials, it is particularly difficult to develop host materials that have triplet excitation energy levels higher than or equal to those of the blue phosphorescent materials and are excellent in terms of a lifetime. Even when a light-emitting layer is composed of quantum dots and made without a host material, the quantum dots enable emission efficiency to be ensured; thus, a light-emitting device that is favorable in terms of a lifetime can be obtained. In the case where the light-emitting layer is composed of quantum dots, the quantum dots preferably have core-shell structures (including core-multishell structures).

In the case of using quantum dots as the light-emitting material in the light-emitting layer, the thickness of the light-emitting layer is set greater than or equal to 3 nm and less than or equal to 100 nm, preferably greater than or equal to 10 nm and less than or equal to 100 nm, and the quantum dot content of the light-emitting layer is greater than or equal to 1 and less than or equal to 100 volume %. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, a blade coating method, a roll coating method, an inkjet method, a printing method, a spray coating method, a curtain coating method, or a Langmuir-Blodgett method) may be employed. For a light-emitting layer using a phosphorescent material, a vacuum evaporation method, as well as the wet process, can be suitably employed.

As the liquid medium used for the wet process, an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like can be used.

<<Pair of Electrodes>>

The electrode 101 and the electrode 102 function as an anode and a cathode of a light-emitting device. The electrode 101 and the electrode 102 can each be formed using a metal, an alloy, a conductive compound, a mixture or a stack thereof, or the like.

One of the electrode 101 and the electrode 102 is preferably formed using a conductive material having a function of reflecting light. Examples of the conductive material include aluminum (Al) and an alloy containing Al. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting device with aluminum. Furthermore, silver (Ag), an alloy containing Ag and N(N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), and gold (Au)), or the like may be used. Examples of the alloy containing silver include an alloy containing silver, palladium, and copper, an alloy containing silver and copper, an alloy containing silver and magnesium, an alloy containing silver and nickel, an alloy containing silver and gold, and an alloy containing silver and ytterbium. Besides, a transition metal such as tungsten, chromium (Cr), molybdenum (Mo), copper, or titanium can be used.

Light emitted from the light-emitting layer is extracted through one or both of the electrode 101 and the electrode 102. Thus, at least one of the electrode 101 and the electrode 102 is preferably formed using a conductive material having a function of transmitting light. An example of the conductive material is a conductive material having a visible light transmittance higher than or equal to 40% and lower than or equal to 100%, preferably higher than or equal to 60% and lower than or equal to 100%, and a resistivity lower than or equal to $1 \times 10^{-2}$ Ω·cm.

The electrode 101 and the electrode 102 may be formed using a conductive material having a function of transmitting light and a function of reflecting light. An example of the conductive material is a conductive material having a visible light reflectivity higher than or equal to 20% and lower than or equal to 80%, preferably higher than or equal to 40% and lower than or equal to 70%, and a resistivity lower than or equal to $1 \times 10^{-2}$ Ω·cm. For example, one or more kinds of conductive metals and alloys, conductive compounds, and the like can be used. Specifically, a metal oxide such as indium tin oxide (hereinafter referred to as ITO), indium tin oxide containing silicon or silicon oxide (abbreviation: ITSO), indium oxide-zinc oxide (Indium Zinc Oxide), indium oxide-tin oxide containing titanium, indium titanium oxide, or indium oxide containing tungsten oxide and zinc oxide can be used, for example. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, as the material having a function of transmitting light, a material that has a function of transmitting visible light and has conductivity is used, and examples of the material include, in addition to the above-described oxide conductor typified by ITO, an oxide semiconductor and an organic conductor containing an organic substance. Examples of the organic conductor containing an organic substance include a composite material in which an organic compound and an electron donor (donor) are mixed and a composite material in which an organic compound and an electron acceptor (acceptor) are mixed. Alternatively, an inorganic carbon-based material such as graphene may be used. The resistivity of the material is preferably lower than or equal to $1 \times 10^5$ Ω·cm, further preferably lower than or equal to $1 \times 10^4$ Ω·cm.

Alternatively, one or both of the electrode 101 and the electrode 102 may be formed by stacking two or more of these materials.

In order to improve the outcoupling efficiency, a material whose refractive index is higher than that of an electrode having a function of transmitting light may be formed in contact with the electrode. The material may be conductive or non-conductive as long as it has a function of transmitting visible light. In addition to the oxide conductors described above, an oxide semiconductor and an organic substance are given as examples. Examples of the organic substance include the materials for the light-emitting layer, the hole-injection layer, the hole-transport layer, the electron-transport layer, and the electron-injection layer given as examples. Alternatively, an inorganic carbon-based material or a metal film thin enough to transmit light can be used, and a plurality of layers with a thickness of several nanometers to several tens of nanometers may be stacked.

In the case where the electrode 101 or the electrode 102 has a function of a cathode, the electrode preferably contains a material with a low work function (3.8 eV or lower). For example, it is possible to use an element belonging to Group 1 or Group 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum and silver, or the like.

When the electrode 101 or the electrode 102 is used as an anode, a material with a high work function (4.0 eV or higher) is preferably used.

The electrode 101 and the electrode 102 may be a stacked layer of a conductive material having a function of reflecting light and a conductive material having a function of transmitting light. This is preferred, in which case the electrode 101 and the electrode 102 can have a function of adjusting the optical length so that desired light from the light-emitting layer resonates to intensify its wavelength.

As the method for forming the electrode 101 and the electrode 102, a sputtering method, an evaporation method, a printing method, a coating method, an MBE (Molecular Beam Epitaxy) method, a CVD method, a pulsed laser deposition method, an ALD (Atomic Layer Deposition) method, or the like can be used as appropriate.

<<Substrate>>

A light-emitting device of one embodiment of the present invention is formed over a substrate made of glass, plastic, or the like. As for the order of forming layers over the substrate, layers may be sequentially stacked from the electrode 101 side or sequentially stacked from the electrode 102 side.

For the substrate where the light-emitting device of one embodiment of the present invention can be formed, glass, quartz, plastic, or the like can be used, for example. Furthermore, a flexible substrate can be used. The flexible substrate means a substrate that can be bent, such as a plastic substrate made of polycarbonate or polyarylate, for example. Furthermore, a film, an inorganic vapor deposition film, or the like can be used. Another material may be used as long as the substrate functions as a support in the fabrication process of the light-emitting device. Another material having a function of protecting the light-emitting device may be used.

In this specification and the like, a light-emitting device can be formed using a variety of substrates, for example. The type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film. Examples of the glass substrate include barium borosilicate glass, aluminoborosilicate glass, and soda lime glass. As examples of the flexible substrate, the attachment film, the base material film, and the like, the following can be given. Examples include plastics typified by polyethylene terephthalate (PET), polyethylene naphthalate (PEN), polyether sulfone (PES), and polytetrafluoroethylene (PTFE). Another example is a resin such as acrylic. Other examples are polypropylene, polyester, polyvinyl fluoride, and polyvinyl chloride. Other examples are polyamide, polyimide, aramid, epoxy, an inorganic vapor deposition film, and paper.

Furthermore, a flexible substrate may be used as the substrate and the light-emitting device may be formed directly on the flexible substrate. Alternatively, a separation layer may be provided between the substrate and the light-emitting device. The separation layer can be used when part or the whole of a light-emitting device formed thereover is separated from the substrate and transferred onto another substrate. In such a case, the light-emitting device can be transferred to a substrate having low heat resistance or a flexible substrate as well. For the above separation layer, a stacked-layer structure of inorganic films of a tungsten film and a silicon oxide film, or a structure in which a resin film of polyimide or the like is formed over a substrate can be used, for example.

In other words, after the light-emitting device is formed using a substrate, the light-emitting device may be transferred to and arranged over another substrate. Examples of the substrate to which the light-emitting device is transferred include, in addition to the above substrates, a cellophane substrate, a stone substrate, a wood substrate, a cloth substrate (including a natural fiber (silk, cotton, or hemp), a synthetic fiber (nylon, polyurethane, or polyester), a regenerated fiber (acetate, cupro, rayon, or regenerated polyester), and the like), a leather substrate, and a rubber substrate. With the use of such a substrate, a light-emitting device with high durability, a light-emitting device with high heat resistance, a light-emitting device with reduced weight, or a light-emitting device with reduced thickness can be obtained.

The light-emitting device 110 may be formed over an electrode electrically connected to a field-effect transistor (FET), for example, that is formed over the above-described substrate. Accordingly, an active matrix display apparatus in which the FET controls the driving of the light-emitting device 110 can be fabricated.

Note that, in this embodiment, one embodiment of the present invention has been described. Furthermore, in any of the other embodiments, one embodiment of the present invention is described. However, embodiments of the present invention are not limited thereto. In other words, since various embodiments of the invention are described in this embodiment and the other embodiments, one embodiment of the present invention is not limited to a particular embodiment. Although the example in which one embodiment of the present invention is used in a light-emitting device is described as an example, one embodiment of the present invention is not limited thereto. For example, depending on the case or according to the circumstances, one embodiment of the present invention is not necessarily used in a light-emitting device.

The structure described above in this embodiment can be used in appropriate combination with the other embodiments.

Embodiment 4

Figure 3:
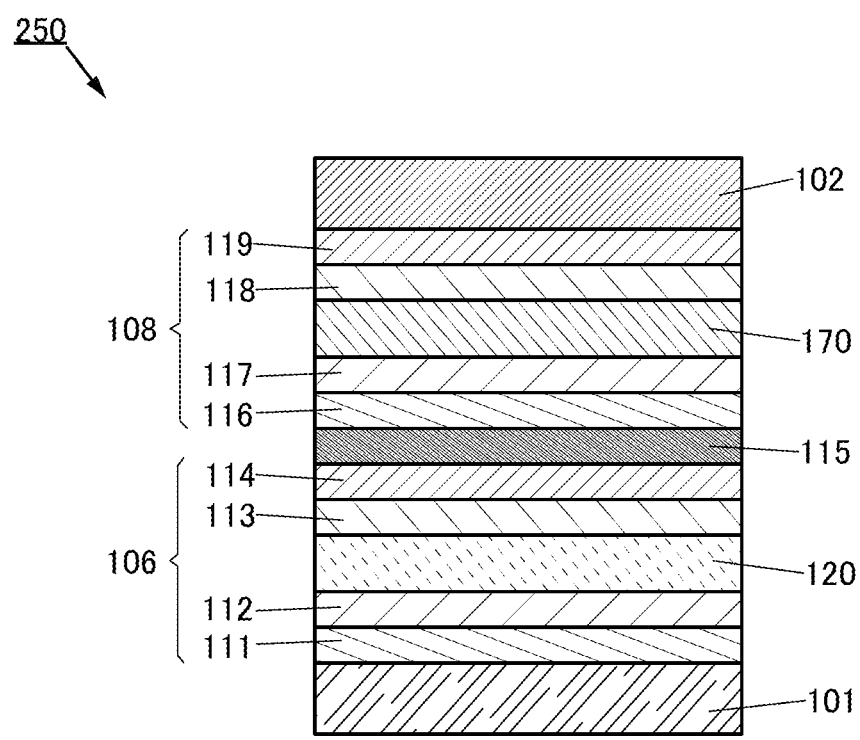
FIG. 3 A schematic view of a light-emitting device of one embodiment of the present invention.

In this embodiment, a light-emitting device having a structure different from the structure of the light-emitting device described in Embodiment 3 will be described below with reference to FIG. 3. In FIG. 3, a portion having a function similar to that of a portion denoted by a reference numeral in FIG. 1(A) is represented by the same hatch pattern and the reference numeral is omitted in some cases. In addition, common reference numerals are used for portions having similar functions, and a detailed description thereof is omitted in some cases.

Structure Example 4 of Light-Emitting Device

FIG. 3 is a schematic cross-sectional view of a light-emitting device 250.

The light-emitting device 250 illustrated in FIG. 3 includes a plurality of light-emitting units (a light-emitting unit 106 and a light-emitting unit 108) between a pair of electrodes (the electrode 101 and the electrode 102). Any one of the plurality of light-emitting units preferably has a structure similar to that of the EL layer 100 or the EL layer 103 illustrated in FIG. 1(A) or FIG. 2(A). That is, it is preferred that the light-emitting device 150 or the light-emitting device 152 illustrated in FIG. 1(A) or FIG. 2(A) include one light-emitting unit, whereas the light-emitting device 250 include a plurality of light-emitting units. Note that the electrode 101 functions as an anode and the electrode 102 functions as a cathode in the light-emitting device 250 in the following description; however, the functions of the electrodes may be reversed as the structure of the light-emitting device 250.

Moreover, in the light-emitting device 250 illustrated in FIG. 3, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable to use a structure similar to that of the EL layer 100 for the light-emitting unit 108.

The light-emitting device 250 includes a light-emitting layer 120 and a light-emitting layer 170. The light-emitting unit 106 includes the hole-injection layer 111, the hole-transport layer 112, an electron-transport layer 113, and an electron-injection layer 114 in addition to the light-emitting layer 170. The light-emitting unit 108 includes a hole-injection layer 116, a hole-transport layer 117, the electron-transport layer 118, and the electron-injection layer 119 in addition to the light-emitting layer 120.

In the light-emitting device 250, any layer of each of the light-emitting unit 106 and the light-emitting unit 108 contains the organic compound of one embodiment of the present invention. Note that the layer containing the organic compound is preferably the light-emitting layer 120 or the light-emitting layer 170.

The charge-generation layer 115 may have either a structure in which a substance having an acceptor property, which is an electron acceptor, is added to a hole-transport material or a structure in which a substance having a donor property, which is an electron donor, is added to an electron-transport material. Alternatively, both of these structures may be stacked.

In the case where the charge-generation layer 115 contains a composite material of an organic compound and a substance having an acceptor property, the composite material that can be used for the hole-injection layer 111 described in Embodiment 3 is used as the composite material. As the organic compound, a variety of compounds such as an aromatic amine compound, a carbazole compound, an aromatic hydrocarbon, and a high molecular compound (an oligomer, a dendrimer, a polymer, and the like) can be used. Note that a substance having a hole mobility of $1 \times 10^{-6}$ cm$^2$/Vs or higher is preferably used as the organic compound. However, other substances may also be used as long as they have a property of transporting more holes than electrons. Since the composite material of an organic compound and a substance having an acceptor property has excellent carrier-injection and carrier-transport properties, low-voltage driving or low-current driving can be achieved. Note that in the case where a surface of a light-emitting unit on the anode side is in contact with the charge-generation layer 115, the charge-generation layer 115 can also serve as a hole-injection layer or a hole-transport layer of the light-emitting unit; thus, a structure in which a hole-injection layer or a hole-transport layer is not provided in the light-emitting unit may be employed. Alternatively, in the case where a surface of a light-emitting unit on the cathode side is in contact with the charge-generation layer 115, the charge-generation layer 115 can also serve as an electron-injection layer or an electron-transport layer of the light-emitting unit; thus, a structure in which an electron-injection layer or an electron-transport layer is not provided in the light-emitting unit may be employed.

Note that the charge-generation layer 115 may have a stacked-layer structure combining a layer containing the composite material of an organic compound and a substance having an acceptor property and a layer formed of another material. For example, a layer containing the composite material of an organic compound and a substance having an acceptor property and a layer containing one compound selected from electron-donating substances and a compound having a high electron-transport property may be used in combination. Moreover, a layer containing the composite material of an organic compound and a substance having an acceptor property and a layer containing a transparent conductive film may be used in combination.

Note that the charge-generation layer 115 sandwiched between the light-emitting unit 106 and the light-emitting unit 108 injects electrons into one of the light-emitting units and injects holes into the other of the light-emitting units when voltage is applied to the electrode 101 and the electrode 102. For example, in FIG. 3, the charge-generation layer 115 injects electrons into the light-emitting unit 106 and injects holes into the light-emitting unit 108 when voltage is applied such that the potential of the electrode 101 is higher than the potential of the electrode 102.

Note that in terms of outcoupling efficiency, the charge-generation layer 115 preferably has a property of transmitting visible light (specifically, the transmittance of visible light through the charge-generation layer 115 is preferably higher than or equal to 40%). Moreover, the charge-generation layer 115 functions even when it has lower conductivity than the pair of electrodes (the electrode 101 and the electrode 102).

Forming the charge-generation layer 115 using the above-described materials can inhibit an increase in driving voltage in the case where the light-emitting layers are stacked.

The light-emitting device having two light-emitting units has been described with reference to FIG. 3; however, a light-emitting device in which three or more light-emitting units are stacked can be similarly employed. When a plurality of light-emitting units partitioned by the charge-generation layer are arranged between a pair of electrodes as in the light-emitting device 250, it is possible to achieve a light-emitting device that can emit high-luminance light with the current density kept low and has a long lifetime. Moreover, a light-emitting device having low power consumption can be achieved.

Note that in each of the above structures, the emission colors exhibited by the guest materials used in the light-emitting unit 106 and the light-emitting unit 108 may be the same or different. In the case where guest materials having a function of exhibiting light emission of the same color are used for the light-emitting unit 106 and the light-emitting unit 108, the light-emitting device 250 can exhibit high emission luminance at a small current value, which is preferred. In the case where guest materials having a function of exhibiting light emission of different colors are used for the light-emitting unit 106 and the light-emitting unit 108, the light-emitting device 250 can exhibit multi-color light emission, which is preferred. In this case, with the use of a plurality of light-emitting materials with different emission wavelengths in one or both of the light-emitting layer 120 and the light-emitting layer 170, the light-emitting device 250 emits light obtained by synthesizing light emission having different emission peaks; thus, its emission spectrum has at least two local maximum values.

The above structure is also suitable for obtaining white light emission. When the light-emitting layer 120 and the light-emitting layer 170 emit light of complementary colors, white light emission can be obtained. It is particularly favorable to select the guest materials so that white light emission with high color rendering properties or light emission of at least red, green, and blue can be obtained.

In the case of a light-emitting device in which three or more light-emitting units are stacked, colors of light emitted from guest materials used in the light-emitting units may be the same or different from each other. In the case where a plurality of light-emitting units that exhibit the same emission color are included, these light-emitting units can exhibit light of the color with higher emission luminance with a smaller current value as compared with light of the other colors. Such a structure can be suitably used for adjustment of emission colors. The structure is particularly suitable when guest materials that emit light of different colors with different emission efficiencies are used. For example, when three layers of light-emitting units are included, the intensity of fluorescence and phosphorescence can be adjusted with two layers of light-emitting units that contain a fluorescent material for the same color and one layer of a light-emitting unit that contains a phosphorescent material that emits light of a color different from the emission color of the fluorescent material. That is, the intensity of emitted light of each color can be adjusted with the number of light-emitting units.

In the case of the light-emitting device including two layers of fluorescent units and one layer of a phosphorescent unit, it is preferable that the light-emitting device include two layers of light-emitting units including a blue fluorescent material and one layer of a light-emitting unit including a yellow phosphorescent material; two layers of light-emitting units including a blue fluorescent material and one layer of a light-emitting-layer unit including a red phosphorescent material and a green phosphorescent material; or two layers of light-emitting units including a blue fluorescent material and one layer of a light-emitting-layer unit including a red phosphorescent material, a yellow phosphorescent material, and a green phosphorescent material, in which case white light emission can be obtained efficiently.

At least one of the light-emitting layer 120 and the light-emitting layer 170 may be further divided into layers and the divided layers may contain different light-emitting materials. That is, at least one of the light-emitting layer 120 and the light-emitting layer 170 can consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. In this case, the light-emitting materials contained in the first light-emitting layer and the second light-emitting layer may be the same or different, and may have functions of exhibiting light emission of the same color or exhibiting light emission of different colors. White light emission with high color rendering properties that is formed of three primary colors or four or more emission colors can also be obtained by using a plurality of light-emitting materials having functions of exhibiting light emission of different colors.

In addition, it is suitable that the light-emitting layer of the light-emitting unit 108 include a phosphorescent compound. When the organic compound of one embodiment of the present invention is used for at least one of the plurality of units, a light-emitting device with high emission efficiency and reliability can be provided.

Note that this embodiment can be combined as appropriate with any of the other embodiments.

Embodiment 5

In this embodiment, a light-emitting apparatus using the light-emitting device described in Embodiment 3 and Embodiment 4 will be described with reference to FIG. 4(A) and FIG. 4(B).

Structure Example 1 of Light-Emitting Apparatus

Figure 4A:
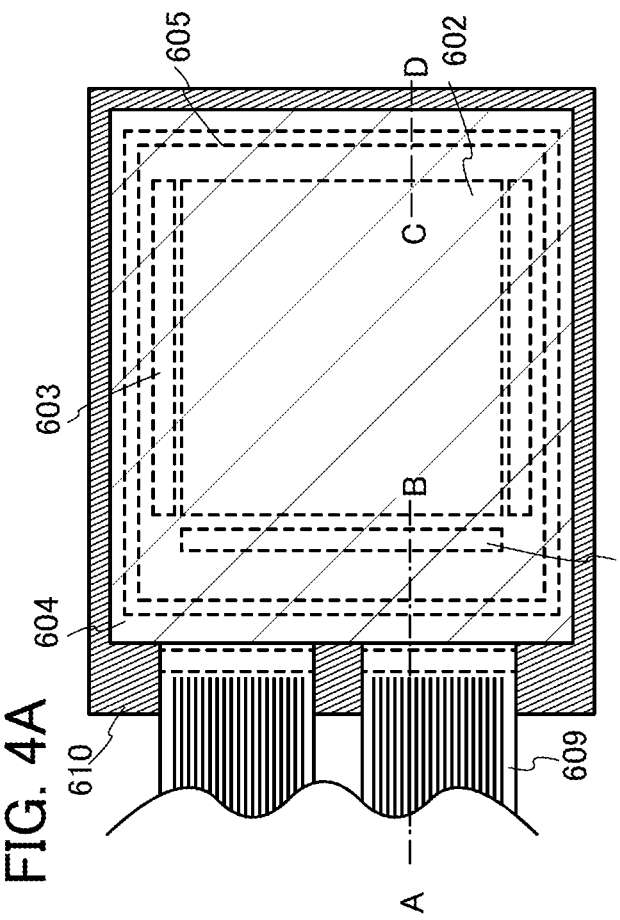
FIG. 4(A), (B) Conceptual views of an active matrix light-emitting apparatus of one embodiment of the present invention.
Figure 4B:
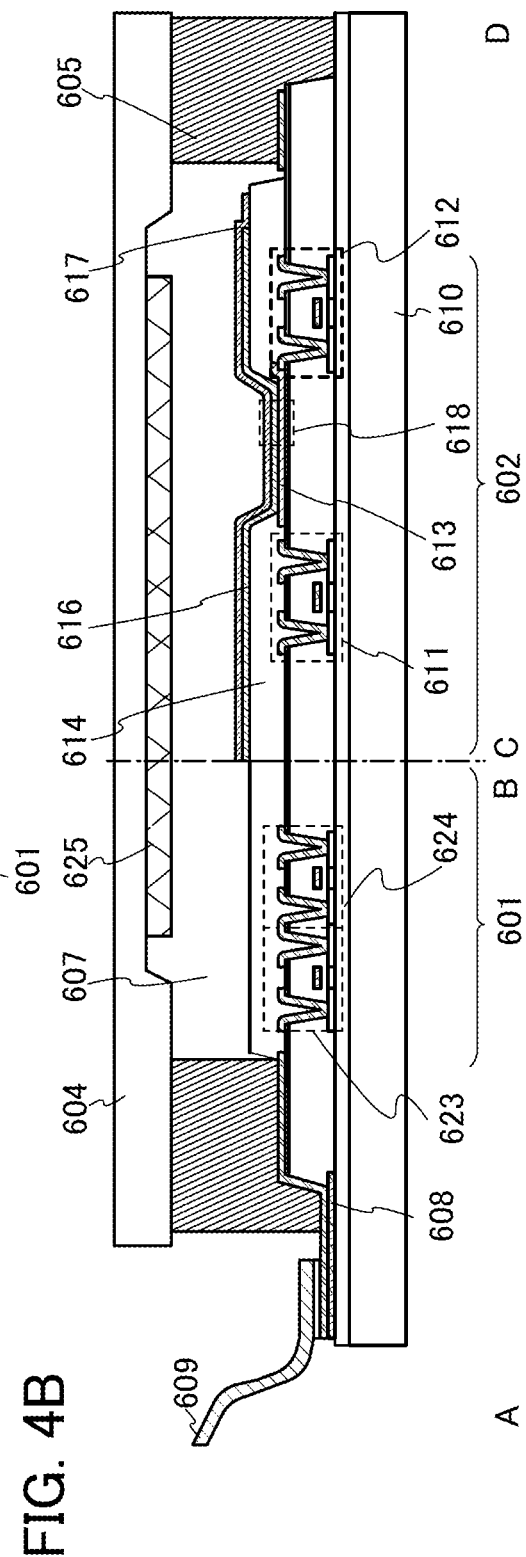

FIG. 4(A) is a top view illustrating the light-emitting device, and FIG. 4(B) is a cross-sectional view along the lines A-B and C-D in FIG. 4(A). This light-emitting apparatus includes a driver circuit portion (a source side driver circuit) 601, a pixel portion 602, and a driver circuit portion (a gate side driver circuit) 603, which are indicated by dotted lines, as components controlling light emission from light-emitting devices. Furthermore, 604 denotes a sealing substrate, 625 denotes a desiccant, 605 denotes a sealant, and a portion surrounded by the sealant 605 is a space 607.

Note that a lead wiring 608 is a wiring for transmitting signals to be input to the source side driver circuit 601 and the gate side driver circuit 603 and receives a video signal, a clock signal, a start signal, a reset signal, and the like from an FPC (flexible printed circuit) 609 serving as an external input terminal. Although only the FPC is illustrated here, a printed wiring board (PWB) may be attached to the FPC. The light-emitting apparatus in this specification includes not only the light-emitting apparatus itself but also the state where an FPC or a PWB is attached thereto.

Next, a cross-sectional structure of the light-emitting apparatus is described with reference to FIG. 4(B). The driver circuit portion and the pixel portion are formed over a device substrate 610; here, the source side driver circuit 601, which is the driver circuit portion, and one pixel in the pixel portion 602 are illustrated.

Note that in the source side driver circuit 601, a CMOS circuit in which an n-channel TFT 623 and a p-channel TFT 624 are combined is formed. The driver circuit may be formed of a variety of CMOS circuits, PMOS circuits, and/or NMOS circuits. Although a driver-integrated type where the driver circuit is formed over the substrate is described in this embodiment, this is not always necessary and the driver circuit can be formed outside instead of over the substrate.

The pixel portion 602 is formed of pixels including a switching TFT 611, a current controlling TFT 612, and a first electrode 613 electrically connected to a drain thereof. Note that an insulator 614 is formed to cover an end portion of the first electrode 613. The insulator 614 can be formed using a positive photosensitive resin film.

In order to improve the coverage with a film formed over the insulator 614, the insulator 614 is formed to have a surface with a curvature at its upper end portion or lower end portion. For example, in the case where photosensitive acrylic is used as a material of the insulator 614, only the upper end portion of the insulator 614 preferably has a curved surface. The radius of curvature of the curved surface is preferably greater than or equal to 0.2 µm and less than or equal to 0.3 µm. Either a negative or positive photosensitive material can be used as the insulator 614.

An EL layer 616 and a second electrode 617 are formed over the first electrode 613. Here, as a material used for the first electrode 613 functioning as an anode, a material with a high work function is desirably used. For example, it is possible to use a single-layer film of an ITO film, an indium tin oxide film containing silicon, an indium oxide film containing zinc oxide at 2 wt % or higher and 20 wt % or lower, a titanium nitride film, a chromium film, a tungsten film, a Zn film, a Pt film, or the like; a stacked layer of titanium nitride and a film containing aluminum as its main component; or a three-layer structure of a titanium nitride film, a film containing aluminum as its main component, and a titanium nitride film. Note that the stacked-layer structure achieves low wiring resistance, a favorable ohmic contact, and a function of the anode.

The EL layer 616 is formed by any of a variety of methods such as an evaporation method using an evaporation mask, an inkjet method, and a spin coating method. A material included in the EL layer 616 may be a low molecular compound or a high molecular compound (including an oligomer and a dendrimer).

As a material used for the second electrode 617, which is formed over the EL layer 616 and functions as a cathode, a material with a low work function (e.g., Al, Mg, Li, Ca, or an alloy or a compound thereof, such as MgAg, MgIn, or AlLi) is preferably used. Note that to transmit light generated in the EL layer 616 through the second electrode 617, a stacked layer of a thin metal film with a reduced thickness and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that the first electrode 613, the EL layer 616, and the second electrode 617 constitute a light-emitting device 618. The light-emitting device 618 is preferably a light-emitting device having any of the structures described in Embodiment 3 and Embodiment 4. The pixel portion includes a plurality of light-emitting devices, and the light-emitting apparatus of this embodiment may include both the light-emitting device with the structure described in Embodiment 3 and Embodiment 4 and a light-emitting device with a different structure.

The sealing substrate 604 and the device substrate 610 are attached to each other using the sealant 605, so that the light-emitting device 618 is provided in the space 607 surrounded by the device substrate 610, the sealing substrate 604, and the sealant 605. Note that the space 607 is filled with a filler, and may be filled with an inert gas (e.g., nitrogen or argon) or one or both of a resin and a desiccant.

Note that an epoxy-based resin or glass frit is preferably used for the sealant 605. Furthermore, these materials are preferably materials that transmit as little moisture or oxygen as possible. As a material used for the sealing substrate 604, in addition to a glass substrate and a quartz substrate, a plastic substrate formed of FRP (Fiber Reinforced Plastics), PVF (polyvinyl fluoride), polyester, acrylic, or the like can be used.

As described above, the light-emitting apparatus including the light-emitting device described in Embodiment 3 and Embodiment 4 can be obtained.

Structure Example 2 of Light-Emitting Apparatus

As examples of display apparatuses, FIG. 5 illustrates examples of light-emitting apparatus including a light-emitting device exhibiting white light emission and a coloring layer (color filter).

FIG. 5(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition wall 1026, an EL layer 1028, a second electrode 1029 of the light-emitting devices, a sealing substrate 1031, a sealant 1032, a red pixel 1044R, a green pixel 1044G, a blue pixel 1044B, a white pixel 1044W, and the like.

In FIG. 5(A) and FIG. 5(B), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black layer is aligned and fixed to the substrate 1001. Note that the coloring layers and the black layer are covered with an overcoat layer 1036. In FIG. 5(A) and FIG. 5(B), there are a light-emitting layer from which light is emitted to the outside without passing through the coloring layer and light-emitting layers from which light is emitted to the outside through the coloring layers of the respective colors. Since light that does not pass through the coloring layer is white and light that passes through the coloring layer is red, blue, or green, an image can be expressed using pixels of the four colors.

FIG. 5(B) illustrates an example in which the red coloring layer 1034R, the green coloring layer 1034G, and the blue coloring layer 1034B) are formed between the gate insulating film 1003 and the first interlayer insulating film 1020. As illustrated in FIG. 5(B), the coloring layers may be provided between the substrate 1001 and the sealing substrate 1031.

The above-described light-emitting apparatuses are a light-emitting apparatus having a structure in which light is extracted toward the substrate 1001 where the TFTs are formed (a bottom emission type), but may be a light-emitting apparatus having a structure in which light is extracted toward the sealing substrate 1031 (a top emission type).

Structure Example 3 of Light-Emitting Apparatus

Figure 6:
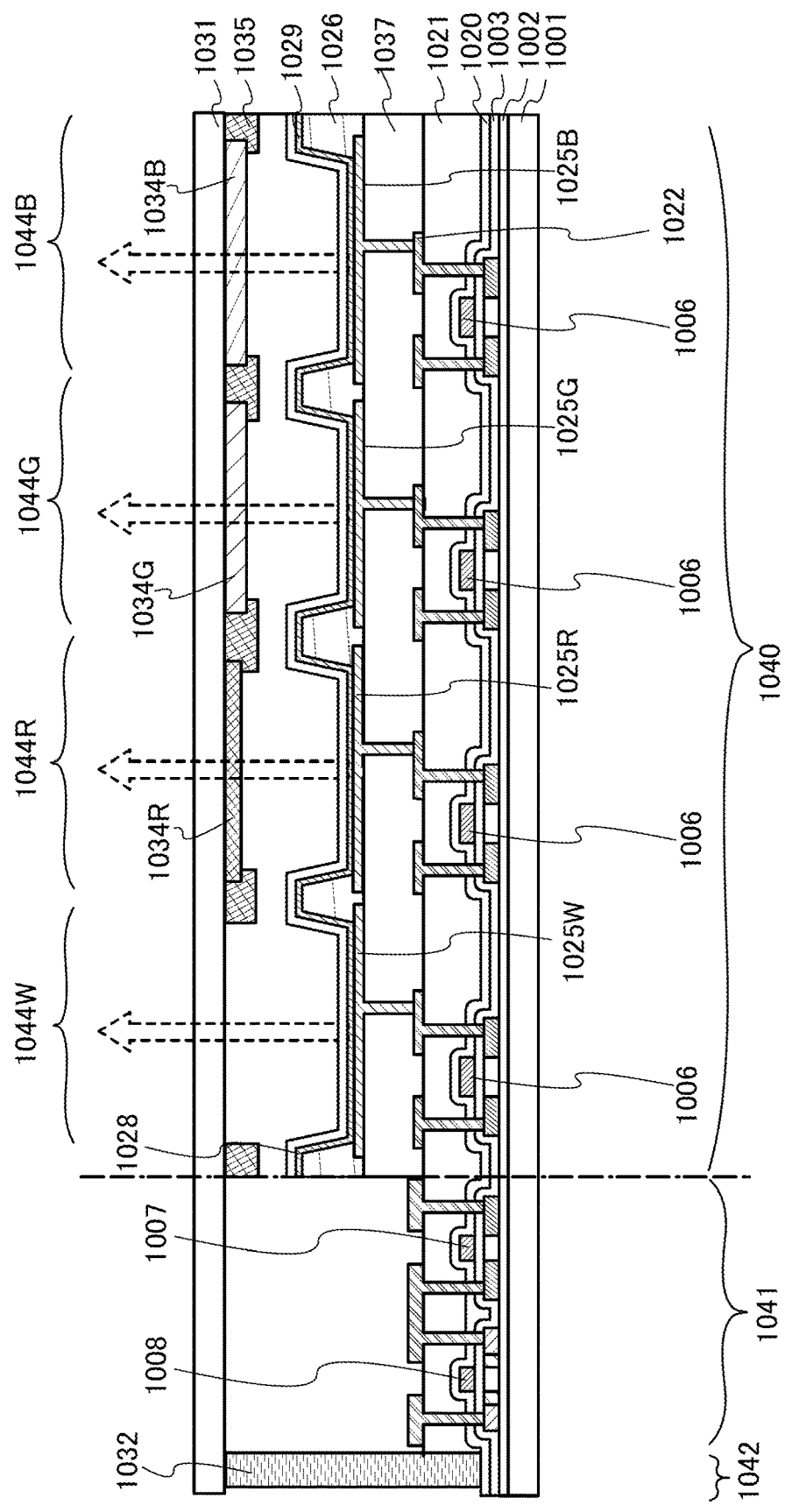
FIG. 6 A conceptual view of an active matrix light-emitting apparatus of one embodiment of the present invention.

FIG. 6 is a cross-sectional view of a top-emission light-emitting apparatus. In this case, a substrate that does not transmit light can be used as the substrate 1001. The process up to the formation of a connection electrode that connects the TFT and the anode of the light-emitting device is performed in a manner similar to that of a bottom-emission light-emitting apparatus. Then, a third interlayer insulating film 1037 is formed to cover an electrode 1022. This insulating film may have a planarization function. The third interlayer insulating film 1037 can be formed using a material similar to that of the second interlayer insulating film 1021 or using other various materials.

A first lower electrode 1025W, a lower electrode 1025R, a lower electrode 1025G, and a lower electrode 1025B of the light-emitting device are anodes here, but may be cathodes. Furthermore, in the case of the top-emission light-emitting apparatus as illustrated in FIG. 6, the lower electrode 1025W, the lower electrode 1025R, the lower electrode 1025G, and the lower electrode 1025B are preferably reflective electrodes. Note that the second electrode 1029 preferably has a function of reflecting light and a function of transmitting light. It is preferable that a microcavity structure be used between the second electrode 1029 and the lower electrode 1025W, the lower electrode 1025R, the lower electrode 1025G, and the lower electrode 1025B, in which case a function of amplifying light with a specific wavelength is provided. The EL layer 1028 has a structure similar to the structure described in Embodiment 3 and Embodiment 4, with which white light emission can be obtained.

In FIG. 5(A), FIG. 5(B), and FIG. 6, the structure of the EL layer for providing white light emission can be achieved, for example, by using a plurality of light-emitting layers or using a plurality of light-emitting units. Note that the structure for providing white light emission is not limited thereto.

In the case of a top emission structure as shown in FIG. 6, sealing can be performed with the sealing substrate 1031 where the coloring layers (the red coloring layer 1034R, the green coloring layer 1034G, and the blue coloring layer 1034B) are provided. The sealing substrate 1031 may be provided with a black layer (black matrix) 1030 positioned between pixels. The coloring layers (the red coloring layer 1034R, the green coloring layer 1034G, and the blue coloring layer 1034B) and the black layer (black matrix) may be covered with an overcoat layer. Note that a substrate having a light-transmitting property is used as the sealing substrate 1031.

Although an example in which full color display is performed using four colors of red, green, blue, and white is shown here, there is no particular limitation and full color display using three colors of red, green, and blue may be performed. Alternatively, full color display using four colors of red, green, blue, and yellow may be performed.

As described above, the light-emitting apparatus including the light-emitting device described in Embodiment 3 and Embodiment 4 can be obtained.

Note that this embodiment can be combined as appropriate with any of the other embodiments.

Embodiment 6

In this embodiment, electronic apparatuses of embodiments of the present invention will be described.

One embodiment of the present invention is a light-emitting device using organic EL, and thus, an electronic apparatus having a flat surface, high emission efficiency, and high reliability can be manufactured. In addition, an electronic apparatus having a curved surface, high emission efficiency, and high reliability can be manufactured according to one embodiment of the present invention. In addition, with the use of the organic compound of one embodiment of the present invention for the electronic apparatus, an electronic apparatus having high emission efficiency and high reliability can be manufactured.

Examples of electronic apparatuses include a television device, a desktop or laptop personal computer, a monitor of a computer and the like, a digital camera, a digital video camera, a digital photo frame, a mobile phone, a portable game machine, a portable information terminal, an audio reproducing device, and a large game machine such as a pachinko machine.

Figure 7A:
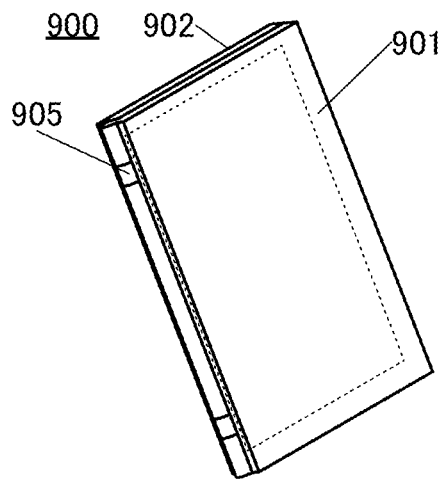
FIG. 7(A) to (D) Views illustrating electronic apparatuses of one embodiment of the present invention.
Figure 7B:
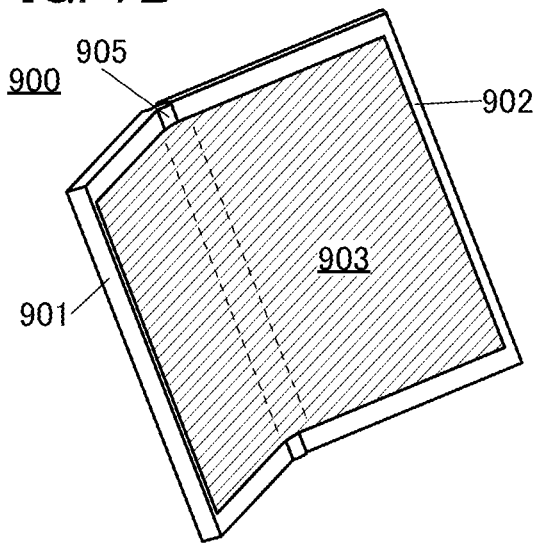

A portable information terminal 900 illustrating in FIGS. 7(A) and 7(B) includes a housing 901, a housing 902, a display portion 903, a hinge portion 905, and the like.

The housing 901 and the housing 902 are joined together by the hinge portion 905. The portable information terminal 900 can be opened as shown in FIG. 7(B) from a closed state (FIG. 7(A)). Thus, the portable information terminal 900 has high portability when carried and excellent visibility with its large display region when used.

In the portable information terminal 900, the flexible display portion 903 is provided across the housing 901 and the housing 902 that are joined together by the hinge portion 905.

The light-emitting apparatus manufactured using one embodiment of the present invention can be used for the display portion 903. Thus, a highly reliable portable information terminal can be manufactured.

The display portion 903 can display at least one of text information, a still image, a moving image, and the like. When text information is displayed on the display portion, the portable information terminal 900 can be used as an e-book reader.

When the portable information terminal 900 is opened, the display portion 903 is held in a state with a large radius of curvature. For example, the display portion 903 is held while including a curved portion with a radius of curvature of greater than or equal to 1 mm and less than or equal to 50 mm, preferably greater than or equal to 5 mm and less than or equal to 30 mm. Part of the display portion 903 can display an image while being curved since pixels are continuously arranged from the housing 901 to the housing 902.

The display portion 903 functions as a touch panel and can be controlled with a finger, a stylus, or the like.

The display portion 903 is preferably formed using one flexible display. Thus, a seamless continuous image can be displayed between the housing 901 and the housing 902. Note that each of the housing 901 and the housing 902 may be provided with a display.

The hinge portion 905 preferably includes a locking mechanism so that an angle formed between the housing 901 and the housing 902 does not become larger than a predetermined angle when the portable information terminal 900 is opened. For example, an angle at which they become locked (they are not opened any further) is preferably greater than or equal to 900 and less than 1800 and can be typically 90°, 120°, 135°, 150°, 175°, or the like. In this way, the convenience, safety, and reliability of the portable information terminal 900 can be improved.

When the hinge portion 905 includes a locking mechanism, excessive force is not applied to the display portion 903; thus, breakage of the display portion 903 can be prevented. Accordingly, a highly reliable portable information terminal can be achieved.

The housing 901 and the housing 902 may be provided with a power button, an operation button, an external connection port, a speaker, a microphone, or the like.

One of the housing 901 and the housing 902 is provided with a wireless communication module, and data can be transmitted and received through a computer network such as the Internet, a LAN (Local Area Network), or Wi-Fi (registered trademark).

Figure 7C:
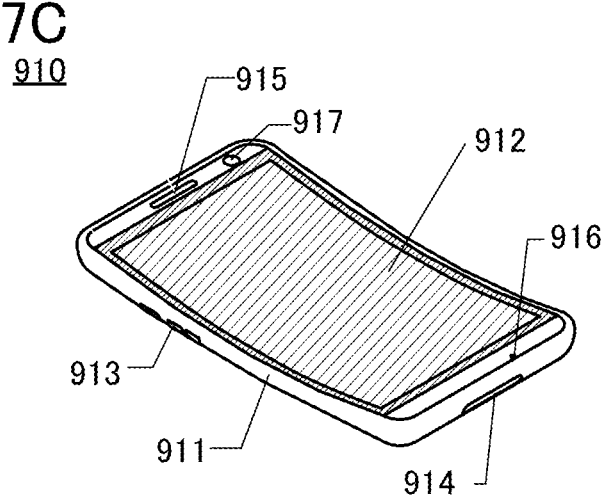

A portable information terminal 910 illustrated in FIG. 7(C) includes a housing 911, a display portion 912, an operation button 913, an external connection port 914, a speaker 915, a microphone 916, a camera 917, and the like.

The light-emitting apparatus manufactured using one embodiment of the present invention can be used for the display portion 912. Thus, a highly reliable portable information terminal can be manufactured.

The portable information terminal 910 includes a touch sensor in the display portion 912. A variety of operations such as making a call and inputting letters can be performed by touch on the display portion 912 with a finger, a stylus, or the like.

The operation of the operation button 913 can switch the power ON and OFF operations and types of images displayed on the display portion 912. For example, switching from a mail creation screen to a main menu screen can be performed.

When a sensing device such as a gyroscope sensor or an acceleration sensor is provided inside the portable information terminal 910, the direction of display on the screen of the display portion 912 can be automatically switched by determining the orientation of the portable information terminal 910 (whether it is placed horizontally or vertically). Furthermore, the direction of display on the screen can be switched by touch on the display portion 912, operation of the operation button 913, sound input using the microphone 916, or the like.

The portable information terminal 910 has, for example, one or more functions selected from a telephone set, a notebook, an information browsing system, and the like. Specifically, the portable information terminal can be used as a smartphone. The portable information terminal 910 is capable of executing a variety of applications such as mobile phone calls, e-mailing, text viewing and writing, music replay, video replay, Internet communication, and games, for example.

Figure 7D:
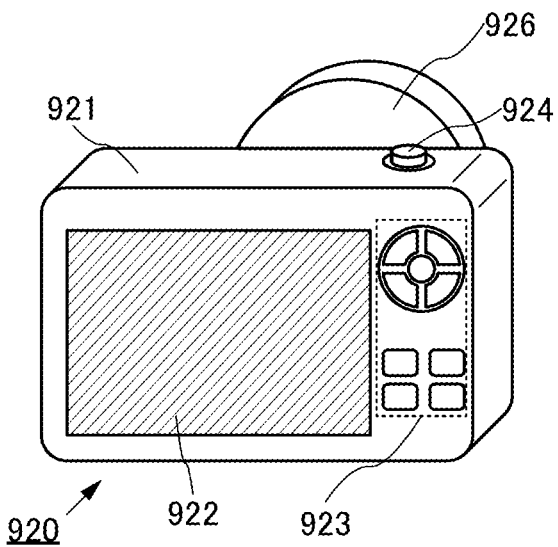

A camera 920 illustrated in FIG. 7(D) includes a housing 921, a display portion 922, operation buttons 923, a shutter button 924, and the like. Furthermore, a detachable lens 926 is attached to the camera 920.

The light-emitting apparatus manufactured using one embodiment of the present invention can be used for the display portion 922. Thus, a highly reliable camera can be fabricated.

Although the camera 920 here is configured such that the lens 926 is detachable from the housing 921 for replacement, the lens 926 may be integrated with the housing 921.

A still image or a moving image can be taken with the camera 920 at the press of the shutter button 924. In addition, the display portion 922 has a function of a touch panel, and images can also be taken by the touch on the display portion 922.

Note that a stroboscope, a viewfinder, or the like can be additionally attached to the camera 920. Alternatively, these may be incorporated into the housing 921.

Figure 8A:
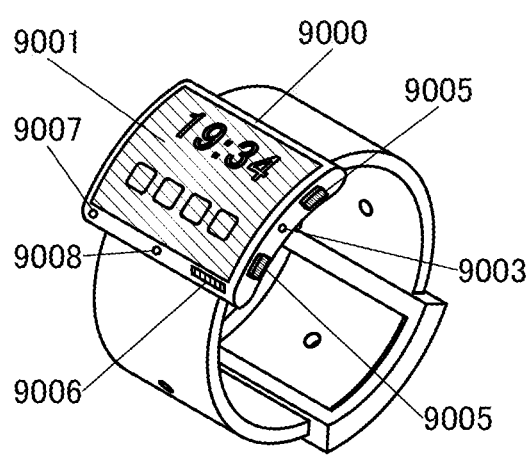
FIG. 8(A) to (E) Views illustrating electronic apparatuses of one embodiment of the present invention.
Figure 8B:
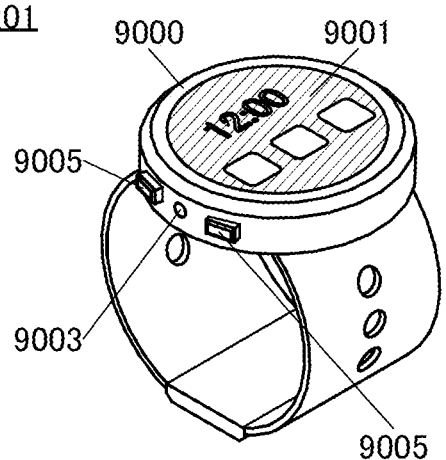

FIG. 8(A) is a perspective view of a wristwatch-type portable information terminal 9200, and FIG. 8(B) is a perspective view of a wristwatch-type portable information terminal 9201. The portable information terminal 9200 can include a speaker 9003, operation keys 9005 (including a power switch or an operation switch), a connection terminal 9006, a sensor 9007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 9008, and the like. The same applies to the portable information terminal 9201.

The portable information terminal 9200 illustrated in FIG. 8(A) is capable of executing a variety of applications such as mobile phone calls, e-mailing, text viewing and writing, music replay, Internet communication, and computer games, for example. The display surface of the display portion 9001 is curved, and display can be performed along the curved display surface. The portable information terminal 9200 can perform near field communication conformable to a communication standard. For example, hands-free calling can be achieved by mutual communication with a headset capable of wireless communication. The portable information terminal 9200 includes the connection terminal 9006, and data can be directly transmitted to and received from another information terminal via a connector. Power charging through the connection terminal 9006 is also possible. Note that the charging operation may be performed by wireless power feeding without through the connection terminal 9006.

Unlike in the portable information terminal illustrated in FIG. 8(A), the display surface of the display portion 9001 is not curved in the portable information terminal 9201 illustrated in FIG. 8(B). Furthermore, the external shape of the display portion of the portable information terminal 9201 is a non-rectangular shape (a circular shape in FIG. 8(B)).

Figure 8C:
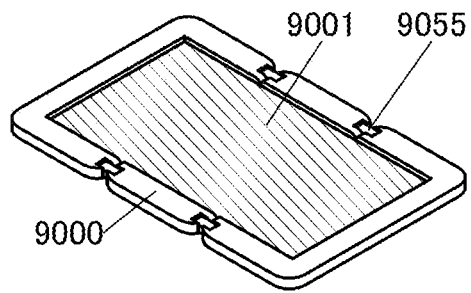
Figure 8D:
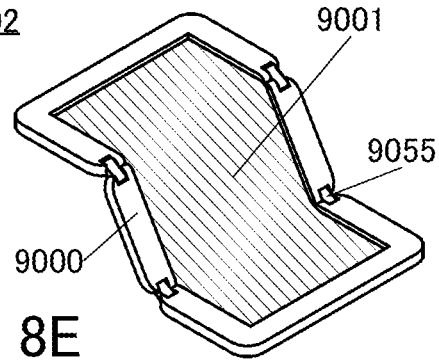
Figure 8E:
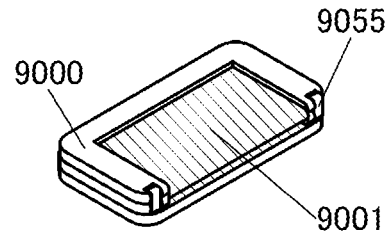

FIGS. 8(C) to 8(E) are perspective views illustrating a foldable portable information terminal 9202. Note that FIG. 8(C) is a perspective view of the portable information terminal 9202 that is opened; FIG. 8(D) is a perspective view of the portable information terminal 9202 that is being changed from one of an opened state and a folded state to the other; and FIG. 8(E) is a perspective view of the portable information terminal 9202 that is folded.

The portable information terminal 9202 is highly portable in the folded state, and is highly browsable with its seamless large display region in the opened state. The display portion 9001 of the portable information terminal 9202 is supported by three housings 9000 joined together by hinges 9055. By being bent between two housings 9000 with the hinges 9055, the portable information terminal 9202 can be reversibly changed in shape from the opened state to the folded state. The portable information terminal 9202 can be bent with a radius of curvature of greater than or equal to 1 mm and less than or equal to 150 mm, for example.

FIG. 9(A) is a schematic view showing an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. The cleaning robot 5100 also includes various sensors such as an infrared sensor, an ultrasonic sensor, an acceleration sensor, a piezo-electric sensor, an optical sensor, and a gyroscope sensor. In addition, the cleaning robot 5100 has a wireless communication means.

The cleaning robot 5100 is self-propelled, detects dust 5120, and can suck up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic apparatus 5140 such as a smartphone. The portable electronic apparatus 5140 can display images taken by the cameras 5102. Accordingly, an owner of the cleaning robot 5100 can monitor the room even from the outside. The display on the display 5101 can be checked by the portable electronic apparatus such as a smartphone.

The light-emitting apparatus of one embodiment of the present invention can be used for the display 5101.

A robot 2100 illustrated in FIG. 9(B) includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107.

The light-emitting apparatus of one embodiment of the present invention can be used for the display 2105.

FIG. 9(C) illustrates an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a second display portion 5002, a support 5012, and an earphone 5013.

The light-emitting apparatus of one embodiment of the present invention can be used for the display portion 5001 and the second display portion 5002.

Figure 10A:
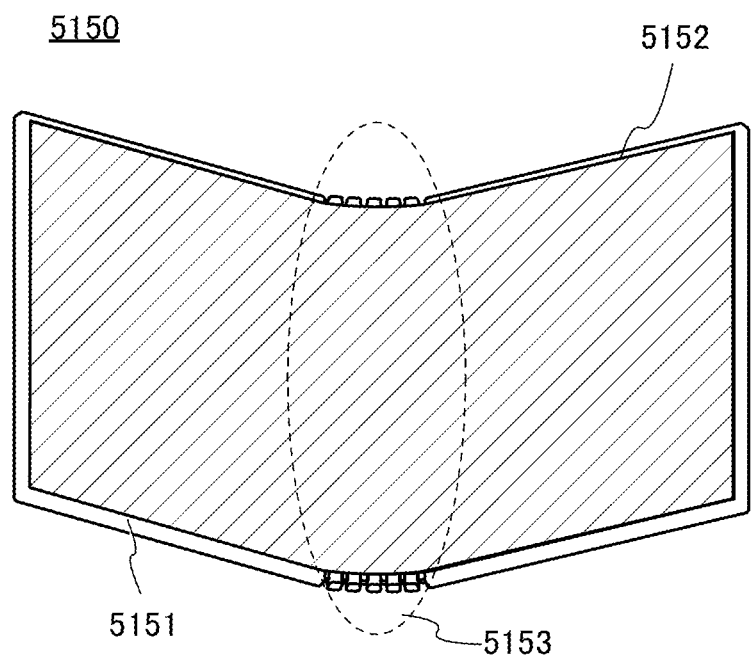
FIG. 10(A), (B) Views illustrating an electronic apparatus of one embodiment of the present invention.
Figure 10B:
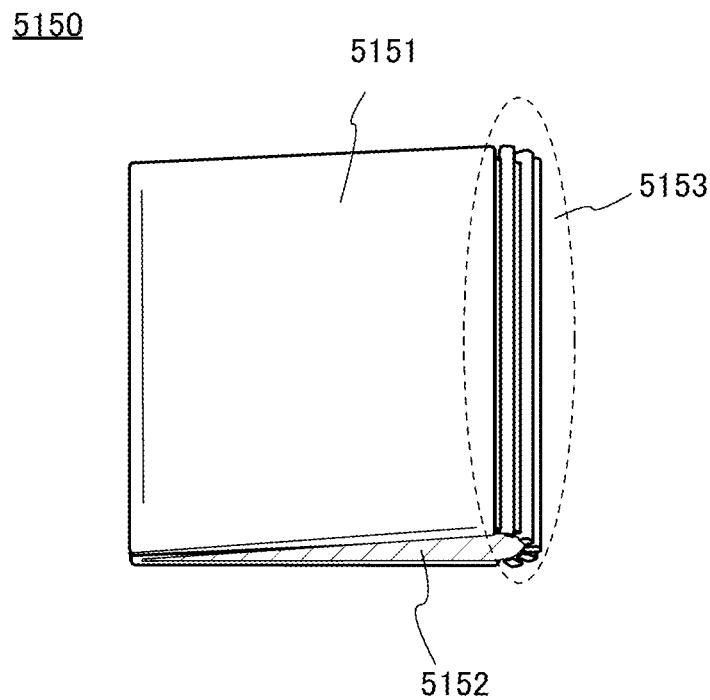

FIGS. 10(A) and 10(B) illustrate a foldable portable information terminal 5150. The foldable portable information terminal 5150 includes a housing 5151, a display region 5152, and a bend portion 5153. FIG. 10(A) illustrates the portable information terminal 5150 that is opened. FIG. 10(B) illustrates the portable information terminal 5150 that is folded. The portable information terminal 5150 is compact in size and has excellent portability when folded, despite its large display region 5152.

The display region 5152 can be folded in half with the bend portion 5153. The bend portion 5153 is formed of a stretchable member and a plurality of supporting members; when the display region is folded, the stretchable member stretches and the bend portion 5153 is folded with a radius of curvature of 2 mm or more, preferably 5 mm or more.

Note that the display region 5152 may be a touch panel (an input/output device) including a touch sensor (an input device). The light-emitting apparatus of one embodiment of the present invention can be used for the display region 5152.

This embodiment can be combined with the other embodiments as appropriate.

Embodiment 7

In this embodiment, examples in which the light-emitting device of one embodiment of the present invention is used for various lighting apparatuses will be described with reference to FIG. 11 and FIG. 12. With the use of the light-emitting device of one embodiment of the present invention, a lighting apparatus having high emission efficiency and high reliability can be manufactured.

Fabricating the light-emitting device of one embodiment of the present invention over a substrate having flexibility enables an electronic apparatus and a lighting apparatus that have a light-emitting region with a curved surface to be obtained.

Furthermore, a light-emitting apparatus in which the light-emitting device of one embodiment of the present invention is used can also be used for lighting for motor vehicles; for example, such lighting can be provided on a windshield, a ceiling, and the like.

Figure 11A:
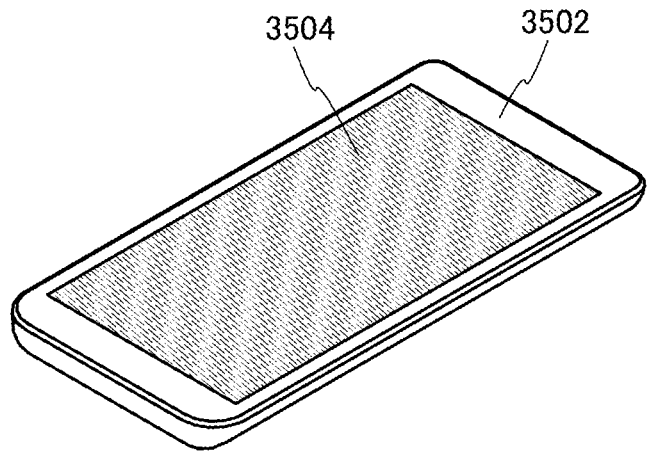
FIG. 11(A) to (C) Views illustrating lighting apparatuses of one embodiment of the present invention.
Figure 11B:
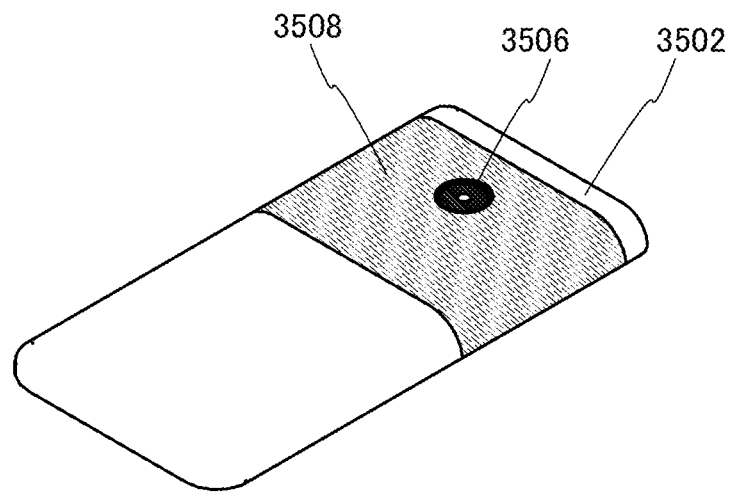

FIG. 11(A) is a perspective view of one surface of a multifunction terminal 3500, and FIG. 11(B) is a perspective view of the other surface of the multifunction terminal 3500. In a housing 3502 of the multifunction terminal 3500, a display portion 3504, a camera 3506, lighting 3508, and the like are incorporated. The light-emitting apparatus of one embodiment of the present invention can be used for the lighting 3508.

The lighting 3508 that includes the light-emitting apparatus of one embodiment of the present invention functions as a planar light source. Thus, unlike a point light source typified by an LED, the lighting 3508 can provide light emission with low directivity. When the lighting 3508 and the camera 3506 are used in combination, for example, an image can be taken by the camera 3506 with the lighting 3508 lighting or flashing. Since the lighting 3508 has a function of a planar light source, a photograph like one taken under natural light can be obtained.

Note that the multifunction terminal 3500 illustrated in FIGS. 11(A) and 11(B) can have a variety of functions, like the electronic apparatuses illustrated in FIG. 8(A) to FIG. 8(C).

The housing 3502 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. When a detection device including a sensor for detecting inclination, such as a gyroscope sensor or an acceleration sensor, is provided inside the multifunction terminal 3500, display on the screen of the display portion 3504 can be automatically changed by determining the orientation of the multifunction terminal 3500 (whether it is placed horizontally or vertically).

The display portion 3504 can function as an image sensor. For example, an image of a palm print, a fingerprint, or the like is taken when the display portion 3504 is touched with the palm or the finger, whereby personal authentication can be performed. Furthermore, with the use of a backlight that emits near-infrared light or a sensing light source that emits near-infrared light in the display portion 3504, an image of a finger vein, a palm vein, or the like can betaken. Note that the light-emitting apparatus of one embodiment of the present invention may be used for the display portion 3504.

Figure 11C:
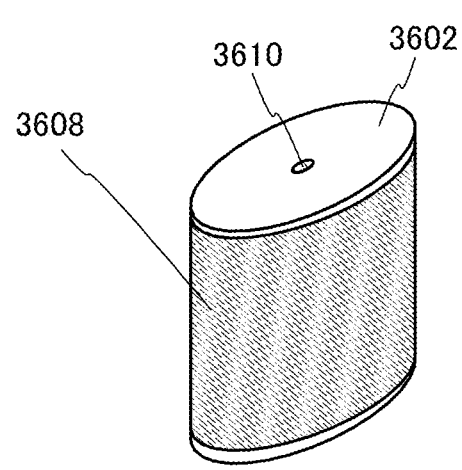

FIG. 11(C) is a perspective view of a security light 3600. The light 3600 includes lighting 3608 on the outside of a housing 3602, and a speaker 3610 and the like are incorporated in the housing 3602. The light-emitting device of one embodiment of the present invention can be used for the lighting 3608.

The light 3600 can emit light when the lighting 3608 is gripped or held, for example. An electronic circuit that can control the manner of light emission from the light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may also be incorporated.

The light 3600 can emit light in any directions; therefore, it is possible to intimidate a thug or the like with light, or light and sound. Moreover, the light 3600 may include a camera such as a digital still camera to have a photography function.

Figure 12:
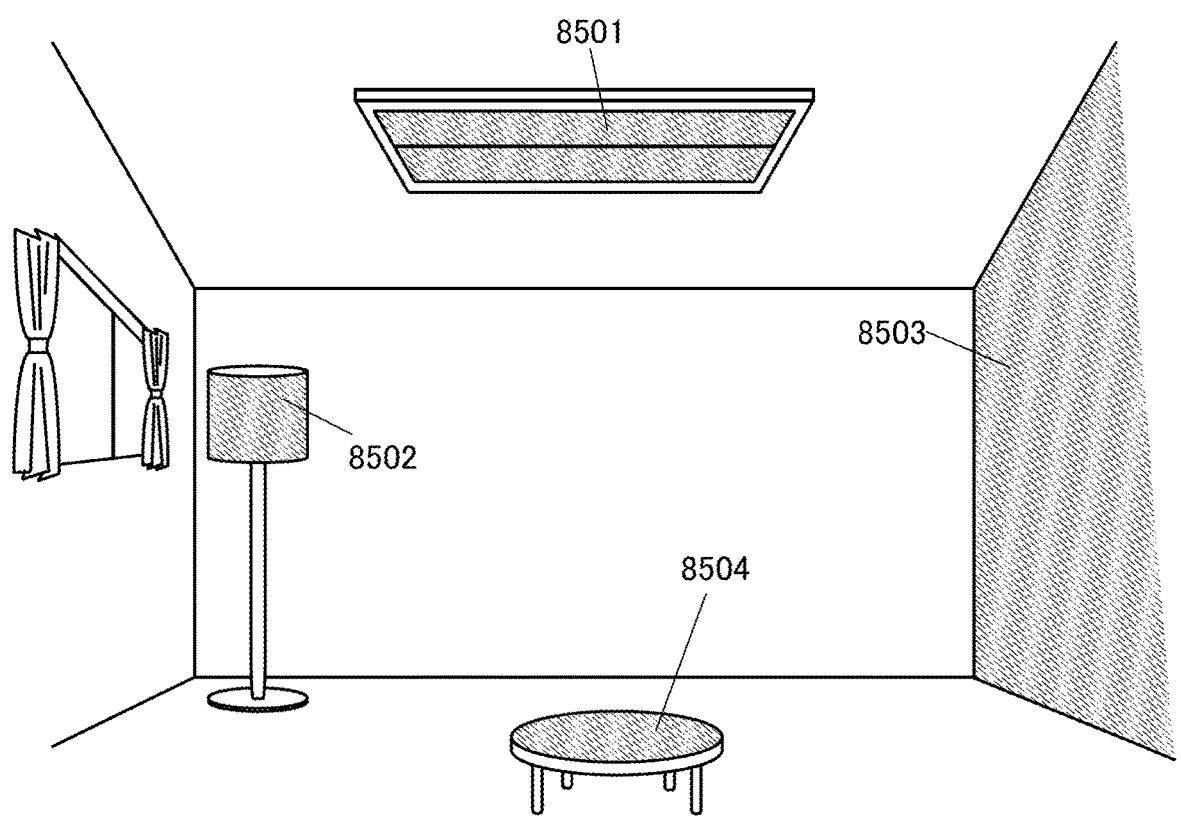
FIG. 12 A view illustrating lighting apparatuses of one embodiment of the present invention.

FIG. 12 illustrates an example in which the light-emitting device is used for an indoor lighting apparatus 8501. Since the light-emitting device can have a larger area, a lighting apparatus having a large area can also be formed. In addition, alighting apparatus 8502 in which a light-emitting region has a curved surface can be formed with the use of a housing with a curved surface. A light-emitting device described in this embodiment is in the form of a thin film, which allows the housing to be designed more freely. Thus, the lighting apparatus can be elaborately designed in a variety of ways. Furthermore, a wall of the room may be provided with a large-sized lighting apparatus 8503. The lighting apparatuses 8501, 8502, and 8503 may be provided with a touch sensor with which power is turned on or off.

When the light-emitting device is used on the surface side of a table, a lighting apparatus 8504 that has a function of a table can be obtained. When the light-emitting device is used as part of other furniture, a lighting apparatus having a function of the furniture can be obtained.

As described above, lighting apparatuses and electronic apparatuses can be obtained by application of the light-emitting apparatus of one embodiment of the present invention. Note that the light-emitting apparatus can be used for electronic apparatuses in a variety of fields without being limited to the lighting apparatuses and the electronic apparatuses described in this embodiment.

The structure described above in this embodiment can be used in combination as appropriate with any of the structures described in the other embodiments.

Example 1

This example will describe a method for synthesizing 4-(9,10-diphenyl-2-anthryl)benzo[a]anthracene (abbreviation: 2aBAPA) (Structural Formula (100)) that is one embodiment of the present invention and is one of the compounds represented by General Formula (G1), and the properties of the compound.

Step 1: Synthesis of 2aBAPA

Into a 100 mL three-necked flask were put 1.1 g (2.4 mmol) of 2-iodo-9,10-diphenylanthracene, 0.80 g (2.9 mmol) of 4-benzo[a]anthracene boronic acid, 0.17 g (0.55 mmol) of tris(2-methylphenyl)phosphine, and 0.71 g (5.1 mmol) of potassium carbonate, and the air in the flask was replaced with nitrogen. To the mixture were added 24 mL of toluene, 3 mL of ethanol, and 3 mL of water, and the mixture was degassed by being stirred under reduced pressure. To this mixture was added 37 mg (0.17 mmol) of palladium(II) acetate, and the mixture was stirred at 80° C. under a nitrogen stream for 11 hours. After the stirring, the mixture was cooled down to room temperature, water was added to the mixture, and an aqueous layer was subjected to extraction with toluene. The obtained organic layer was washed with saturated saline, and then the organic layer was dried with magnesium sulfate. The mixture was subjected to gravity filtration and the filtrate was concentrated, whereby a solid was obtained. A toluene solution of the obtained solid was subjected to suction filtration through Celite (Wako Pure Chemical Industries, Ltd., Catalog No. 537-02305), Florisil (Wako Pure Chemical Industries, Ltd., Catalog No. 066-05265), and aluminum oxide, and the filtrate was condensed to give a solid. The obtained solid was purified by silica gel column chromatography (toluene:hexane=1:6) and then purified by high-performance liquid chromatography (developing solvent: chloroform). The obtained solid was washed with methanol, so that 1.0 g of a target pale yellow powder was obtained at a yield of 74%. The synthesis scheme is shown in (A-1) below.

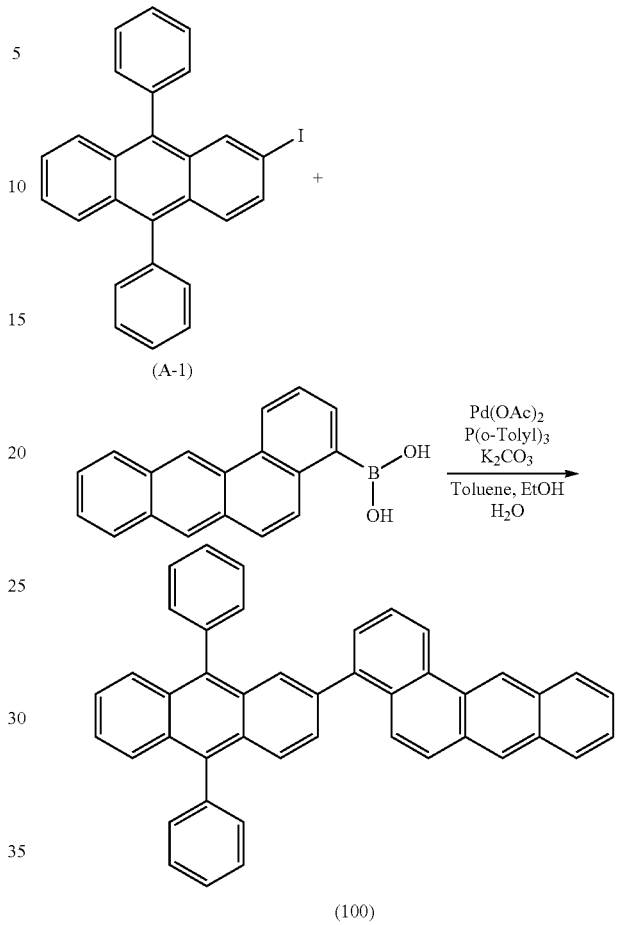

[Chemical Formula 27]

By a train sublimation method, 1.5 g of the obtained solid was sublimated and purified. The sublimation purification was performed by heating at 270° C. for 16 hours under conditions where the pressure was 4.0 Pa and the flow rate of argon was 5 mL/min. After the sublimation purification, 0.90 g of a yellow powder of 4-(9,10-diphenyl-2-anthryl)benzo[a]anthracene was obtained at a collection rate of 91%.

Analysis data of the obtained solid by nuclear magnetic resonance spectroscopy (H NMR) are shown below.

$^1$H NMR (CDCl$_3$, 300 MHz): δ=7.33-7.78 (m, 21H), 7.82-7.86 (m, 2H), 8.01-8.04 (m, 1H), 8.11-8.15 (m, 1H), 8.33 (s, 1H), 8.85 (d, J=7.8 Hz, 1H), 9.20 (s, 1H).

Figure 13A:
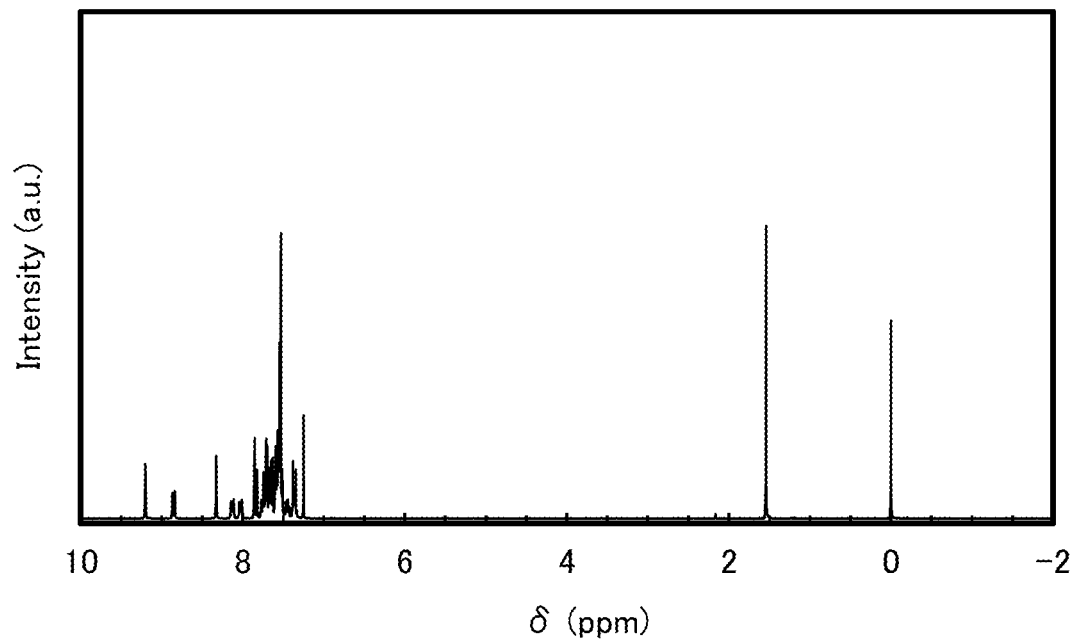
FIG. 13(A), (B) Diagrams showing an NMR chart of a compound in Example.
Figure 13B:
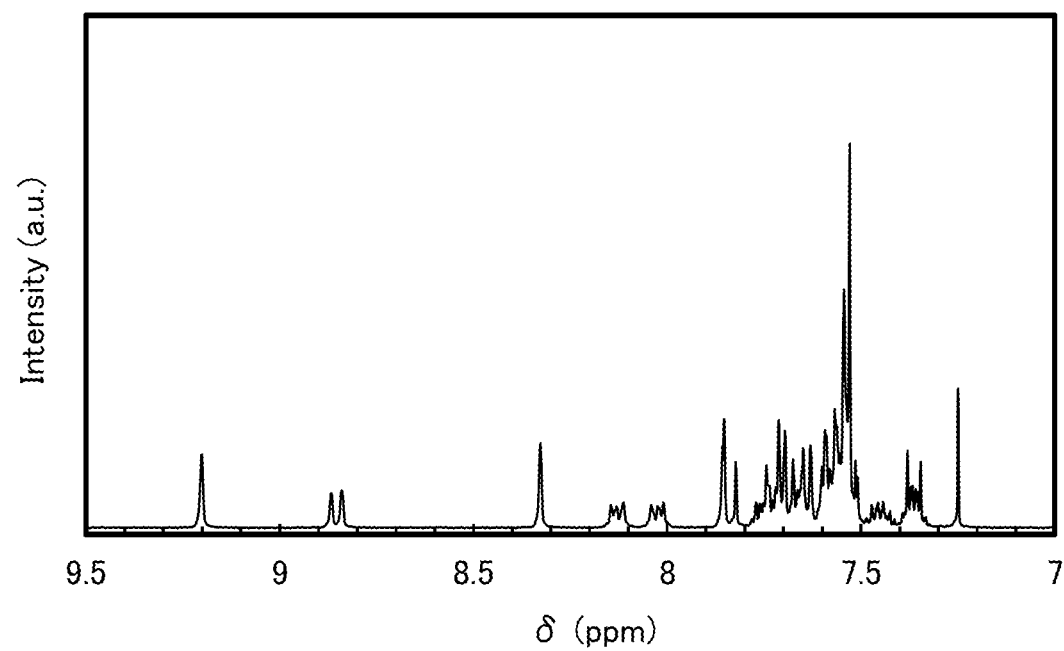

FIG. 13(A) and FIG. 13(B) show $^1$H NMR charts of the obtained solid. Note that FIG. 13(B) is an enlarged diagram of the range of 7.0 ppm to 9.5 ppm of FIG. 13(A). The measurement results indicate that 2aBAPA, which was the target substance, was obtained.

<Properties of 2aBAPA>

Figure 14:
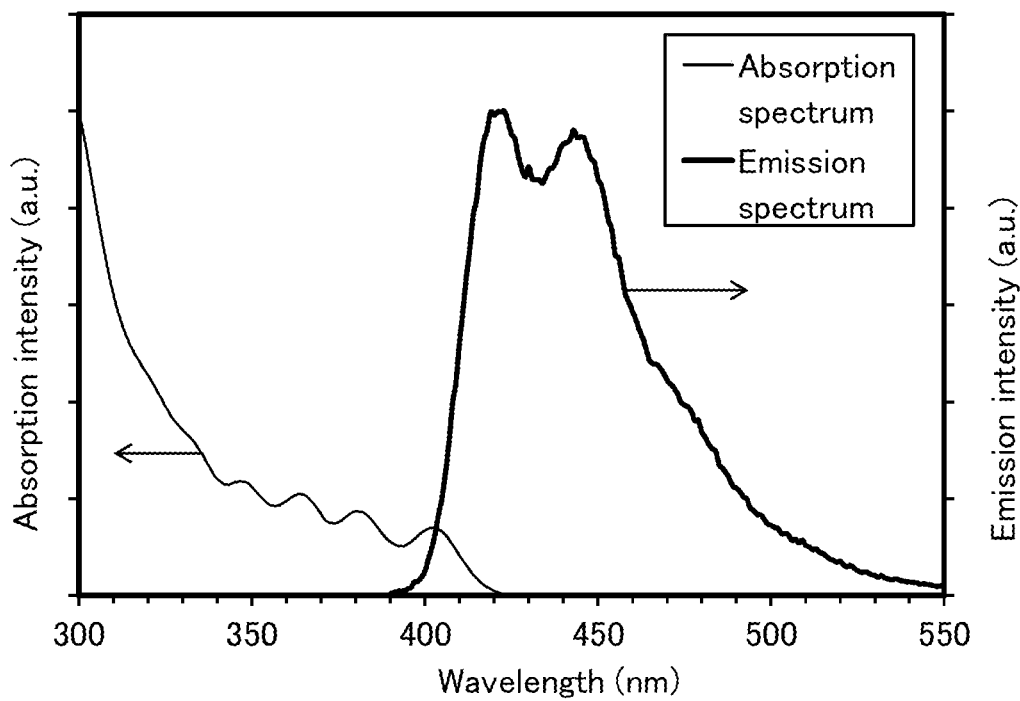
FIG. 14 A diagram showing an absorption spectrum and an emission spectrum of a compound in Example.
Figure 15:
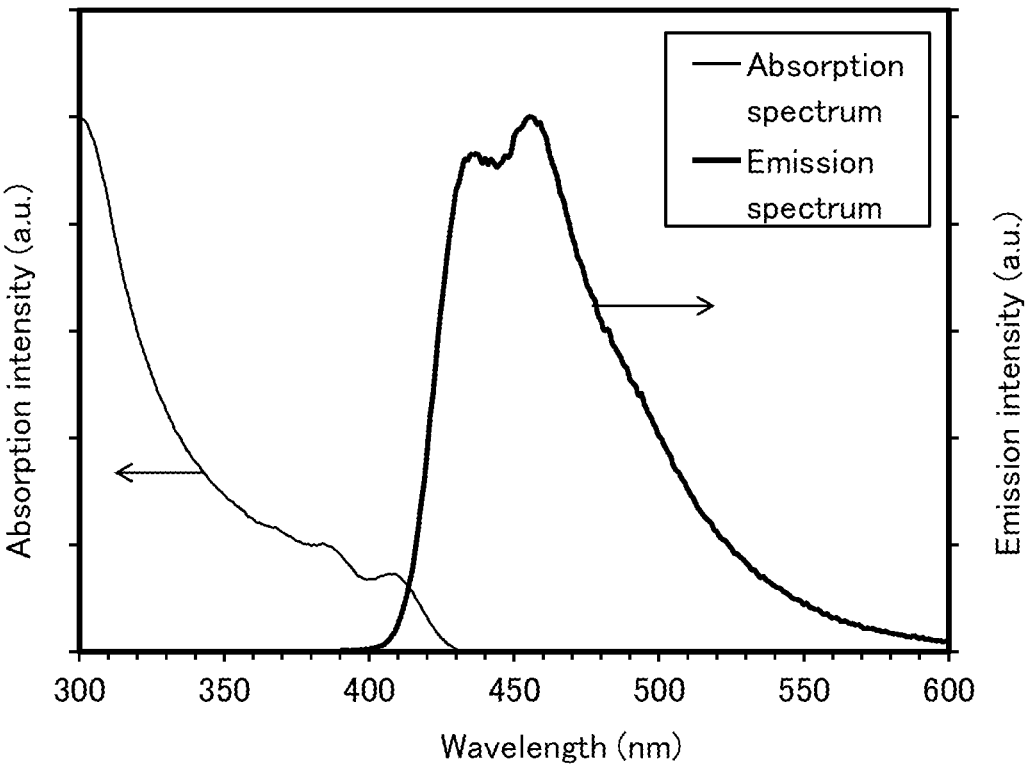
FIG. 15 A diagram showing an absorption spectrum and an emission spectrum of a compound in Example.

FIG. 14 shows the absorption spectrum and the emission spectrum of 2aBAPA in a toluene solution. FIG. 15 shows the absorption spectrum and the emission spectrum of a thin film. The solid thin film was formed over a quartz substrate by a vacuum evaporation method. The absorption spectrum in the toluene solution was measured using an ultraviolet-visible spectrophotometer (V550, produced by JASCO Corporation). The absorption spectrum of the 2aBAPA solution shown in FIG. 14 was obtained by subtracting the absorption spectrum of toluene measured when only toluene was put in a quartz cell from the absorption spectrum of 2aBAPA in the toluene solution. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.).

From FIG. 14, the toluene solution of 2aBAPA was observed to have absorption peaks at around 402 nm, 381 nm, 364 nm, and 347 nm; also from FIG. 14, the emission wavelength peaks were at 421 and 443 nm (excitation wavelength: 381 nm). From FIG. 15, the thin film of 2aBAPA was observed to have absorption peaks at around 408 nm, 384 nm, and 368 nm; also from FIG. 15, the emission wavelength peaks were observed at around 437 and 456 nm (excitation wavelength: 380 nm). 2aBAPA was confirmed to emit blue light. The compound of one embodiment of the present invention can be used as a host for a light-emitting substance or a substance that exhibits fluorescence in the visible region.

Furthermore, the thin film of 2aBAPA was found to have a good film quality with little change in shape, hardly being aggregated even under air.

The HOMO level and the LUMO level of 2aBAPA were calculated on the basis of a cyclic voltammetry (CV) measurement. The calculation method is shown below.

An electrochemical analyzer (model No. ALS model 600A or 600C, manufactured by BAS Inc.) was used as a measurement apparatus. To prepare a solution for the CV measurement, dehydrated dimethylformamide (DMF) (produced by Sigma-Aldrich Inc., 99.8%, catalog No. 22705-6) was used as a solvent, tetra-n-butylammonium perchlorate (n-Bu$_4$NClO$_4$) (produced by Tokyo Chemical Industry Co., Ltd., catalog No. T0836) as a supporting electrolyte was dissolved at a concentration of 100 mmol/L, and the object to be measured was also dissolved at a concentration of 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag+ electrode (RE7 reference electrode for non-aqueous solvent, manufactured by BAS Inc.) was used as a reference electrode. Note that the measurement was performed at room temperature (20 to 25° C.). The scan speed in the CV measurement was fixed to 0.1 V/sec, and an oxidation potential Ea [V] and a reduction potential Ec [V] with respect to the reference electrode were measured. Ea was an intermediate potential of an oxidation-reduction wave, and Ec was an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]−4.94−Ea and LUMO level [eV]−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the HOMO level was found to be −5.79 eV in the measurement of the oxidation potential Ea [V] of 2aBAPA. In contrast, the LUMO level was found to be −2.78 eV in the measurement of the reduction potential Ec [V].

Example 2

This example will describe a method for synthesizing 7-(9,10-diphenyl-2-anthryl)benzo[a]anthracene (abbreviation: 2aBAPA-02) (abbreviation: 2aBAPA-02) (Structural Formula (101)) that is one embodiment of the present invention and is one of the compounds represented by General Formula (G1), and the properties of the compound.

Step 1: Synthesis of 2aBAPA-02

Into a 200 mL three-necked flask were put 2.3 g (5.0 mmol) of 2-iodo-9,10-diphenylanthracene, 1.4 g (5.0 mmol) of benzo[a]anthracene-7-boronic acid, 0.15 g (0.50 mmol) of tri(ortho-tolyl)phosphine, and 1.4 g (10 mmol) of potassium carbonate, and the air in the flask was replaced with nitrogen. To the mixture were added 20 mL of toluene, 5.0 mL of ethanol, and 5.0 mL of water, and the mixture was degassed by being stirred under reduced pressure. To this mixture was added 56 mg (0.25 mmol) of palladium(II) acetate, and the mixture was stirred at 80° C. under a nitrogen stream for 8 hours. After the stirring, the aqueous layer of this mixture was subjected to extraction with toluene, the extracted solution and the organic layer were combined and washed with saturated saline, and magnesium sulfate was added for drying. The oily substance obtained by concentrating a filtrate obtained by gravity filtration of this mixture was purified by silica gel column chromatography (hexane:toluene=4:1), and then was recrystallized with toluene, whereby 2.3 g of a target yellow solid was obtained at a yield of 83%. The synthesis scheme is shown in Formula (A-2) below.

[Chemical Formula 28]

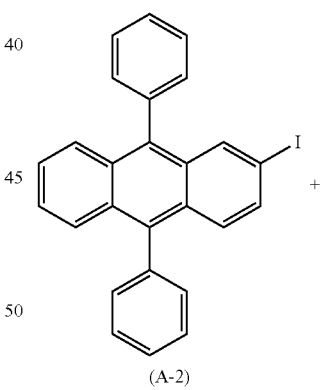

(A-2)

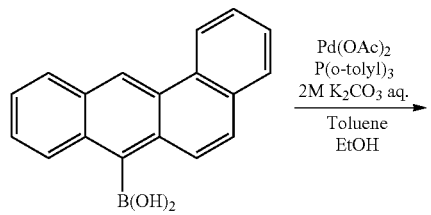

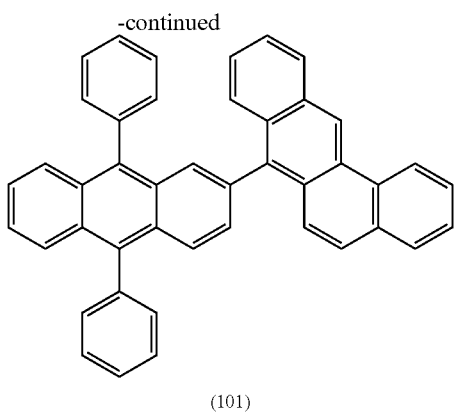

(101)

By the train sublimation method, 2.3 g of the obtained yellow solid was sublimated and purified. The sublimation purification was performed by heating at 260° C. under conditions where the pressure was 4.0 Pa and the flow rate of argon was 5.0 mL/min. After the sublimation purification, 2.1 g of a pale yellow solid was obtained at a collection rate of 93%.

Analysis data of the obtained solid by nuclear magnetic resonance spectroscopy (H NMR) are shown below.

$^1$H NMR (DMSO-$d_6$, 300 MHz): δ=7.37-7.75 (m, 23H), 7.86 (d, J=9.3 Hz, 2H), 8.27 (d, J=8.4 Hz, 1H), 8.99 (d, J=8.1 Hz, 1H), 9.45 (s, 1H).

Figure 16A:
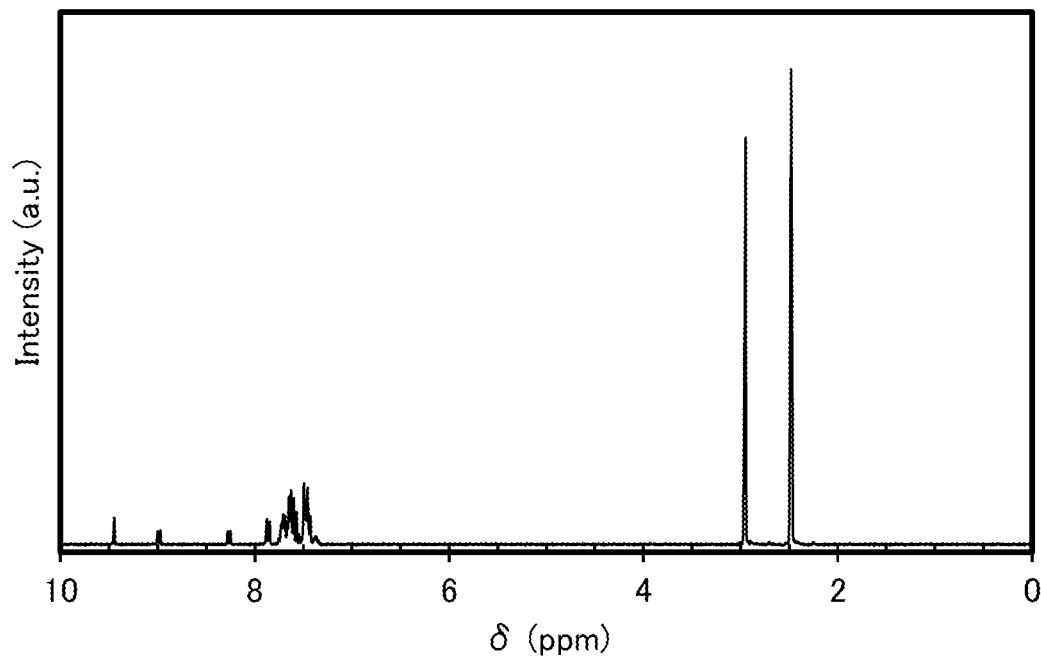
FIG. 16(A), (B) Diagrams showing an NMR chart of a compound in Example.
Figure 16B:
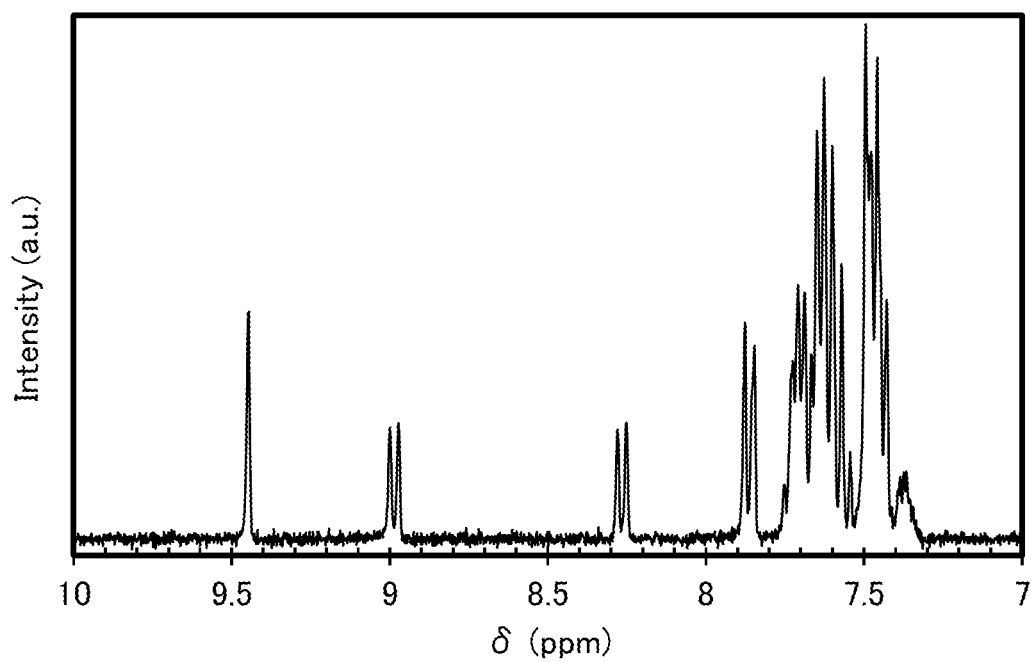

FIG. 16(A) and FIG. 16(B) show $^1$H NMR charts of the obtained solid. Note that FIG. 16(B) is an enlarged diagram of the range of 7.0 ppm to 10.0 ppm of FIG. 16(A). The measurement results indicate that 2aBAPA-02, which was the target substance, was obtained.

<Properties of 2aBAPA-02>

Figure 17:
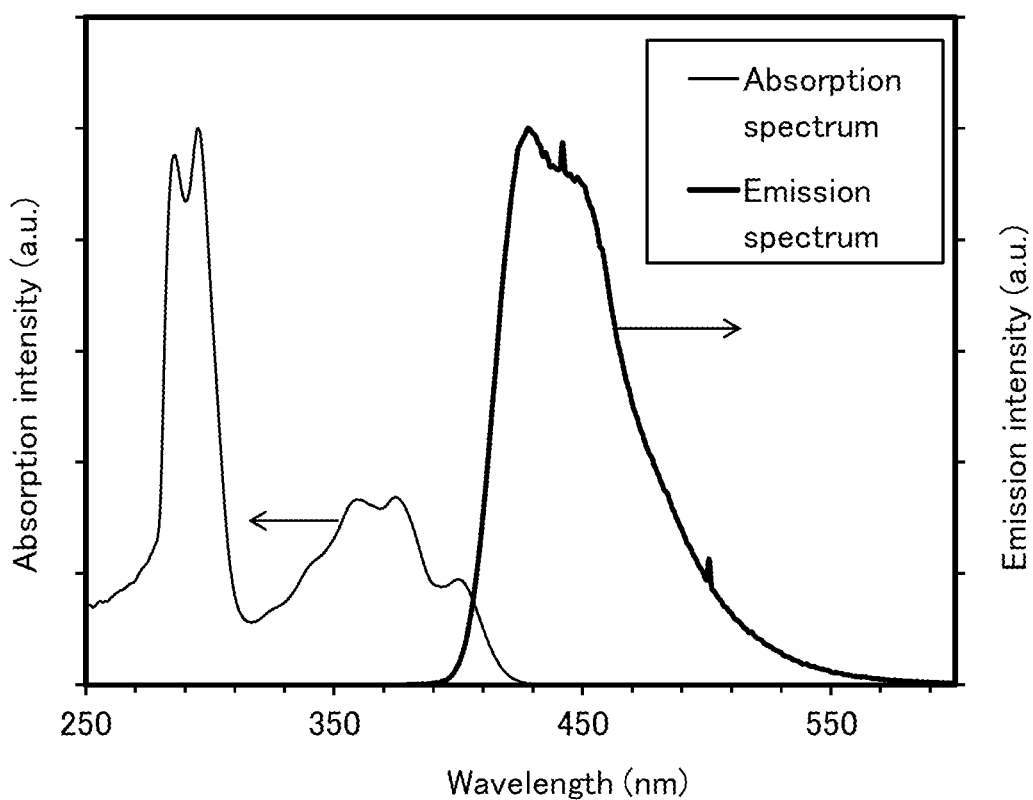
FIG. 17 A diagram showing an absorption spectrum and an emission spectrum of a compound in Example.
Figure 18:
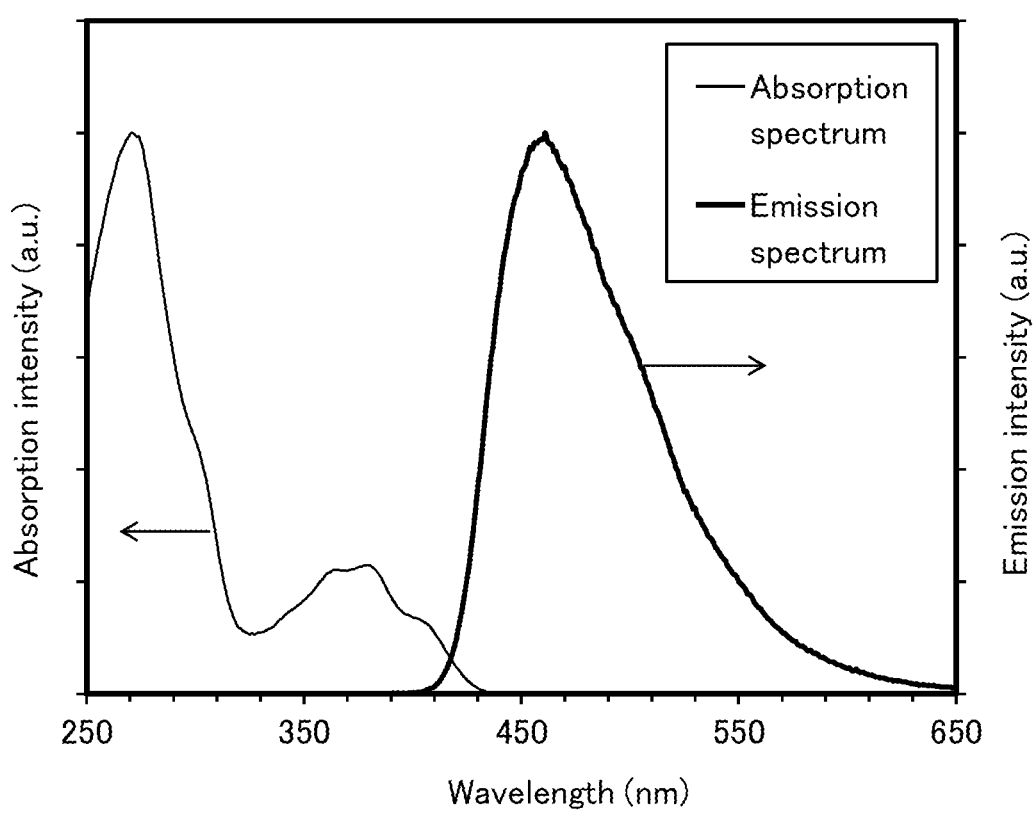
FIG. 18 A diagram showing an absorption spectrum and an emission spectrum of a compound in Example.

Next, FIG. 17 shows the measurement results of the absorption spectrum and the emission spectrum of 2aBAPA-02 in a toluene solution. FIG. 18 shows the absorption spectrum and the emission spectrum of a thin film. The measurement was performed in a manner similar to that in Example 1.

From the results in FIG. 17, for the toluene solution of 2aBAPA-02, the absorption peaks were observed at around 400 nm, 375 nm, 360 nm, and 340 nm, and the emission wavelength peak was observed at 429 nm (excitation wavelength: 375 nm). From the results in FIG. 18, for the solid thin film of 2aBAPA-02, the absorption peaks were observed at around 403 nm, 379 nm, 363 nm, 344 nm, and 302 nm, and the emission wavelength peak was observed at around 461 nm (excitation wavelength: 380 nm).

Note that 2aBAPA-02 was confirmed to emit blue light. The organic compound of one embodiment of the present invention, 2aBAPA-02, can be used as a host for a light-emitting substance or a substance that exhibits fluorescence in the visible region. Furthermore, the thin film of 2aBAPA-02 was found to have a good film quality with little change in shape, hardly being aggregated even under air.

Next, CV measurement was performed on 2aBAPA-02. The measurement was performed in a manner similar to that in Example 1.

As a result, the HOMO level was found to be −5.80 eV in the measurement of the oxidation potential Ea [V] of 2aBAPA-02. In contrast, the LUMO level was found to be −2.78 eV in the measurement of the reduction potential Ec [V]. In addition, when the oxidation-reduction wave was repeatedly measured and the waveform of the first cycle was compared with that in the hundredth cycle, 82% of the peak intensity was maintained in the Ea measurement, and 82% of the peak intensity was maintained in the Ec measurement; thus, resistance to oxidation and reduction of 2aBAPA-02 was found to be extremely high.

Example 3

This example will describe a method for synthesizing 4-[9,10-di(1-naphthyl)-2-anthryl]benzo[a]anthracene (abbreviation: 2aBAαDNA) (Structural Formula (102)) that is one embodiment of the present invention and is one of the compounds represented by General Formula (G1), and the properties of the compound.

Step 1: Synthesis of 2aBAαDNA

Into a 200 mL three-necked flask were put 1.1 g (2.2 mmol) of 2-bromo-9,10-di(1-naphthyl)anthracene, 0.82 g (5.0 mmol) of benzo[a]anthracene-4-boronic acid, 67 mg (0.22 mmol) of tri(ortho-tolyl)phosphine, and 0.61 g (4.4 mmol) of potassium carbonate, and the air in the flask was replaced with nitrogen. To the mixture were added 9.0 mL of toluene, 2.0 mL of ethanol, and 2.0 mL of water, and the mixture was degassed by being stirred under reduced pressure. To this mixture was added 25 mg (0.11 mmol) of palladium(II) acetate, and the mixture was stirred at 80° C. under a nitrogen stream for 4 hours. After the stirring, the solid obtained by performing suction filtration on this mixture was purified by silica gel column chromatography (hexane:toluene=4:1), and then was recrystallized with toluene, whereby 1.0 g of a target pale yellow solid was obtained at a yield of 71%. The synthesis scheme is shown in Formula (A-3) below.

[Chemical Formula 29]

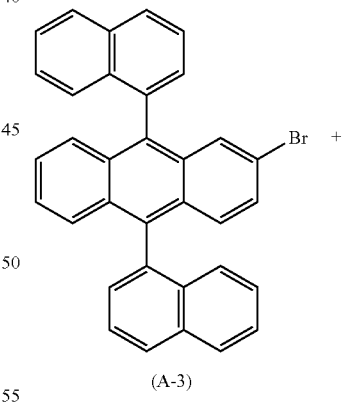

(A-3)

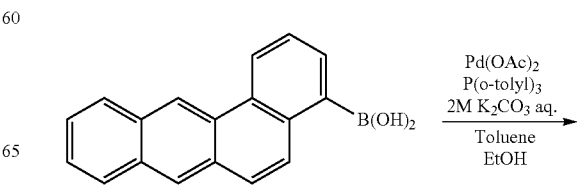

-continued

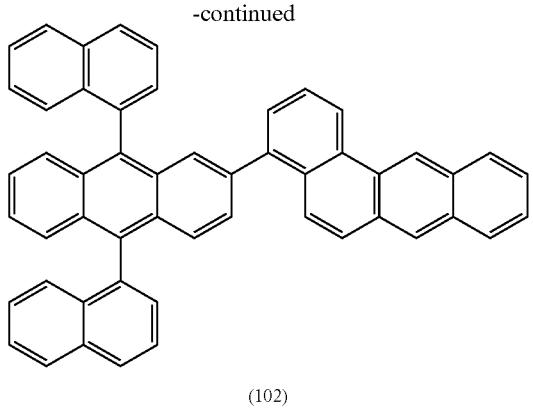

(102)

By the train sublimation method, 0.95 g of the obtained pale yellow solid was sublimated and purified. The sublimation purification was performed by heating at 290° C. under conditions where the pressure was 4.0 Pa and the flow rate of argon was 5.0 mL/min. After the sublimation purification, 0.89 g of a yellow solid was obtained at a collection rate of 94%.

Analysis data of the obtained solid by nuclear magnetic resonance spectroscopy ($^1$H NMR) are shown below.

$^1$H NMR (DMSO-$d_6$, 300 MHz): δ=7.16-7.88 (m, 23H), 8.02-8.09 (m, 3H), 8.13-8.23 (m, 3H), 8.40 (s, 1H), 8.89 (d, J=8.1 Hz, 1H), 9.33 (s, 1H).

Figure 19A:
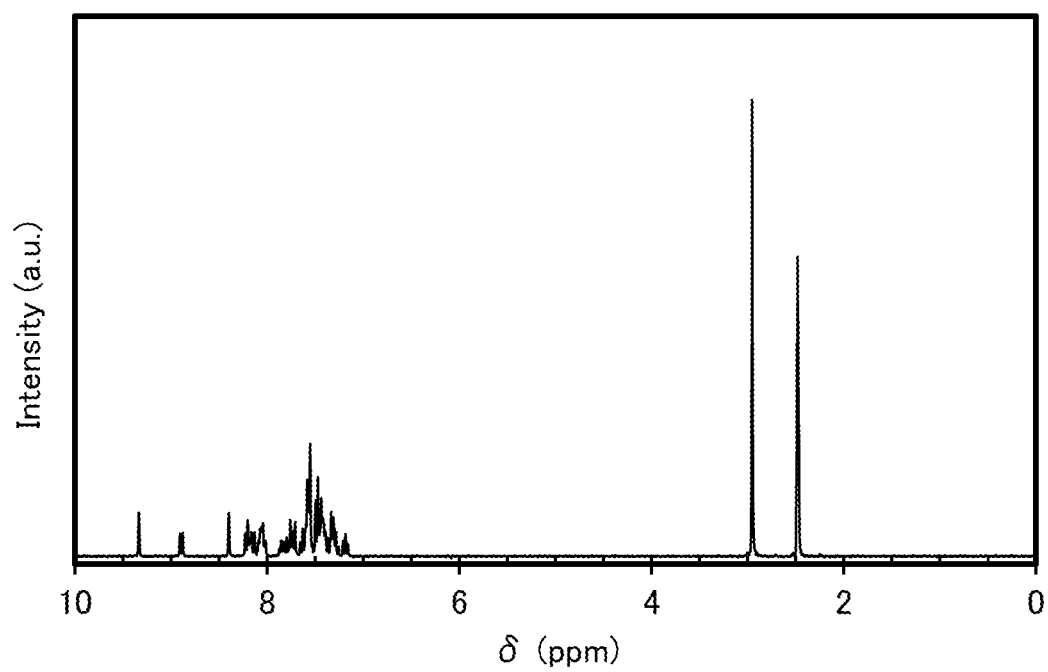
FIG. 19(A), (B) Diagrams showing an NMR chart of a compound in Example.
Figure 19B:
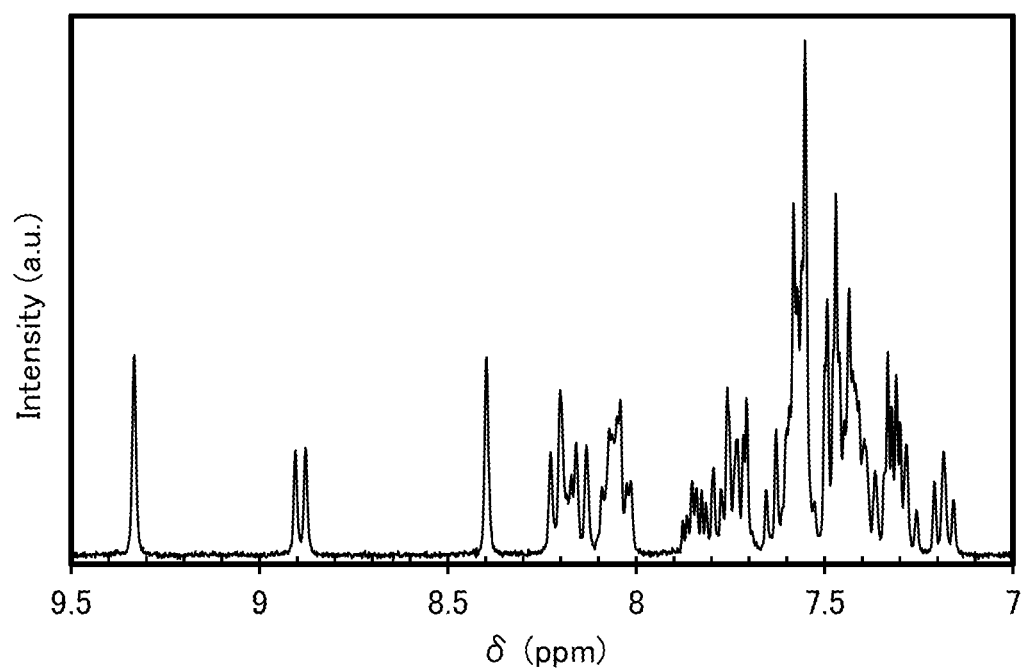

FIG. 19(A) and FIG. 19(B) show $^1$H NMR charts of the obtained solid. Note that FIG. 19(B) is an enlarged diagram of the range of 7.0 ppm to 9.5 ppm of FIG. 19(A). The measurement results indicate that 2aBAαDNA, which was the target substance, was obtained.

<Properties of 2aBAαDNA>

Figure 20:
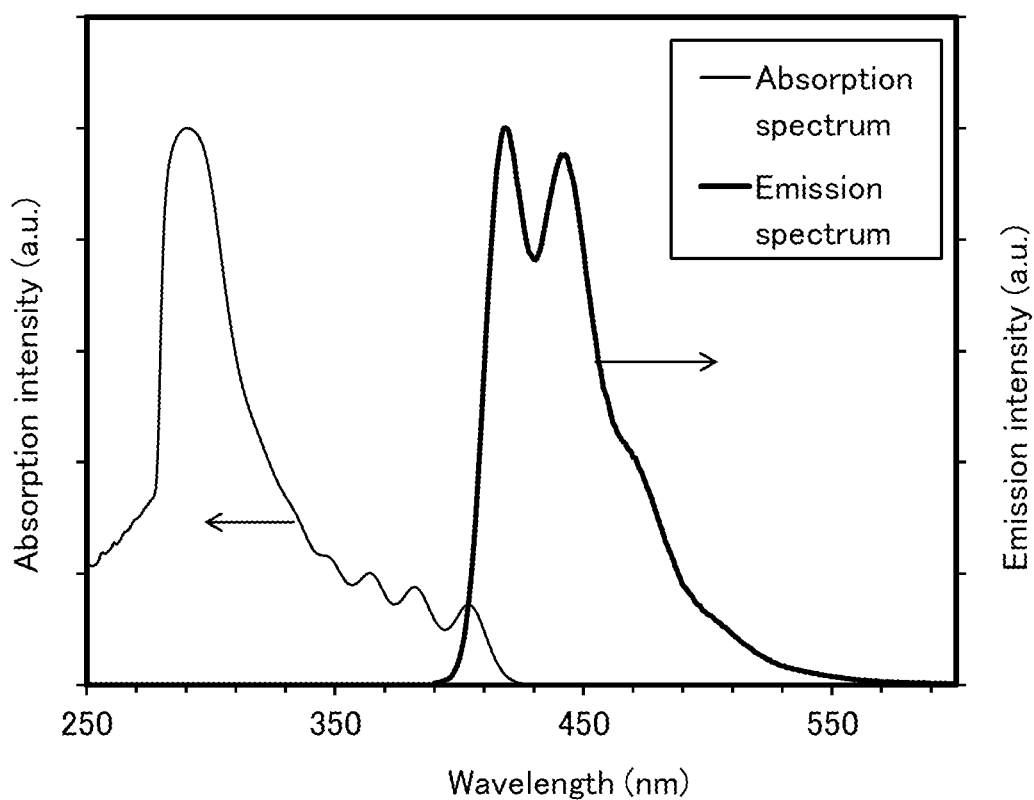
FIG. 20 A diagram showing an absorption spectrum and an emission spectrum of a compound in Example.
Figure 21:
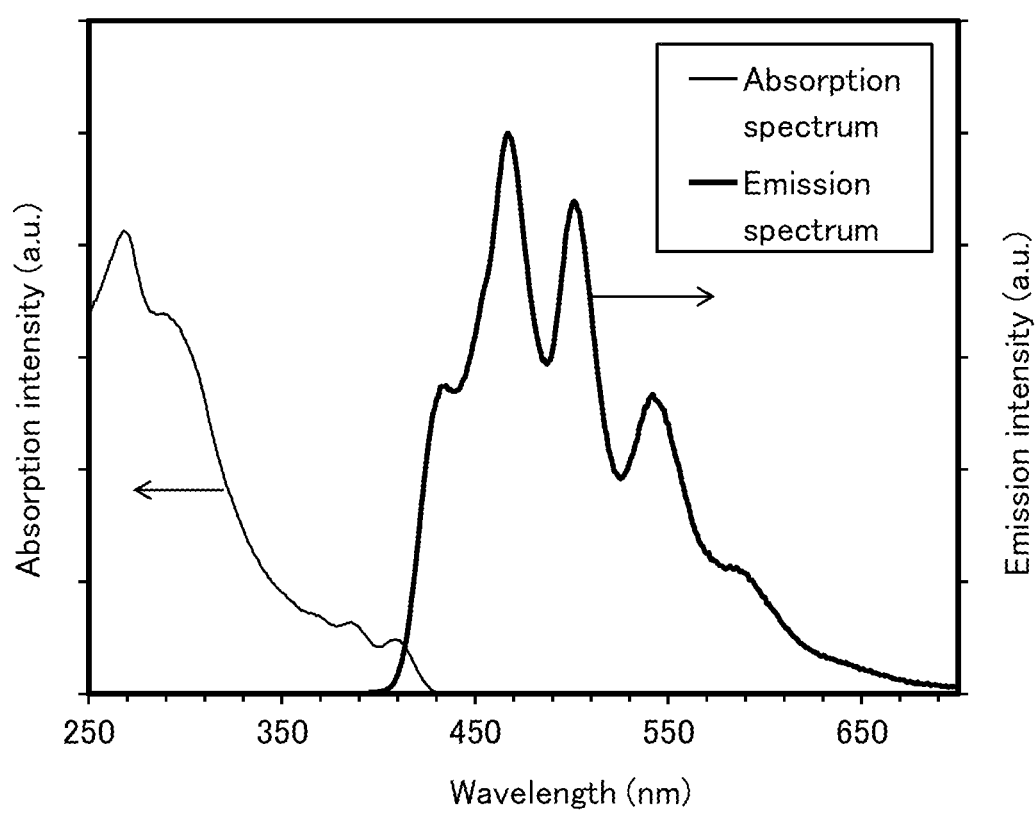
FIG. 21 A diagram showing an absorption spectrum and an emission spectrum of a compound in Example.

Next, FIG. 20 shows the measurement results of the absorption spectrum and the emission spectrum of 2aBAαDNA in a toluene solution. FIG. 21 shows the absorption spectrum and the emission spectrum of a thin film. The measurement was performed in a manner similar to that in Example 1.

From FIG. 20, for the toluene solution of 2aBAαDNA, the absorption peaks were observed at around 404 nm, 382 nm, 364 nm, and 347 nm, and the emission wavelength peaks were observed at around 419 nm and 442 nm (excitation wavelength: 382 nm). From the results in FIG. 21, for the solid thin film of 2aBAαDNA, the absorption peaks were observed at around 409 nm, 386 nm, 367 nm, 289 nm, and 269 nm, and the emission wavelength peaks were observed at around 434 nm, 467 nm, 501 nm, 542 nm, and 585 nm (excitation wavelength: 390 nm).

Note that 2aBAαDNA was confirmed to emit blue light. The organic compound of one embodiment of the present invention, 2aBAαDNA, can be used as a host for a light-emitting substance or a substance that exhibits fluorescence in the visible region. Furthermore, the thin film of 2aBAαDNA was found to have a good film quality with little change in shape, hardly being aggregated even under air.

Next, CV measurement was performed on 2aBAαDNA. The measurement was performed in a manner similar to that in Example 1.

As a result, the HOMO level was found to be −5.83 eV in the measurement of the oxidation potential Ea [V] of 2aBAαDNA. In contrast, the LUMO level was found to be −2.81 eV in the measurement of the reduction potential Ec [V]. In addition, when the oxidation-reduction wave was repeatedly measured and the waveform of the first cycle was compared with that in the hundredth cycle, 70% of the peak intensity was maintained in the Ea measurement, and 74% of the peak intensity was maintained in the Ec measurement; thus, resistance to oxidation and reduction of 2aBAαDNA was found to be high.

Example 4

This example will describe a method for synthesizing 4-[10-(1-naphthyl)-9-phenyl-2-anthryl]benzo[a]anthracene (abbreviation: 3aBA-αNPhA) (Structural Formula (103)) that is one embodiment of the present invention and is one of the compounds represented by General Formula (G1), and the properties of the compound.

Step 1: Synthesis of 3aBA-αNPhA

Into a 200 mL three-necked flask were put 2.0 g (4.8 mmol) of 2-chloro-10-(1-naphthyl)-9-phenylanthracene, 1.3 g (4.8 mmol) of benzo[a]anthracene-4-boronic acid, 0.17 g (0.48 mmol) of di(1-adamanthyl)-n-butylphosphine, 3.2 g (15 mmol) of tripotassium phosphate, and 1.1 g (15 mmol) of tert-butyl alcohol, and the air in the flask was replaced with nitrogen. To the mixture was added 24 mL of diethylene glycol dimethyl ether, and the mixture was degassed by being stirred under reduced pressure. To this mixture was added 54 mg (0.24 mmol) of palladium(II) acetate, and the mixture was stirred at 140° C. under a nitrogen stream for 12 hours. After the stirring, the solid obtained by performing suction filtration on this mixture was dissolved in toluene, and the solution was subjected to suction filtration through Celite, aluminum oxide, and Florisil. The solid obtained by concentrating the obtained filtrate was purified by high-performance liquid chromatography (HPLC) and then recrystallized with toluene to give 1.2 g of a target pale yellow solid at a yield of 42%. The synthesis scheme is shown in Formula (A-4) below.

[Chemical Formula 30]

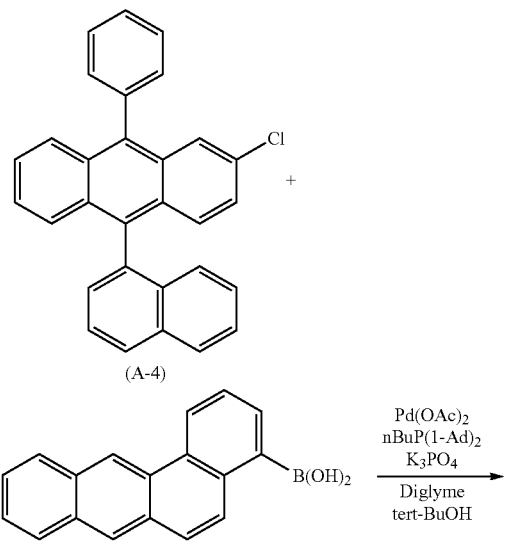

(A-4)

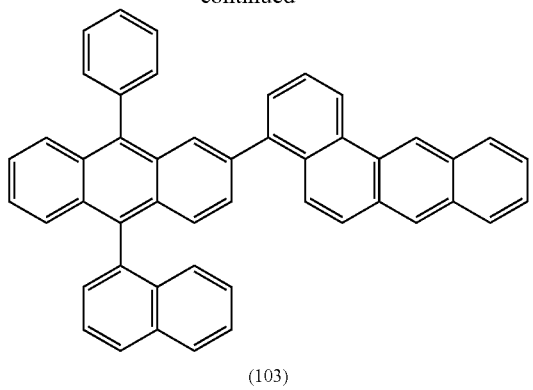

(103)

By the train sublimation method, 1.2 g of the obtained pale yellow solid was purified by sublimation. The sublimation purification was performed by heating at 290° C. under conditions where the pressure was 4.0 Pa and the flow rate of argon was 5.0 mL/min. After the sublimation purification, 1.1 g of a white solid was obtained at a collection rate of 93%.

Analysis data of the obtained solid by nuclear magnetic resonance spectroscopy (H NMR) are shown below.

$^1$H NMR (DMSO-$d_6$, 300 MHz): δ=7.12 (d, J=7.8 Hz, 1H), 7.32-7.84 (m, 22H), 8.09-8.23 (m, 4H), 8.46 (s, 1H), 8.98 (d, J=7.8 Hz, 1H), 9.40 (s, 1H).

Figure 22A:
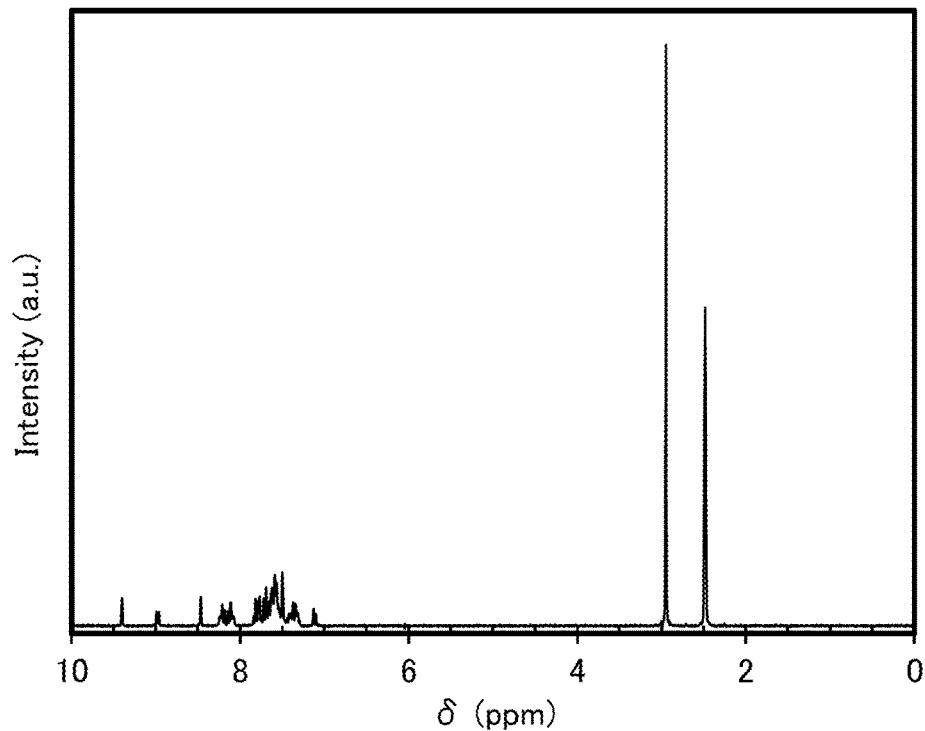
FIG. 22(A), (B) Diagrams showing an NMR chart of a compound in Example.
Figure 22B:
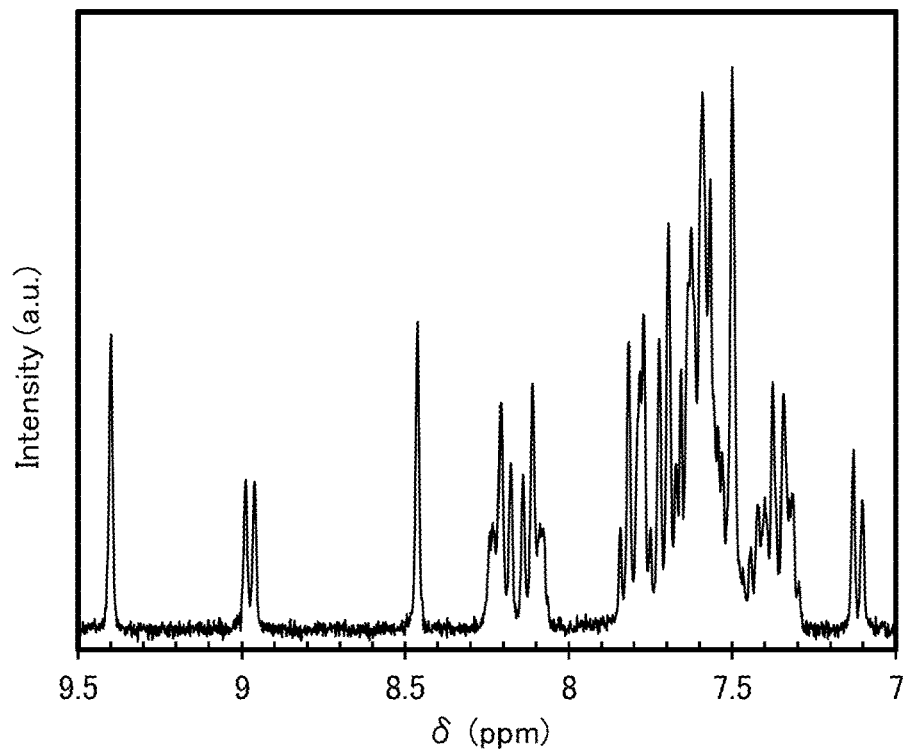

FIG. 22(A) and FIG. 22(B) show $^1$H NMR charts of the obtained solid. Note that FIG. 22(B) is an enlarged diagram of the range of 7.0 ppm to 9.5 ppm of FIG. 22(A). The measurement results indicate that 3aBA-αNPhA, which was the target substance, was obtained.

<Properties of 3aBA-αNPhA>

Figure 23:
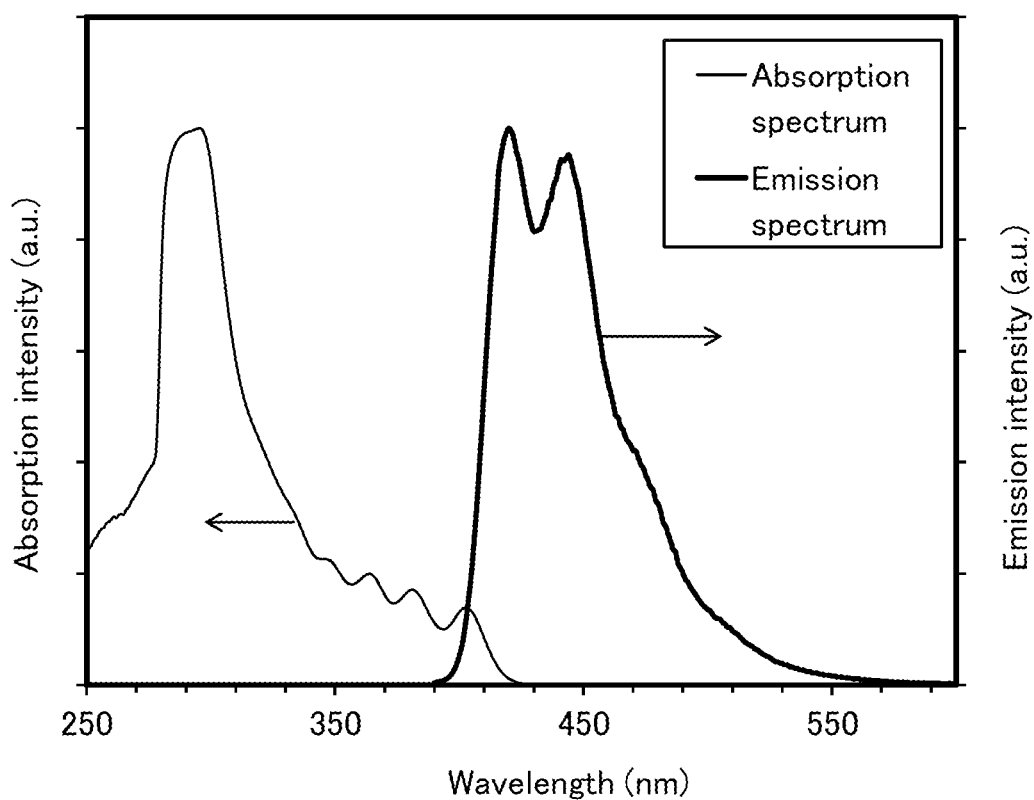
FIG. 23 A diagram showing an absorption spectrum and an emission spectrum of a compound in Example.
Figure 24:
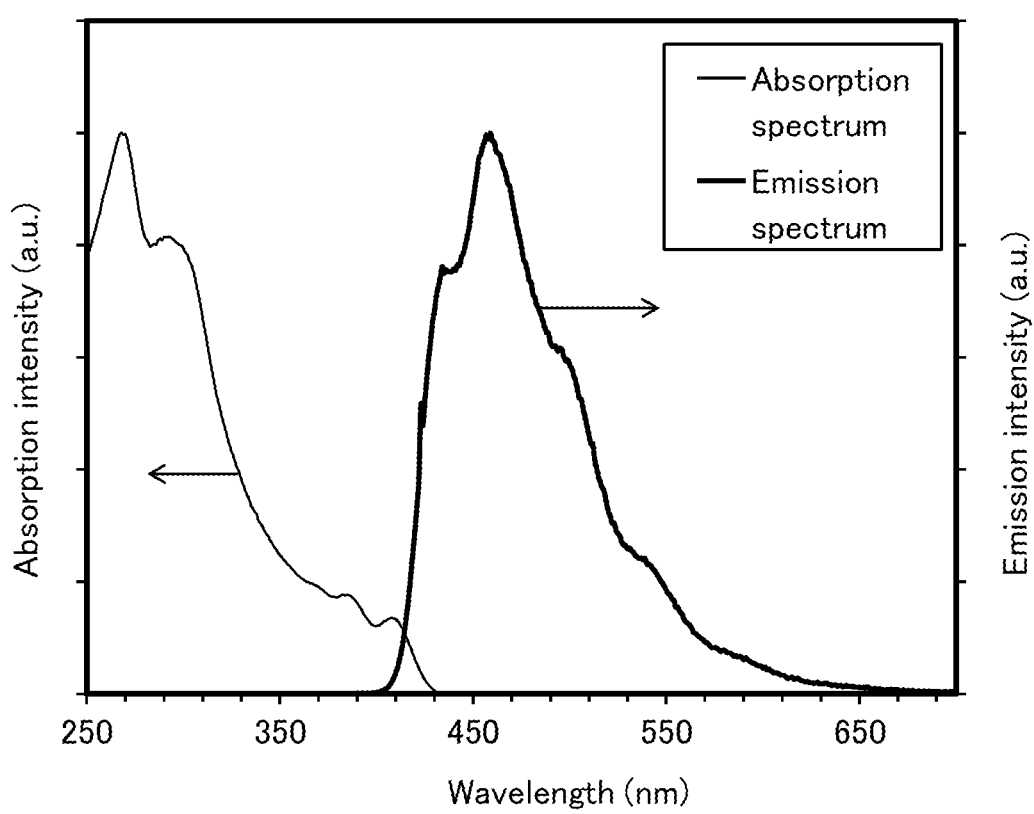
FIG. 24 A diagram showing an absorption spectrum and an emission spectrum of a compound in Example.

Next, FIG. 23 shows the measurement results of the absorption spectrum and the emission spectrum of 3aBA-αNPhA in a toluene solution. FIG. 24 shows the absorption spectrum and the emission spectrum of a thin film. The measurement was performed in a manner similar to that in Example 1.

From the results in FIG. 23, for the toluene solution of 3aBA-αNPhA, the absorption peaks were observed at around 403 nm, 381 nm, 364 nm, and 348 nm, and the emission wavelength peaks were observed at 420 nm and 443 nm (excitation wavelength: 381 nm). From the results in FIG. 24, for the solid thin film of 3aBA-αNPhA, the absorption peaks were observed at around 408 nm, 385 nm, 367 nm, 293 nm, and 268 nm, and the emission wavelength peaks were observed at around 434 nm, 459 nm, 496 nm, 540 nm, and 590 nm (excitation wavelength: 380 nm).

Note that 3aBA-αNPhA was confirmed to emit blue light. The organic compound of one embodiment of the present invention, 3aBA-αNPhA, can be used as a host for a light-emitting substance or a substance that exhibits fluorescence in the visible region. Furthermore, the thin film of 3aBA-αNPhA was found to have a good film quality with little change in shape, hardly being aggregated even under air.

Next, CV measurement was performed on 3aBA-αNPhA. The measurement was performed in a manner similar to that in Example 1.

As a result, the HOMO level was found to be −5.81 eV in the measurement of the oxidation potential Ea [V] of 3aBA-αNPhA. In contrast, the LUMO level was found to be −2.80 eV in the measurement of the reduction potential Ec [V]. In addition, when the oxidation-reduction wave was repeatedly measured and the waveform of the first cycle was compared with that of the hundredth cycle, 72% of the peak intensity was maintained in the Ea measurement, and 69% of the peak intensity was maintained in the Ec measurement, which confirmed that 3aBA-αNPhA had high resistance to oxidation and reduction.

Example 5

This example will describe a method for synthesizing 4-[9-(1-naphthyl)-10-phenyl-2-anthryl]benzo[a]anthracene (abbreviation: 2aBA-αNPhA) (Structural Formula (104)) that is one embodiment of the present invention and is one of the compounds represented by General Formula (G1), and the properties of the compound.

Step 1: Synthesis of 2aBA-αNPhA

Into a 200 mL three-necked flask were put 3.0 g (7.1 mmol) of 2-chloro-9-(1-naphthyl)-10-phenylanthracene, 2.7 g (10 mmol) of benzo[a]anthracene-4-boronic acid, 0.26 g (0.72 mmol) of di(1-adamantyl)-n-butylphosphine, 4.5 g (21 mmol) of tripotassium phosphate, and 1.6 g (21 mmol) of tert-butyl alcohol, and the air in the flask was replaced with nitrogen. To the mixture was added 36 mL of diethylene glycol dimethyl ether, and the mixture was degassed by being stirred under reduced pressure. To this mixture was added 80 mg (0.36 mmol) of palladium(II) acetate, and the mixture was stirred at 130° C. under a nitrogen stream for 4 hours. After the stirring, the solid obtained by performing suction filtration on this mixture was dissolved in toluene, and the solution was subjected to suction filtration through Celite, aluminum oxide, and Florisil. The solid obtained by concentrating the obtained filtrate was purified by high-performance liquid chromatography (HPLC) and then recrystallized with toluene to give 2.3 g of a target pale yellow solid at a yield of 52%. The synthesis scheme is shown in Formula (A-5) below.

[Chemical Formula 31]

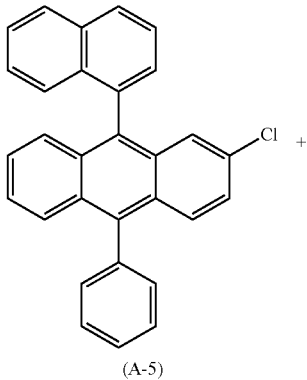

(A-5)

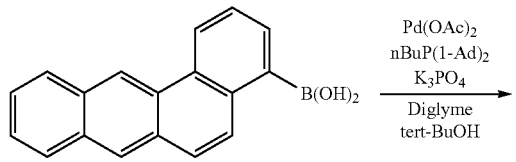

-continued

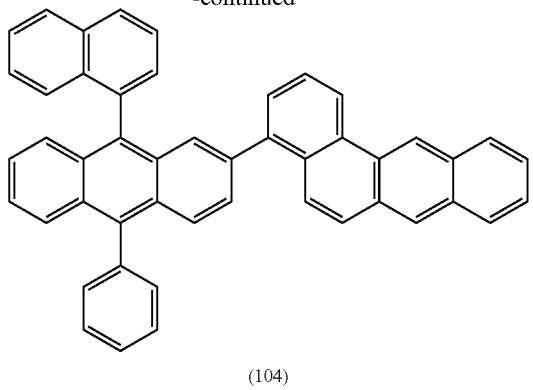

(104)

By the train sublimation method, 2.3 g of the obtained pale yellow solid was sublimated and purified. The sublimation purification was performed by heating at 300° C. under the conditions where the pressure was 3.8 Pa and the argon flow rate was 5.0 mL/min. After the sublimation purification, 2.1 g of a white solid was obtained at a collection rate of 95%.

Analysis data of the obtained solid by nuclear magnetic resonance spectroscopy (H NMR) are shown below.

$^1$H NMR (DMSO-$d_6$, 300 MHz): δ=7.14 (d, J=8.1 Hz, 1H), 7.30-7.74 (m, 21H), 7.84 (d, J=8.7 Hz, 1H), 8.00-8.10 (m, 3H), 8.18-8.21 (m, 1H), 8.41 (s, 1H), 8.90 (d, J=8.1 Hz, 1H), 9.34 (s, 1H).

Figure 25A:
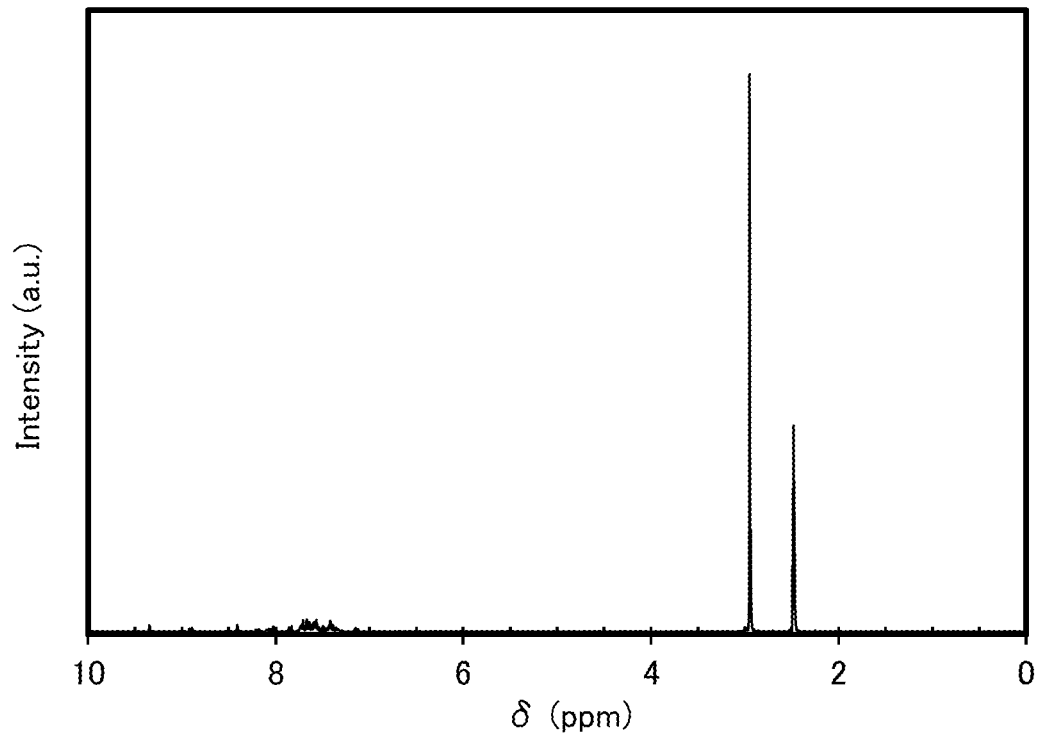
FIG. 25(A), (B) Diagrams showing an NMR chart of a compound in Example.
Figure 25B:
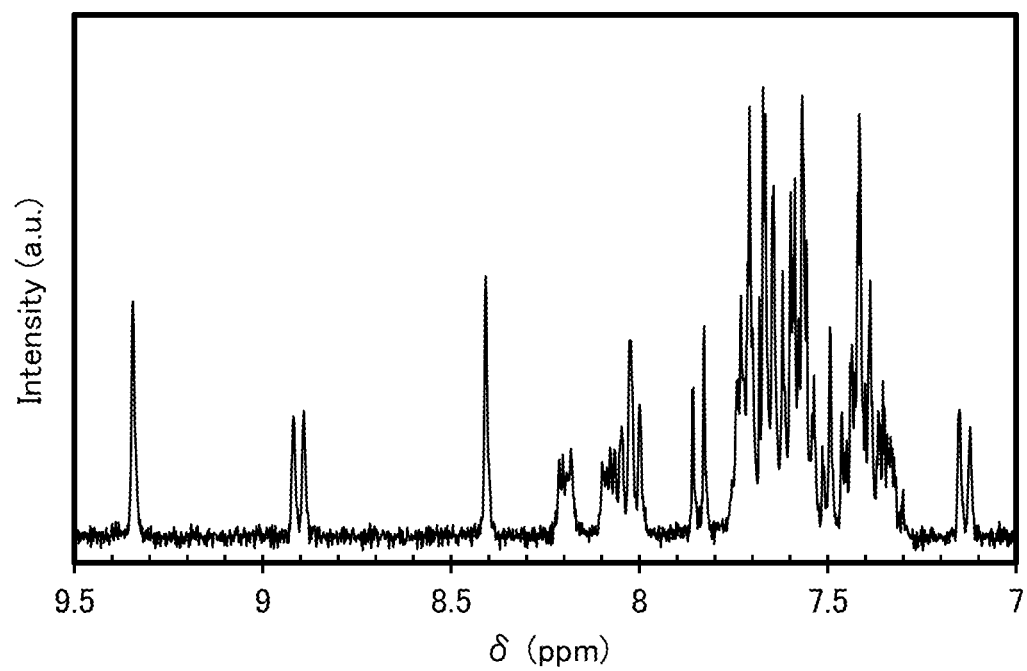

FIG. 25(A) and FIG. 25(B) show $^1$H NMR charts of the obtained solid. Note that FIG. 25(B) is an enlarged diagram of the range of 7.0 ppm to 9.5 ppm of FIG. 25(A). The measurement results indicate that 2aBA-αNPhA, which was the target substance, was obtained.

<Properties of 2aBA-αNPhA>

Figure 26:
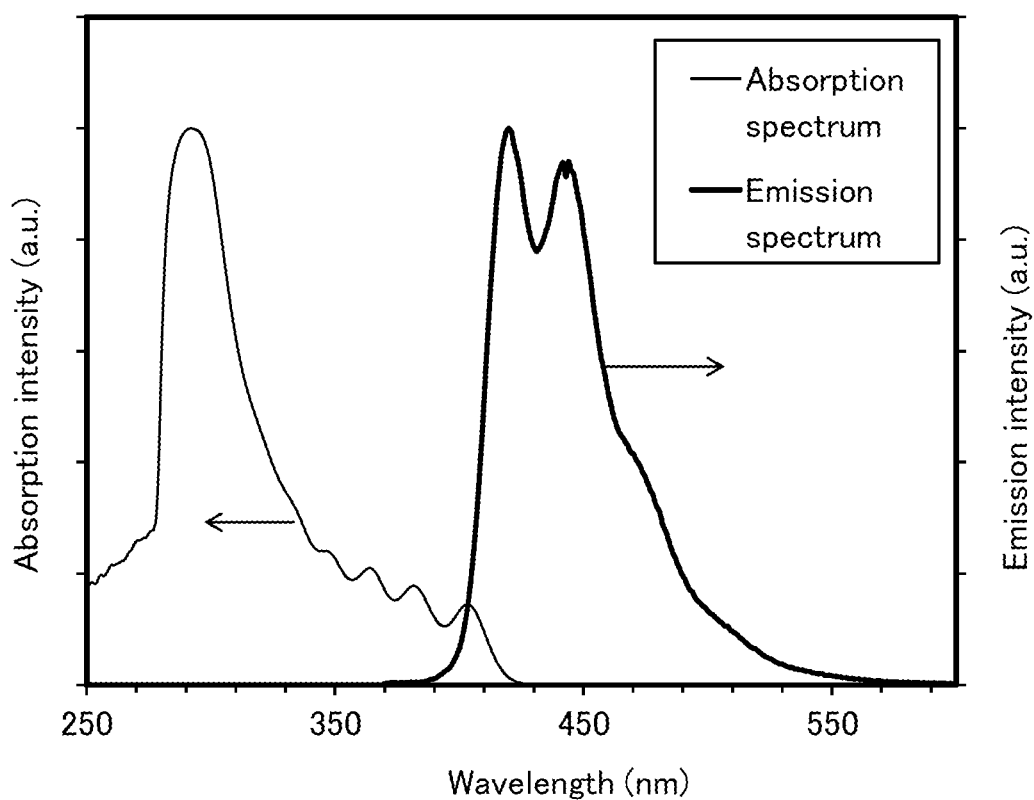
FIG. 26 A diagram showing an absorption spectrum and an emission spectrum of a compound in Example.
Figure 27:
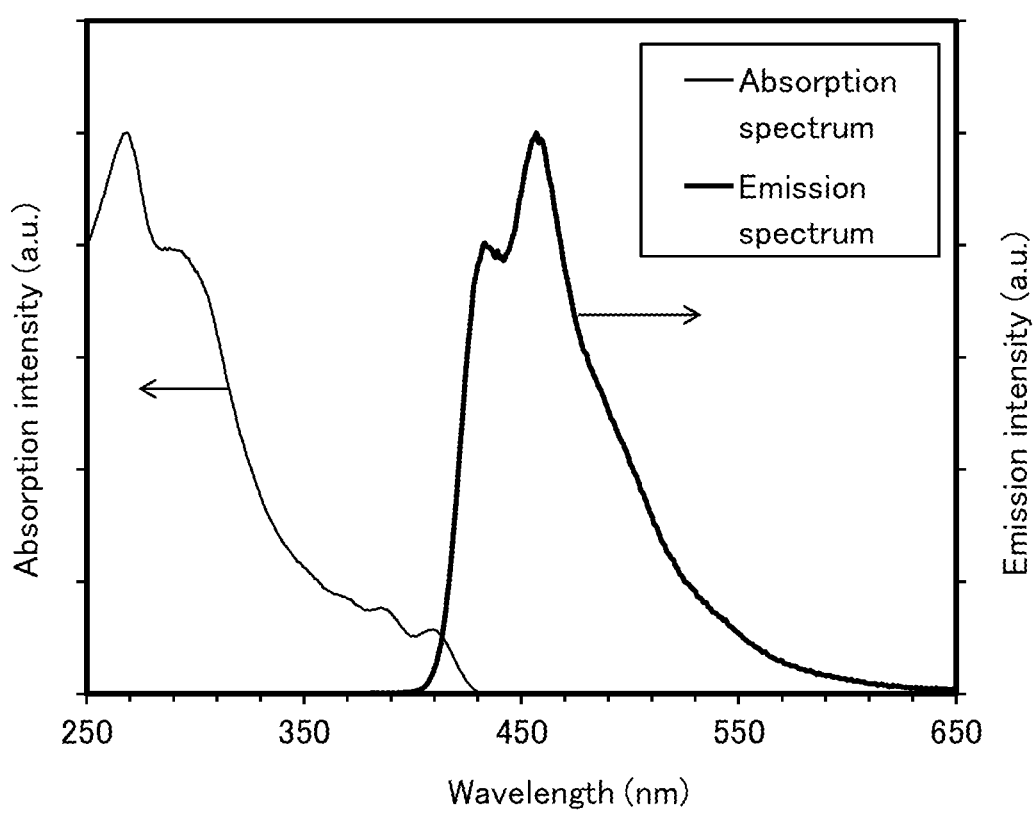
FIG. 27 A diagram showing an absorption spectrum and an emission spectrum of a compound in Example.

Next, FIG. 26 shows the measurement results of the absorption spectrum and the emission spectrum of 2aBA-αNPhA in a toluene solution. FIG. 27 shows the absorption spectrum and the emission spectrum of a thin film. The measurement was performed in a manner similar to that in Example 1.

From the results in FIG. 26, for the toluene solution of 2aBA-αNPhA, the absorption peaks were observed at around 403 nm, 382 nm, 364 nm, and 346 nm, and the emission wavelength peaks were observed at 420 nm and 443 nm (excitation wavelength: 382 nm). From the results in FIG. 27, for the solid thin film of 2aBA-αNPhA, the absorption peaks were observed at around 410 nm, 386 nm, 368 nm, 291 nm, and 269 nm, and the emission wavelength peaks were observed at around 433 nm and 457 nm (excitation wavelength: 370 nm).

Note that 2aBA-αNPhA was confirmed to emit blue light. The organic compound of one embodiment of the present invention, 2aBA-αNPhA, can be used as a host for a light-emitting substance or a substance that exhibits fluorescence in the visible region. Furthermore, the thin film of 2aBA-αNPhA was found to have a good film quality with little change in shape, hardly being aggregated even under air.

Next, CV measurement was performed on 2aBA-αNPhA. The measurement was performed in a manner similar to that in Example 1.

As a result, the HOMO level was found to be −5.82 eV in the measurement of the oxidation potential Ea [V] of 2aBA-αNPhA. In contrast, the LUMO level was found to be −2.79 eV in the measurement of the reduction potential Ec [V]. In addition, when the oxidation-reduction wave was repeatedly measured and the waveform of the first cycle was compared with that in the hundredth cycle, 73% of the peak intensity was maintained in the Ea measurement, and 72% of the peak intensity was maintained in the Ec measurement; thus, resistance to oxidation and reduction of 2aBA-αNPhA was found to be high.

Example 6

Differential scanning calorimetry (DSC) was performed on 2aBAPA, 2aBA-αNPhA, and 3aBA-αNPhA, each of which was synthesized in the above manner. As the measurement apparatus, Pyris 1 DSC manufactured by PerkinElmer, Inc. was used. In the first cycle of the measurement of 2aBAPA, the temperature was increased from −10° C. to 300° C. at a rate of 40° C./min, held at 300° C. for one minute, and then decreased from 300° C. to −10° C. at a rate of 100° C./min. In the second cycle, the measurement was performed under the same conditions as the first cycle except that the rate of temperature increase was 10° C./min. In the third cycle, the measurement was performed under the same conditions as the first cycle. In the first cycle for 2aBA-αNPhA, the temperature was increased from −10° C. to 360° C. at a rate of 40° C./min, held at 360° C. for one minute, and then decreased from 360° C. to −10° C. at a rate of 100° C./min. In the second cycle, the measurement was performed under the same conditions as the first cycle except that the rate of temperature increase was 10° C./min. In the third cycle, the measurement was performed under the same conditions as the first cycle. In the first cycle for 3aBA-αNPhA, the temperature was increased from −10° C. to 340° C. at a rate of 40° C./min, held at 340° C. for one minute, and then decreased from 340° C. to −10° C. at a rate of 100° C./min. In the second cycle, the measurement was performed under the same conditions as the first cycle except that the rate of temperature increase was 10° C./min. In the third cycle, the measurement was performed under the same conditions as the first cycle.

In this measurement, three cycles were performed, and the glass transition temperature Tg was read from the results at the time of the temperature increase in the third cycle. The results are shown in Table 1.

TABLE 1

|  | Tg (° C.) |
| --- | --- |
| 2aBAPA | 154 |
| 2aBA-αNPhA | 174 |
| 3aBA-αNPhA | 178 |

It was found from Table 1 that each organic compound of one embodiment of the present invention is a material that has excellent heat resistance with Tg exceeding 150° C. It was found that 2aBA-αNPhA and 3aBA-αNPhA have higher heat resistance than 2aBAPA by more than 20° C.

Example 7

This example will describe fabrication examples of a light-emitting device including the organic compound of one embodiment of the present invention and a comparative light-emitting device and the characteristics of the light-emitting devices. FIG. 1(A) illustrates a stacked-layer structure of the light-emitting devices fabricated in this example. Table 2 shows the details of the device structures. The organic compounds used in this example are shown below. Note that other embodiments or examples can be referred to for other organic compounds.

[Chemical Formula 32]

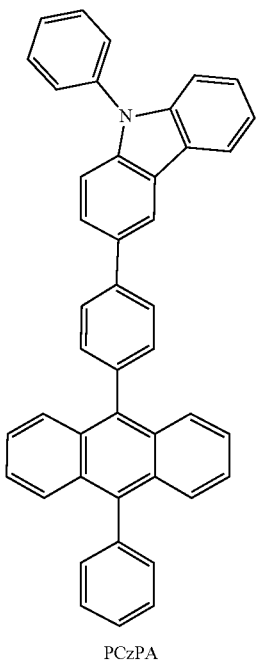

PCzPA

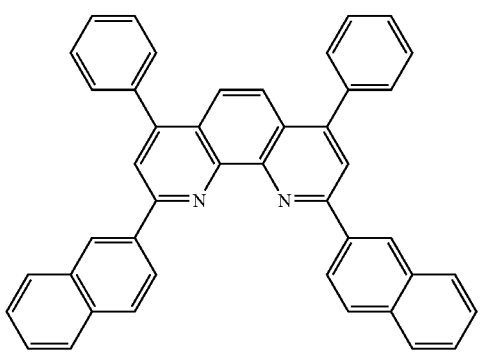

NBPhen

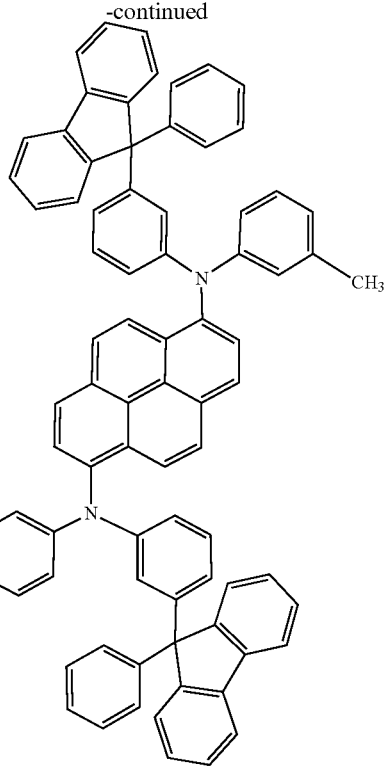

1,6mMemFLPAPrn

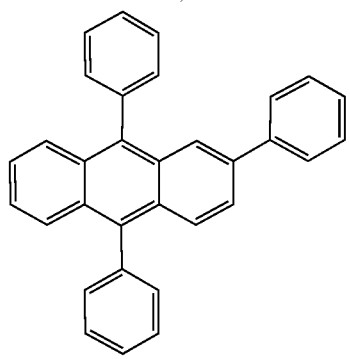

2PPA

TABLE 2

| | Layer | Reference numeral | Thickness (nm) | Material | Weight ratio |
|---|---|---|---|---|---|
| Comparative Light-emitting device 1 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2PPA | — |
| | Light-emitting layer | 140 | 25 | 2PPA: 1,6mMemFLPAPrn | 1:0.03 |
| | Hole-transport layer | 112 | 30 | PCzPA | — |
| | Hole-injection layer | 111 | 10 | PCzPA: MoO₃ | 1:0.5 |
| | Electrode | 101 | 70 | ITSO | — |
| Light-emitting device 2 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2aBAPA | — |
| | Light-emitting layer | 140 | 25 | 2aBAPA: 1,6mMemFLPAPrn | 1:0.03 |
| | Hole-transport layer | 112 | 30 | PCzPA | — |
| | Hole-injection layer | 111 | 10 | PCzPA: MoO₃ | 1:0.5 |
| | Electrode | 101 | 70 | ITSO | — |

<<Fabrication of Comparative Light-Emitting Device 1>>

As the electrode 101, an ITSO film was formed to a thickness of 70 nm over a glass substrate by a sputtering method. Note that the electrode area of the electrode 101 was set to 4 mm² (2 mm×2 mm). Next, as pretreatment for forming alight-emitting device over the substrate, a surface of the substrate was washed with water, drying was performed at 200° C. for one hour, and then UV ozone treatment was performed for 370 seconds. After that, the substrate was transferred into a vacuum evaporation apparatus where the degree of vacuum was kept at approximately 1×10⁻⁴ Pa, and baking was performed at 170° C. for 30 minutes. Then, the substrate was allowed to cool for approximately 30 minutes.

Next, as the hole-injection layer 111, PCzPA and molybdenum(VI) oxide (Mo₃) were deposited over the electrode 101 by co-evaporation in a weight ratio (PCzPA:MoO₃) of 1:0.5 to a thickness of 10 nm.

Next, as the hole-transport layer 112, PCzPA was deposited over the hole-injection layer 111 by evaporation to a thickness of 30 nm.

Then, as the light-emitting layer 140, 2,9,10-triphenylanthracene (abbreviation: 2PPA) and 1,6mMemFLPAPrn were deposited over the hole-transport layer 112 by co-evaporation in a weight ratio (2PPA:1,6mMemFLPAPrn) of 1:0.03 to a thickness of 25 nm. Note that in the light-emitting layer 140, 1,6mMemFLPAPrn is a guest material that exhibits fluorescence.

Next, as an electron-transport layer 118(1), 2PPA was deposited over the light-emitting layer 140 by evaporation to a thickness of 15 nm. Then, as an electron-transport layer 118(2), NBPhen was sequentially deposited over the electron-transport layer 118(1) by evaporation to a thickness of 10 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the light-emitting device 1 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm² and heat treatment at 80° C. for one hour were performed. Through the above steps, the comparative light-emitting device 1 was obtained.

<<Fabrication of Light-Emitting Device 2>>

The fabrication process of the light-emitting device 2 is the same as that of the comparative light-emitting device 1 described above, except for the fabrication steps of the light-emitting layer 140 and the electron-transport layer 118(1). The device structure of the light-emitting device 2 is as shown in Table 2; hence, the detailed description of the fabrication process is omitted. Note that the light-emitting layer 140 and the electron-transport layer 118(1) of the light-emitting device 2 were formed by a vacuum evaporation method, as in the comparative light-emitting device 1.

The device structures of the comparative light-emitting device 1 and the light-emitting device 2 are the same, except for a host material used for the light-emitting layer 140 and a material used for the electron-transport layer 118(1). Note that the light-emitting device 2 uses 2aBAPA, which is the organic compound of one embodiment of the present invention, and the comparative light-emitting device 1 uses 2PPA, which is a comparative substance.

<Characteristics of Light-Emitting Devices>

Next, the characteristics of the comparative light-emitting device 1 and the light-emitting device 2, which were fabricated as above, were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 28:
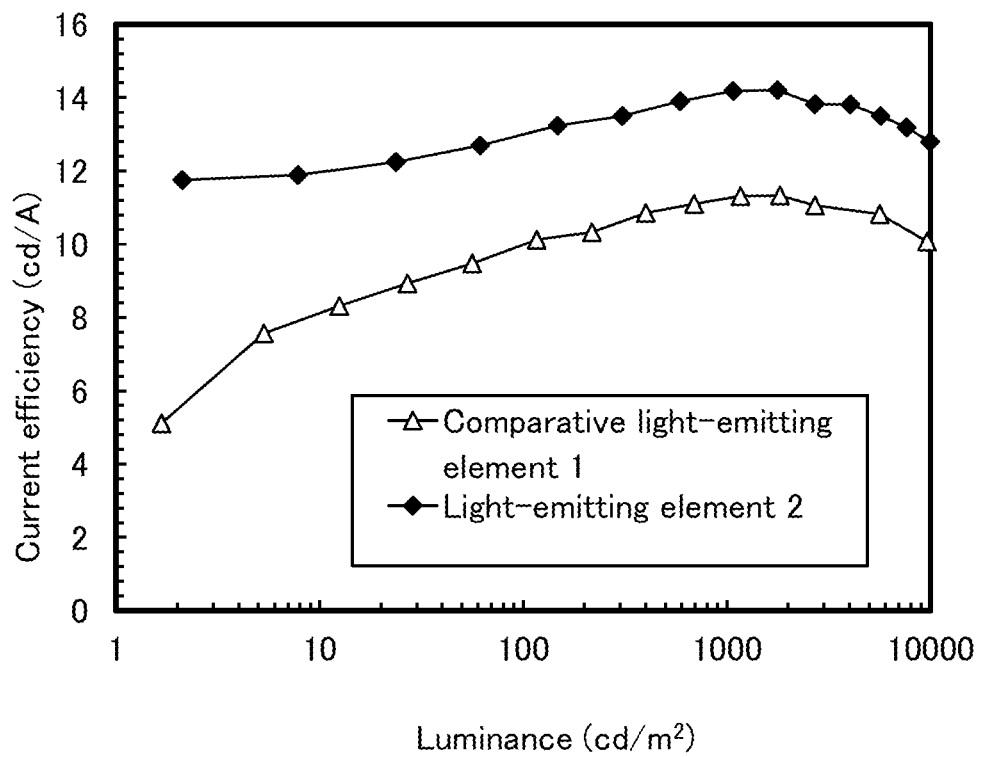
FIG. 28 A diagram showing current efficiency-luminance characteristics of light-emitting devices in Example.
Figure 29:
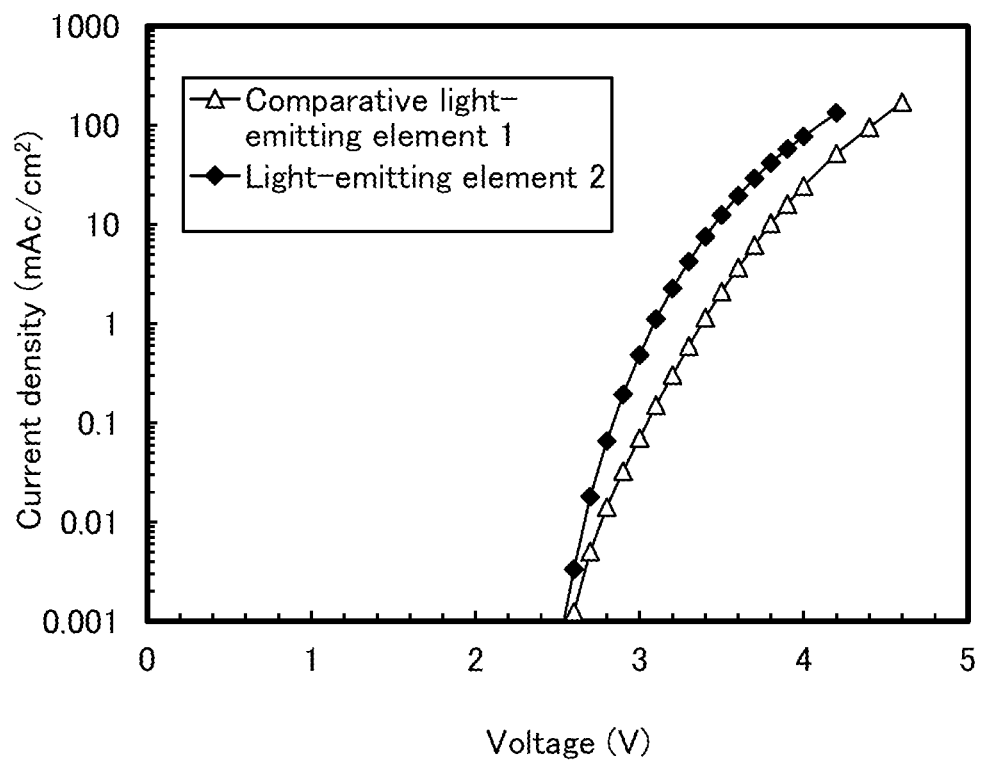
FIG. 29 A diagram showing current density-voltage characteristics of light-emitting devices in Example.
Figure 30:
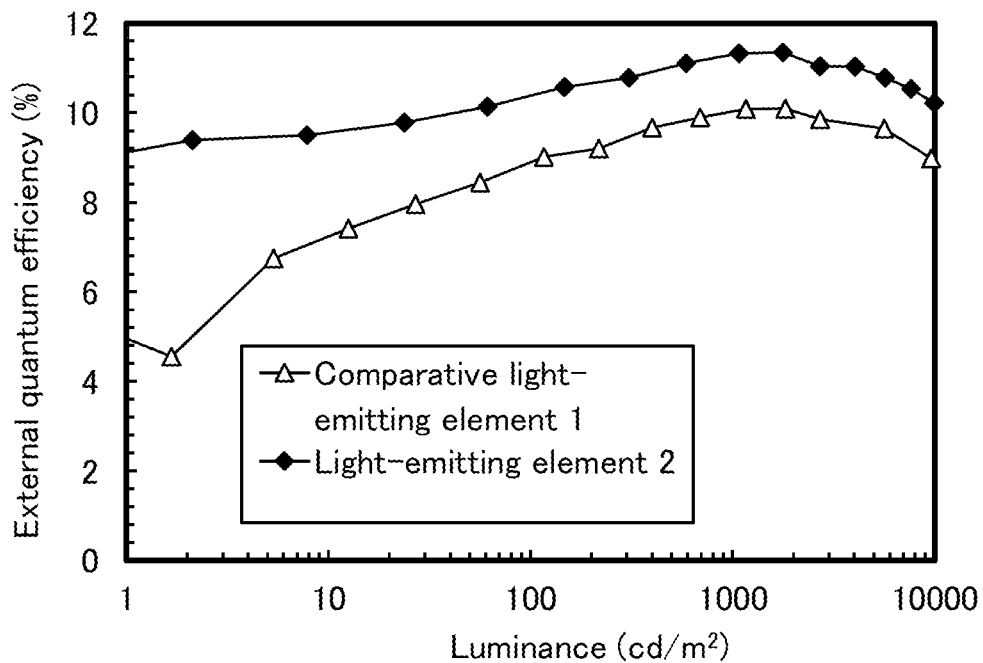
FIG. 30 A diagram showing external quantum efficiency-luminance characteristics of light-emitting devices in Example.
Figure 31:
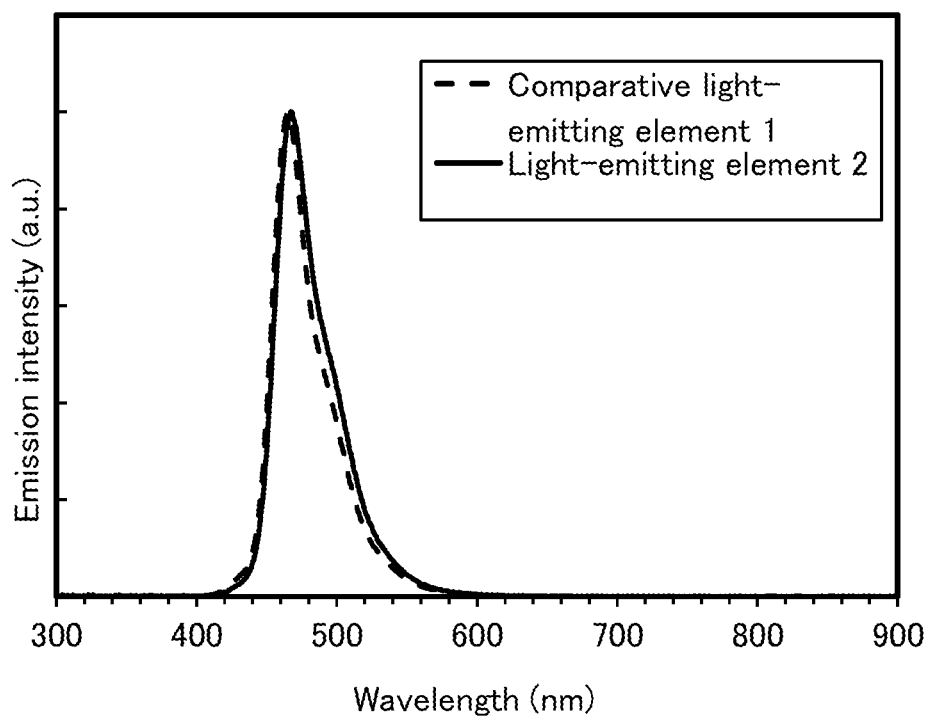
FIG. 31 A diagram showing emission spectra of light-emitting devices in Example.

FIG. 28 shows the current efficiency-luminance characteristics of the comparative light-emitting device 1 and the light-emitting device 2. FIG. 29 shows the current density-voltage characteristics. FIG. 30 shows the external quantum efficiency-luminance characteristics. Note that the measurement of the light-emitting devices was performed at room temperature (in an atmosphere maintained at 23° C.). FIG. 31 shows emission spectra in the case where current at a current density of 12.5 mA/cm² was supplied to the comparative light-emitting device 1 and the light-emitting device 2.

Table 3 shows the device characteristics of the comparative light-emitting device 1 and the light-emitting device 2 at around 1000 cd/m².

TABLE 3

| | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Comparative Light-emitting device 1 | 3.80 | 10.3 | (0.138, 0.153) | 1165.0 | 11.3 | 9.4 | 10.1 |
| Light-emitting device 2 | 3.40 | 7.59 | (0.137, 0.183) | 1076.0 | 14.2 | 13.1 | 11.3 |

As shown in FIG. 28 and Table 3, the comparative light-emitting device 1 and the light-emitting device 2 exhibited high current efficiency. In particular, despite emitting blue light with a low luminosity factor, the light-emitting device 2 using the organic compound of one embodiment of the present invention exhibited a current efficiency exceeding 14 cd/A, which is extremely high for a blue fluorescent device.

As shown in FIG. 30 and Table 3, the comparative light-emitting device 1 and the light-emitting device 2 exhibited high external quantum efficiency. In particular, the light-emitting device 2 using the organic compound of one embodiment of the present invention exhibited an external quantum efficiency exceeding 11%, which is extreme for a fluorescent device. Thus, it was found that the light-emitting device using the organic compound having a benzo[a]anthracene skeleton at the 2-position of the anthracene skeleton can be a light-emitting device having high current efficiency and high external quantum efficiency. It was also found that the organic compound having a benzo[a]anthracene skeleton at the 2-position of the anthracene skeleton enables fabrication of a light-emitting device having higher emission efficiency than in the case of using the organic compound having a phenyl group at the 2-position of the anthracene skeleton.

Note that since the generation probability of singlet excitons which are generated by recombination of carriers (holes and electrons) injected from the pair of electrodes is 25%, the theoretical external quantum efficiency of a fluorescent device in the case where the light extraction efficiency to the outside is 30% is at most 7.5%. Each of the comparative light-emitting device 1 and the light-emitting device 2 obtains higher efficiency than the theoretical limit value. This is probably because in the comparative light-emitting device 1 and the light-emitting device 2, some of the triplet excitons are converted into singlet excitons by TTA described in Embodiment 3 and contribute to fluorescence in addition to light emission derived from the singlet excitons generated by recombination of carriers injected from the pair of electrodes.

As shown in FIG. 29 and Table 3, the comparative light-emitting device 1 and the light-emitting device 2 each have favorable driving voltage. FIG. 29 shows that the light-emitting device 2 of one embodiment of the present invention has lower driving voltage than the comparative light-emitting device 1. Thus, it was found that the light-emitting device using the organic compound having a benzo[a]anthracene skeleton at the 2-position of the anthracene skeleton has lower driving voltage than the light-emitting device using the organic compound having a phenyl group at the 2-position of the anthracene skeleton.

As shown in FIG. 31, the emission spectra of the comparative light-emitting device 1 and the light-emitting device 2 respectively have a spectral peak at around 465 nm and 467 nm and a full width at half maximum of approximately 36 nm and 40 nm; hence, the comparative light-emitting device 1 and the light-emitting device 2 exhibited favorable blue light emission originating from 1,6mMemFLPAPrn, which is the guest material.

<Reliability of Light-Emitting Devices>

Figure 32:
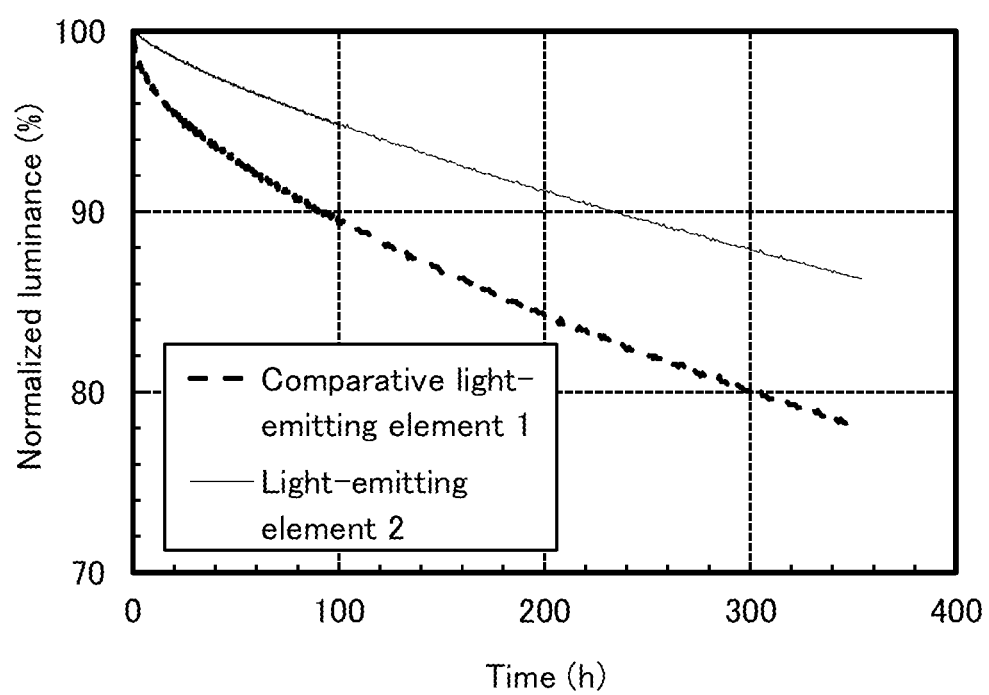
FIG. 32 A diagram showing results of a reliability test on light-emitting devices in Example.

Next, driving tests at a constant current of 2 mA were performed on the comparative light-emitting device 1 and the light-emitting device 2. FIG. 32 shows the results. It was found from FIG. 32 that the comparative light-emitting device 1 and the light-emitting device 2 have high reliability. In particular, it was found that $LT_{90}$ (time taken for 10% luminance reduction) of the light-emitting device 2 exceeds 230 hours, demonstrating particularly high reliability. It was also found from FIG. 32 that the light-emitting device 2 has higher reliability than the comparative light-emitting device 1. Thus, it was found that the light-emitting device using the organic compound having a benzo[a]anthracene skeleton at the 2-position of the anthracene skeleton has higher reliability than the light-emitting device using the organic compound having a phenyl group at the 2-position of the anthracene skeleton.

As described above, with the use of the compound of one embodiment of the present invention in the light-emitting layer, a light-emitting device that exhibits high emission efficiency, favorable driving voltage, and high reliability can be fabricated. In addition, it was found that the light-emitting device using the organic compound of one embodiment of the present invention has higher emission efficiency and higher reliability than the light-emitting device using the organic compound having a phenyl group at the 2-position of the anthracene skeleton.

Example 8

This example will describe fabrication examples of light-emitting devices each of which includes the organic compound of one embodiment of the present invention and is different from that in Example 7, and the characteristics of the light-emitting devices. FIG. 1(A) illustrates a stacked-layer structure of the light-emitting devices fabricated in this example. Table 4 shows the details of the device structures. The organic compounds used in this example are shown below. Note that other embodiments or examples can be referred to for other organic compounds.

[Chemical Formula 33]

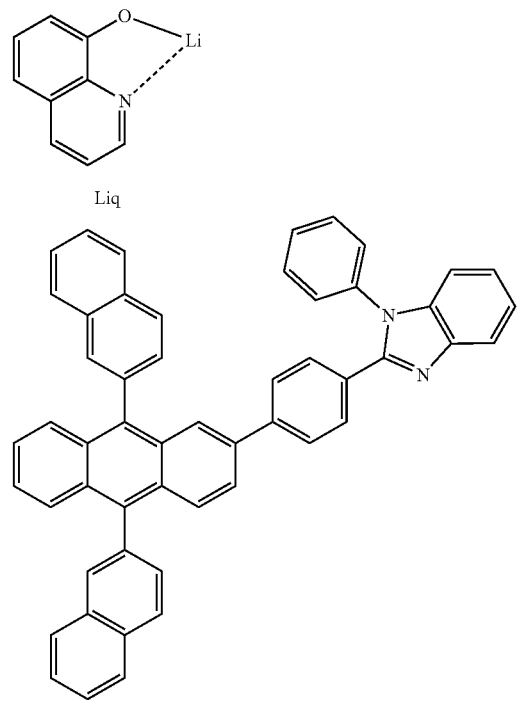

Liq

ZADN

-continued

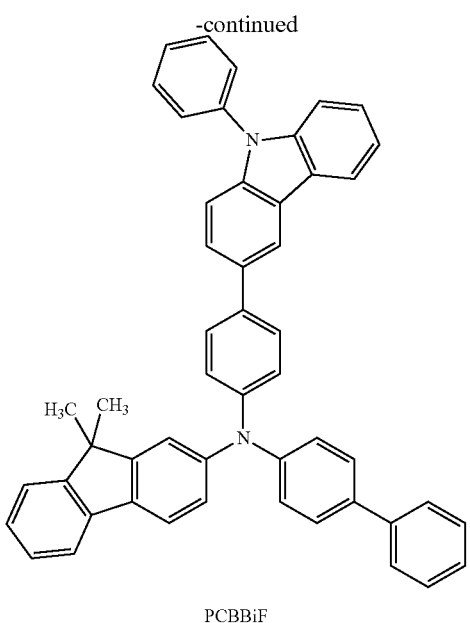

PCBBiF (2aBAPA:BD-001) of 1:0.03 to a thickness of 25 nm. Note that in the light-emitting layer 140, BD-001 is a guest material that exhibits fluorescence.

Next, as the electron-transport layer 118, 2-{4-[9,10-di(naphthalen-2-yl)-2-anthryl]-1-phenyl-1H-benzimidazole (abbreviation: ZADN) and 8-hydroxyquinolinato-lithium (abbreviation: Liq) were deposited over the light-emitting layer 140 by co-evaporation in a weight ratio (ZADN:Liq) of 1:1 to a thickness of 25 nm.

Then, as the electron-injection layer 119, Liq was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the light-emitting device 1 was sealed. Specifically, a drying agent was attached to the counter substrate, and the counter

TABLE 4

| | Layer | Reference numeral | Thickness (nm) | Material | Weight ratio |
|---|---|---|---|---|---|
| Light-emitting device 3 | Electrode | 102 | 200 | Al | — |
| | Electron-injection layer | 119 | 1 | Liq | — |
| | Electron-transport layer | 118 | 25 | ZADN: Liq | 1:1 |
| | Light-emitting layer | 140 | 25 | 2aBAPA: BD-001 | 1:0.03 |
| | Hole-transport layer | 112(2) | 10 | HT602 | |
| | | 112(1) | 20 | PCBBiF | — |
| | Hole-injection layer | 111 | 10 | PCBBiF: NDP-9 | 1:0.1 |
| | Electrode | 101 | 70 | ITSO | — |
| Light-emitting device 4 | Electrode | 102 | 200 | Al | — |
| | Electron-injection layer | 119 | 1 | Liq | — |
| | Electron-transport layer | 118 | 25 | ZADN: Liq | 1:1 |
| | Light-emitting layer | 140 | 25 | 3aBA-αNPhA: BD-001 | 1:0.03 |
| | Hole-transport layer | 112(2) | 10 | HT602 | |
| | | 112(1) | 20 | PCBBiF | — |
| | Hole-injection layer | 111 | 10 | PCBBiF: NDP-9 | 1:0.1 |
| | Electrode | 101 | 70 | ITSO | — |

<<Fabrication of Light-Emitting Device 3>>

As the hole-injection layer 111 of the light-emitting device 3, PCBBiF and NDP-9 (produced by Analysis Atelier Corporation, material serial No. 1S20170124) were deposited over the electrode 101 by co-evaporation in a weight ratio (PCBBiF:NDP-9) of 1:0.1 to a thickness of 10 nm.

Next, as a hole-transport layer 112(1), PCBBiF was deposited over the hole-injection layer 111 by evaporation to a thickness of 20 nm, and subsequently, as a hole-transport layer 112(2), HT602 (produced by Analysis Atelier Corporation, material serial No. 1S20160920) was deposited by evaporation to a thickness of 10 nm. Note that the hole-transport layer 112(2) has a function of an electron-blocking layer.

Then, as the light-emitting layer 140, 2aBAPA and BD-001 (produced by Analysis Atelier Corporation, material serial No. 1S20160602) were deposited over the hole-transport layer 112 by co-evaporation in a weight ratio substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm$^2$ and heat treatment at 80° C. for one hour were performed. Through the above steps, the light-emitting device 3 was obtained.

<<Fabrication of Light-Emitting Device 4>>

The fabrication process of the light-emitting device 4 is the same as that of the aforementioned light-emitting device 3, except for the fabrication step of the light-emitting layer 140. The device structure of the light-emitting device 4 is as shown in Table 4; hence, the detailed description of the fabrication process is omitted. Note that the light-emitting layer 140 of the light-emitting device 4 was formed by a vacuum evaporation method, as in the light-emitting device 4.

The device structures of the light-emitting device 3 and the light-emitting device 4 are the same, except for a host material used for the light-emitting layer 140. 2aBAPA is used in the light-emitting device 3, and 3aBA-αNPhA is used in the light-emitting device 4. The difference between these two organic compounds is that 2aBAPA has a phenyl group at the 9-position and the 10-position of the anthracene skeleton, whereas 3aBA-αNPhA has a phenyl group at the 9-position of the anthracene skeleton and a naphthyl group at the 10-position. That is, 2aBAPA has the same aryl groups at the 9-position and the 10-position, whereas 3aBA-αNPhA has different aryl groups as substitutes at the 9-position and the 10-position of the anthracene skeleton.

<Characteristics of Light-Emitting Devices>

Next, the characteristics of the fabricated light-emitting device 3 and light-emitting device 4 were measured. The measurement conditions of the light-emitting devices were similar to those in Example above.

Figure 33:
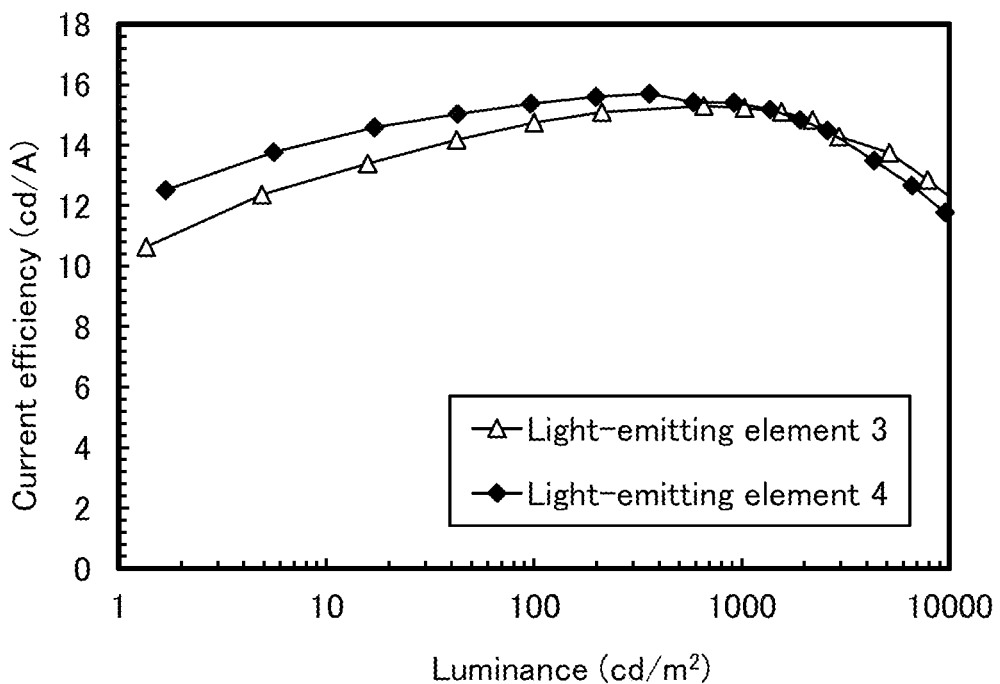
FIG. 33 A diagram showing current efficiency-luminance characteristics of light-emitting devices in Example.
Figure 34:
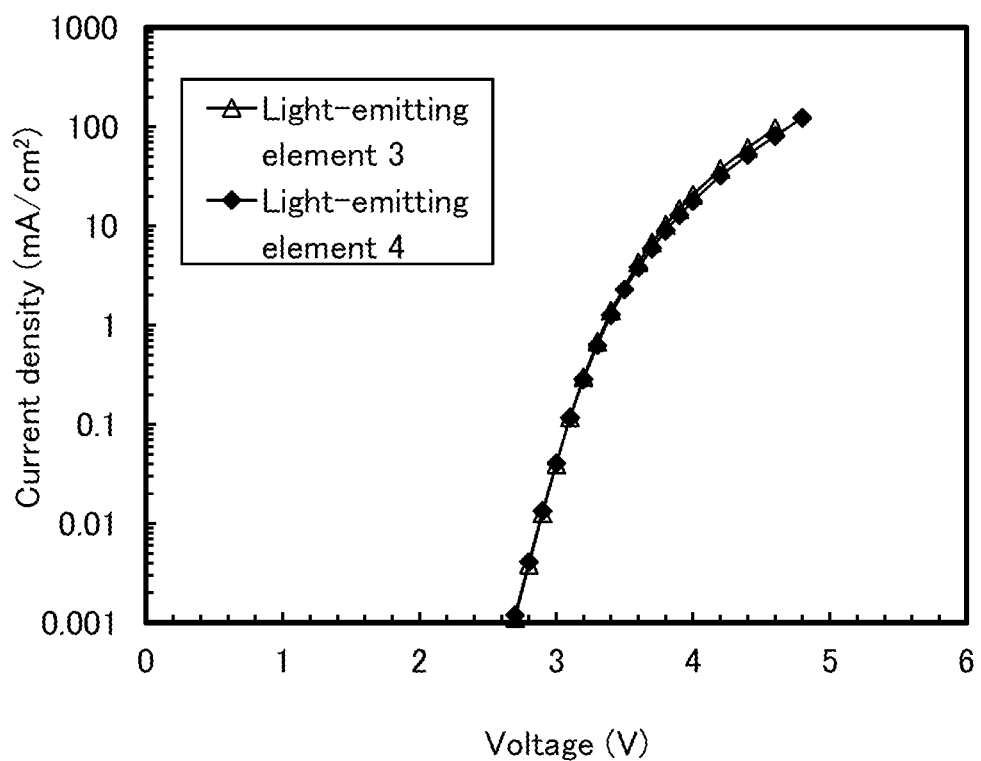
FIG. 34 A diagram showing current density-voltage characteristics of light-emitting devices in Example.
Figure 35:
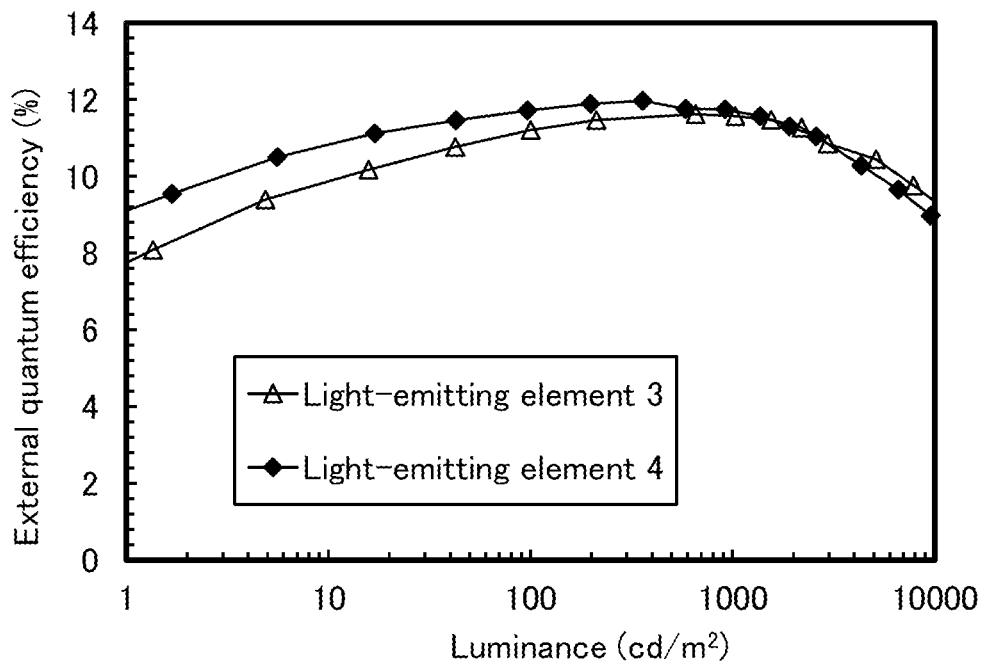
FIG. 35 A diagram showing external quantum efficiency-luminance characteristics of light-emitting devices in Example.
Figure 36:
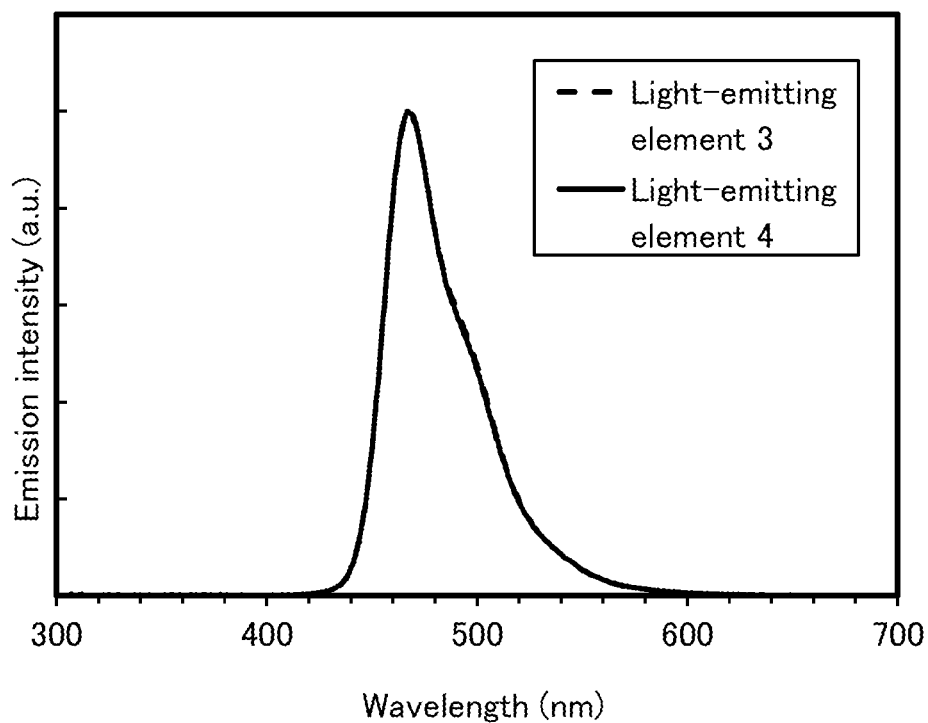
FIG. 36 A diagram showing emission spectra of light-emitting devices in Example.

FIG. 33 shows the current efficiency-luminance characteristics of the light-emitting device 3 and the light-emitting device 4. FIG. 34 shows the current density-voltage characteristics. FIG. 35 shows the external quantum efficiency-luminance characteristics. FIG. 36 shows emission spectrum in the case where current at a current density of 12.5 mA/cm$^2$ was supplied to the light-emitting device 3 and the light-emitting device 4.

Table 5 shows the device characteristics of the light-emitting device 3 and the light-emitting device 4 at around 1000 cd/m$^2$.

TABLE 5

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 3 | 3.70 | 6.78 | (0.139, 0.197) | 1032 | 15.2 | 12.9 | 11.6 |
| Light-emitting device 4 | 3.70 | 5.96 | (0.139, 0.196) | 919 | 15.4 | 13.1 | 11.7 |

As shown in FIG. 33 and Table 5, despite emitting blue light with a low luminosity factor, the light-emitting device 3 and the light-emitting device 4 exhibited a current efficiency exceeding 15 cd/A, which is extremely high for a blue fluorescent device. The light-emitting device 3 and the light-emitting device 4 had an equivalent current efficiency.

As shown in FIG. 35 and Table 5, the light-emitting device 3 and the light-emitting device 4 exhibited an external quantum efficiency exceeding 11%, which is extremely high for a fluorescent device. The light-emitting device 3 and the light-emitting device 4 had an equivalent external quantum efficiency. Note that the external quantum efficiencies of the light-emitting device 3 and the light-emitting device 4 are higher than 7.5%, which is the theoretical maximum value. This is probably because of the effects due to TTA, as described above.

As shown in FIG. 34 and Table 5, the light-emitting device 3 and the light-emitting device 4 each have favorable driving voltage. The light-emitting device 3 and the light-emitting device 4 had an equivalent current efficiency.

From FIG. 36, the emission spectra of the light-emitting device 3 and the light-emitting device 4 respectively have a spectral peak at around 468 nm and 467 nm, and both have a full width at half maximum of approximately 44 nm; hence, the light-emitting device 3 and the light-emitting device 4 exhibited favorable blue light emission originating from BD-001, which is the guest material.

<Reliability of Light-Emitting Devices>

Figure 37:
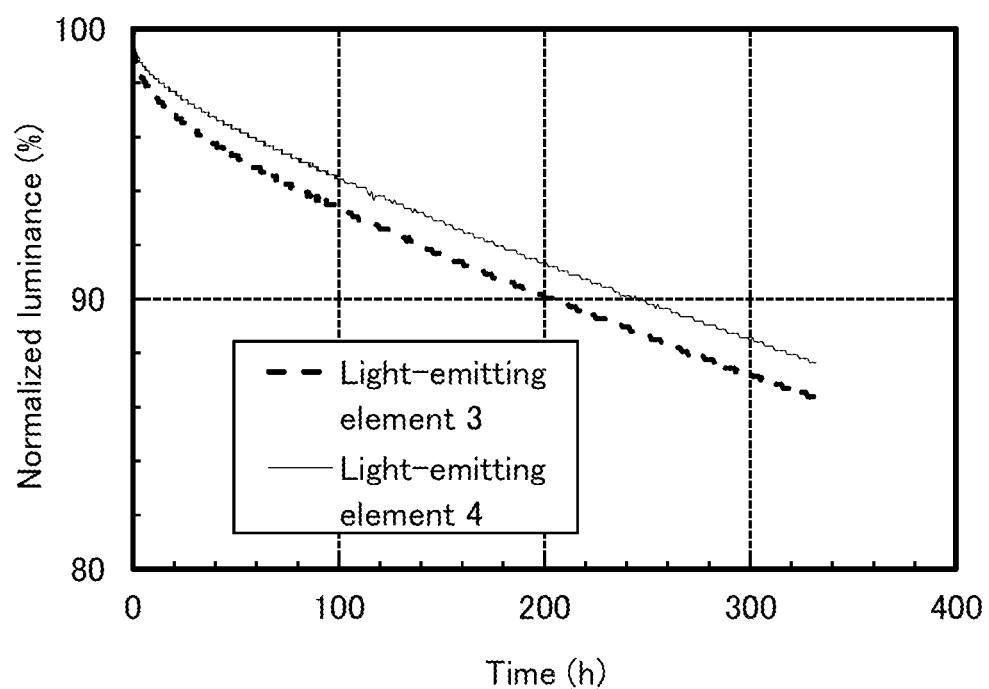
FIG. 37 A diagram showing results of a reliability test on light-emitting devices in Example.

Next, driving tests at a constant current of 2 mA were performed on the light-emitting device 3 and the light-emitting device 4. FIG. 37 shows the results. It was found from FIG. 37 that the light-emitting device 3 and the light-emitting device 4 have LT$_{90}$ exceeding 200 hours and thus have high reliability. It was also found from FIG. 37 that the light-emitting device 4 has higher reliability than the light-emitting device 3. Accordingly, it was found that the light-emitting device using the organic compound that has a benzo[a]anthracene skeleton at the 2-position of the anthracene skeleton and has different aryl groups at the 9-position and the 10-position of the anthracene skeleton can be a light-emitting device having extremely high reliability.

Example 9

This example will describe fabrication examples of light-emitting devices each of which includes the organic compound of one embodiment of the present invention and is different from those in Examples above, and the characteristics of the light-emitting devices. FIG. 1(A) illustrates a stacked-layer structure of the light-emitting devices fabricated in this example. Table 6 shows the details of the device structures. The organic compounds used in this example are shown below. Note that other embodiments or examples can be referred to for other organic compounds.

[Chemical Formula 34]
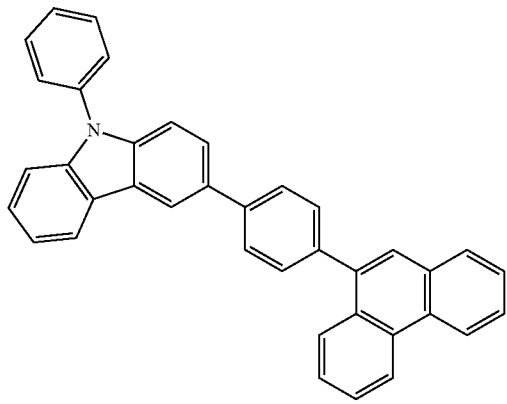
PCPPn
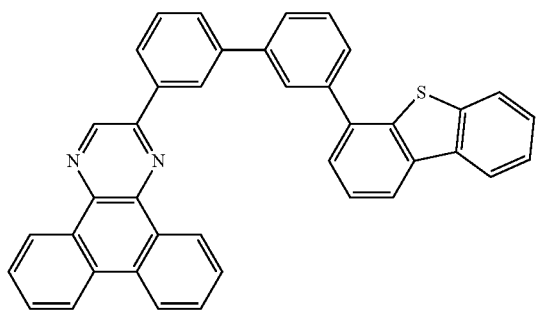
2mDBTBPDBq-II
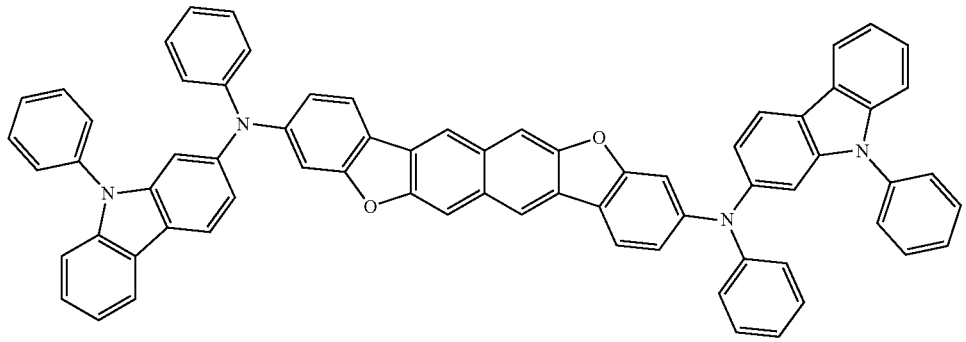
3.10PCA2Nbf(IV)-02
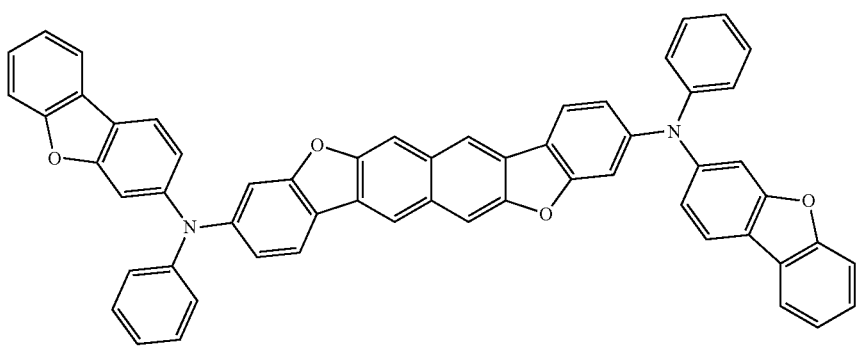
3.10FrA2Nbf(IV)-02

TABLE 6

| Layer | | Reference numeral | Thickness (nm) | Material | Weight ratio |
|---|---|---|---|---|---|
| Light-emitting device 5 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBAPA: 3,10PCA2Nbf(IV)-02 | 1:0.015 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |
| Light-emitting device 6 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBAPA: 3,10FrA2Nbf(IV)-02 | 1:0.015 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |
| Light-emitting device 7 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBA-αNPhA: 3,10PCA2Nbf(IV)-02 | 1:0.015 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |
| Light-emitting device 8 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBA-αNPhA: 3,10FrA2Nbf(IV)-02 | 1:0.015 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |

<<Fabrication of Light-Emitting Device 5>>

As the hole-injection layer 111 of the light-emitting device 5, PCPPn and MoO$_3$ were deposited over the electrode 101 by co-evaporation in a weight ratio (PCPPn: MoO$_3$) of 1:0.5 to a thickness of 10 nm.

Next, as the hole-transport layer 112, PCPPn was deposited over the hole-injection layer 111 by evaporation to a thickness of 30 nm.

Then, as the light-emitting layer 140, 2aBAPA and 3,10-bis[N-(9-phenyl-9H-carbazol-2-yl)-N-phenylamino]naphtho[2,3-b; 6,7-b']bisbenzofuran (abbreviation: 3,10PCA2Nbf(IV)-02) were deposited over the hole-transport layer 112 by co-evaporation at a weight ratio (2aBAPA: 3,10PCA2Nbf(IV)-02) of 1:0.015 to a thickness of 25 nm. Note that in the light-emitting layer 140, 3,10PCA2Nbf(IV)-02 is a guest material exhibiting fluorescence.

Next, as the electron-transport layer 118(1), 2mDBTBPDBq-II was deposited over the light-emitting layer 140 by evaporation to a thickness of 15 nm. Then, as the electron-transport layer 118(2), NBPhen was sequentially deposited over the electron-transport layer 118(1) by evaporation to a thickness of 10 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the light-emitting device 5 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm$^2$ and heat treatment at 80° C. for one hour were performed. Through the above steps, the light-emitting device 5 was obtained.

<<Fabrication of Light-Emitting Device 6 to Light-Emitting Device 8>>

The fabrication process of the light-emitting device 6 to the light-emitting device 8 is the same as that of the aforementioned light-emitting device 5, except for the fabrication step of the light-emitting layer 140. The device structures of the light-emitting device 6 to the light-emitting device 8 are as shown in Table 6; hence, the detailed description of the fabrication process is omitted. Note that in Table 6, 3,10-bis[N-(dibenzofuran-3-yl)-N-phenylamino] naphtho[2,3-b; 6,7-b']bisbenzofuran (abbreviation: 3,10FrA2Nbf(IV)-02) was used as a guest material of the light-emitting device 6 to the light-emitting device 8. The light-emitting layer 140 of each of the light-emitting device 6 to the light-emitting device 8 was formed by a vacuum evaporation method, as in the light-emitting device 5.

The light-emitting device 5 and the light-emitting device 7 contain the same guest material but different host materials. Similarly, the light-emitting device 6 and the light-emitting device 8 contain the same guest material but different host materials. The light-emitting device 5 and the light-emitting device 6 contain the same host material but different guest materials. Similarly, the light-emitting device 7 and the light-emitting device 8 contain the same host material but different guest materials.

The light-emitting device 5 to the light-emitting device 8 are examples of light-emitting devices using a host material having a benzo[a]anthracene skeleton and a guest material having a benzofuran skeleton in a luminophore.

<Characteristics of Light-Emitting Devices>

Next, the characteristics of the fabricated light-emitting device 5 to light-emitting device 8 were measured. The measurement conditions of the light-emitting devices were similar to those described in Example above.

Figure 38:
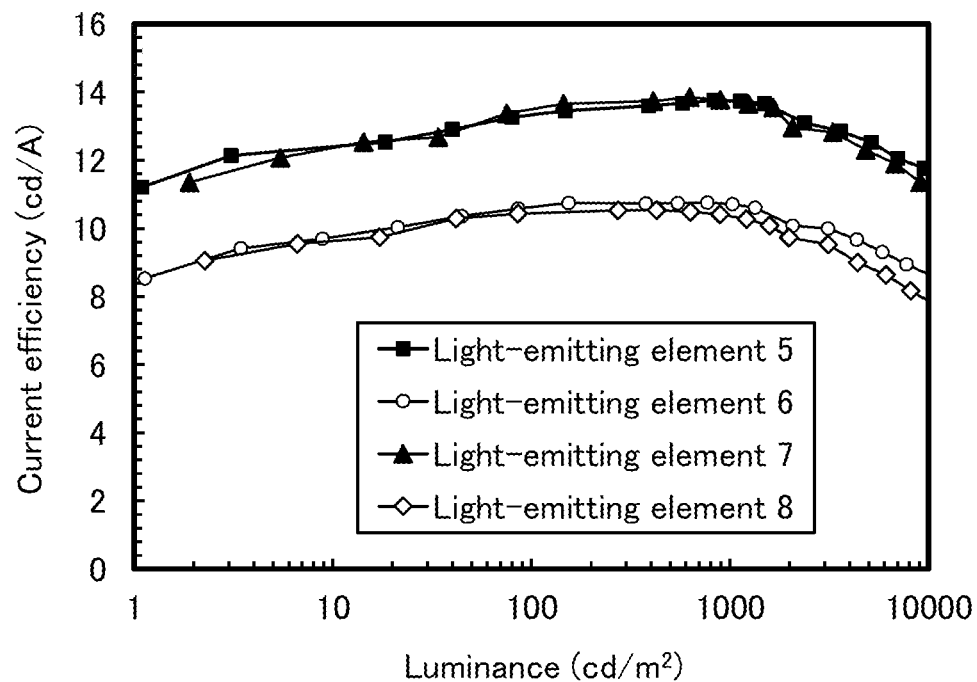
FIG. 38 A diagram showing current efficiency-luminance characteristics of light-emitting devices in Example.
Figure 39:
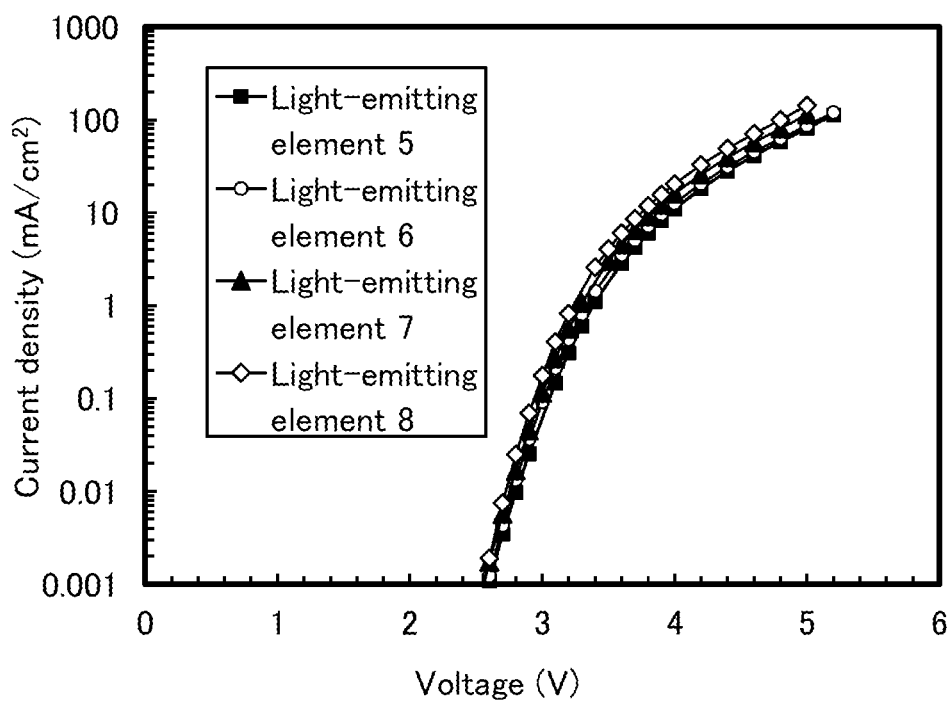
FIG. 39 A diagram showing current density-voltage characteristics of light-emitting devices in Example.
Figure 40:
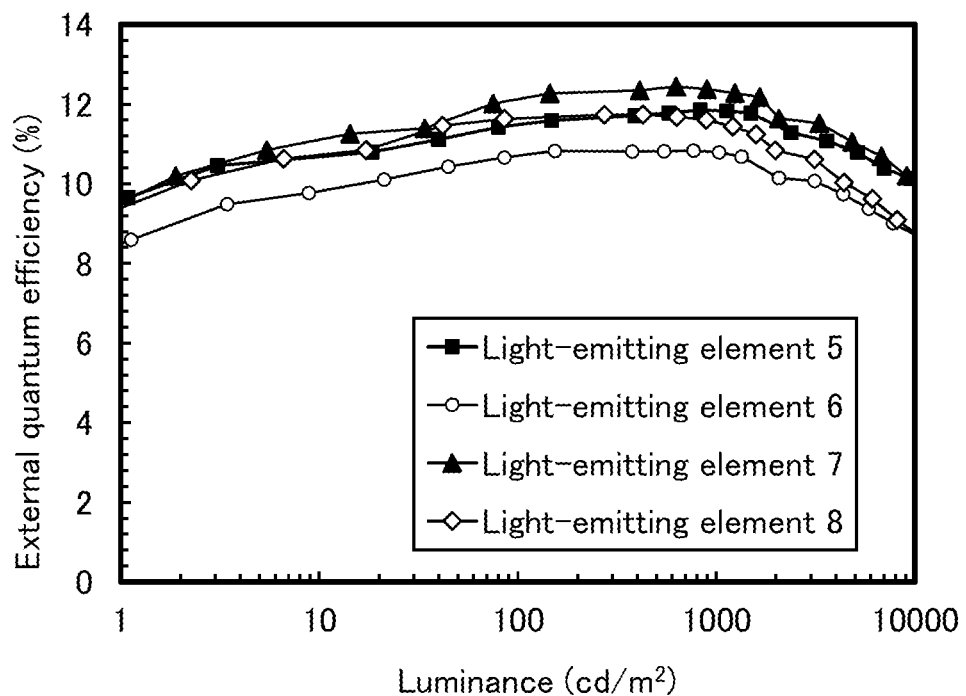
FIG. 40 A diagram showing external quantum efficiency-luminance characteristics of light-emitting devices in Example.
Figure 41:
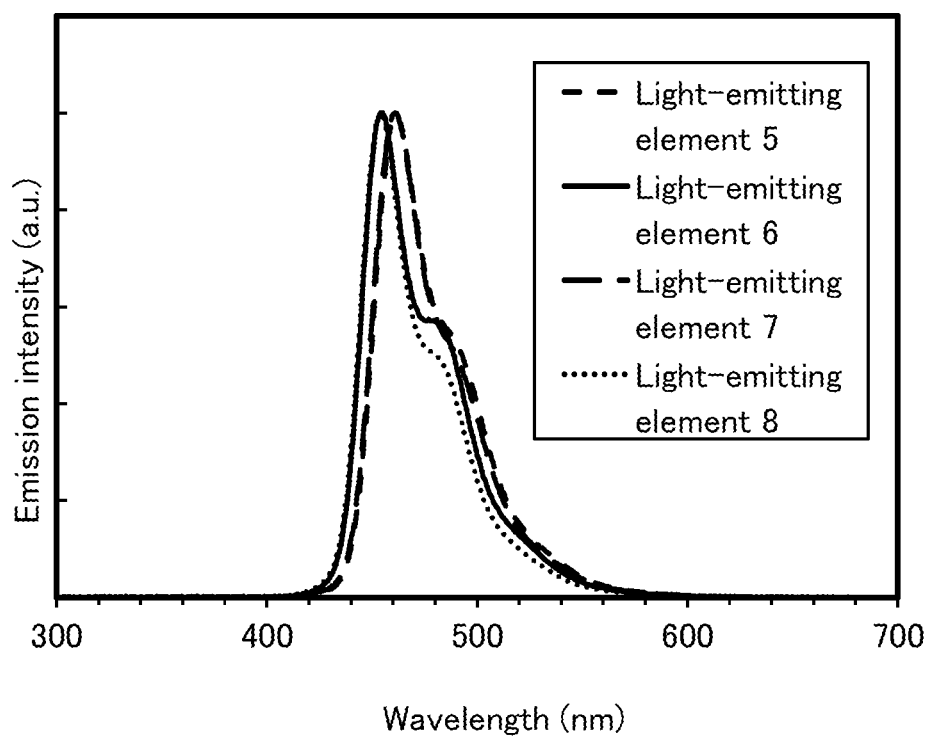
FIG. 41 A diagram showing emission spectra of light-emitting devices in Example.

FIG. 38 shows the current efficiency-luminance characteristics of the light-emitting device 5 to the light-emitting device 8. FIG. 39 shows the current density-voltage characteristics. FIG. 40 shows the external quantum efficiency-luminance characteristics. FIG. 41 shows emission spectra when current at a current density of 12.5 mA/cm$^2$ was supplied to the light-emitting device 5 to the light-emitting device 8.

Table 7 shows the device characteristics of the light-emitting device 5 to the light-emitting device 8 at around 1000 cd/m$^2$.

As shown in FIG. 39 and Table 7, the light-emitting device 5 to the light-emitting device 8 each have favorable driving voltage. The light-emitting device 5 to the light-emitting device 8 had equivalent driving voltage.

FIG. 41 shows that the emission spectra of the light-emitting device 5 to the light-emitting device 8 respectively have a spectral peak at around 462 nm, 454 nm, 461 nm, and 454 nm and a full width at half maximum of approximately 43 nm, 45 nm, 41 nm, and 37 nm; hence, the light-emitting device 5 to the light-emitting device 8 exhibited favorable blue light emission originating from their guest materials.

<Reliability of Light-Emitting Devices>

Figure 42:
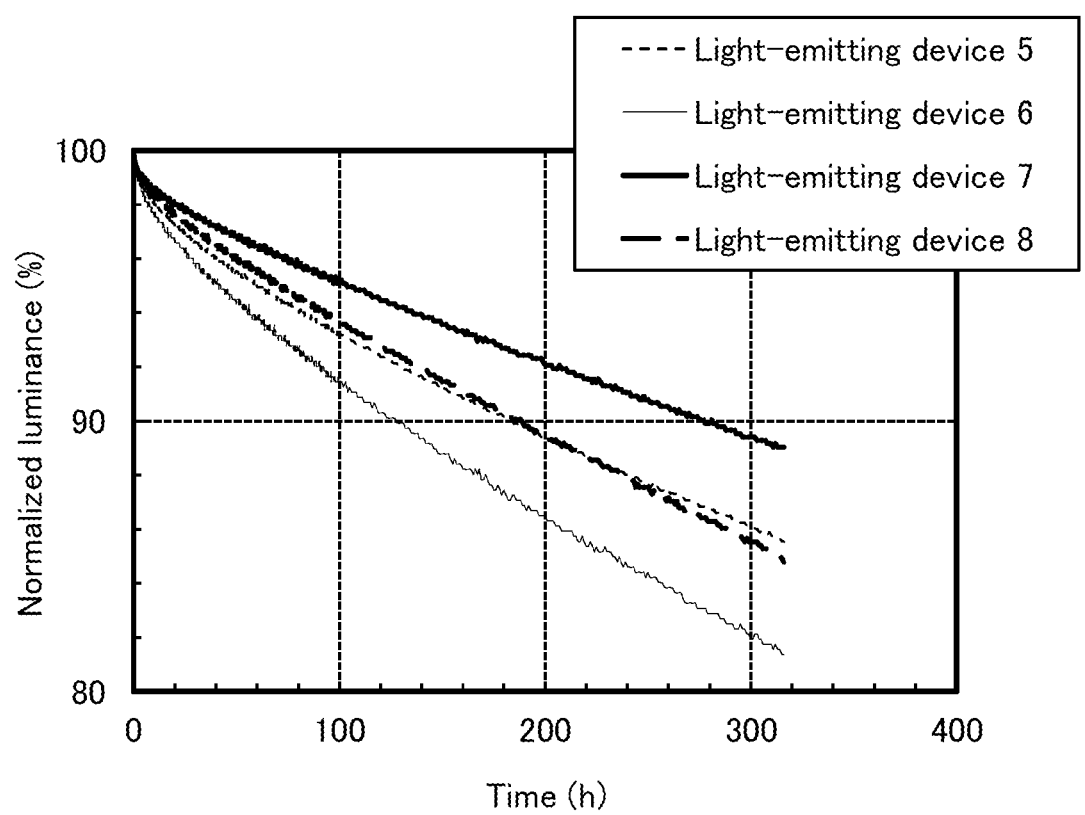
FIG. 42 A diagram showing results of a reliability test on of light-emitting devices in Example.

Next, driving tests at a constant current of 2 mA were performed on the light-emitting device 5 to the light-emitting device 8. FIG. 42 shows the results. It was found from FIG. 42 that the light-emitting device 5 to the light-emitting device 8 each have high reliability. When the light-emitting device 5 and the light-emitting device 7, which contain the same guest material, are compared to each other and the light-emitting device 6 and the light-emitting device 8,

TABLE 7

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 5 | 3.90 | 8.24 | (0.140, 0.156) | 1131 | 13.7 | 11.1 | 11.8 |
| Light-emitting device 6 | 3.90 | 9.63 | (0.141, 0.121) | 1031 | 10.7 | 8.6 | 10.8 |
| Light-emitting device 7 | 3.70 | 6.51 | (0.140, 0.146) | 897 | 13.8 | 11.7 | 12.4 |
| Light-emitting device 8 | 3.70 | 8.54 | (0.141, 0.104) | 889 | 10.4 | 8.8 | 11.6 |

As shown in FIG. 38 and Table 7, despite emitting blue light with a low luminosity factor, the light-emitting device 5 to the light-emitting device 8 each exhibited a current efficiency exceeding 10 cd/A, which is high for a blue fluorescent device. The light-emitting device 5 and the light-emitting device 7 have an equivalent current efficiency, and the light-emitting device 6 and the light-emitting device 8 have an equivalent current efficiency. Meanwhile, when the light-emitting device 5 and the light-emitting device 7 are compared with the light-emitting device 6 and the light-emitting device 8, the light-emitting device 5 and the light-emitting device 7 have a higher current efficiency. This is because light emission exhibited by the guest material contained in the light-emitting device 5 and the light-emitting device 7 has a higher luminosity factor than light emission exhibited by the guest material contained in the light-emitting device 6 and the light-emitting device 8. Note that there is no difference in current efficiency between the host materials.

As shown in FIG. 40 and Table 7, the light-emitting device 5 to the light-emitting device 8 exhibited an external quantum efficiency exceeding 10%, which is extremely high for a fluorescent device. The light-emitting device 5 to the light-emitting device 8 had an equivalent external quantum efficiency. Note that the external quantum efficiencies of the light-emitting device 5 to the light-emitting device 8 are higher than 7.5%, which is the theoretical maximum value. This is probably because of the effects due to TTA, as described above.

which contain the same guest material, are compared to each other, the light-emitting device 7 and the light-emitting device 8 have higher reliability. These results demonstrate that, as in Example 8, the light-emitting device using the organic compound that has the benzo[a]anthracene skeleton at the 2-position of the anthracene skeleton and has different aryl groups at the 9-position and the 10-position of the anthracene skeleton can be a light-emitting device having extremely high reliability.

From the above results, the use of the host material having a benzo[a]anthracene skeleton and the guest material having a benzofuran skeleton in a luminophore enables fabrication of a light-emitting device having high emission efficiency and high reliability.

Example 10

This example will describe a fabrication example of light-emitting devices each of which includes the organic compound of one embodiment of the present invention and is different from that in Example 7, and the characteristics of the light-emitting devices. FIG. 1(A) illustrates a stacked-layer structure of the light-emitting devices fabricated in this example. Table 8 shows the details of the device structures. The organic compound used in this example is shown below. Note that other embodiments or examples can be referred to for other organic compounds.

[Chemical Formula 35]

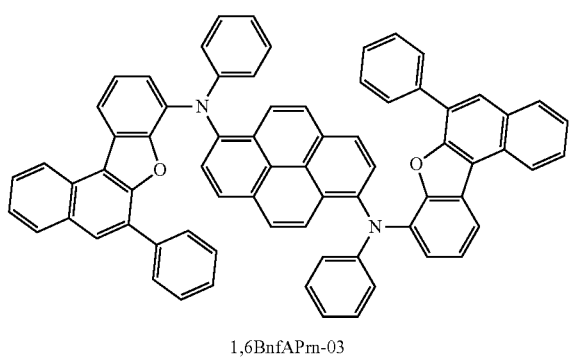

1,6BnfAPrn-03

<<Fabrication of Light-Emitting Device 9 and Light-Emitting Device 10>>

The fabrication process of the light-emitting device 9 and the light-emitting device 10 is the same as that of the aforementioned light-emitting device 5, except for the fabrication step of the light-emitting layer 140. The device structures of the light-emitting device 9 and the light-emitting device 10 are as shown in Table 8; hence, the detailed description of the fabrication process is omitted. Note that in Table 8, N,N-(pyrene-1,6-diyl)bis[(6,N-diphenylbenzo[b]naphtho[1,2-d]furan)-8-amine] (abbreviation: 1,6BnfAPrn-03) was used as a guest material of the light-emitting device 9. The light-emitting layer 140 of each of the light-emitting device 9 and the light-emitting device 10 was formed by a vacuum evaporation method, as in the light-emitting device 5.

The luminophore of the guest material used in the light-emitting device 9 is a pyrene skeleton and does not have a benzofuran skeleton. Meanwhile, the luminophore of the guest material used in the light-emitting device 10 is a naphthobisbenzofuran skeleton; i.e., it has a benzofuran skeleton. That is, the light-emitting device 10 is an example of a light-emitting device using a host material having a benzo[a]anthracene skeleton and a guest material having a benzofuran skeleton in a luminophore.

<Characteristics of Light-Emitting Devices>

Next, the characteristics of the fabricated light-emitting device 9 and light-emitting device 10 were measured. The measurement conditions of the light-emitting devices were similar to those described in Example above.

TABLE 8

| | Layer | Reference numeral | Thickness (nm) | Material | Weight ratio |
|---|---|---|---|---|---|
| Light-emitting device 9 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBAPA: 1,6BnfAPrn-03 | 1:0.03 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |
| Light-emitting device 10 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBAPA: 3,10PCA2Nbf(IV)-02 | 1:0.03 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |

Figure 43:
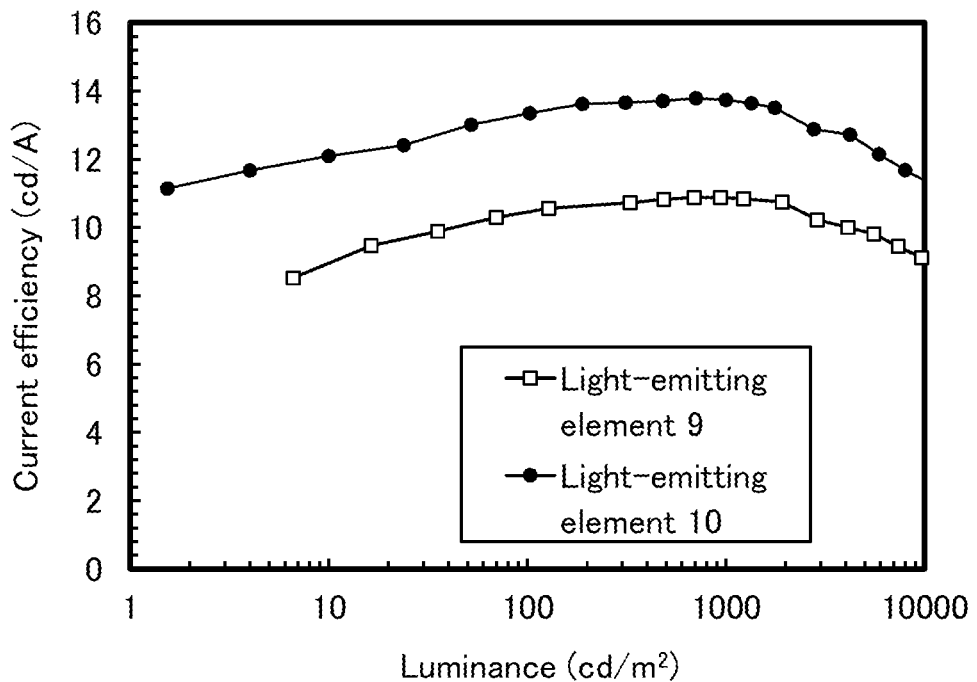
FIG. 43 A diagram showing current efficiency-luminance characteristics of light-emitting devices in Example.
Figure 44:
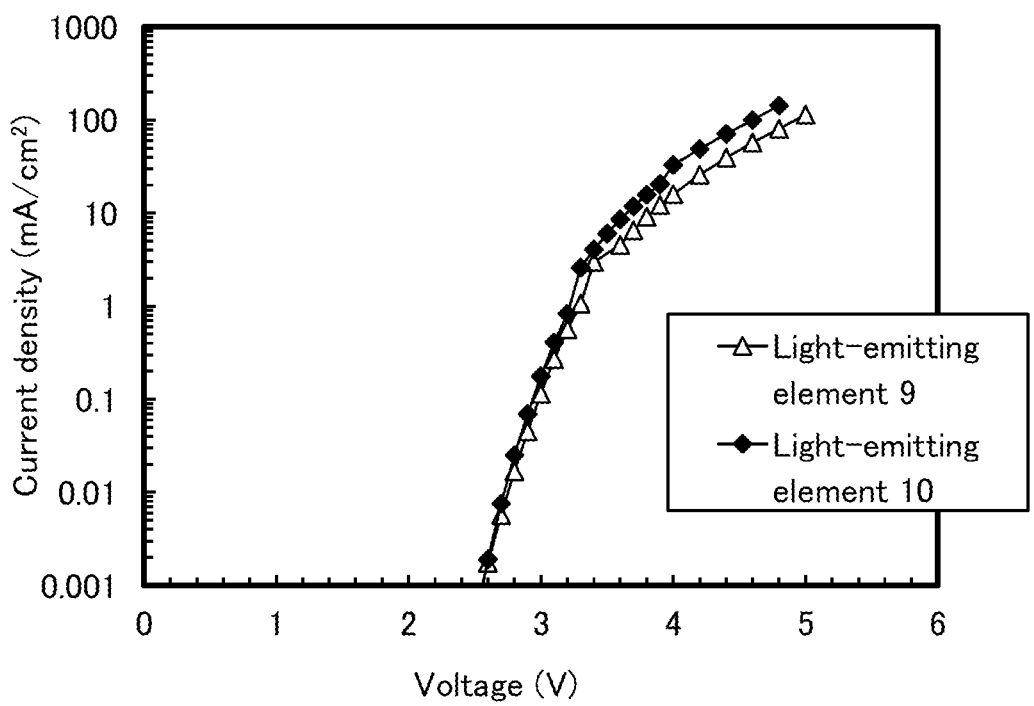
FIG. 44 A diagram showing current density-voltage characteristics of light-emitting devices in Example.
Figure 45:
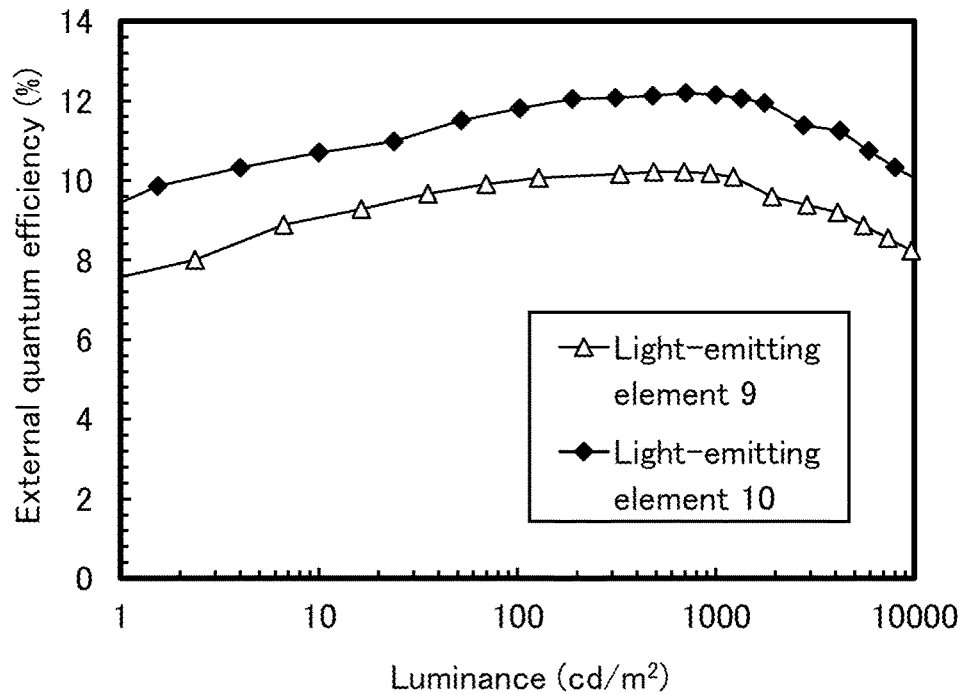
FIG. 45 A diagram showing external quantum efficiency-luminance characteristics of light-emitting devices in Example.
Figure 46:
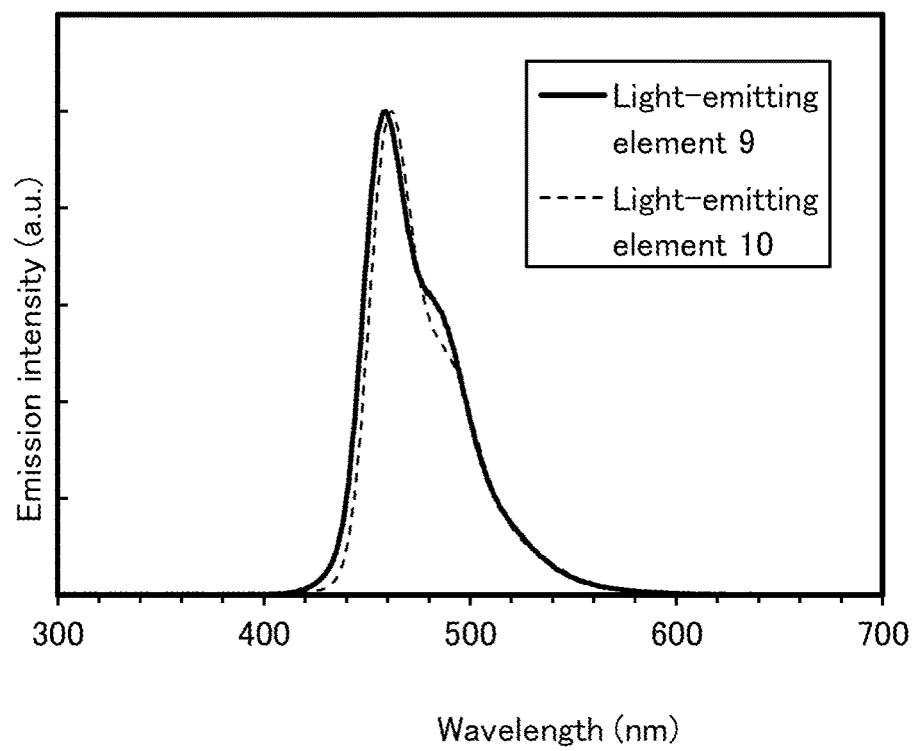
FIG. 46 A diagram showing emission spectra of light-emitting devices in Example.

FIG. 43 shows the current efficiency-luminance characteristics of the light-emitting device 9 and the light-emitting device 10. FIG. 44 shows the current density-voltage characteristics. FIG. 45 shows the external quantum efficiency-luminance characteristics. FIG. 46 shows emission spectra when current at a current density of 12.5 mA/cm$^2$ was supplied to the light-emitting device 9 and the light-emitting device 10.

Table 9 shows the device characteristics of the light-emitting device 9 and the light-emitting device 10 at around 1000 cd/m$^2$.

TABLE 9

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 9 | 3.90 | 8.64 | (0.140, 0.137) | 937 | 10.8 | 8.7 | 10.2 |
| Light-emitting device 10 | 3.80 | 7.29 | (0.140, 0.150) | 1001 | 13.7 | 11.4 | 12.1 |

As shown in FIG. 43 and Table 9, despite emitting blue light with a low luminosity factor, the light-emitting device 9 and the light-emitting device 10 each exhibited a current efficiency exceeding 10 cd/A, which is high for a blue fluorescent device. In particular, the light-emitting device 10 exhibited a current efficiency exceeding 13 cd/A, which is extremely high for a blue fluorescent device.

As shown in FIG. 45 and Table 9, the light-emitting device 9 and the light-emitting device 10 exhibited an external quantum efficiency exceeding 10%, which is high for a fluorescent device. In particular, the light-emitting device 10 exhibited an external quantum efficiency exceeding 13%, which is extreme for a fluorescent device. It was thus found that in the case of using the host material having a benzo[a]anthracene skeleton, the light-emitting device using the guest material having a benzofuran skeleton in the luminophore obtained higher emission efficiency than the light-emitting device using a pyrene skeleton in the luminophore. Note that the external quantum efficiencies of the light-emitting device 9 and the light-emitting device 10 are higher than 7.5%, which is the theoretical maximum value. This is probably because of the effects due to TTA, as described above.

As shown in FIG. 44 and Table 9, the light-emitting device 9 and the light-emitting device 10 each have favorable driving voltage. It was found from FIG. 44 that the light-emitting device 10 has lower driving voltage than the light-emitting device 9. It was thus found that in the case of using the host material having a benzo[a]anthracene skeleton, the light-emitting device using the guest material having a benzofuran skeleton in the luminophore demonstrates lower driving voltage than the light-emitting device using an anthracene skeleton in the luminophore.

As shown in FIG. 46, the emission spectra of the light-emitting device 9 and the light-emitting device 10 respectively have a spectrum peak at around 459 nm and 462 nm and a full width at half maximum of approximately 46 nm and 40 nm; thus, the light-emitting device 9 and the light-emitting device 10 exhibited blue light emission derived from their guest materials.

<Reliability of Light-Emitting Devices>

Figure 47:
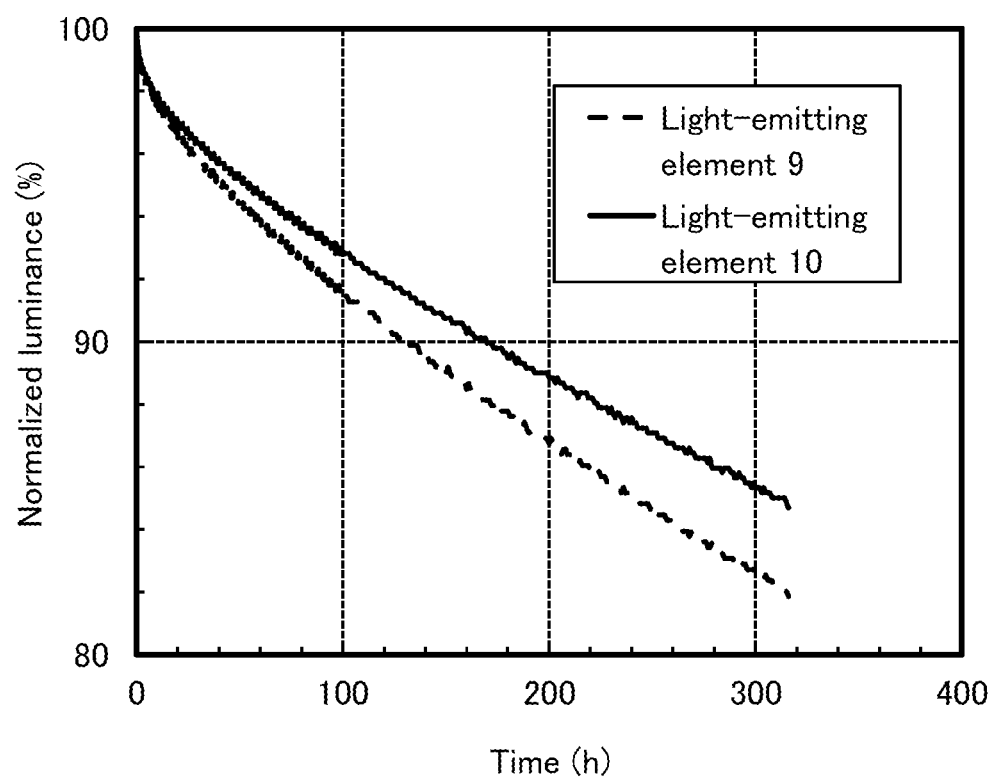
FIG. 47 A diagram showing results of a reliability test on light-emitting devices in Example.

Next, driving tests at a constant current of 2 mA were performed on the light-emitting device 9 and the light-emitting device 10. FIG. 47 shows the results. It was found from FIG. 47 that the light-emitting device 9 and the light-emitting device 10 have high reliability. It was also found from FIG. 47 that the light-emitting device 10 has higher reliability than the light-emitting device 9. It was thus found that in the case of using the host material having a benzo[a]anthracene skeleton, the light-emitting device using the guest material having a benzofuran skeleton in the luminophore has higher reliability than the light-emitting device using a pyrene skeleton in the luminophore.

Example 11

This example will describe fabrication examples of light-emitting devices each of which includes the organic compound of one embodiment of the present invention and is different from those in Examples above, and the characteristics of the light-emitting devices. FIG. 1(A) illustrates a stacked-layer structure of the light-emitting devices fabricated in this example. Table 10 shows the details of the device structures. Note that other embodiments or examples can be referred to for organic compounds used in this example.

TABLE 10

| | Layer | Reference numeral | Thickness (nm) | Material | Weight ratio |
|---|---|---|---|---|---|
| Light-emitting device 11 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2aBAPA | — |
| | Light-emitting layer | 140 | 25 | 2aBAPA: 1,6BnfAPrn-03 | 1:0.03 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |
| Light-emitting device 12 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2aBAPA-02 | — |
| | Light-emitting layer | 140 | 25 | 2aBAPA-02: 1,6BnfAPrn-03 | 1:0.03 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |

<<Fabrication of Light-Emitting Device 11>>

As the hole-injection layer 111 of the light-emitting device 11, PCPPn and MoO$_3$ were deposited over the electrode 101 by co-evaporation in a weight ratio (PCPPn:MoO$_3$) of 1:0.5 to a thickness of 10 nm.

Next, as the hole-transport layer 112, PCPPn was deposited over the hole-injection layer 111 by evaporation to a thickness of 30 nm.

Then, as the light-emitting layer 140, 2aBAPA and 1,6BnfAPrn-03 were deposited over the hole-transport layer 112 by co-evaporation at a weight ratio (2aBAPA:1,6BnfAPrn-03) of 1:0.03 to a thickness of 25 nm. Note that in the light-emitting layer 140, 1,6BnfAPrn-03 is a guest material that exhibits fluorescence.

Next, as the electron-transport layer 118(1), 2aBAPA was deposited over the light-emitting layer 140 by evaporation to a thickness of 15 nm. Then, as the electron-transport layer 118(2), NBPhen was sequentially deposited over the electron-transport layer 118(1) by evaporation to a thickness of 10 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the light-emitting device 11 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm$^2$ and heat treatment at 80° C. for one hour were performed. Through the above steps, the light-emitting device 11 was obtained.

<<Fabrication of Light-Emitting Device 12>>

The fabrication process of the light-emitting device 12 is the same as that of the light-emitting device 11 described above, except for the fabrication steps of the light-emitting layer 140 and the electron-transport layer 118(1). The device structure of the light-emitting device 12 is as shown in Table 10; hence, the detailed description of the fabrication process is omitted. The light-emitting layer 140 and the electron-transport layer 118(1) of the light-emitting device 11 were formed by a vacuum evaporation method, as in the light-emitting device 11.

The device structures of the light-emitting device 11 and the light-emitting device 12 are the same, except for a host material used for the light-emitting layer 140 and a material used for the electron-transport layer 118(1). 2aBAPA is used in the light-emitting device 11, and 2aBAPA-02 is used in the light-emitting device 12. The difference between these two organic compounds is the bonding position between benzo[a]anthracene and anthracene. 2aBAPA is an organic compound in which an anthracene skeleton is bonded to the 4-position of benzo[a]anthracene, whereas 2aBAPA-02 is an organic compound in which an anthracene skeleton is bonded to the 7-position of benzo[a]anthracene.

<Characteristics of Light-Emitting Devices>

Next, the characteristics of the fabricated light-emitting device 11 and light-emitting device 12 were measured. The measurement conditions of the light-emitting devices were similar to those described in Example above.

Figure 48:
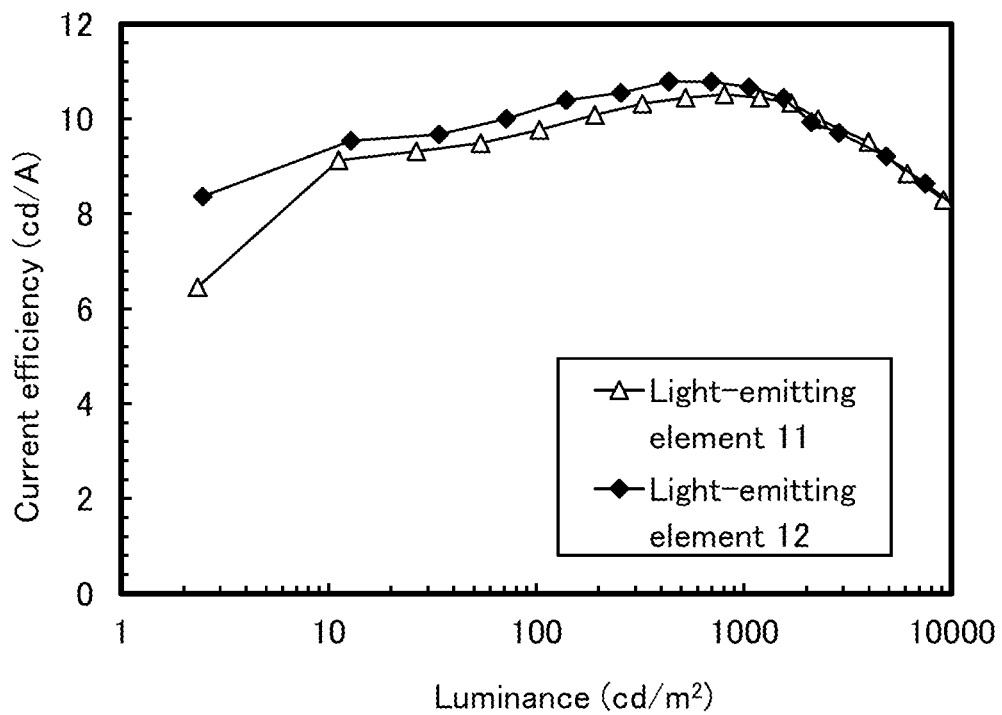
FIG. 48 A diagram showing current efficiency-luminance characteristics of light-emitting devices in Example.
Figure 49:
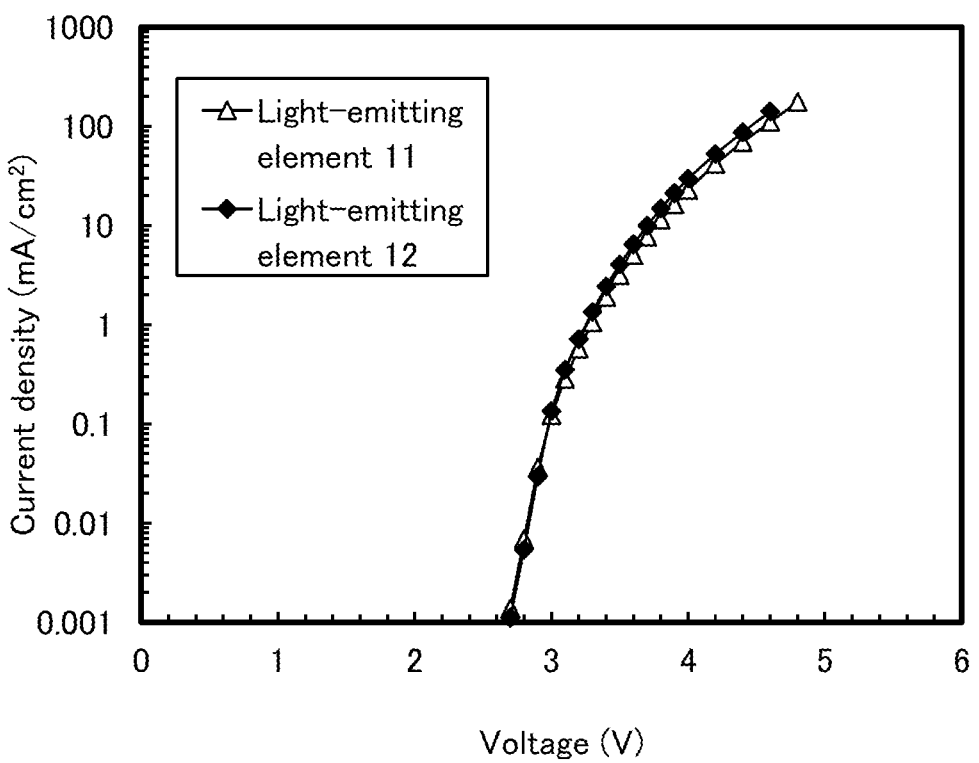
FIG. 49 A diagram showing current density-voltage characteristics of light-emitting devices in Example.
Figure 50:
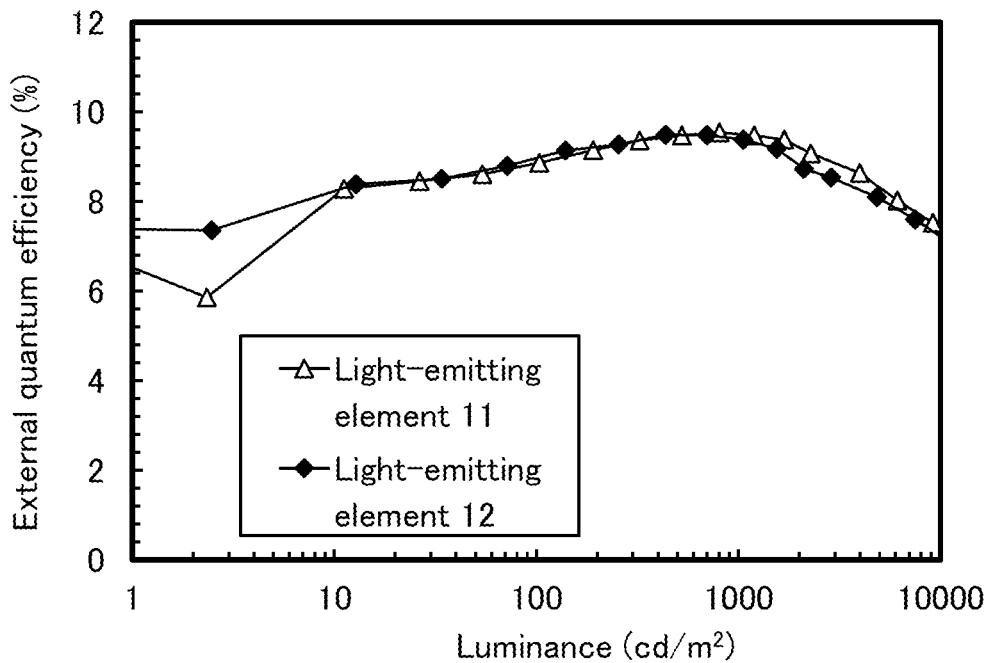
FIG. 50 A diagram showing external quantum efficiency-luminance characteristics of light-emitting devices in Example.
Figure 51:
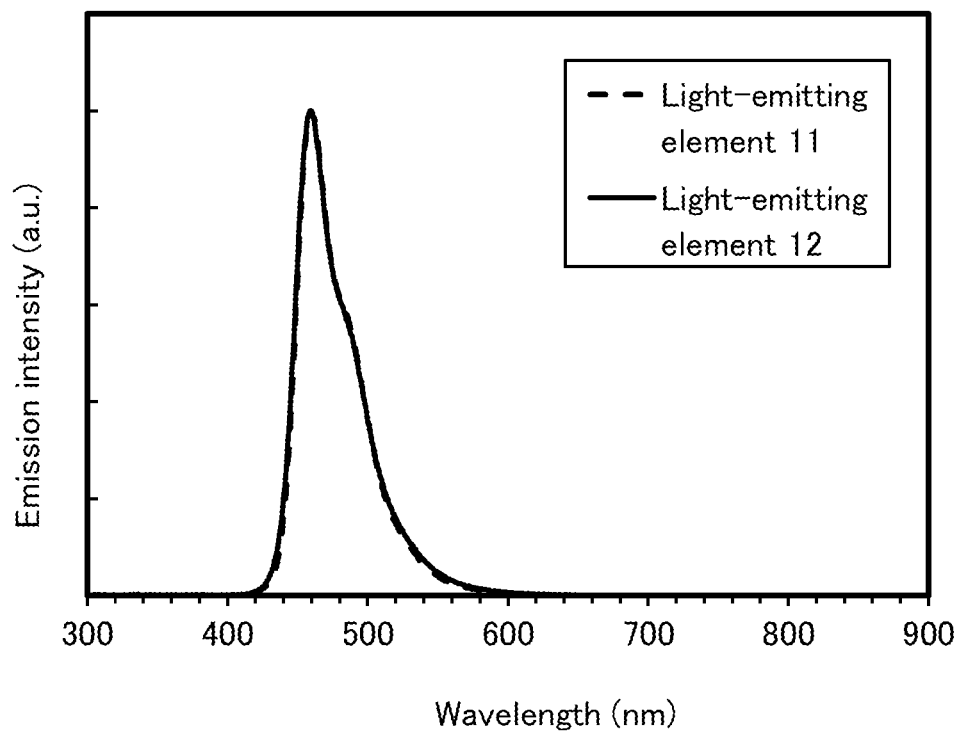
FIG. 51 A diagram showing emission spectra of light-emitting devices in Example.

FIG. 48 shows the current efficiency-luminance characteristics of the light-emitting device 11 and the light-emitting device 12. FIG. 49 shows the current density-voltage characteristics. FIG. 50 shows the external quantum efficiency-luminance characteristics. FIG. 51 shows emission spectra in the case where current at a current density of 12.5 mA/cm$^2$ was supplied to the light-emitting device 11 and the light-emitting device 12.

Table 11 shows the device characteristics of the light-emitting device 11 and the light-emitting device 12 at around 1000 cd/m$^2$.

As shown in FIG. 48 and Table 11, despite emitting blue light with a low luminosity factor, the light-emitting device 11 and the light-emitting device 12 each exhibited a current efficiency exceeding 10 cd/A, which is high for a blue fluorescent device. The light-emitting device 11 and the light-emitting device 12 have an equivalent current efficiency.

As shown in FIG. 50 and Table 11, the light-emitting device 11 and the light-emitting device 12 exhibited an external quantum efficiency exceeding 9%, which is high for a fluorescent device. The light-emitting device 11 and the light-emitting device 12 had an equivalent external quantum efficiency. Note that the external quantum efficiencies of the light-emitting device 11 and the light-emitting device 12 are higher than 7.5%, which is the theoretical maximum value. This is probably because of the effects due to TTA, as described above.

As shown in FIG. 49 and Table 11, the light-emitting device 11 and the light-emitting device 12 each have favorable driving voltage. The light-emitting device 11 and the light-emitting device 12 had equivalent driving voltage.

From FIG. 51, the emission spectra of the light-emitting device 11 and the light-emitting device 12 both have a spectral peak at around 459 nm and a full width at half maximum of approximately 45 nm; hence, the light-emitting device 11 and the light-emitting device 12 exhibited blue light emission originating from 1,6BnfAPrn-03, which is the guest material.

<Reliability of Light-Emitting Devices>

Figure 52:
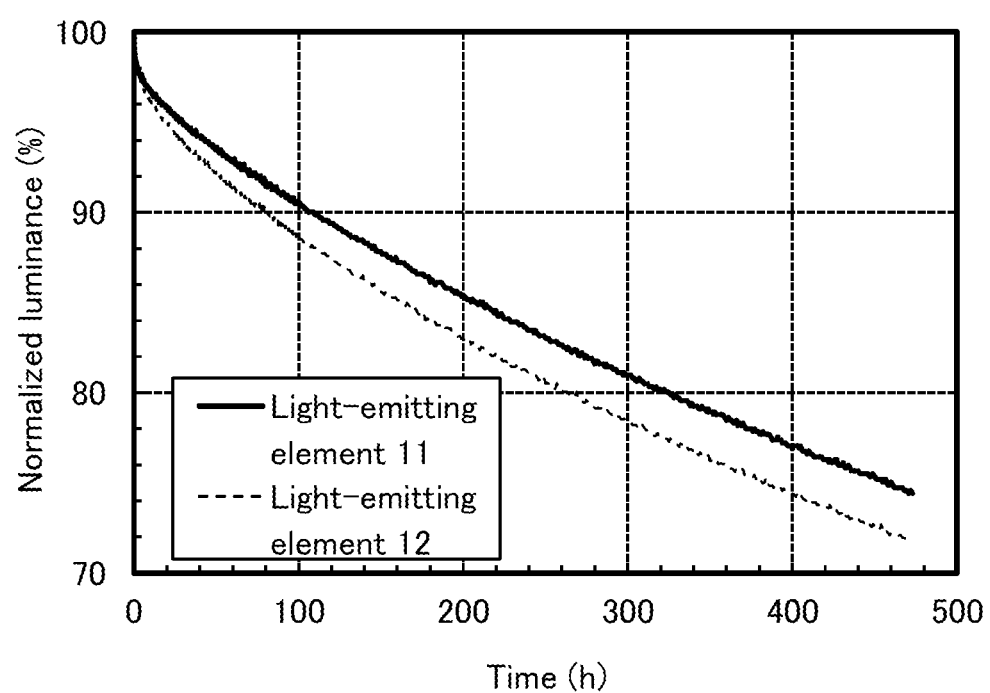
FIG. 52 A diagram showing results of a reliability test on light-emitting devices in Example.

Next, driving tests at a constant current of 2 mA were performed on the light-emitting device 11 and the light-emitting device 12. FIG. 52 shows the results. It was found from FIG. 52 that the light-emitting device 11 and the light-emitting device 12 have high reliability. It was also found from FIG. 52 that the light-emitting device 11 has higher reliability than the light-emitting device 12. Accordingly, it was found that the organic compound in which the anthracene skeleton is bonded to the 4-position of the benzo[a]anthracene skeleton enables fabrication of a light-emitting device having higher reliability than in the case of using the organic compound in which the anthracene skeleton is bonded to the 7-position of the benzo[a]anthracene skeleton.

Example 12

This example will describe a fabrication example of a light-emitting device that includes the organic compound of one embodiment of the present invention and is different from those in Examples above, and the characteristics of the light-emitting device. FIG. 1(A) illustrates a stacked-layer structure of the light-emitting device fabricated in this example. Table 12 shows the details of the device structure. Note that other embodiments or examples can be referred to for organic compounds used in this example.

TABLE 11

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 11 | 3.70 | 7.66 | (0.141, 0.143) | 805 | 10.5 | 8.9 | 9.5 |
| Light-emitting device 12 | 3.70 | 9.93 | (0.144, 0.148) | 1059 | 10.7 | 9.1 | 9.4 |

TABLE 12

| Layer | | Reference numeral | Thickness (nm) | Material | Weight ratio |
|---|---|---|---|---|---|
| Light-emitting device 13 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBAPA: 1,6mMemFLPAPrn | 1:0.03 |
| | Hole-transport layer | 112 | 30 | PCPPn | — |
| | Hole-injection layer | 111 | 10 | PCPPn: MoO$_3$ | 1:0.5 |
| | Electrode | 101 | 70 | ITSO | — |

<<Fabrication of Light-Emitting Device 13>>

As the hole-injection layer 111 of the light-emitting device 13, PCPPn and MoO$_3$ were deposited over the electrode 101 by co-evaporation in a weight ratio (PCPPn:MoO$_3$) of 1:0.5 to a thickness of 10 nm.

Next, as the hole-transport layer 112, PCPPn was deposited over the hole-injection layer 111 by evaporation to a thickness of 30 nm.

Then, as the light-emitting layer 140, 2aBAPA and 1,6mMemFLPAPrn were deposited over the hole-transport layer 112 by co-evaporation in a weight ratio (2aBAPA:1,6mMemFLPAPrn) of 1:0.03 to a thickness of 25 nm. Note that in the light-emitting layer 140, 1,6mMemFLPAPrn is a guest material that exhibits fluorescence.

Next, as the electron-transport layer 118(1), 2mDBT-BPDBq-II was deposited over the light-emitting layer 140 by evaporation to a thickness of 15 nm. Then, as the electron-transport layer 118(2), NBPhen was sequentially deposited over the electron-transport layer 118(1) by evaporation to a thickness of 10 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the light-emitting device 13 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm$^2$ and heat treatment at 80° C. for one hour were performed. Through the above steps, the light-emitting device 13 was obtained.

<Characteristics of Light-Emitting Device>

Next, the characteristics of the fabricated light-emitting device 13 were measured. The measurement conditions of the light-emitting device were similar to those described in Example above.

Figure 53:
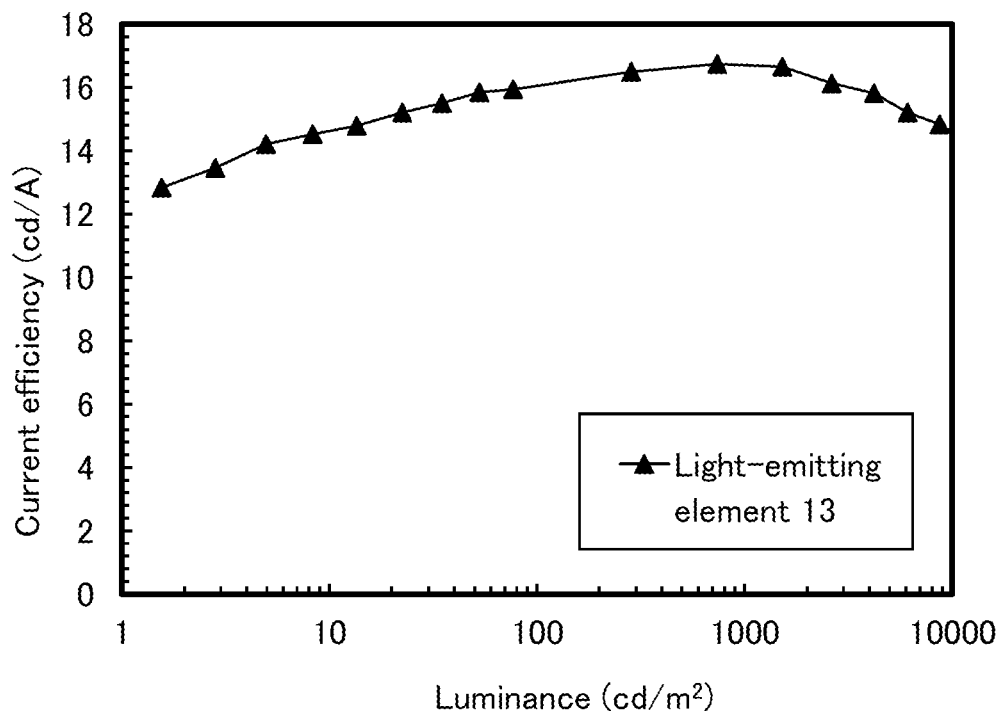
FIG. 53 A diagram showing current efficiency-luminance characteristics of a light-emitting device in Example.
Figure 54:
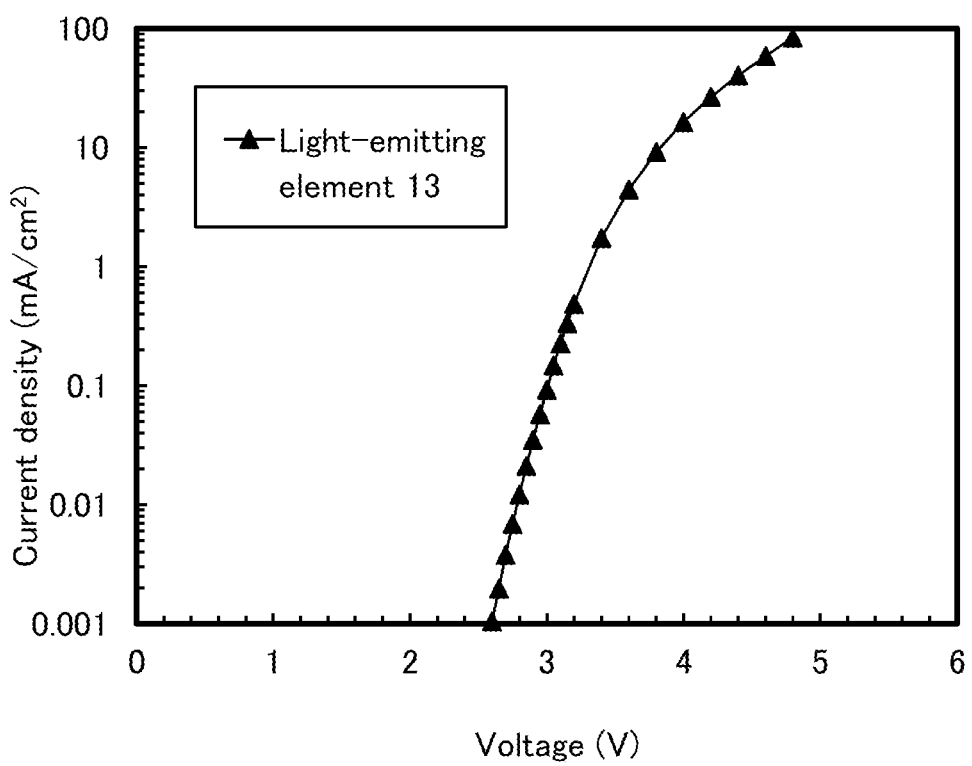
FIG. 54 A diagram showing current density-voltage characteristics of a light-emitting device in Example.
Figure 55:
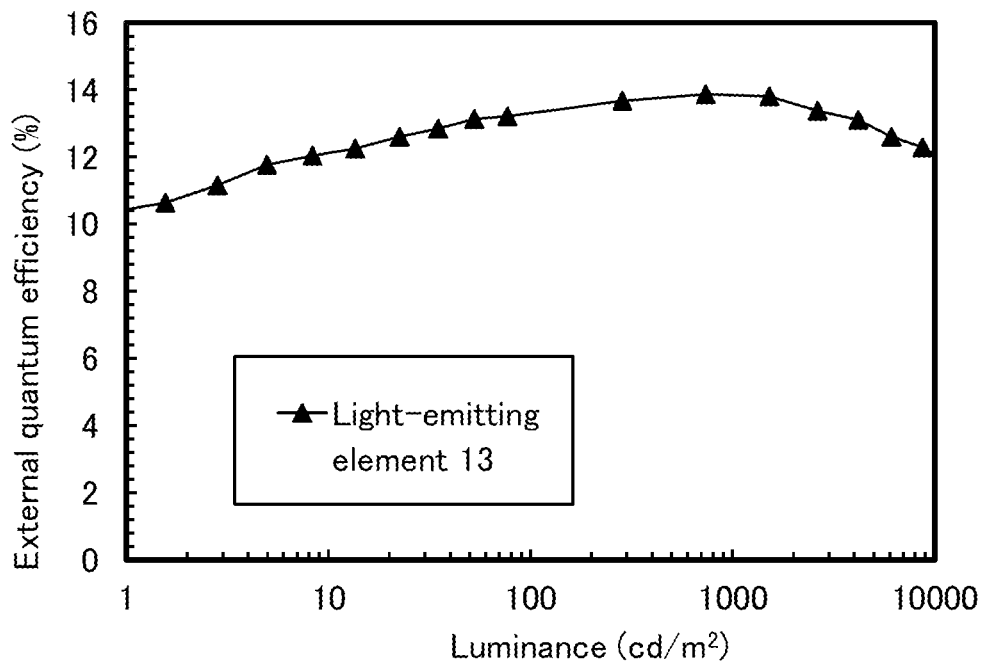
FIG. 55 A diagram showing external quantum efficiency-luminance characteristics of a light-emitting device in Example.
Figure 56:
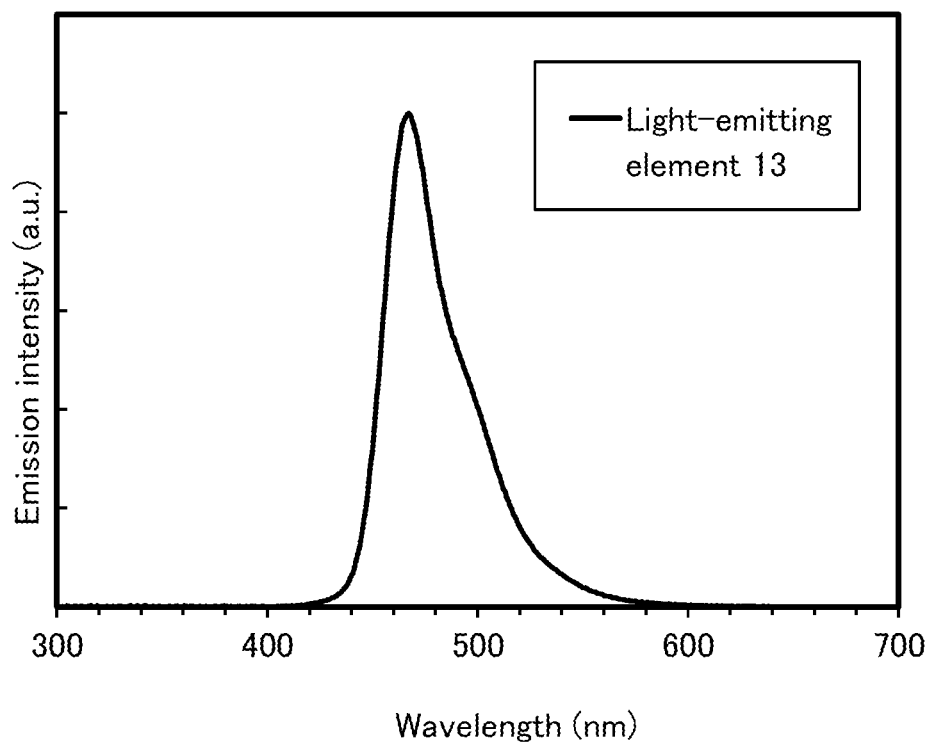
FIG. 56 A diagram showing an emission spectrum of a light-emitting device in Example.

FIG. 53 shows current efficiency-luminance characteristics of the light-emitting device 13. FIG. 54 shows the current density-voltage characteristics. FIG. 55 shows the external quantum efficiency-luminance characteristics. FIG. 56 shows emission spectrum in the case where current at a current density of 12.5 mA/cm$^2$ was supplied to the light-emitting device 13.

Table 13 shows the device characteristics of the light-emitting device 13 at around 1000 cd/m$^2$.

TABLE 13

| | Voltage (V) | Current density (mA/cm$^2$) | CIE chromaticity (x, y) | Luminance (cd/m$^2$) | Current efficiency (cd/A) | Power efficiency (lm/w) | External quantum efficiency (%) |
|---|---|---|---|---|---|---|---|
| Light-emitting device 13 | 3.60 | 4.41 | (0.138, 0.172) | 738 | 16.7 | 14.6 | 13.9 |

As shown in FIG. 53 and Table 13, although the light-emitting device 13 emits blue light with a low luminosity factor, it exhibited a current efficiency exceeding 16 cd/A, which is high for a blue fluorescent device.

As shown in FIG. 55 and Table 13, the light-emitting device 13 exhibited an external quantum efficiency exceeding 13%, which is high for a fluorescent device. Note that the external quantum efficiency of the light-emitting device 13 is higher than 7.5%, which is the theoretical maximum value. This is probably because of the effects due to TTA, as described above.

As shown in FIG. 54 and Table 13, the light-emitting device 13 was found to have favorable driving voltage.

As shown in FIG. 56, the emission spectrum of the light-emitting device 13 has a spectrum peak at around 467 nm and a full width at half maximum of approximately 39 nm; hence, the light-emitting device 13 exhibited blue light emission derived 1,6mMemFLPAPrn, which is the guest material.

<Delayed Fluorescence Measurement of Light-Emitting Device>

Next, to investigate the effect of TTA in the light-emitting device 13, the fluorescence lifetime was calculated using transient electroluminescence measurement.

Figure 57:
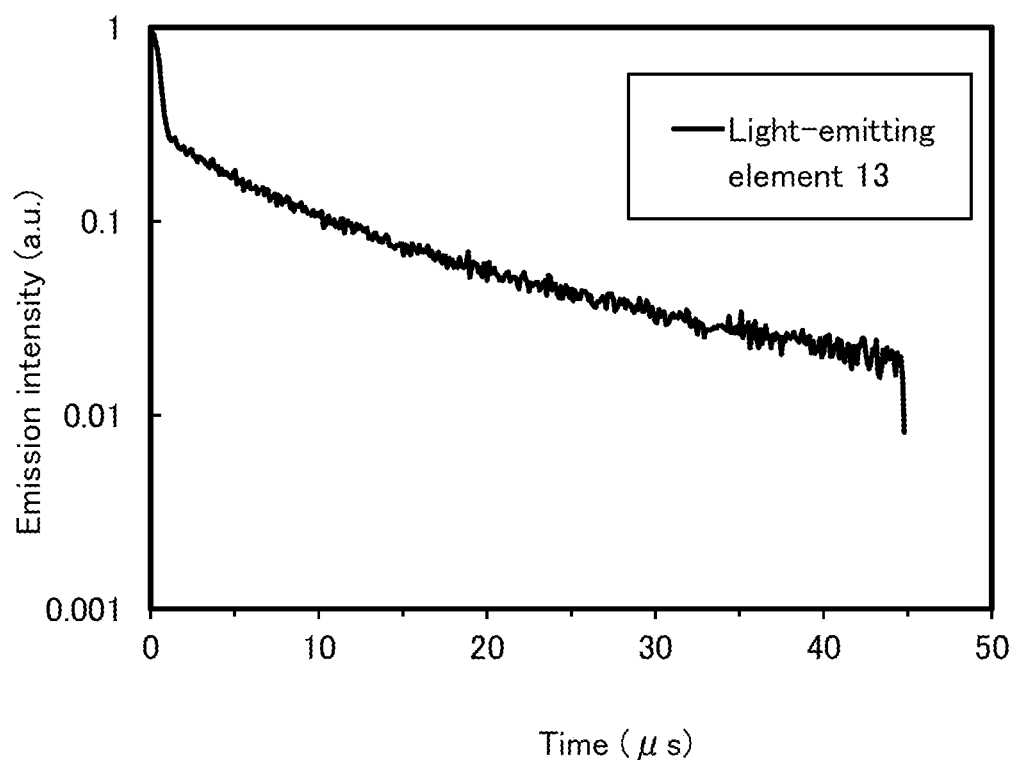
FIG. 57 A diagram showing emission lifetime measurement results of a light-emitting device in Example.

A picosecond fluorescence lifetime measurement system (manufactured by Hamamatsu Photonics K.K.) was used for the measurement. In this measurement, to measure the fluorescence lifetime of the light-emitting device, a rectangular pulse voltage was applied to the light-emitting device, and time-resolved measurement of light emission, which was attenuated from the falling of the voltage, was performed with a streak camera. The pulse voltage was applied at a frequency of 10 Hz, and data with a high S/N ratio was obtained by integrating data obtained by repeated measurements. The measurement was performed at room temperature (300 K) under the conditions of an applied pulse voltage of approximately 3 V to 4 V, an applied pulse time width of 100 psec, a negative bias voltage of −1 V (when the device is not driven), and a measurement time range of 50 psec so that the current efficiency of the light-emitting device becomes the maximum. FIG. 57 shows the measurement results. Note that in FIG. 57, the vertical axis represents the emission intensity normalized to that in a state where carriers are steadily injected (the pulse voltage is applied). The horizontal axis represents time elapsed after the falling of the pulse voltage.

The attenuation curve shown in FIG. 57 was fitted with Formula (1) below.
[Formula 1]

In Formula (1), L represents normalized emission intensity, and t represents elapsed time. As a result of fitting the attenuation curve, fitting was achieved when n was 2. The fitting result of the attenuation curve showed that two delayed fluorescence components with a lifetime of 6.0 μs and 25.0 μs were included. In addition, the proportion of the delayed fluorescence components in light emission was calculated to be 27.4%. Therefore, the light-emitting device 13 was found to have a large proportion of delayed fluorescence components.

Example 13

This example will describe a fabrication example of a light-emitting device that includes the organic compound of one embodiment of the present invention and is different from those in Examples above, and the characteristics of the light-emitting device. FIG. 1(A) illustrates a stacked-layer structure of the light-emitting device fabricated in this example. Table 14 shows the details of the device structure. Note that other embodiments or examples can be referred to for organic compounds used in this example.

thickness of 10 nm. Note that the hole-transport layer 112(2) has a function of an electron-blocking layer.

Then, as the light-emitting layer 140, 2aBA-αNPhA and 1,6BnfAPrn-03 were deposited over the hole-transport layer 112 by co-evaporation at a weight ratio (2aBA-αNPhA:1,6BnfAPrn-03) of 1:0.03 to a thickness of 25 nm. Note that in the light-emitting layer 140, 1,6BnfAPrn-03 is a guest material that exhibits fluorescence.

Next, as the electron-transport layer 118, ZADN and Liq were deposited over the light-emitting layer 140 by co-evaporation at a weight ratio (ZADN:Liq) of 1:1 to a thickness of 25 nm.

Then, as the electron-injection layer 119, Liq was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the light-emitting device 14 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm$^2$ and heat treatment at 80° C. for one hour were performed. Through the above steps, the light-emitting device 14 was obtained.

<Characteristics of Light-Emitting Device>

Next, the characteristics of the fabricated light-emitting device 14 were measured. The measurement conditions of

TABLE 14

| | Layer | Reference numeral | Thickness (nm) | Material | Weight ratio |
|---|---|---|---|---|---|
| Light-emitting device 14 | Electrode | 102 | 200 | Al | — |
| | Electron-injection layer | 119 | 1 | Liq | — |
| | Electron-transport layer | 118 | 25 | ZADN: Liq | 1:1 |
| | Light-emitting layer | 140 | 25 | 2aBA-αNPhA: 1,6BnfAPrn-03 | 1:0.03 |
| | Hole-transport layer | 112(2) | 10 | HT602 | — |
| | | 112(1) | 20 | PCBBiF | — |
| | Hole-injection layer | 111 | 10 | PCBBiF: NDP-9 | 1:0.1 |
| | Electrode | 101 | 70 | ITSO | — |

<<Fabrication of Light-Emitting Device 14>>

As the hole-injection layer 111 of the light-emitting device 14, PCBBiF and NDP-9 were deposited over the electrode 101 by co-evaporation at a weight ratio (PCBBiF:NDP-9) of 1:0.1 to a thickness of 10 nm.

Next, as the hole-transport layer 112(1), PCBBiF was deposited over the hole-injection layer 111 by evaporation to a thickness of 20 nm, and subsequently, as the hole-transport layer 112(2), HT602 was deposited by evaporation to a the light-emitting device were similar to those described in Example above.

Figure 58:
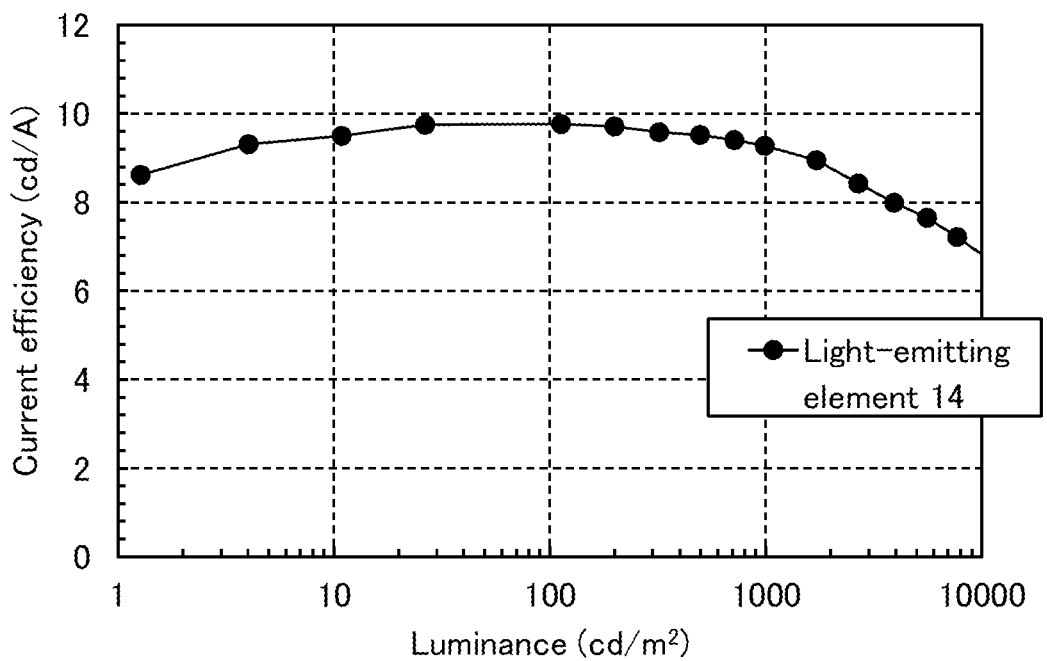
FIG. 58 A diagram showing current efficiency-luminance characteristics of a light-emitting device in Example.
Figure 59:
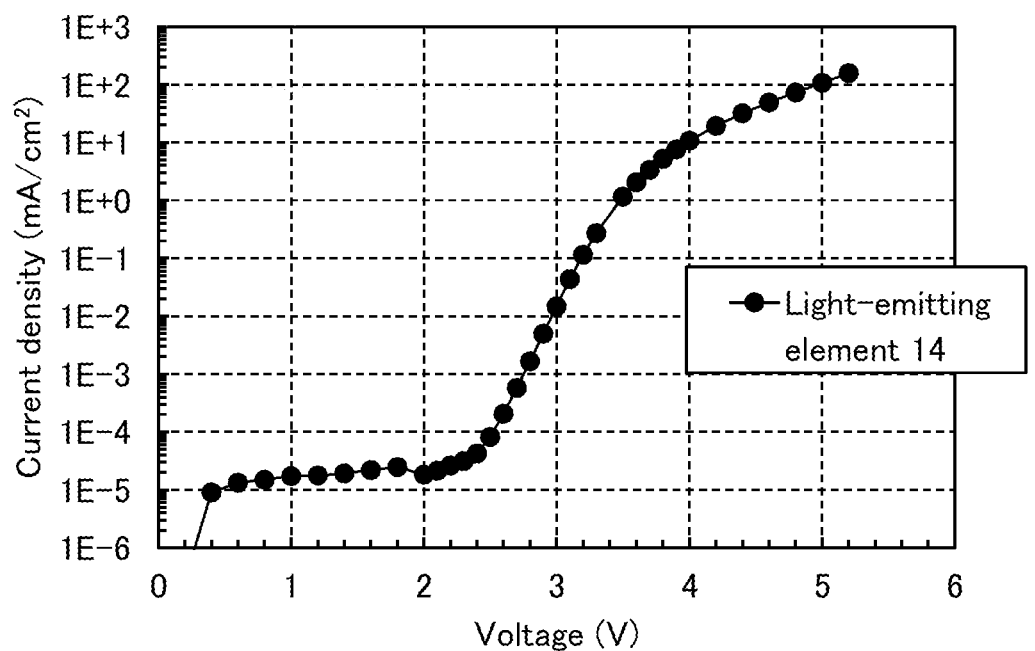
FIG. 59 A diagram showing current density-voltage characteristics of a light-emitting device in Example.
Figure 60:
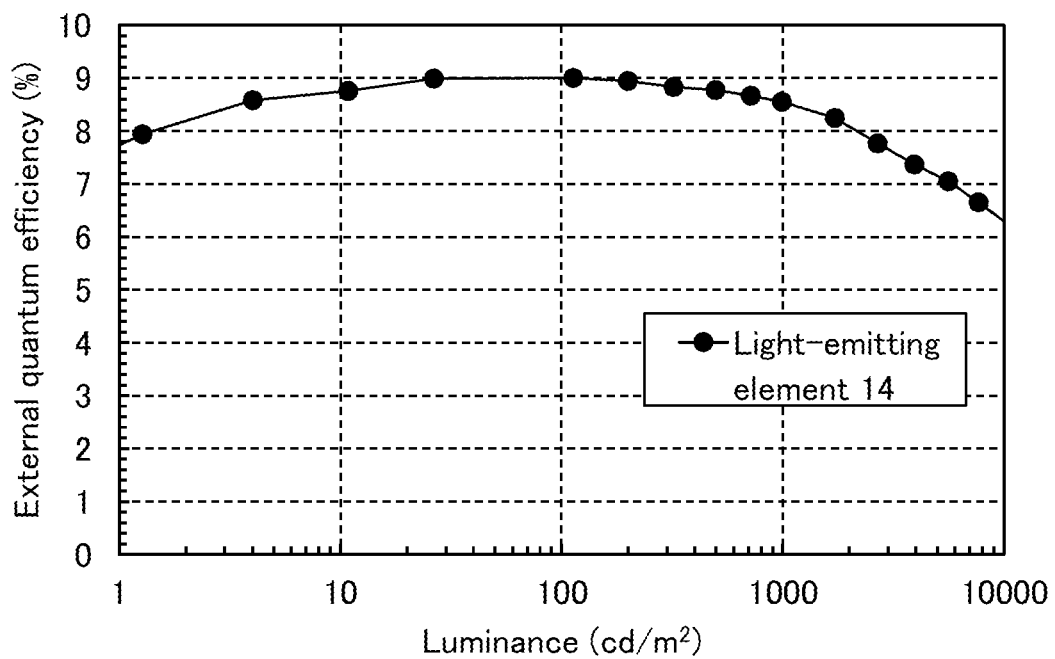
FIG. 60 A diagram showing external quantum efficiency-luminance characteristics of a light-emitting device in Example.
Figure 61:
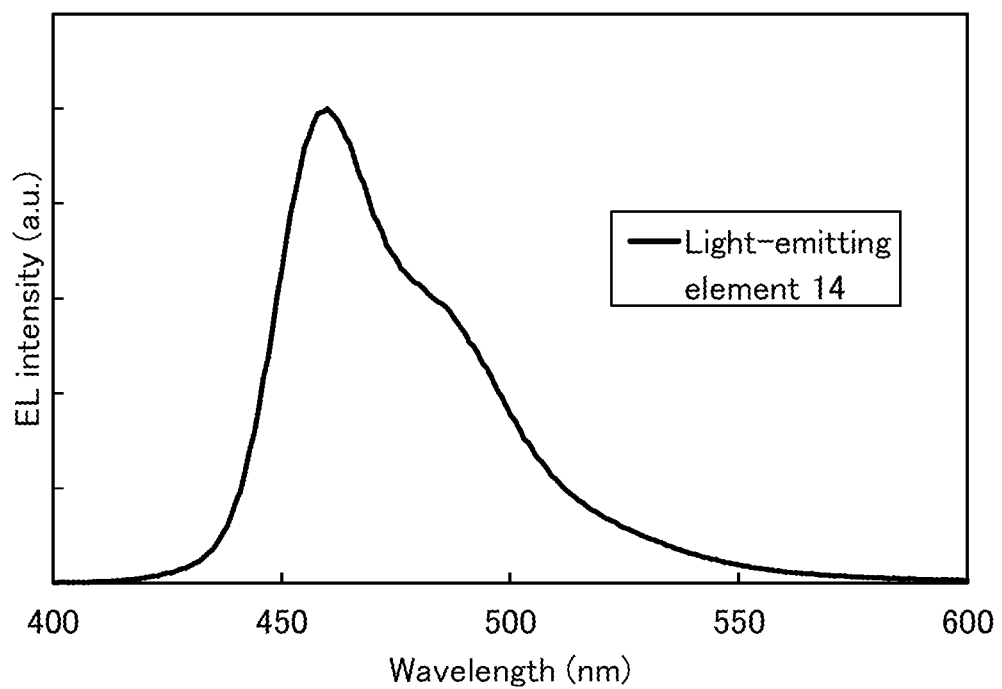
FIG. 61 A diagram showing an emission spectrum of a light-emitting device in Example.

FIG. 58 shows current efficiency-luminance characteristics of the light-emitting device 14. FIG. 59 shows the current density-voltage characteristics. FIG. 60 shows the external quantum efficiency-luminance characteristics. FIG. 61 shows emission spectra when current at a current density of 12.5 mA/cm$^2$ was supplied to the light-emitting device 14.

Table 15 shows the device characteristics of the light-emitting device 14 at around 1000 cd/m².

TABLE 15

| | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting device 14 | 4.00 | 10.67 | (0.141, 0.142) | 990 | 9.3 | 7.3 | 8.5 |

As shown in FIG. 58 and Table 15, although the light-emitting device 14 emits blue light with a low luminosity factor, it exhibited a current efficiency exceeding 9 cd/A, which is high for a blue fluorescent device.

As shown in FIG. 60 and Table 15, the light-emitting device 14 exhibited an external quantum efficiency exceeding 8%, which is high for a fluorescent device. Note that the external quantum efficiency of the light-emitting device 14 is higher than 7.5%, which is the theoretical maximum value. This is probably because of the effects due to TTA, as described above.

As shown in FIG. 59 and Table 15, it is found that the light-emitting device 14 has favorable driving voltage.

As shown in FIG. 61, the emission spectrum of the light-emitting device 14 has a spectrum peak at around 460 nm and a full width at half maximum of approximately 45 nm; hence, the light-emitting device 14 exhibited blue light emission derived from 1,6BnfAPrn-03, which is the guest material.

<Reliability of Light-Emitting Device>

Figure 62:
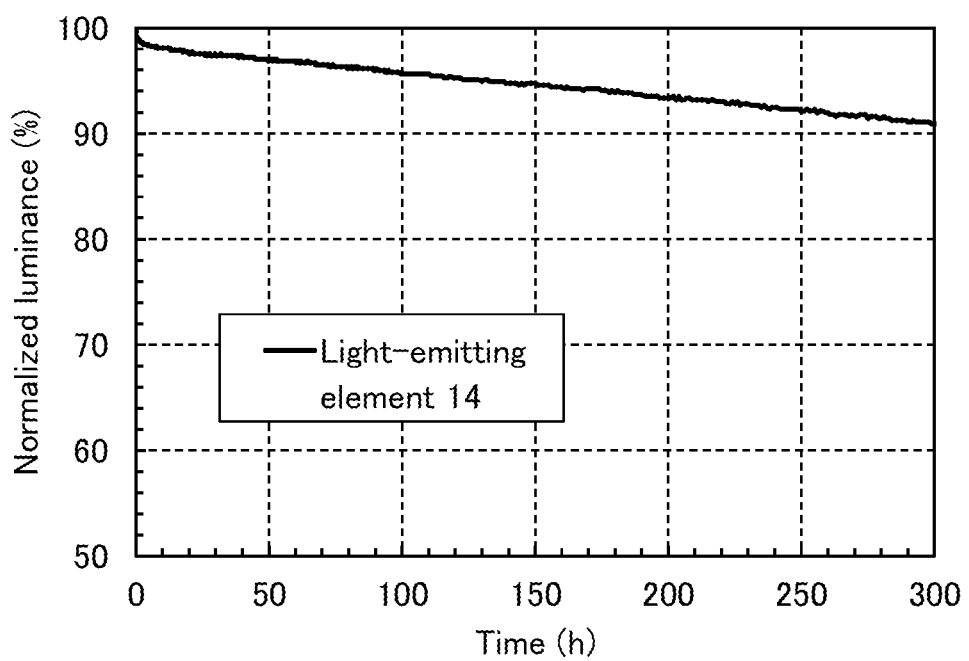
FIG. 62 A diagram showing results of a reliability test on a light-emitting device in Example.

Next, a driving test at a constant current of 2 mA was performed on the light-emitting device 14. FIG. 62 shows the results. It was found from FIG. 62 that the light-emitting device 14 has extremely high reliability with $LT_{90}$ of 300 hours or longer.

Example 14

This example will describe a fabrication example of alight-emitting device that includes the organic compound of one embodiment of the present invention and is different from those in Examples above, and the characteristics of the light-emitting device. FIG. 1(A) illustrates a stacked-layer structure of light-emitting devices fabricated in this example. Table 16 shows the details of the device structures. Note that other embodiments or examples can be referred to for organic compounds used in this example.

TABLE 16

| | Layer | Reference numeral | Thickness (nm) | Material | Weight ratio |
|---|---|---|---|---|---|
| Comparative Light-emitting device 15 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 140 | 25 | cgDBCzPA: 1,6BnfAPrn-03 | 1:0.03 |
| | Hole-transport layer | 112 | 30 | PCPPn | — |
| | Hole-injection layer | 111 | 10 | PCPPn: MoO₃ | 1:0.5 |
| | Electrode | 101 | 70 | ITSO | — |
| Light-emitting device 16 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBA-αNPhA: 3,10PCA2Nbf(IV)-02 | 1:0.015 |
| | Hole-transport layer | 112(2) | 10 | HT602 | — |
| | | 112(1) | 20 | PCBBiF | — |
| | Hole-injection layer | 111 | 10 | PCBBiF: NDP-9 | 1:0.1 |
| | Electrode | 101 | 70 | ITSO | — |

<<Fabrication of Comparative Light-Emitting Device 15>>

As the hole-injection layer 111 of the comparative light-emitting device 15, PCPPn and MoO₃ were deposited over the electrode 101 by co-evaporation in a weight ratio (PCPPn:MoO₃) of 1:0.5 to a thickness of 10 nm.

Next, as the hole-transport layer 112, PCPPn was deposited over the hole-injection layer 111 by evaporation to a thickness of 30 nm.

Then, as the light-emitting layer 140, cgDBCzPA and 1,6BnfAPrn-03 were deposited over the hole-transport layer 112 by co-evaporation at a weight ratio (cgDBCzPA:1, 6BnfAPrn-03) of 1:0.03 to a thickness of 25 nm. Note that in the light-emitting layer 140, 1,6BnfAPrn-03 is a guest material that exhibits fluorescence.

Next, as the electron-transport layer 118(1), cgDBCzPA was deposited over the light-emitting layer 140 by evaporation to a thickness of 15 nm. Then, as the electron-transport layer 118(2), NBPhen was sequentially deposited over the electron-transport layer 118(1) by evaporation to a thickness of 10 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the comparative light-emitting device 15 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm$^2$ and heat treatment at 80° C. for one hour were performed. Through the above steps, the comparative light-emitting device 15 was obtained.

<<Fabrication of Light-Emitting Device 16>>

As the hole-injection layer 111 of the light-emitting device 16, PCBBiF and NDP-9 were deposited over the electrode 101 by co-evaporation at a weight ratio (PCBBiF:NDP-9) of 1:0.1 to a thickness of 10 nm.

Next, as the hole-transport layer 112(1), PCBBiF was deposited over the hole-injection layer 111 by evaporation to a thickness of 20 nm, and subsequently, as the hole-transport layer 112(2), HT602 was deposited by evaporation to a thickness of 10 nm. Note that the hole-transport layer 112(2) has a function of an electron-blocking layer.

Then, as the light-emitting layer 140, 2aBA-αNPhA and 3,10PCA2Nbf(IV)-02 were deposited over the hole-transport layer 112 by co-evaporation at a weight ratio (2aBA-αNPhA:3,10PCA2Nbf(IV)-02) of 1:0.015 to a thickness of 25 nm. Note that in the light-emitting layer 140, 3,10PCA2Nbf(IV)-02 is a guest material that exhibits fluorescence.

Next, as the electron-transport layer 118(1), 2mDBTBPDBq-II was deposited over the light-emitting layer 140 by evaporation to a thickness of 15 nm. Then, as the electron-transport layer 118(2), NBPhen was sequentially deposited over the electron-transport layer 118(1) by evaporation to a thickness of 10 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the light-emitting device 16 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other. Then, irradiation with ultraviolet light having a wavelength of 365 nm at 6 J/cm$^2$ and heat treatment at 80° C. for one hour were performed. Through the above steps, the light-emitting device 16 was obtained.

<Characteristics of Light-Emitting Devices>

Next, the characteristics of the comparative light-emitting device 15 and the light-emitting device 16, which were fabricated as above, were measured. The measurement conditions of the light-emitting devices were similar to those described in Example above.

Figure 63:
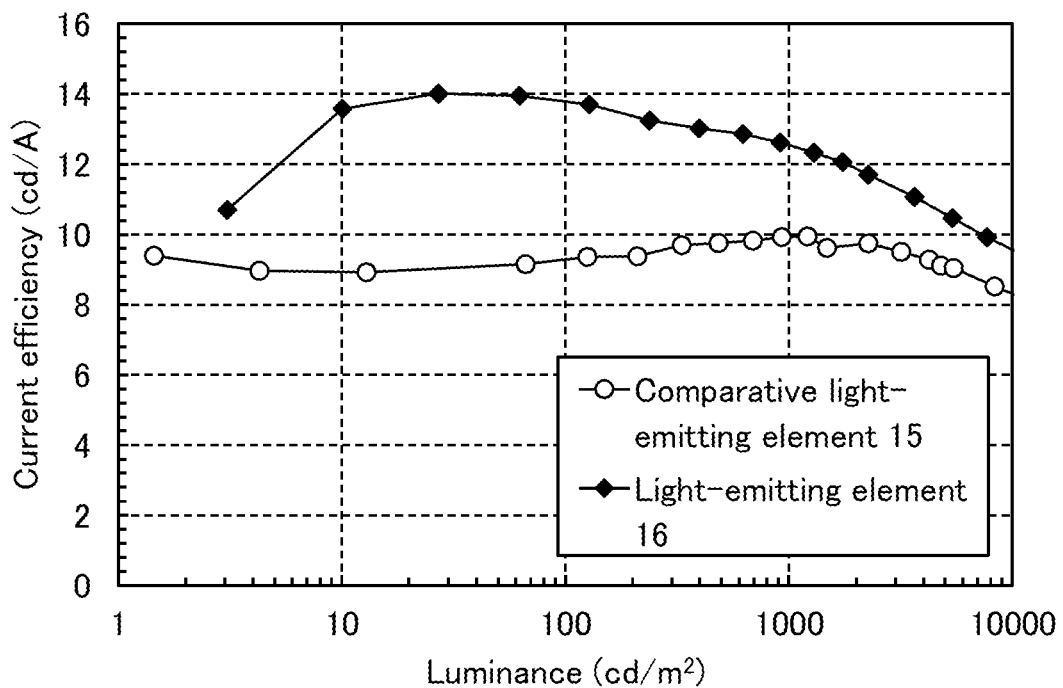
FIG. 63 A diagram showing current efficiency-luminance characteristics of light-emitting devices in Example.
Figure 64:
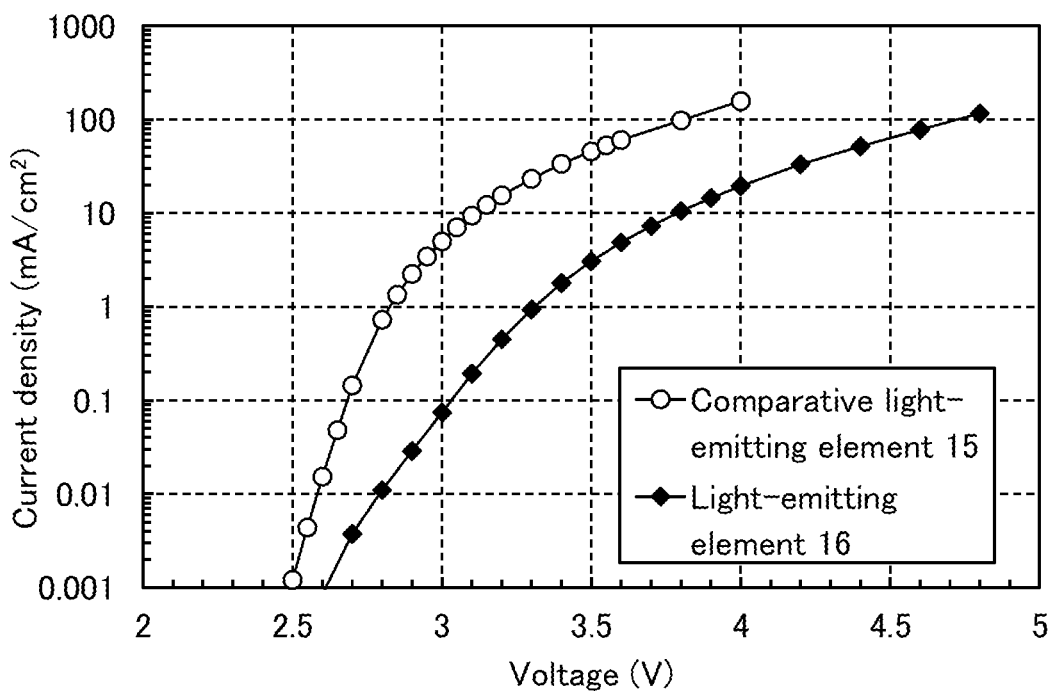
FIG. 64 A diagram showing current density-voltage characteristics of light-emitting devices in Example.
Figure 65:
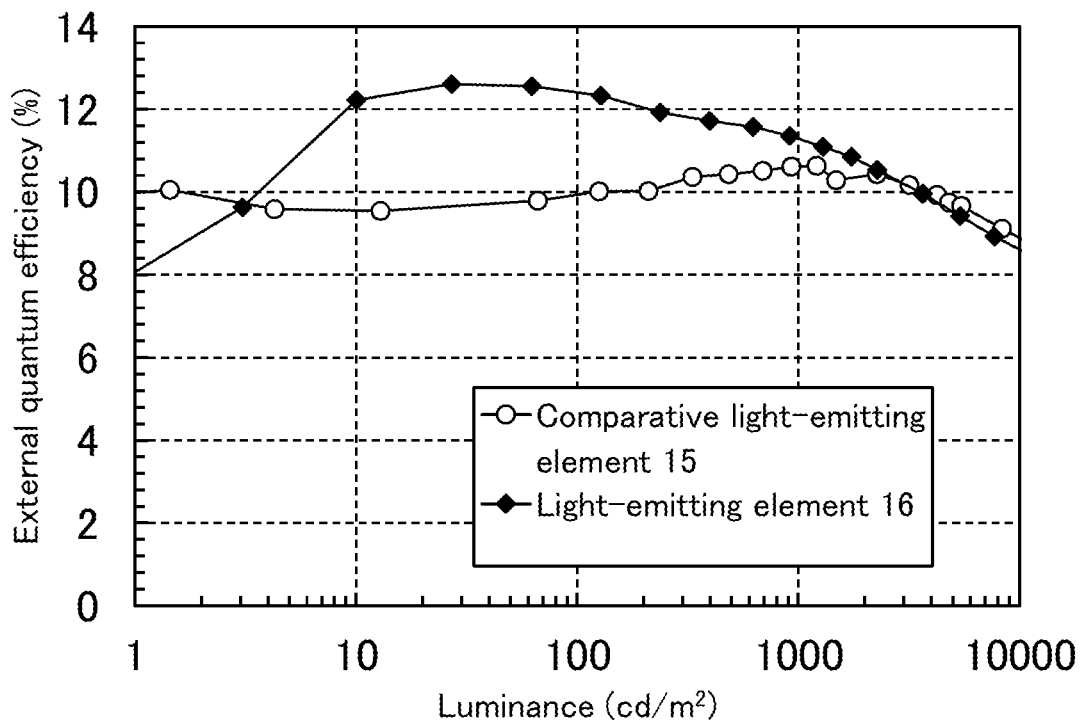
FIG. 65 A diagram showing external quantum efficiency-luminance characteristics of light-emitting devices in Example.
Figure 66:
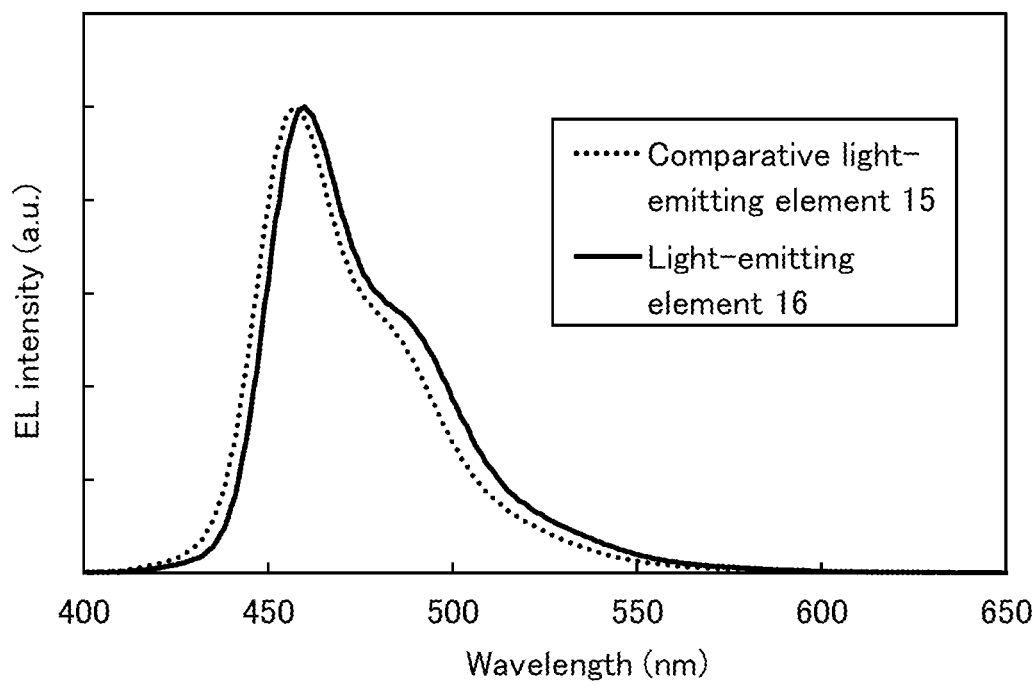
FIG. 66 A diagram showing emission spectra of light-emitting devices in Example.

FIG. 63 shows the current efficiency-luminance characteristics of the comparative light-emitting device 15 and the light-emitting device 16. FIG. 64 shows the current density-voltage characteristics. FIG. 65 shows the external quantum efficiency-luminance characteristics. FIG. 66 shows emission spectra when current at a current density of 12.5 mA/cm$^2$ was supplied to the comparative light-emitting device 15 and the light-emitting device 16.

Table 17 shows the device characteristics of the comparative light-emitting device 15 and the light-emitting device 16 at around 1000 cd/m$^2$.

TABLE 17

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Comparative Light-emitting device 15 | 3.10 | 9.4 | (0.140, 0.114) | 931.1 | 9.9 | 10.1 | 10.6 |
| Light-emitting device 16 | 3.70 | 7.25 | (0.141, 0.148) | 915.6 | 12.6 | 10.7 | 11.4 |

As shown in FIG. 63 and Table 17, although the comparative light-emitting device 15 and the light-emitting device 16 emit blue light with a low luminosity factor, they exhibited a current efficiency exceeding 9 cd/A, which is high for a blue fluorescent device.

As shown in FIG. 65 and Table 17, the comparative light-emitting device 15 and the light-emitting device 16 exhibited an external quantum efficiency exceeding 10%, which is high for a fluorescent device. Note that the external quantum efficiencies of the comparative light-emitting device 15 and the light-emitting device 16 are higher than 7.5%, which is the theoretical maximum value. This is probably because of the effects due to TTA, as described above.

As shown in FIG. 64 and Table 17, the comparative light-emitting device 15 and the light-emitting device 16 each have favorable driving voltage.

As shown in FIG. 66, the emission spectra of the comparative light-emitting device 15 and the light-emitting device 16 respectively have a spectrum peak at around 457 nm and 460 nm and a full width at half maximum of approximately 41 nm and 45 nm; hence, the comparative light-emitting device 15 and the light-emitting device 16 exhibited blue light emission derived from their guest materials.

<Reliability of Light-Emitting Devices>

Figure 67A:
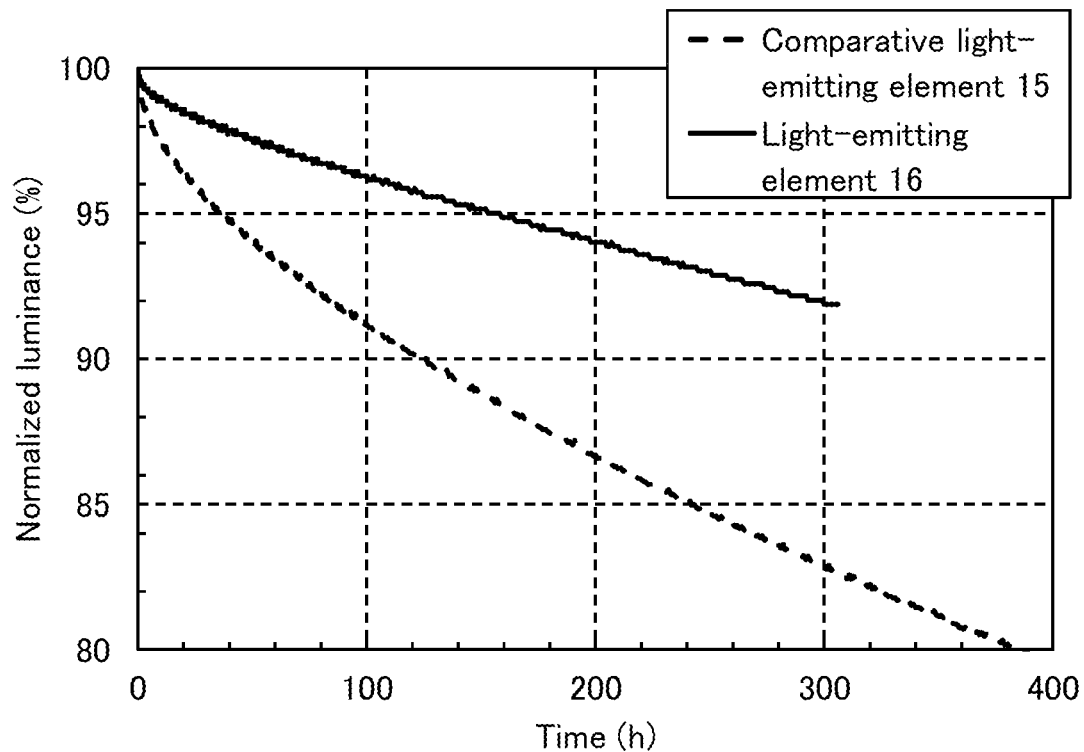
FIG. 67(A), (B) Diagrams showing results of a reliability test on light-emitting devices in Example.
Figure 67B:
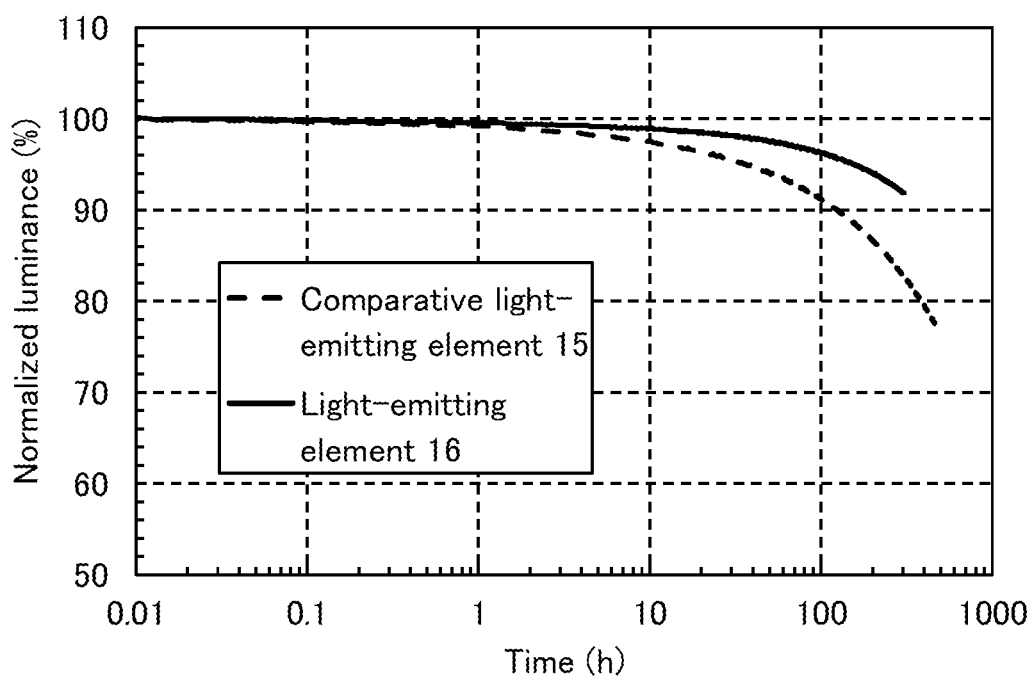

Next, driving tests at a constant current of 2 mA were performed on the comparative light-emitting device 15 and the light-emitting device 16. The results are shown in FIGS. 67(A) and 67(B). The horizontal axis in FIG. 67(A) is on a linear scale, and the horizontal axis in FIG. 67(B) is on a log scale. It was found from FIGS. 67(A) and 67(B) that the comparative light-emitting device 15 and the light-emitting device 16 each have high reliability with $LT_{90}$ of 100 hours or longer. In particular, the estimated $LT_{90}$ of the light-emitting device 16 exceeds 400 hours, demonstrating extremely high reliability. Furthermore, the light-emitting device 16 was found to be a device having a lifetime at least four times that of the comparative light-emitting device 15.

Example 15

This example will describe a method for synthesizing 4-[9-(1-naphthyl)-10-(3-biphenylyl)-2-anthryl]benzo[a]anthracene (abbreviation: 2aBA-αNmBPhA) (Structural Formula (120)) that is the organic compound of one embodiment of the present invention represented by General Formula (G1).

Step 1: Synthesis of 2aBA-αNmBPhA

Into a 50 mL three-necked flask were put 1.3 g (2.6 mmol) of 2-chloro-9-(1-naphthyl)-10-(3-biphenylyl)anthracene, 0.81 g (3.0 mmol) of benzo[a]anthracene-4-boronic acid, 93 mg (0.26 mmol) of di(1-adamanthyl)-n-butylphosphine, 1.7 g (7.8 mmol) of tripotassium phosphate, and 0.58 g (7.8 mmol) of tert-butyl alcohol, and the air in the flask was replaced with nitrogen. To the mixture was added 13 mL of diethylene glycol dimethyl ether, and the mixture was degassed by being stirred under reduced pressure. To this mixture was added 29 mg (0.13 mmol) of palladium(II) acetate, and the mixture was stirred at 120° C. under a nitrogen stream for 20 hours.

After the stirring, water was added to this mixture, the solid obtained by performing suction filtration was dissolved in toluene, and the solution was subjected to suction filtration through Celite, alumina, and Florisil. The solid obtained by concentrating the obtained filtrate was purified by high-performance liquid chromatography (HPLC) and then recrystallized with toluene/hexane to give 1.0 g of a target pale yellow solid at a yield of 57%. The synthesis scheme of the above synthesis method is shown in Formula (A-6) below.

[Chemical Formula 36]

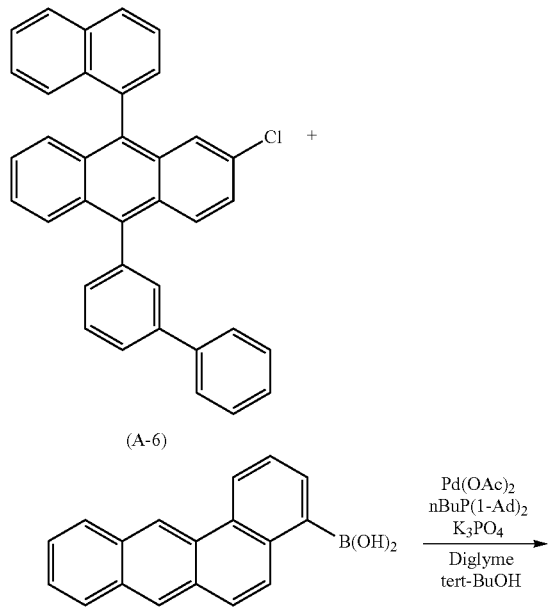

(A-6)

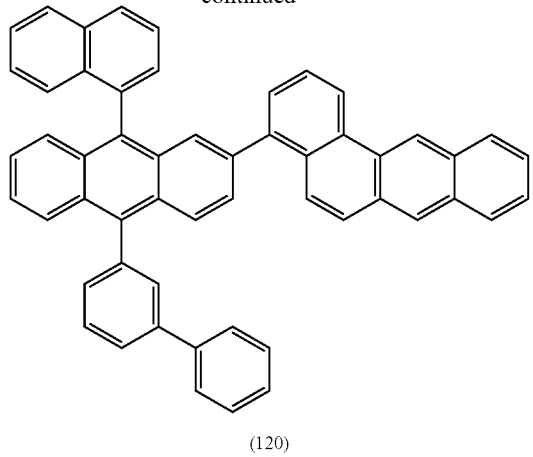

(120)

By the train sublimation method, 1.0 g of the obtained pale yellow solid was sublimated and purified. The sublimation purification was performed by heating the pale yellow solid at 330° C. under the conditions where the pressure was 3.5 Pa and the argon flow rate was 5.0 mL/min. After the sublimation purification, 0.68 g of a yellow solid was obtained at a collection rate of 68%.

Figure 68A:
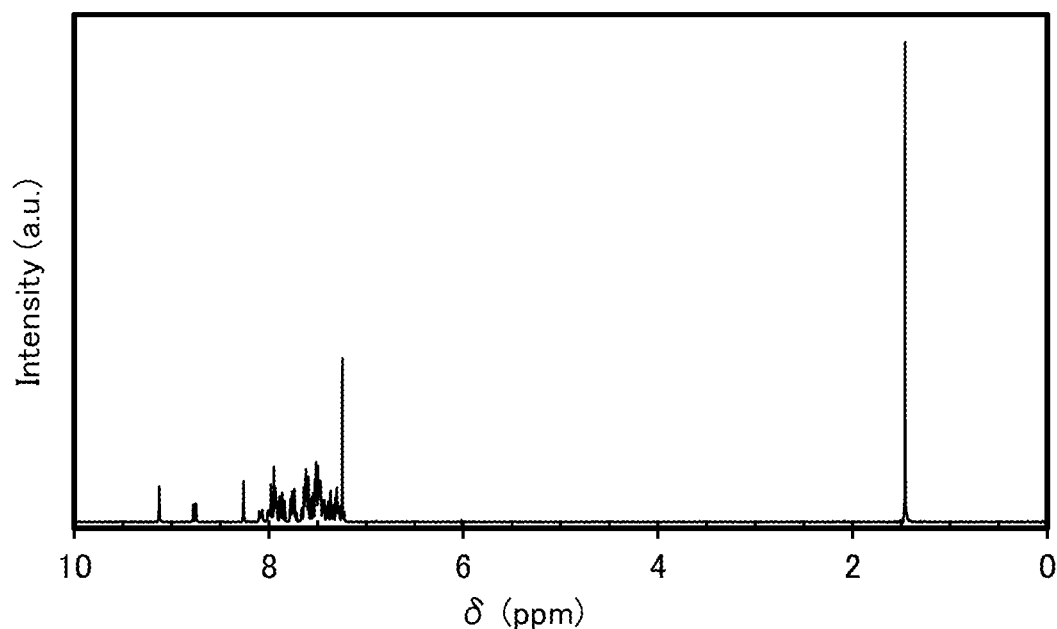
FIG. 68(A), (B) Diagrams showing an NMR chart of a compound in Example.
Figure 68B:
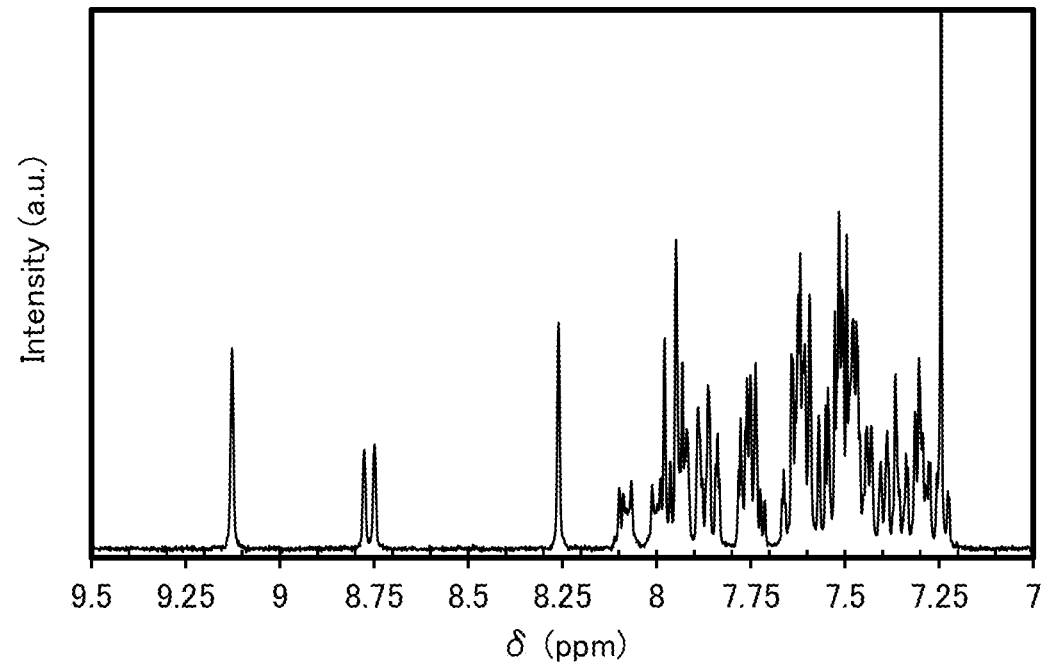

Analysis results of the obtained yellow solid by nuclear magnetic resonance spectroscopy ($^1$H-NMR) are shown below. FIGS. 68(A) and 68(B) show $^1$H-NMR charts. Note that FIG. 68(B) is a chart showing an enlarged view of the range of 7.0 ppm to 9.5 ppm in FIG. 68(A). These results revealed that 2aBA-αNmBPhA, which is the organic compound of one embodiment of the present invention represented by Structural Formula (120) above, was obtained in this example.

$^1$H NMR (CDCl$_3$, 300 MHz): δ=7.22-7.66 (m, 20H), 7.71-8.10 (m, 11H), 8.26 (s, 1H), 8.76 (d, J=7.8 Hz, 1H), 9.13 (s, 1H).

<Properties of 2aBA-αNmBPhA>

Figure 69:
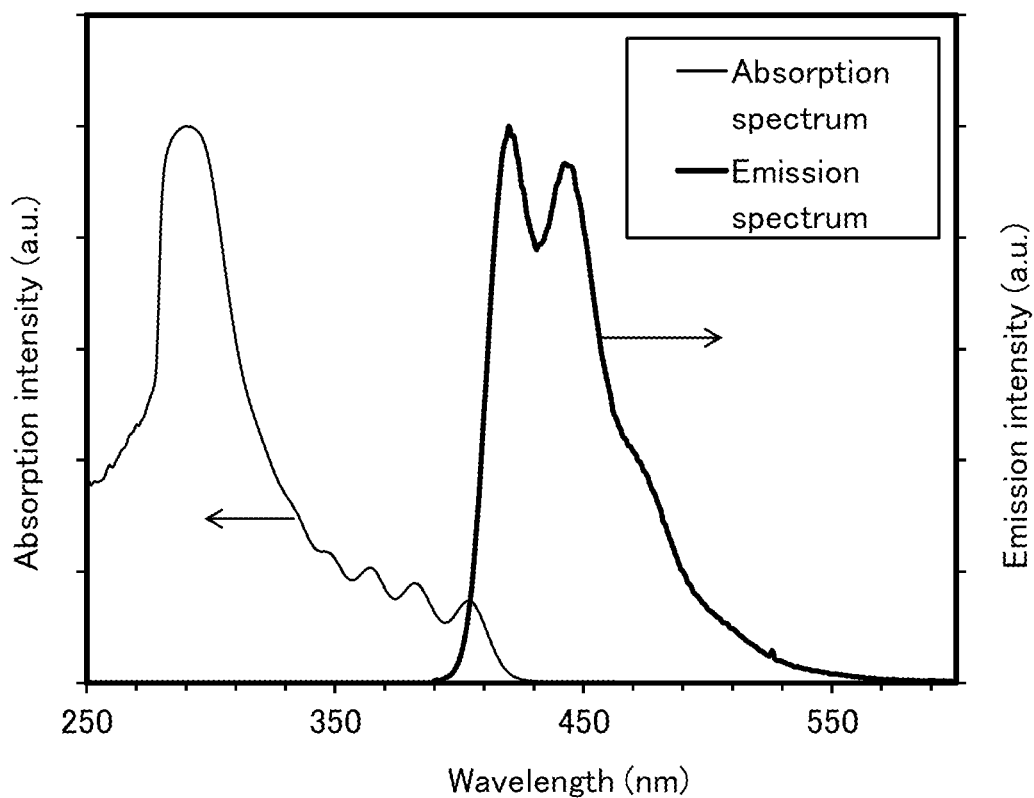
FIG. 69 A diagram showing an absorption spectrum and an emission spectrum of a compound in Example.
Figure 70:
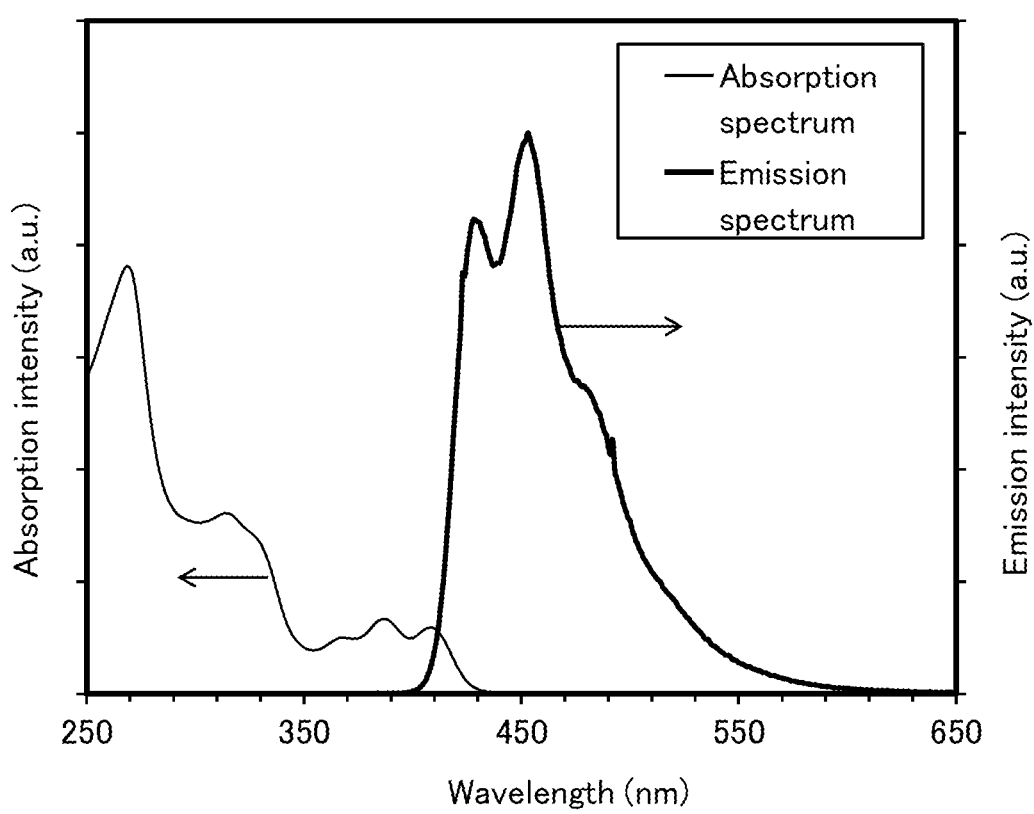
FIG. 70 A diagram showing an absorption spectrum and an emission spectrum of a compound in Example.

Next, FIG. 69 shows the measurement results of the absorption spectrum and the emission spectrum of 2aBA-αNmBPhA in a toluene solution. FIG. 70 shows the absorption spectrum and the emission spectrum of a thin film. The measurement was performed in a manner similar to that in Example 1.

From the results in FIG. 69, for the toluene solution of 2aBA-αNmBPhA, the absorption peaks were observed at around 404 nm, 382 nm, 364 nm, and 348 nm, and the emission wavelength peaks were observed at around 443 nm and 420 nm (excitation wavelength: 382 nm). From the results in FIG. 70, for the solid thin film of 2aBA-αNmBPhA, the absorption peaks were observed at around 408 nm, 386 nm, 368 nm, 329 nm, 316 nm, and 269 nm, and the emission wavelength peaks were observed at around 453 nm and 428 (excitation wavelength: 370 nm).

Note that 2aBA-αNmBPhA was confirmed to emit blue light. The organic compound of one embodiment of the present invention, 2aBA-αNmBPhA, can be used as a host for a light-emitting substance or a substance that exhibits fluorescence in the visible region. Furthermore, the thin film of 2aBA-αNmBPhA was found to have a good film quality with little change in shape, hardly being aggregated even under air.

Next, CV measurement was performed on 2aBA-αNmBPhA. The measurement was performed in a manner similar to that in Example 1.

As a result, the HOMO level was found to be −5.81 eV in the measurement of the oxidation potential Ea [V] of 2aBA-αNmBPhA. In contrast, the LUMO level was found to be −2.80 eV in the measurement of the reduction potential Ec [V].

Example 16

This example will describe a method for synthesizing 4-[9-(2-naphthyl)-10-phenyl-2-anthryl]benzo[a]anthracene (abbreviation: 2aBA-βNPhA) (Structural Formula (115)) that is one embodiment of the present invention and is one of the compounds represented by General Formula (G1).

Step 1: Synthesis of 2aBA-βNPhA

Into a 50 mL three-necked flask were put 1.1 g (2.7 mmol) of 2-chloro-9-(2-naphthyl)-10-phenylanthracene, 074 g (2.7 mmol) of benzo[a]anthracene-4-boronic acid, 30 mg (0.14 mmol) of di(1-adamanthyl)-n-butylphosphine, 1.7 g (8.1 mmol) of tripotassium phosphate, and 0.60 g (8.1 mmol) of tert-butyl alcohol, and the air in the flask was replaced with nitrogen. To the mixture was added 13 mL of diethylene glycol dimethyl ether, and the mixture was degassed by being stirred under reduced pressure. To this mixture was added 30 mg (0.14 mmol) of palladium(II) acetate, and the mixture was stirred at 80° C. under a nitrogen stream for 8 hours.

After the stirring, water was added to this mixture, the solid obtained by performing suction filtration was dissolved in toluene, and the solution was subjected to suction filtration through Celite, aluminum oxide, and Florisil. The solid obtained by concentrating the obtained filtrate was purified by high-performance liquid chromatography (HPLC) and then recrystallized with toluene/hexane to give 0.72 g of a target pale yellow solid at a yield of 44%. The synthesis scheme of the above synthesis method is shown in the Formula (A-7) below.

[Chemical Formula 37]

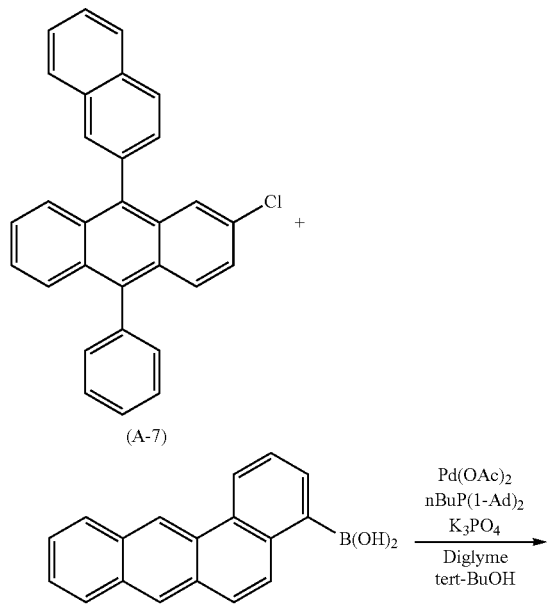

(A-7)

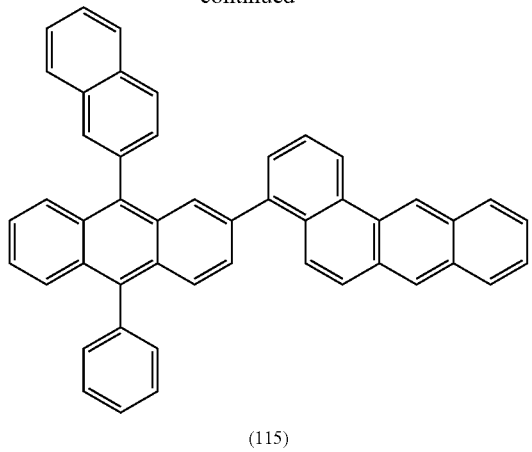

(115)

By the train sublimation method, 0.72 g of the obtained pale yellow solid was purified by sublimation. The sublimation purification was performed by heating the pale yellow solid at 260° C. under the conditions where the pressure was 3.8 Pa and the argon flow rate was 5.0 mL/min. After the sublimation purification, 0.65 g of a pale yellow solid was obtained at a collection rate of 90%.

Figure 71A:
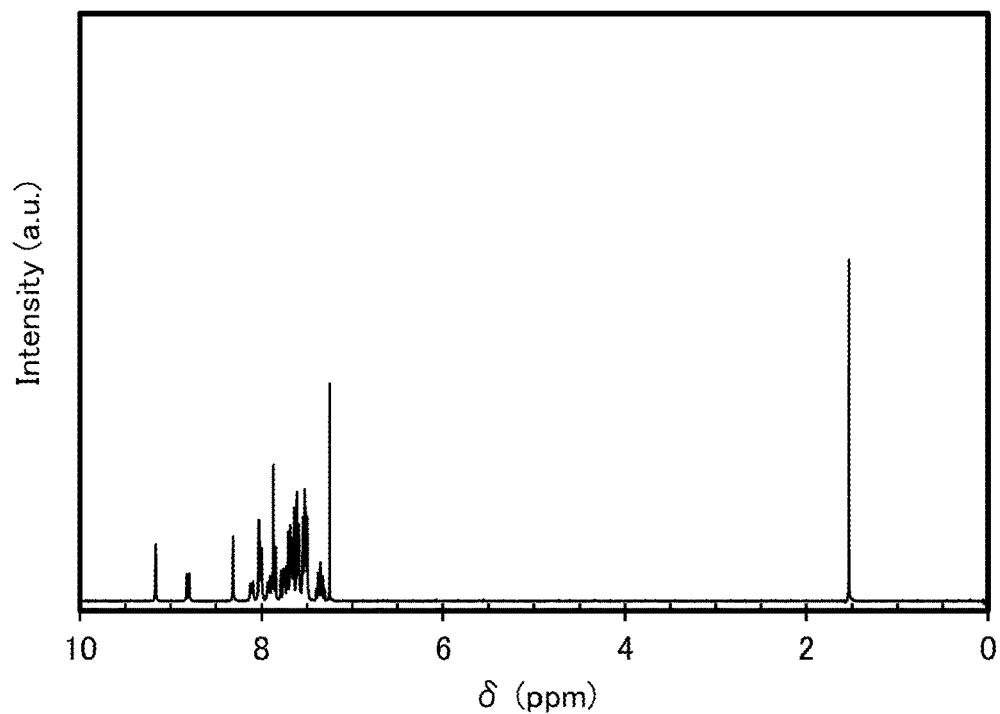
FIG. 71(A), (B) Diagrams showing an NMR chart of a compound in Example.
Figure 71B:
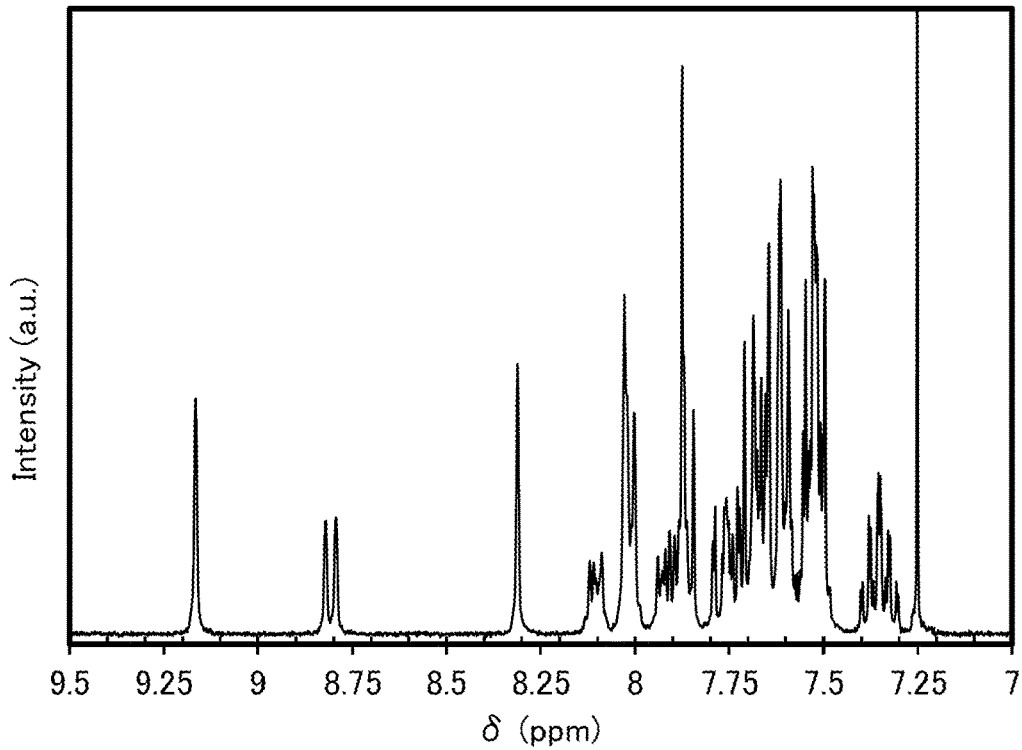

Analysis results of the obtained pale yellow solid by nuclear magnetic resonance spectroscopy ($^1$H-NMR) are shown below. FIGS. 71(A) and 71(B) show $^1$H-NMR charts. Note that FIG. 71(B) is a chart showing an enlarged view of the range of 7.0 ppm to 9.5 ppm in FIG. 71(A). These results revealed that 2aBA-βNPhA, which is the organic compound of one embodiment of the present invention represented by Structural Formula (115) above, was obtained in this example.

$^1$H NMR (CDCl$_3$, 300 MHz): δ=7.30-7.40 (m, 2H), 7.48-7.79 (m, 17H), 7.85-7.94 (m, 4H), 8.00-8.03 (m, 3H), 8.09-8.12 (m, 1H), 8.31 (s, 1H), 8.81 (d, J=7.5 Hz, 1H), 9.17 (s, 1H).

<Properties of 2aBA-βNPhA>

Figure 72:
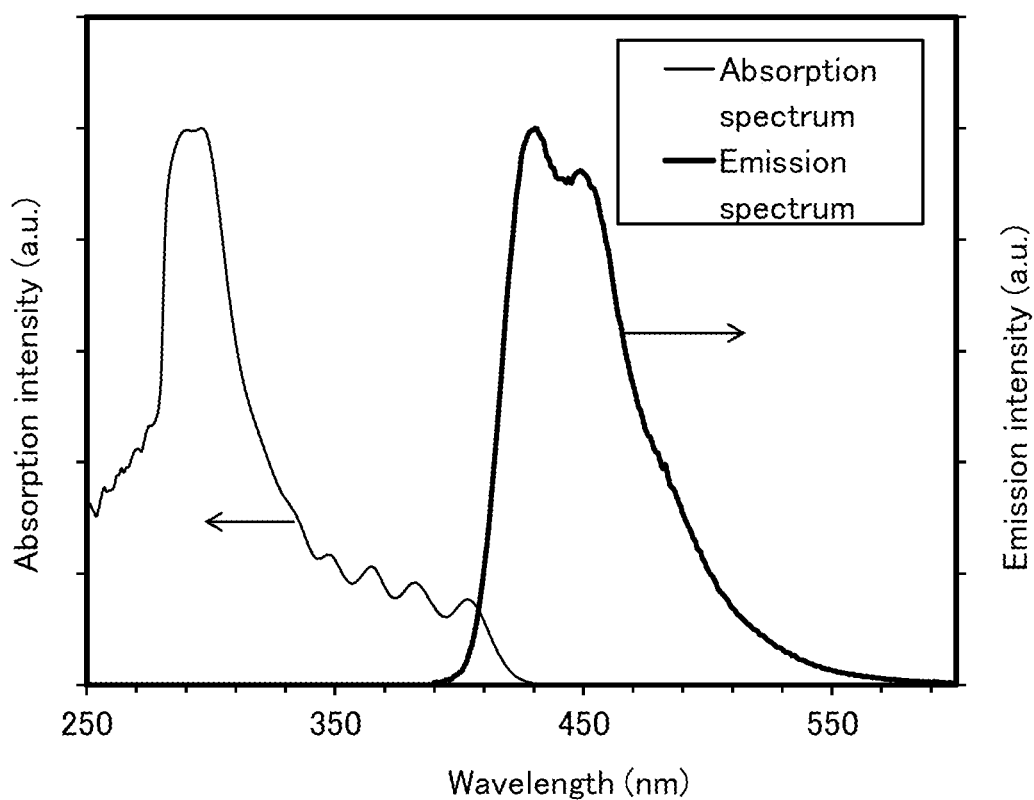
FIG. 72 A diagram showing an absorption spectrum and an emission spectrum of a compound in Example.
Figure 73:
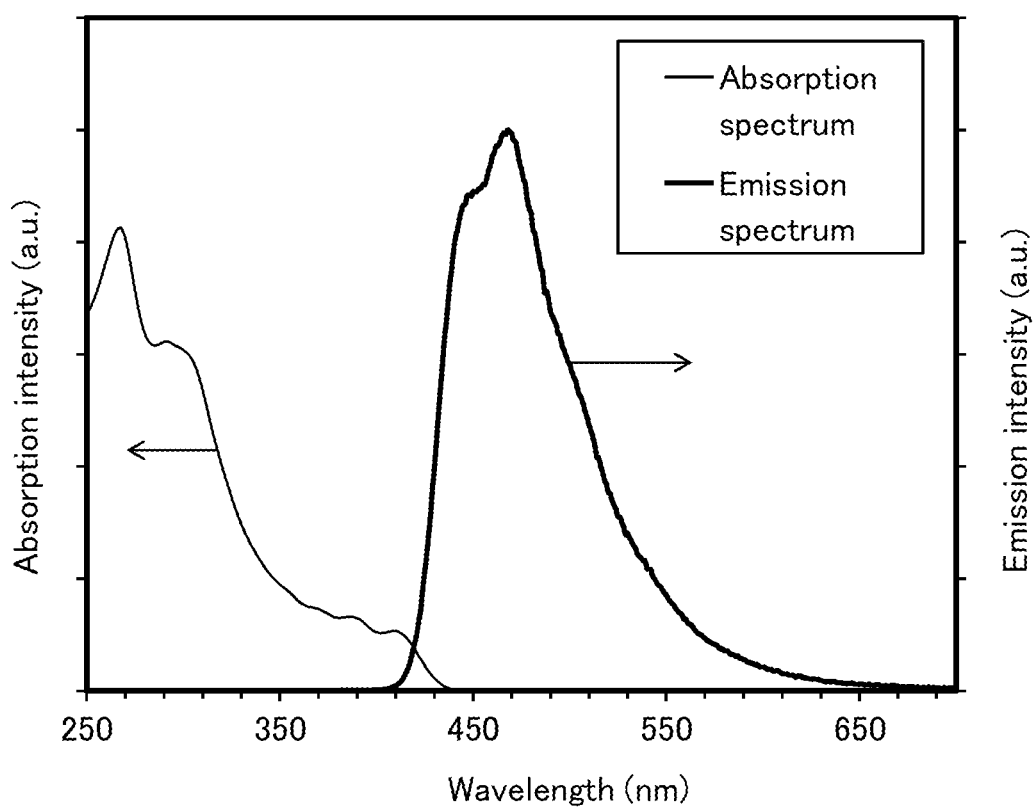
FIG. 73 A diagram showing an absorption spectrum and an emission spectrum of a compound in Example.

Next, FIG. 72 shows the measurement results of the absorption spectrum and the emission spectrum of 2aBA-βNPhA in a toluene solution. FIG. 73 shows the absorption spectrum and the emission spectrum of a thin film. The measurement was performed in a manner similar to that in Example 1.

From the results in FIG. 72, for the toluene solution of 2aBA-βNPhA, the absorption peaks were observed at around 403 nm, 382 nm, 365 nm, 347 nm, and 296 nm, and the emission wavelength peaks were observed at around 449 nm and 430 nm (excitation wavelength: 382 nm). From the results in FIG. 73, for the solid thin film of 2aBA-βNPhA, the absorption peaks were observed at around 410 nm, 388 nm, 370 nm, 305 nm, and 292 nm, and the emission wavelength peaks were observed at around 468 nm and 447 nm (excitation wavelength: 370 nm).

Note that 2aBA-βNPhA was confirmed to emit blue light. The organic compound of one embodiment of the present invention, 2aBA-βNPhA, can be used as a host for a light-emitting substance or a substance that exhibits fluorescence in the visible region. Furthermore, the thin film of 2aBA-βNPhA was found to have a good film quality with little change in shape, hardly being aggregated even under air.

Next, CV measurement was performed on 2aBA-βNPhA. The measurement was performed in a manner similar to that in Example 1.

As a result, the HOMO level was found to be −5.79 eV in the measurement of the oxidation potential Ea [V] of 2aBA-βNPhA. In contrast, the LUMO level was found to be −2.78 eV in the measurement of the reduction potential Ec [V].

Example 17

This example will describe a method for synthesizing 4-[10-(1-naphthyl)-9-(3-biphenylyl)-2-anthryl]benzo[a]anthracene (abbreviation: 3aBA-αNmBPhA) (Structural Formula (167)) that is one embodiment of the present invention and is one of the compounds represented by General Formula (G1).

Step 1: Synthesis of 3aBA-αNmBPhA

Into a 200 mL three-necked flask were put 2.3 g (4.7 mmol) of 2-chloro-10-(1-naphthyl)-9-(3-biphenylyl)anthracene, 1.4 g (5.2 mmol) of benzo[a]anthracene-4-boronic acid, 0.17 g (0.48 mmol) of di(1-adamanthyl)-n-butylphosphine, 3.0 g (14 mmol) of tripotassium phosphate, and 1.0 g (14 mmol) of tert-butyl alcohol, and the air in the flask was replaced with nitrogen. To the mixture was added 24 mL of diethylene glycol dimethyl ether, and the mixture was degassed by being stirred under reduced pressure. To this mixture was added 54 mg (0.24 mmol) of palladium(II) acetate, and the mixture was stirred at 130° C. under a nitrogen stream for 18 hours.

After the stirring, water was added to this mixture, the solid obtained by performing suction filtration was dissolved in toluene, and the solution was subjected to suction filtration through Celite, aluminum oxide, and Florisil. The solid obtained by concentrating the obtained filtrate was purified by high-performance liquid chromatography (HPLC) and then recrystallized with toluene to give 1.2 g of a target pale yellow solid at a yield of 38%. The synthesis scheme of the above synthesis method is shown in Formula (A-8) below.

[Chemical Formula 38]

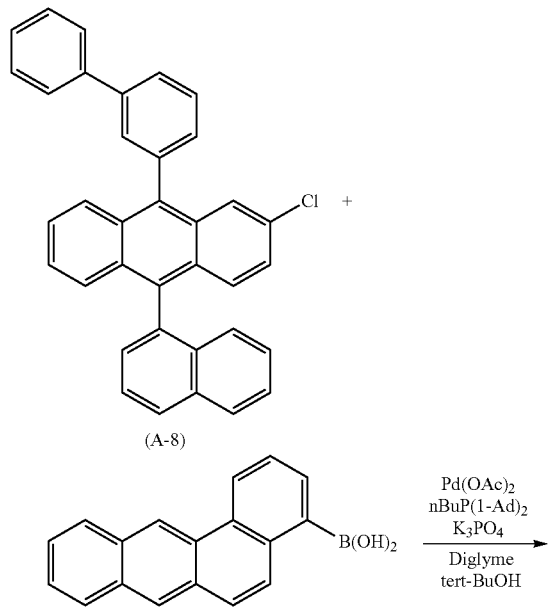

(A-8)

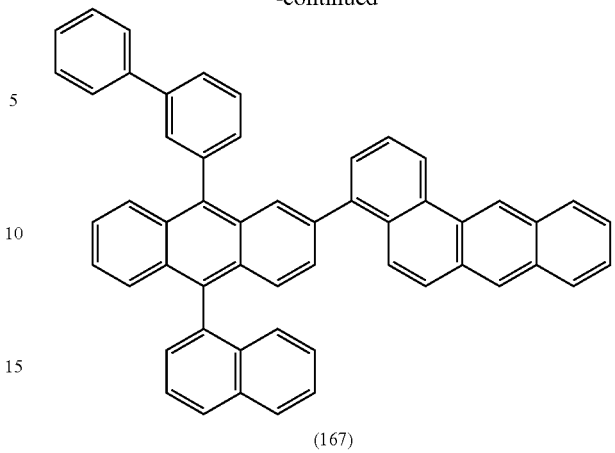

(167)

By the train sublimation method, 1.2 g of the obtained pale yellow solid was purified by sublimation. In the purification by sublimation, the pale yellow solid was heated at 310° C. under a pressure of 3.6 Pa with an argon flow rate of 5.0 mL/min. After the purification by sublimation, 1.0 g of a pale yellow solid was obtained at a collection rate of 83%.

Figure 74A:
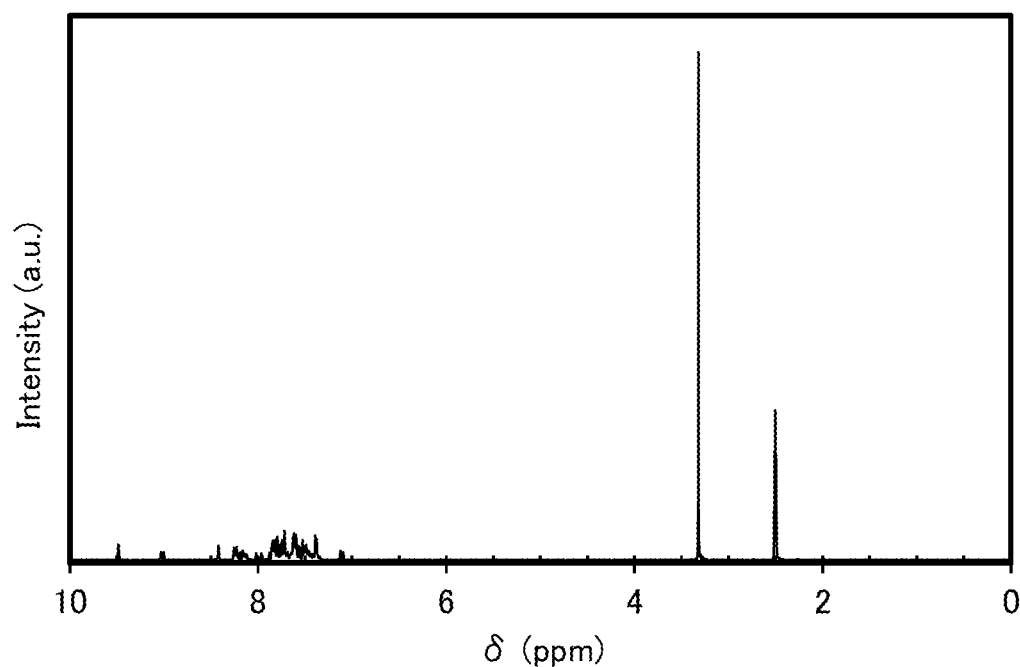
FIG. 74(A), (B) Diagrams showing an NMR chart of a compound in Example.
Figure 74B:
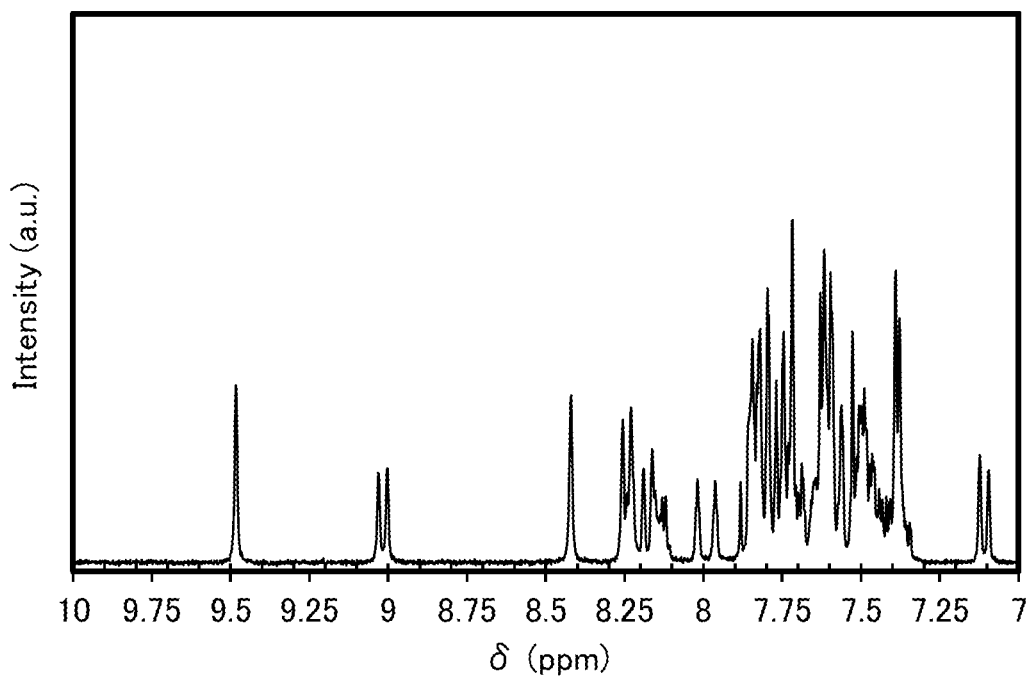

Analysis results of the obtained pale yellow solid by nuclear magnetic resonance spectroscopy ($^1$H-NMR) are shown below. FIGS. 74(A) and 74(B) show $^1$H-NMR charts. Note that FIG. 74(B) is a chart showing an enlarged view of the range of 7.0 ppm to 10 ppm in FIG. 74(A). These results revealed that 3aBA-αNmBPhA, which is the organic compound of one embodiment of the present invention represented by Structural Formula (167) above, was obtained in this example.

$^1$H NMR (DMSO, 300 MHz): δ=7.11 (d, J=8.4 Hz, 1H), 7.35-7.88 (m, 25H), 7.99 (d, J=17 Hz, 1H), 8.12-8.26 (m, 4H), 8.42 (s, 1H), 9.02 (d, J=4.5 Hz, 1H), 9.48 (s, 1H).

<Properties of 3aBA-αNmBPhA>

Figure 75:
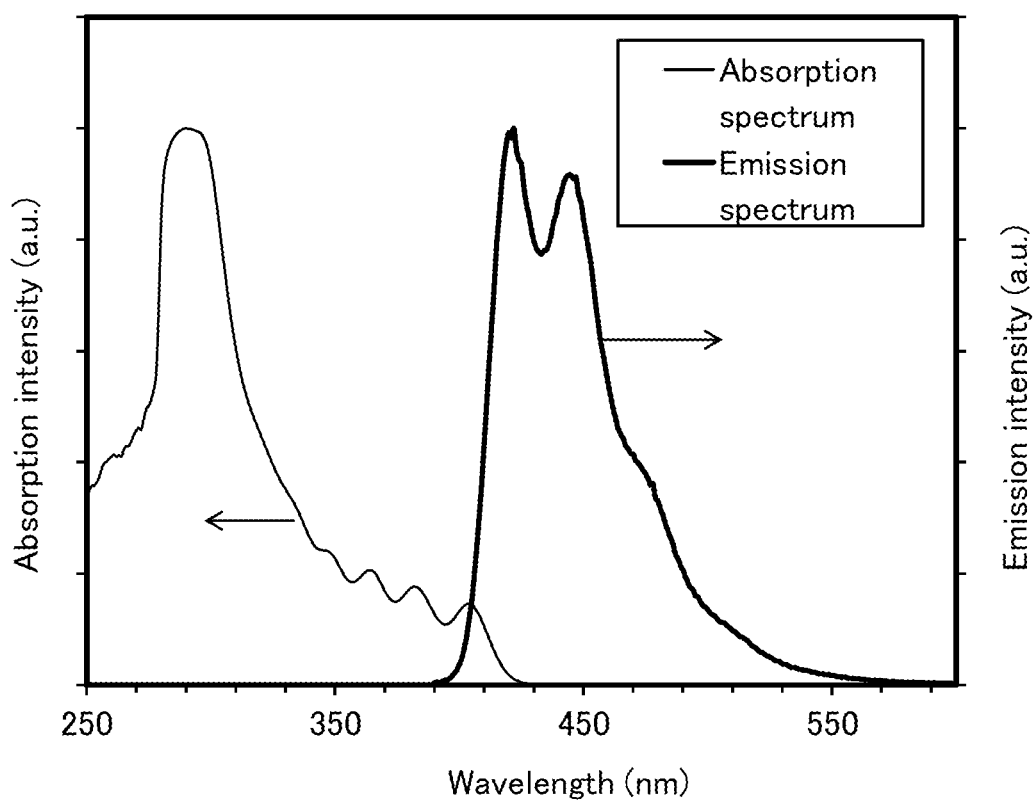
FIG. 75 A diagram showing an absorption spectrum and an emission spectrum of a compound in Example.
Figure 76:
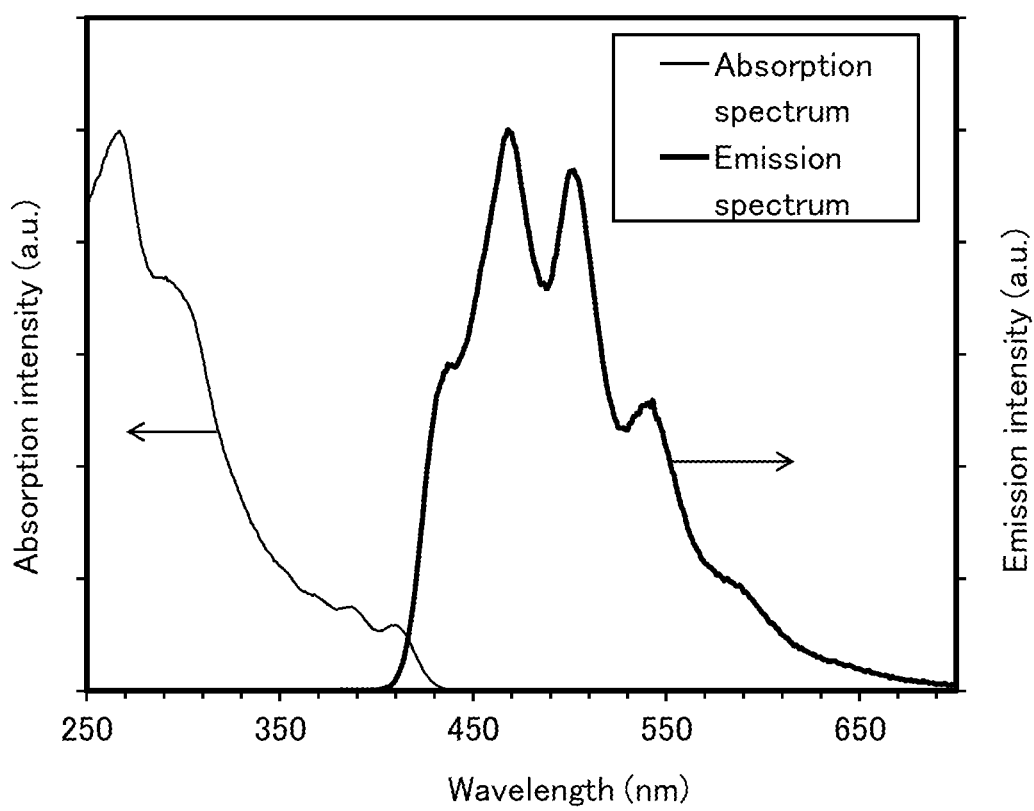
FIG. 76 A diagram showing an absorption spectrum and an emission spectrum of a compound in Example.

Next, FIG. 75 shows the measurement results of the absorption spectrum and the emission spectrum of 3aBA-αNmBPhA in a toluene solution. FIG. 76 shows the absorption spectrum and the emission spectrum of a thin film. The measurement was performed in a manner similar to that in Example 1.

From the results in FIG. 75, for the toluene solution of 3aBA-αNmBPhA, the absorption peaks were observed at around 404 nm, 383 nm, 364 nm, and 347 nm, and the emission wavelength peaks were observed at around 445 nm and 421 nm (excitation wavelength: 382 nm). From the results in FIG. 76, for the solid thin film of 3aBA-αNmBPhA, the absorption peaks were observed at around 409 nm, 387 nm, 368 nm, and 291 nm, and the emission wavelength peaks were observed at around 588 nm, 543 nm, 502 nm, 468 nm, and 437 nm (excitation wavelength: 370 nm).

Note that 3aBA-αNmBPhA was confirmed to emit blue light. The organic compound of one embodiment of the present invention, 3aBA-αNmBPhA, can be used as a host for a light-emitting substance or a substance that exhibits fluorescence in the visible region. Furthermore, the thin film of 3aBA-αNmBPhA was found to have a good film quality with little change in shape, hardly being aggregated even under air.

Next, CV measurement was performed on 3aBA-αNmBPhA. The measurement was performed in a manner similar to that in Example 1.

As a result, the HOMO level was found to be −5.82 eV in the measurement of the oxidation potential Ea [V] of 3aBA-αNmBPhA. In contrast, the LUMO level was found to be −2.81 eV in the measurement of the reduction potential Ec [V].

Example 18

This example will describe a method for synthesizing 4-[10-(2-naphthyl)-9-phenyl-2-anthryl]benzo[a]anthracene (abbreviation: 3aBA-βNPhA) (Structural Formula (117)) that is one embodiment of the present invention and is one of the compounds represented by General Formula (G1).

Step 1: Synthesis of 3aBA-βNPhA

Into a 50 mL three-necked flask were put 1.6 g (3.9 mmol) of 2-chloro-10-(2-naphthyl)-9-phenylanthracene, 1.1 g (3.9 mmol) of benzo[a]anthracene-4-boronic acid, 0.14 g (0.40 mmol) of di(1-adamanthyl)-n-butylphosphine, 2.5 g (12 mmol) of tripotassium phosphate, and 0.89 g (12 mmol) of tert-butyl alcohol, and the air in the flask was replaced with nitrogen. To the mixture was added 20 mL of diethylene glycol dimethyl ether, and the mixture was degassed by being stirred under reduced pressure. To this mixture was added 45 mg (0.20 mmol) of palladium(II) acetate, and the mixture was stirred at 90° C. under a nitrogen stream for 14 hours.

After the stirring, water was added to this mixture, the solid obtained by performing suction filtration was dissolved in toluene, and the solution was subjected to suction filtration through Celite, aluminum oxide, and Florisil. The solid obtained by concentrating the obtained filtrate was purified by high-performance liquid chromatography (HPLC) and then recrystallized with toluene/hexane to give 1.0 g of a target pale yellow solid at a yield of 41%. The synthesis scheme of the above synthesis method is shown in Formula (A-9) below.

[Chemical Formula 39]

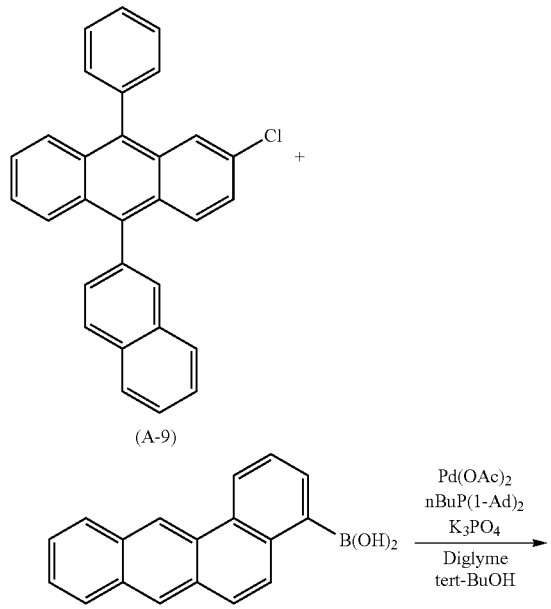

(A-9)

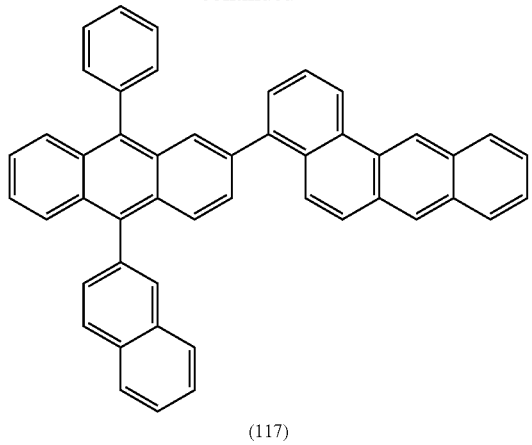

(117)

By the train sublimation method, 1.0 g of the obtained pale yellow solid was sublimated and purified. The sublimation purification was performed by heating the pale yellow solid at 270° C. under the conditions where the pressure was 3.8 Pa and the argon flow rate was 5.0 mL/min. After the sublimation purification, 0.88 g of a pale yellow solid was obtained at a collection rate of 88%.

Figure 77A:
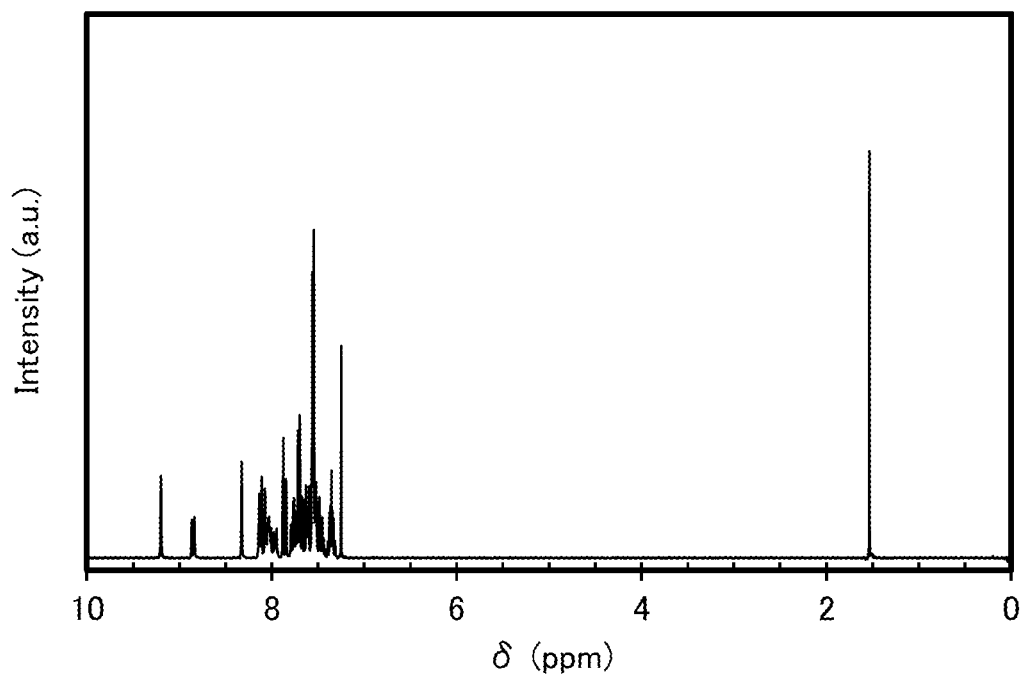
FIG. 77(A), (B) Diagrams showing an NMR chart of a compound in Example.
Figure 77B:
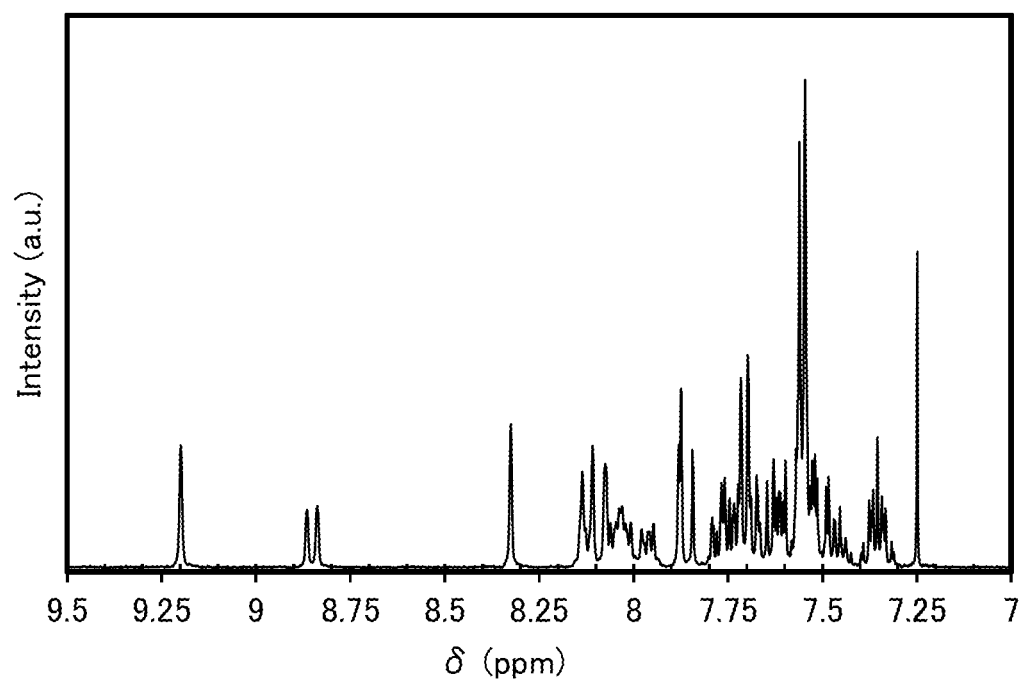

Analysis results of the obtained pale yellow solid by nuclear magnetic resonance spectroscopy ($^1$H-NMR) are shown below. FIGS. 77(A) and 77(B) show $^1$H-NMR charts. Note that FIG. 77(B) is a chart showing an enlarged view of the range of 7.0 ppm to 9.5 ppm in FIG. 77(A). These results revealed that 3aBA-βNPhA, which is the organic compound of one embodiment of the present invention represented by Structural Formula (117) above, was obtained in this example.

$^1$H NMR (CDCl$_3$, 300 MHz): δ=7.31-7.40 (m, 2H), 7.42-7.80 (m, 17H), 7.84-7.88 (m, 2H), 7.95-8.14 (m, 6H), 8.33 (s, 1H), 8.84 (d, J=8.1 Hz, 1H), 9.20 (s, 1H)

<Properties of 3aBA-βNPhA>

Figure 78:
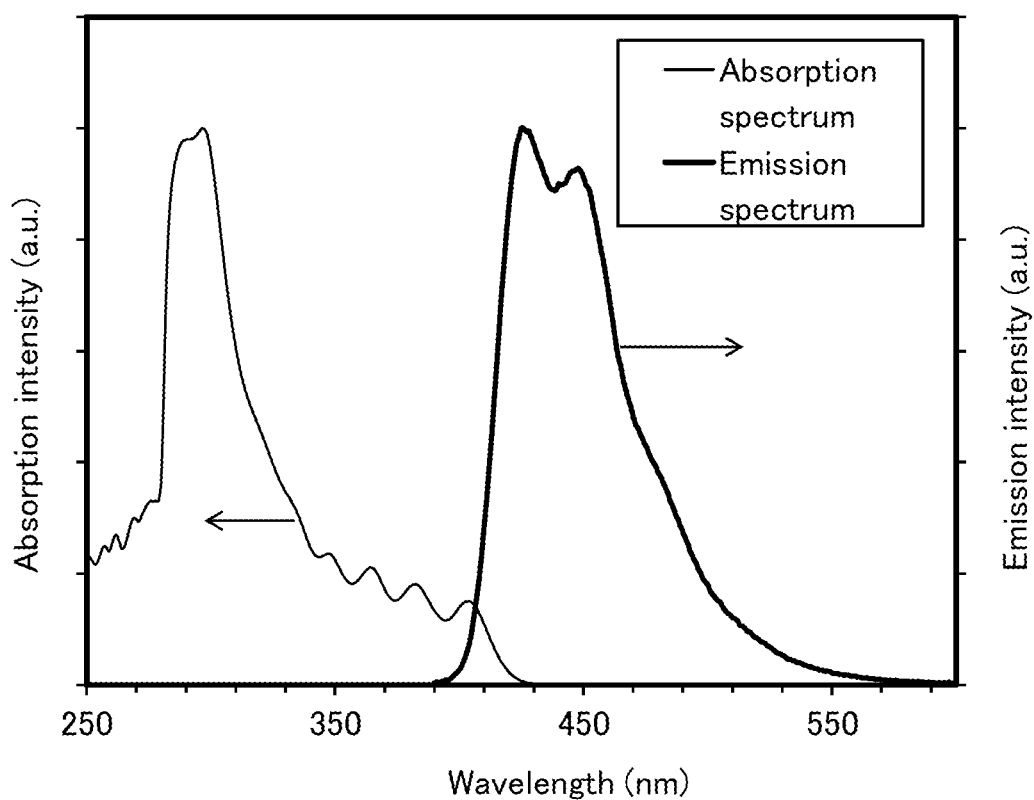
FIG. 78 A diagram showing an absorption spectrum and an emission spectrum of a compound in Example.
Figure 79:
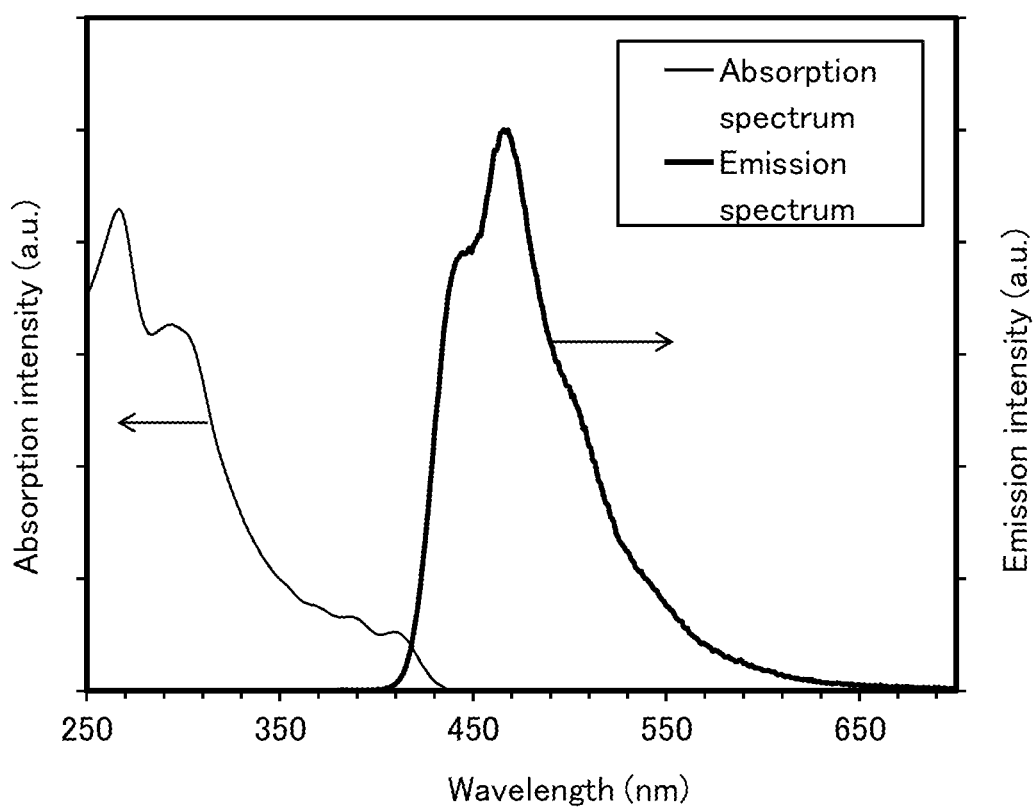
FIG. 79 A diagram showing an absorption spectrum and an emission spectrum of a compound in Example.

Next, FIG. 78 shows the measurement results of the absorption spectrum and the emission spectrum of 3aBA-βNPhA in a toluene solution. FIG. 79 shows the absorption spectrum and the emission spectrum of a thin film. The measurement was performed in a manner similar to that in Example 1.

From the results in FIG. 78, for the toluene solution of 3aBA-βNPhA, the absorption peaks were observed at around 403 nm, 382 nm, 364 nm, 348 nm, and 297 nm, and the emission wavelength peaks were observed at around 447 nm and 426 nm (excitation wavelength: 382 nm). From the results in FIG. 79, for the solid thin film of 3aBA-βNPhA, the absorption peaks were observed at around 410 nm, 389 nm, 370 nm, 302 nm, and 293 nm, and the emission wavelength peaks were observed at around 466 nm and 444 nm (excitation wavelength: 370 nm).

Note that 3aBA-βNPhA was confirmed to emit blue light. The organic compound of one embodiment of the present invention, 3aBA-βNPhA, can be used as a host for a light-emitting substance or a substance that exhibits fluorescence in the visible region. Furthermore, the thin film of 3aBA-βNPhA was found to have a good film quality with little change in shape, hardly being aggregated even under air.

Next, CV measurement was performed on 3aBA-βNPhA. The measurement was performed in a manner similar to that in Example 1.

As a result, the HOMO level was found to be −5.79 eV in the measurement of the oxidation potential Ea [V] of 3aBA-βNPhA. In contrast, the LUMO level was found to be −2.78 eV in the measurement of the reduction potential Ec [V].

Example 19

This example will describe fabrication examples of light-emitting devices of embodiments of the present invention and the characteristics of the light-emitting devices. The structure of each of the light-emitting devices fabricated in this example is the same as that in FIG. 1(A). Table 18 shows the details of the device structures. The structures and abbreviations of organic compounds that were used are shown below. Note that the above examples and embodiments can be referred to for other organic compounds.

TABLE 18

| | Layer | Reference numeral | Thickness (nm) | Material | Weight ratio |
|---|---|---|---|---|---|
| Light-emitting device 17 | Electrode | 102 | 200 | Al | — |
| | Electron-injection layer | 119 | 1 | LiF | — |
| | Electron-transport layer | 118(2) | 5 | NBPhen | — |
| | | 118(1) | 15 | 2mDBTBPDBq-II | — |
| | Light-emitting layer | 140 | 25 | 2aBA-αNmBPhA: 3,10PCA2Nbf(IV)-02 | 1:0.015 |
| | Hole-transport layer | 112(2) | 10 | HT602 | — |
| | | 112(1) | 20 | PCBBiF | — |
| | Hole-injection layer | 111 | 10 | PCBBiF: NDP-9 | 1:0.1 |
| | Electrode | 101 | 70 | ITSO | — |
| Light-emitting device 18 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 3aBA-αNmBPhA: 3,10PCA2Nbf(IV)-02 | 1:0.015 |
| | Hole-transport layer | 112(2) | 10 | HT602 | — |
| | | 112(1) | 20 | PCBBiF | — |
| | Hole-injection layer | 111 | 10 | PCBBiF: NDP-9 | 1:0.1 |
| | Electrode | 101 | 70 | ITSO | — |
| Light-emitting device 19 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 2aBA-βNPhA: 3,10PCA2Nbf(IV)-02 | 1:0.03 |
| | Hole-transport layer | 112(2) | 10 | HT602 | — |
| | | 112(1) | 20 | PCBBiF | — |
| | Hole-injection layer | 111 | 10 | PCBBiF: NDP-9 | 1:0.1 |
| | Electrode | 101 | 70 | ITSO | — |
| Light-emitting device 20 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | 2mDBTBPDBq-II | — |
| | Light-emitting layer | 140 | 25 | 3aBA-βNPhA: 3,10PCA2Nbf(IV)-02 | 1:0.03 |
| | Hole-transport layer | 112(2) | 10 | HT602 | — |
| | | 112(1) | 20 | PCBBiF | — |
| | Hole-injection layer | 111 | 10 | PCBBiF: NDP-9 | 1:0.1 |
| | Electrode | 101 | 70 | ITSO | — |

<<Fabrication of Light-Emitting Device 17 to Light-Emitting Device 20>>

A light-emitting device 17 to a light-emitting device 20 are different from the above light-emitting device 16 only in the structure of the light-emitting layer 130 (the structure of the electron-transport layer 118 as well for the light-emitting device 17), and fabrication steps of the other components are the same as those in the fabrication method for the light-emitting device 16. The details of the device structures are as shown in Table 18; thus, the details of the fabrication method are omitted.

<Characteristics of Light-Emitting Devices>

Next, the characteristics of the fabricated light-emitting device 17 to light-emitting device 20 were measured. The measurement was performed in a manner similar to that in Example 7.

Figure 80:
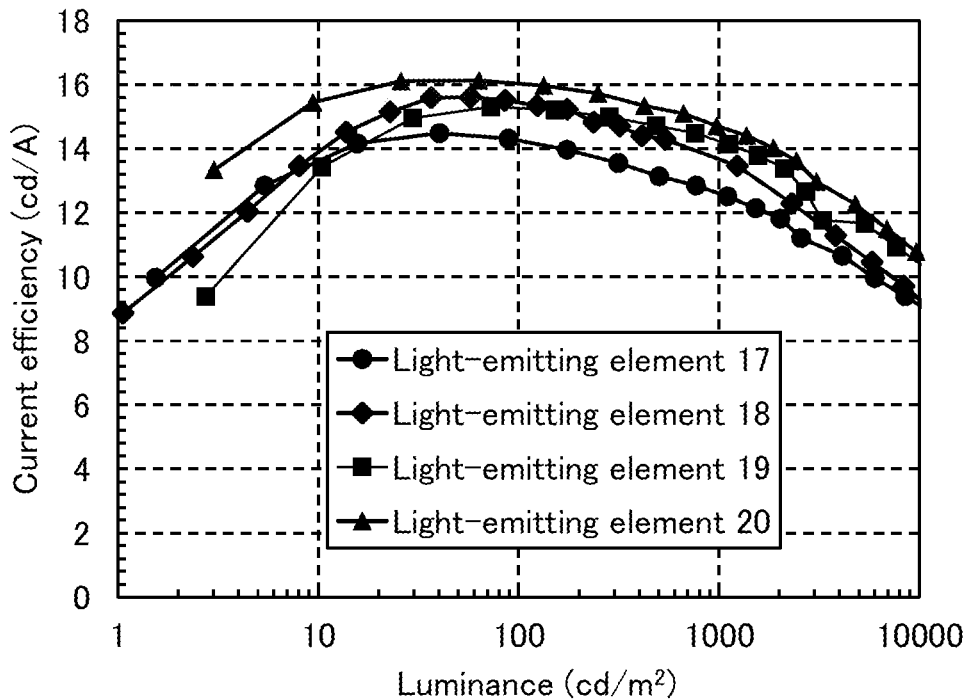
FIG. 80 A diagram showing current efficiency-luminance characteristics of light-emitting devices in Example.
Figure 81:
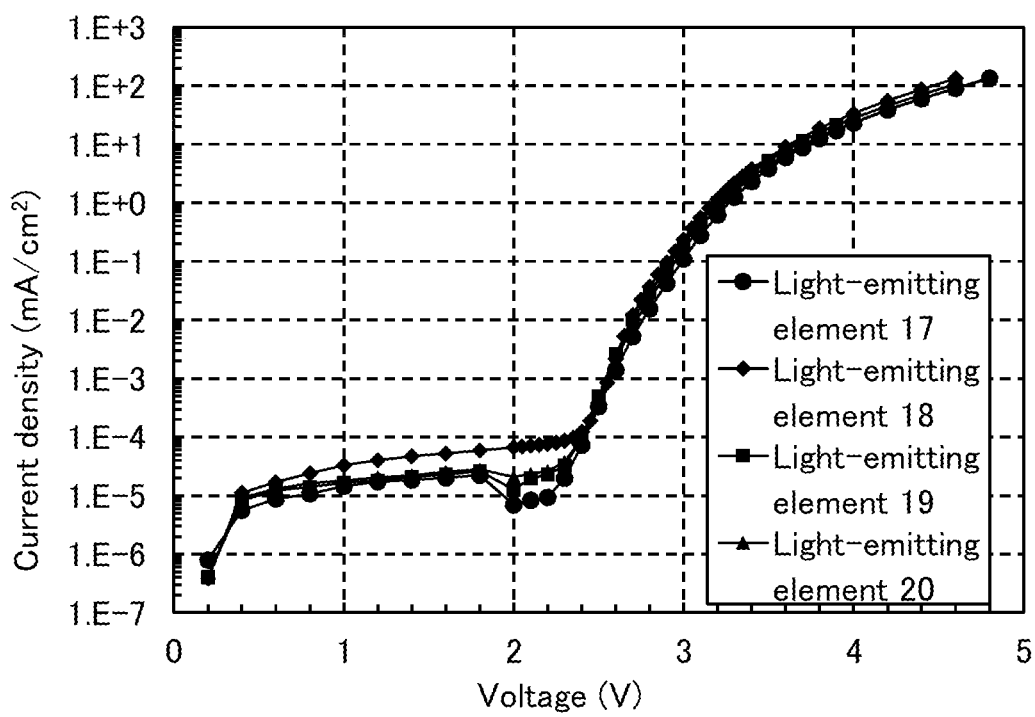
FIG. 81 A diagram showing current density-voltage characteristics of light-emitting devices in Example.
Figure 82:
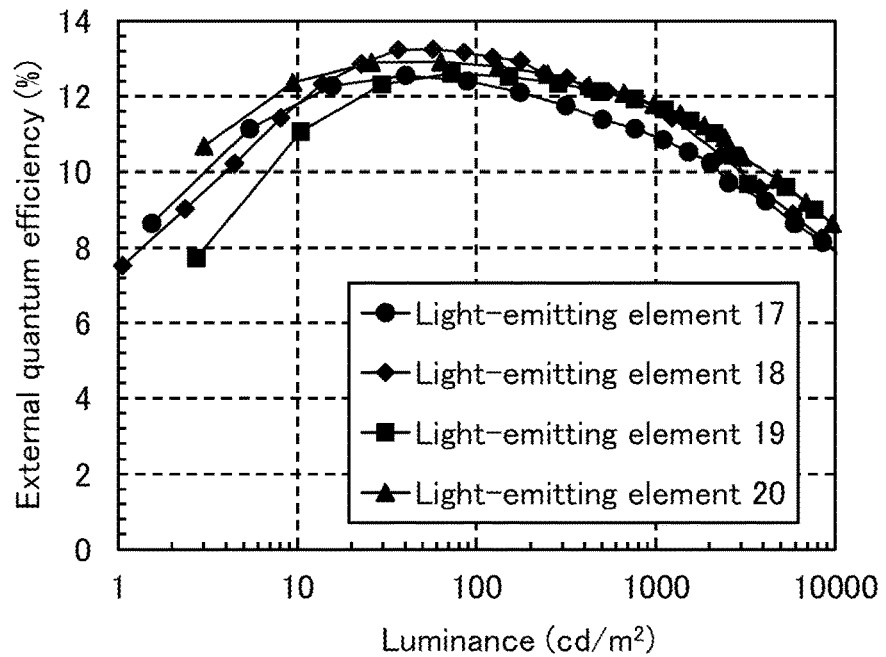
FIG. 82 A diagram showing external quantum efficiency-luminance characteristics of light-emitting devices in Example.
Figure 83:
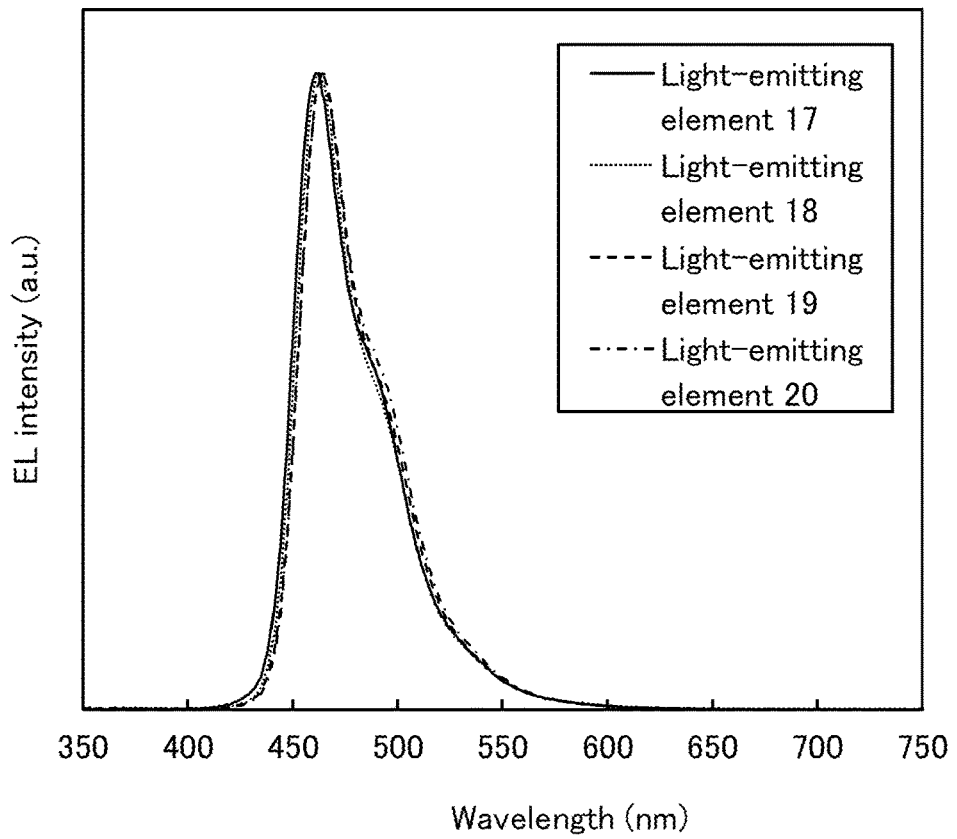
FIG. 83 A diagram showing emission spectra of light-emitting devices in Example.

FIG. 80 shows the current efficiency-luminance characteristics of the light-emitting device 17 to the light-emitting device 20. FIG. 81 shows the current density-voltage characteristics. FIG. 82 shows the external quantum efficiency-luminance characteristics. FIG. 83 shows emission spectra in the case where current at a current density of 12.5 mA/cm$^2$ was supplied to the light-emitting device 17 to the light-emitting device 20.

Table 19 shows the device characteristics of the light-emitting device 17 to the light-emitting device 20 at around 1000 cd/m$^2$.

TABLE 19

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 17 | 3.70 | 8.8 | (0.141, 0.154) | 1101.0 | 12.5 | 10.6 | 10.8 |
| Light-emitting device 18 | 3.60 | 9.19 | (0.142, 0.162) | 1237.0 | 13.5 | 11.7 | 11.4 |
| Light-emitting device 19 | 3.60 | 7.9 | (0.140, 0.172) | 1121.0 | 14.1 | 12.3 | 11.6 |
| Light-emitting device 20 | 3.60 | 6.64 | (0.140, 0.178) | 977.2 | 14.7 | 12.8 | 11.8 |

As shown in FIG. 80 and Table 19, despite emitting blue light with a low luminosity factor, the light-emitting device 17 to the light-emitting device 20 exhibited a current efficiency exceeding 12 cd/A, which is high for a blue fluorescent device.

As shown in FIG. 82 and Table 19, the light-emitting device 17 to the light-emitting device 20 exhibited an external quantum efficiency exceeding 10%, which is high for a fluorescent device. Note that the external quantum efficiencies of the light-emitting device 17 to the light-emitting device 20 are higher than 7.5%, which is the theoretical maximum value. This is probably because of the effects due to TTA, as described above.

As shown in FIG. 81 and Table 19, the light-emitting device 17 to the light-emitting device 20 have favorable driving voltage characteristics.

From FIG. 83, the emission spectra of the light-emitting device 17 to the light-emitting device 20 each have a spectral peak at around 464 nm and a full width at half maximum of approximately 42 nm; hence, the light-emitting device 17 to the light-emitting device 20 exhibited favorable blue light emission originating from 3,10PCA2Nbf(IV)-02, which is the guest material.

<Reliability of Light-Emitting Devices>

Figure 84:
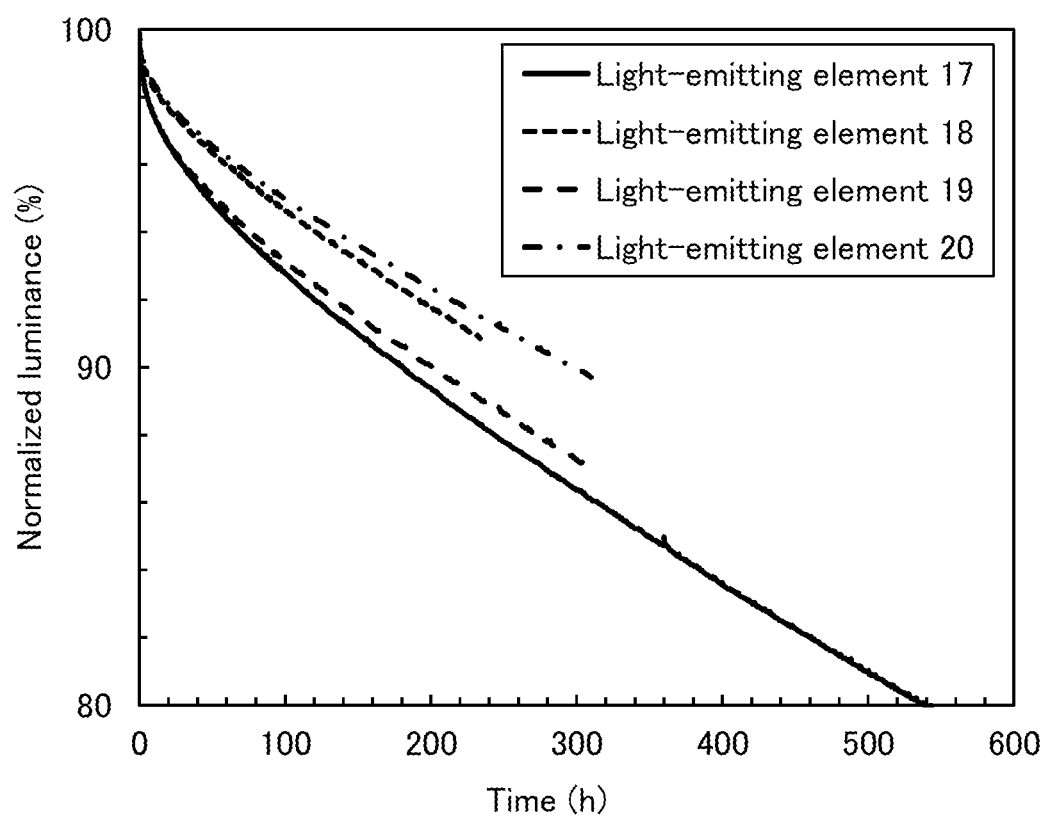
FIG. 84 A diagram showing results of a reliability test on light-emitting devices in Example.

Next, driving tests at a constant current of 2 mA were performed on the light-emitting device 17 to the light-emitting device 20. The results are shown in FIG. 84. It was found from FIG. 84 that the light-emitting device 17 to the light-emitting device 20 have high reliability with LT$_{90}$ of 180 hours or longer. In particular, the light-emitting device 18 and the light-emitting device 20 were found to have extremely high reliability with LT$_{90}$ of 250 hours or longer.

Example 20

This example will describe fabrication examples of light-emitting devices of embodiments of the present invention and the characteristics of the light-emitting devices. The structure of each of the light-emitting devices fabricated in this example is the same as that in FIG. 1(A). Table 20 shows the details of the device structures. The structure and abbreviation of an organic compound that was used are shown below. Note that the above examples and embodiments can be referred to for other organic compounds.

[Chemical Formula 40]

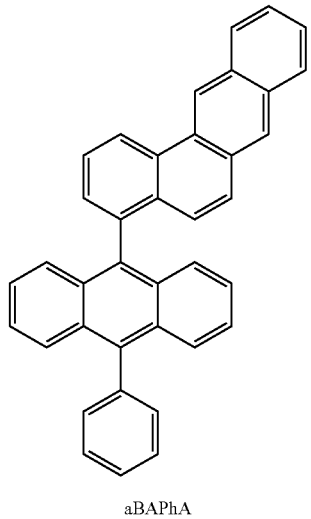

aBAPhA

TABLE 20

| | Layer | Reference numeral | Thickness (nm) | Material | Weight ratio |
|---|---|---|---|---|---|
| Comparative Light-emitting device 21 | Electrode | 102 | 200 | Al | — |
| | Electron-injection layer | 119 | 1 | LiF | — |
| | Electron-transport layer | 118 | 25 | NBPhen | — |
| | Light-emitting layer | 140 | 25 | aBAPhA: 1,6BnfAprn-03 | 1:0.03 |
| | Hole-transport layer | 112 | 30 | PCPPn | — |
| | Hole-injection layer | 111 | 10 | PCPPn: MoO$_3$3 | 1:0.5 |
| | Electrode | 101 | 70 | ITSO | — |

TABLE 20-continued

| | Layer | Reference numeral | Thickness (nm) | Material | Weight ratio |
|---|---|---|---|---|---|
| Light-emitting device 22 | Electrode | 102 | 200 | Al | — |
| | Electron-injection layer | 119 | 1 | LiF | — |
| | Electron-transport layer | 118 | 25 | NBPhen | — |
| | Light-emitting layer | 140 | 25 | 2aBAPA: 1,6BnfAprn-03 | 1:0.03 |
| | Hole-transport layer | 112 | 30 | PCPPn | — |
| | Hole-injection layer | 111 | 10 | PCPPn: $MoO_3$ | 1:0.5 |
| | Electrode | 101 | 70 | ITSO | — |
| Light-emitting device 23 | Electrode | 102 | 200 | Al | — |
| | Electron-injection layer | 119 | 1 | LiF | — |
| | Electron-transport layer | 118 | 25 | NBPhen | — |
| | Light-emitting layer | 140 | 25 | 2aBA-αNPhA: 1,6BnfAprn-03 | 1:0.03 |
| | Hole-transport layer | 112 | 30 | PCPPn | — |
| | Hole-injection layer | 111 | 10 | PCPPn: $MoO_3$ | 1:0.5 |
| | Electrode | 101 | 70 | ITSO | — |

<<Fabrication of Comparative Light-Emitting Device 21>>

As the electrode 101, an ITSO film was formed to a thickness of 70 nm over a glass substrate by a sputtering method. Note that the electrode area of the electrode 101 was set to 4 mm² (2 mm×2 mm). Next, as pretreatment for forming alight-emitting device over the substrate, a surface of the substrate was washed with water, drying was performed at 200° C. for one hour, and then UV ozone treatment was performed for 370 seconds. After that, the substrate was transferred into a vacuum evaporation apparatus where the degree of vacuum was kept at approximately $1×10^4$ Pa, and baking was performed at 170° C. for 30 minutes. Then, the substrate was allowed to cool for approximately 30 minutes.

Next, as the hole-injection layer 111, PCPPn and molybdenum(VI) oxide ($MoO_3$) were deposited over the electrode 101 by co-evaporation in a weight ratio (PCPPn:$MoO_3$) of 1:0.5 to a thickness of 10 nm.

Then, as the hole-transport layer 112, PCPPn was deposited over the hole-injection layer 111 by evaporation to a thickness of 30 nm.

Next, as the light-emitting layer 140, 4-(10-phenyl-9-anthryl)benzo[a]anthracene (abbreviation: aBAPhA) and 1,6BnfAPrn-03 were deposited over the hole-transport layer 112 by co-evaporation at a weight ratio (aBAPhA:1,6BnfAPrn-03) of 1:0.03 to a thickness of 25 nm. Note that in the light-emitting layer 140, 1,6BnfAPrn-03 is a guest material that exhibits fluorescence.

Then, as the electron-transport layer 118, NBPhen was deposited over the light-emitting layer 140 by evaporation to a thickness of 25 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, the substrate over which the light-emitting device was formed was fixed to a substrate (a counter substrate) that differs from the substrate over which the light-emitting device was formed for sealing with a sealant, whereby the comparative light-emitting device 21 was sealed. Specifically, a drying agent was attached to the counter substrate, and the counter substrate in which the sealant was applied to the surrounding of a portion where the light-emitting device was formed and the glass substrate over which the light-emitting device was formed were bonded to each other.

Then, irradiation with ultraviolet light having a wavelength of 365 nm at 6 J/cm² and heat treatment at 80° C. for one hour were performed. Through the above steps, the comparative light-emitting device 21 was obtained.

<<Fabrication of Light-Emitting Device 22 and Light-Emitting Device 23>>

The fabrication process of the light-emitting device 22 to the light-emitting device 23 is the same as that of the comparative light-emitting device 21 described above, except for the fabrication step of the light-emitting layer 140. The device structures of the light-emitting device 22 and the light-emitting device 23 are as shown in Table 20; hence, the detailed description of the fabrication process is omitted.

The device structures of the comparative light-emitting device 21, the light-emitting device 22, and the light-emitting device 23 are the same, except for a host material used for the light-emitting layer 140. Note that the light-emitting device 22 and the light-emitting device 23 respectively use 2aBAPA and 2aBA-αNPhA, each of which is the organic compound of one embodiment of the present invention, and the comparative light-emitting device 1 uses aBAPhA, which is a comparative substance. In 2aBAPA and 2aBA-αNPhA, the benzoanthracene skeleton is bonded to the 2-position of the anthracene skeleton, whereas in aBAPhA, the benzoanthracene skeleton is bonded to the 9-position of the anthracene skeleton.

<Reliability of Light-Emitting Devices>

Figure 85:
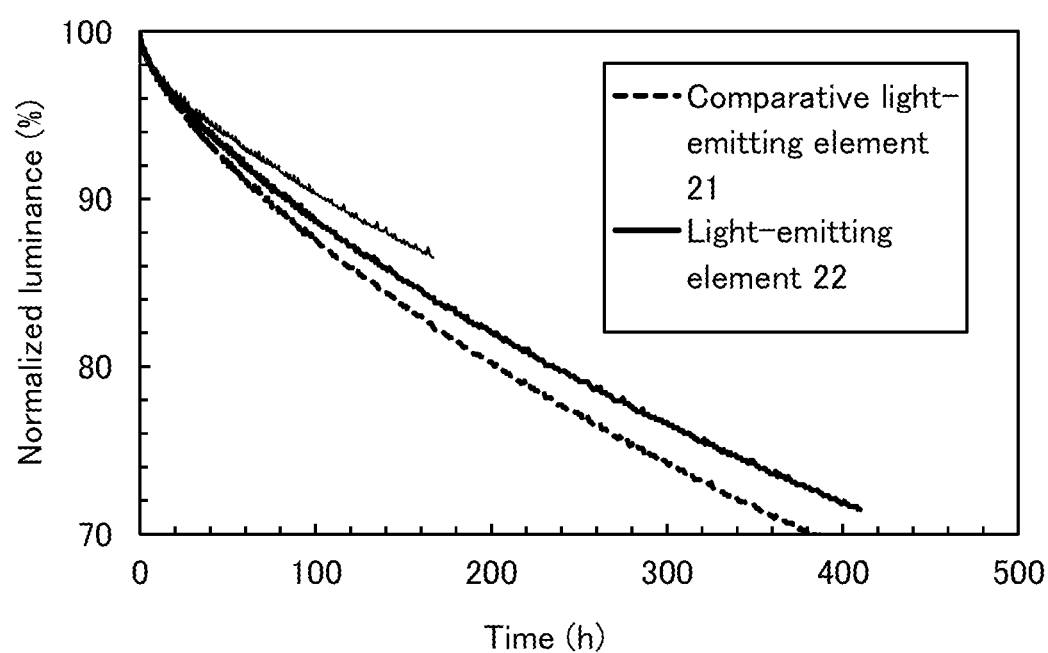
FIG. 85 A diagram showing results of a reliability test on light-emitting devices in Example.

Next, driving tests at a constant current of 2 mA were performed on the comparative light-emitting device 21, the light-emitting device 22, and the light-emitting device 23. The results are shown in FIG. 85. FIG. 85 shows that the light-emitting device 22 and the light-emitting device 23 have higher reliability than the comparative light-emitting device 21. It was thus found that as a host material used in a blue fluorescent device, the compound in which the benzoanthracene skeleton is bonded to the 2-position of the anthracene skeleton exhibits higher reliability than the compound in which the benzoanthracene skeleton is bonded to the 9-position of the anthracene skeleton.

REFERENCE NUMERALS

100: EL layer, 101: electrode, 102: electrode, 103: EL layer, 106: light-emitting unit, 108: light-emitting unit, 110: light-emitting device, 111: hole-injection layer, 112: hole-transport layer, 112-a: hole-transport layer, 112-b: hole-transport layer, 112-c: hole-transport layer, 113: electron-transport layer, 114: electron-injection layer, 115: charge-generation layer, 116: hole-injection layer, 117: hole-transport layer, 118: electron-transport layer, 119: electron-injection layer, 120: light-emitting layer, 121: host material, 122: guest material, 131: hole-injection layer material, 132: hole-transport material, 133: hole-transport material, 134: hole-transport material, 140: light-emitting layer, 141: host material, 142: guest material, 150: light-emitting device, 152: light-emitting device, 170: light-emitting layer, 250: light-emitting device, 600A: ALS model, 601: source side driver circuit, 602: pixel portion, 603: gate side driver circuit, 604: sealing substrate, 605: sealant, 607: space, 608: wiring, 610: device substrate, 611: switching TFT, 612: current controlling TFT, 613: electrode, 614: insulator, 616: EL layer, 617: electrode, 618: light-emitting device, 623: n-channel TFT, 624: p-channel TFT, 900: portable information terminal, 901: housing, 902: housing, 903: display portion, 905: hinge portion, 910: portable information terminal, 911: housing, 912: display portion, 913: operation button, 914: external connection port, 915: speaker, 916: microphone, 917: camera, 920: camera, 921: housing, 922: display portion, 923: operation button, 924: shutter button, 926: lens, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: electrode, 1024G: electrode, 1024R: electrode, 1024W: electrode, 1025B: lower electrode, 1025G: lower electrode, 1025R: lower electrode, 1025W: lower electrode, 1026: partition wall, 1028: EL layer, 1029: electrode, 1030: black layer, 1031: sealing substrate, 1032: sealant, 1033: base material, 1034B: coloring layer, 1034G: coloring layer, 1034R: coloring layer, 1035: black layer, 1036: overcoat layer, 1037: interlayer insulating film, 1040: pixel portion, 1041: driver circuit portion, 1042: peripheral portion, 1044B: blue pixel, 1044G: green pixel, 1044R: red pixel, 1044W: white pixel, 2100: robot, 2101: illuminance sensor, 2102: microphone, 2103: upper camera, 2104: speaker, 2105: display, 2106: lower camera, 2107: obstacle sensor, 2108: moving mechanism, 2110: arithmetic device, 3500: multifunction terminal, 3502: housing, 3504: display portion, 3506: camera, 3508: lighting, 3600: light, 3602: housing, 3608: lighting, 3610: speaker, 5000: housing, 5001: display portion, 5002: display portion, 5003: speaker, 5004: LED ramp, 5006: connection terminal, 5007: sensor, 5008: microphone, 5012: support, 5013: earphone, 5100: cleaning robot, 5101: display, 5102: camera, 5103: brush, 5104: operation button, 5120: dust, 5140: portable electronic apparatus, 5150: portable information terminal, 5151: housing, 5152: display region, 5153: bend portion, 8501: lighting apparatus, 8502: lighting apparatus, 8503: lighting apparatus, 8504: lighting apparatus, 9000: housing, 9001: display portion, 9003: speaker, 9005: operation key, 9006: connection terminal, 9007: sensor, 9008: microphone, 9055: hinge, 9200: portable information terminal, 9201: portable information terminal, 9202: portable information terminal This application is based on Japanese Patent Application Serial No. 2018-104950 filed with Japan Patent Office on May 31, 2018 and Japanese Patent Application Serial No. 2018-154845 filed with Japan Patent Office on Aug. 21, 2018, the entire contents of which are hereby incorporated herein by reference.

The invention claimed is:

1. An organic compound comprising a substituted or unsubstituted benzo[a]anthracene skeleton and a substituted anthracene skeleton, wherein the benzo[a]anthracene skeleton is bonded to a 2-position of the anthracene skeleton, and wherein a 9-position of the anthracene skeleton and a 10-position of the anthracene skeleton each independently comprise a substituted or unsubstituted aryl group having 6 to 13 carbon atoms.

2. An organic compound represented by General Formula (G1):

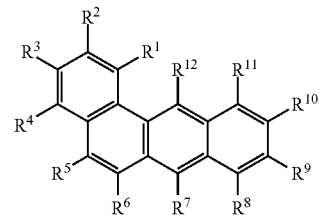

(G1)

wherein any one of $R^1$ to $R^{12}$ is a substituent represented by General Formula (g1), and the other $R^1$ to $R^{12}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring,

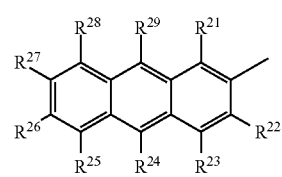

(g1)

wherein $R^{21}$ to $R^{23}$ and $R^{25}$ to $R^{28}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring, and wherein $R^{24}$ and $R^{29}$ each independently represent a substituted or unsubstituted aryl group having 6 to 13 carbon atoms.

3. An organic compound represented by General Formula (G2):

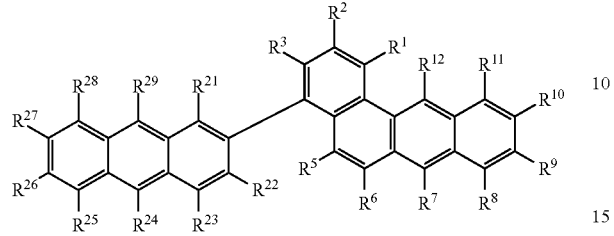
(G2)

wherein $R^1$ to $R^3$, $R^5$ to $R^{12}$, and $R^{21}$ to $R^{23}$ and $R^{25}$ to $R^{28}$ each independently represent any one of hydrogen, an alkyl group having 1 to 6 carbon atoms, a cycloalkyl group having 3 to 6 carbon atoms, and a substituted or unsubstituted aryl group having 6 to 13 carbon atoms in a ring, and wherein $R^{24}$ and $R^{29}$ each independently represent a substituted or unsubstituted aryl group having 6 to 13 carbon atoms.

4. The organic compound according to claim 3, wherein $R^1$ to $R^3$ and $R^5$ to $R^{12}$ each represent hydrogen.

5. The organic compound according to claim 2, wherein $R^{24}$ and $R^{29}$ each independently represent a substituted or unsubstituted phenyl group or a substituted or unsubstituted naphthyl group.

6. The organic compound according to claim 2, wherein $R^{24}$ is a substituted or unsubstituted phenyl group, and $R^{29}$ is a substituted or unsubstituted naphthyl group.

7. An organic compound represented by any one of Structural Formulae (100) to (104), (115), (117), (120), and (167).

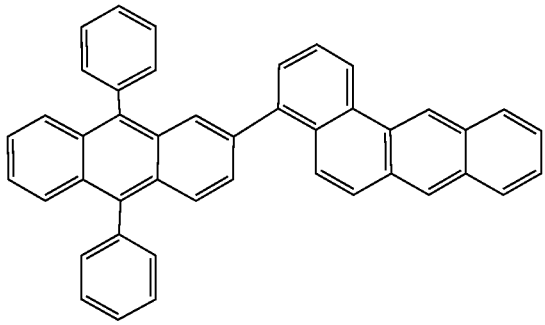
(100)

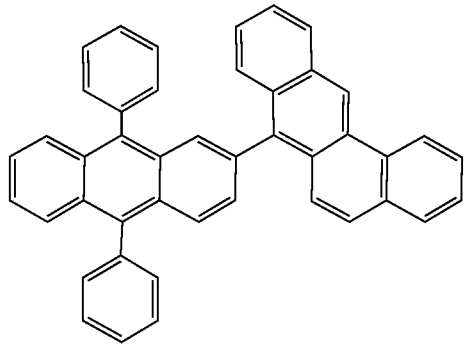
(101)

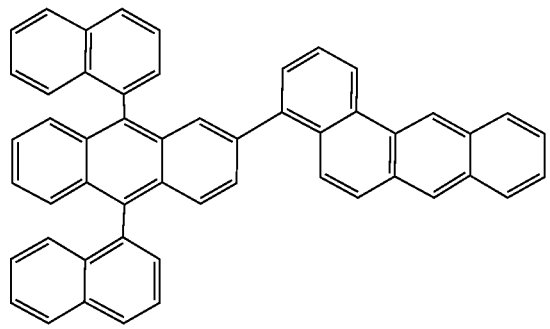
(102)

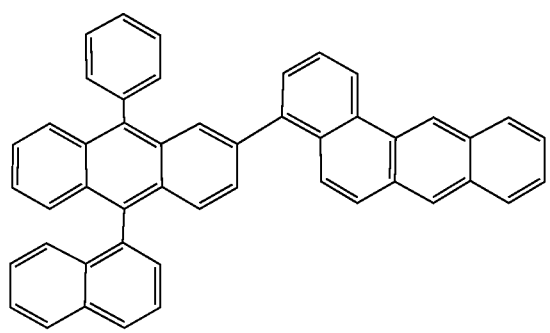
(103)

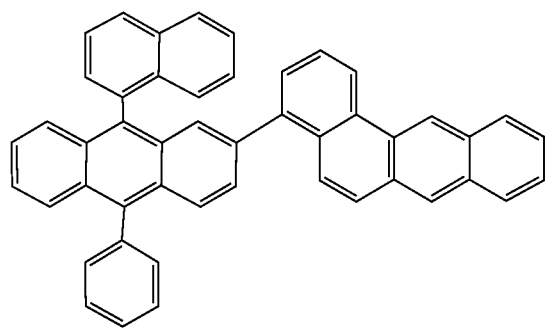
(104)

(120)
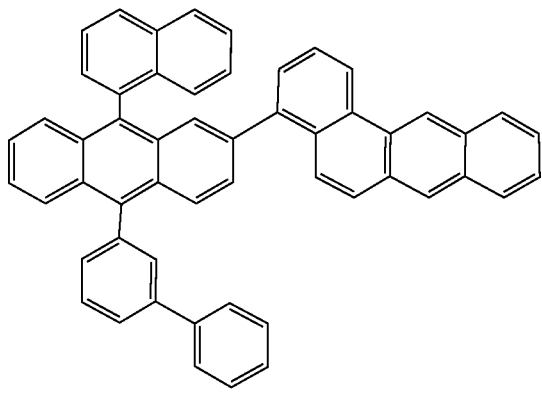

(115)
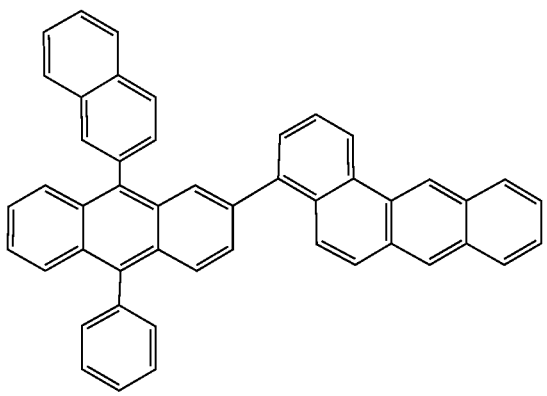

(167)
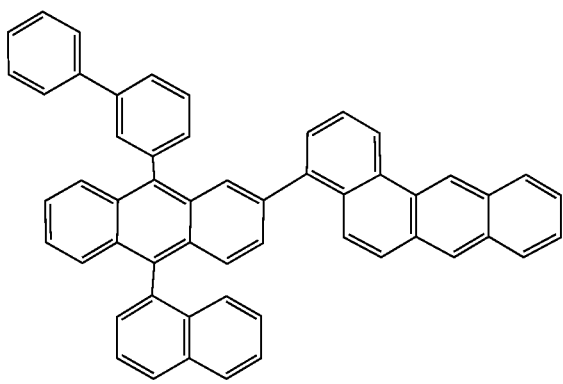

(117)
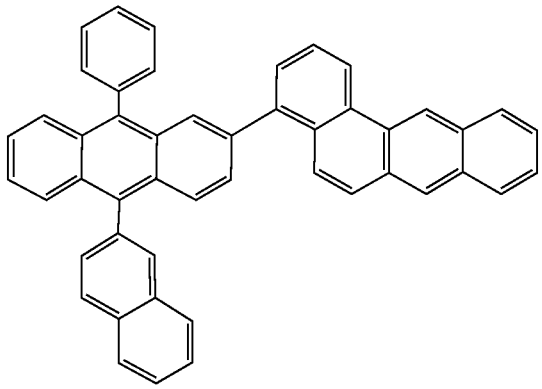

8. A light-emitting device comprising an EL layer between a pair of electrodes,
   wherein the EL layer comprises the organic compound according to claim 1.

9. A light-emitting device comprising a light-emitting layer between a pair of electrodes,
   wherein the light-emitting layer comprises the organic compound according to claim 1.

10. A light-emitting device comprising a light-emitting layer between a pair of electrodes,
    wherein the light-emitting layer comprises a host material and a guest material,
    wherein the host material comprises a benzo[a]anthracene skeleton and a substituted anthracene skeleton,
    wherein the benzo[a]anthracene skeleton is bonded to a 2-position of the anthracene skeleton,
    wherein a 9-position of the anthracene skeleton and a 10-position of the anthracene skeleton each independently comprise a substituted or unsubstituted aryl group having 6 to 13 carbon atoms,
    wherein the guest material comprises a luminophore, and
    wherein the luminophore comprises a benzofuran skeleton.

11. A light-emitting apparatus comprising:
    the light-emitting device according to claim 8, and
    at least one of a color filter and a transistor.

12. An electronic apparatus comprising:
    the light-emitting apparatus according to claim 11, and
    at least one of a housing and a touch sensor.

13. A lighting apparatus comprising:
    the light-emitting device according to claim 8, and
    at least one of a housing and a touch sensor.

* * * * *